US007407744B2

(12) United States Patent
Liu et al.

(10) Patent No.: US 7,407,744 B2
(45) Date of Patent: Aug. 5, 2008

(54) CYTOMEGALOVIRUS GENE FUNCTION AND METHODS FOR DEVELOPING ANTIVIRALS, ANTI-CMV VACCINES, AND CMV-BASED VECTORS

(75) Inventors: Fenyong Liu, Berkeley, CA (US); Walter Dunn, Cupertino, CA (US); Cassie Chou, Cupertino, CA (US)

(73) Assignee: The Regents of the University of California, Oakland, CA (US)

( * ) Notice: Subject to any disclaimer, the term of this patent is extended or adjusted under 35 U.S.C. 154(b) by 414 days.

(21) Appl. No.: 10/897,508

(22) Filed: Jul. 23, 2004

(65) Prior Publication Data

US 2005/0064394 A1 Mar. 24, 2005

Related U.S. Application Data

(60) Provisional application No. 60/490,200, filed on Jul. 25, 2003.

(51) Int. Cl.
*C12Q 1/70* (2006.01)

(52) U.S. Cl. ........................................................ 435/5

(58) Field of Classification Search ...................... 435/5
See application file for complete search history.

(56) References Cited

OTHER PUBLICATIONS

Chee et al., Analysis of the Protein-Coding Content of the Sequence of Human Cytomegalovirus Strain AD169, (1990) Curr Top Microbiol Immunol, 154: 125-169.

Dargan et al., The Published DNA Sequence of Human Cytomegalovirus Strain AD169 Lacks 929 Base Pairs Affecting Genes UL42 and UL43, (1997), J Virol, 71 (12): 9833-9836.

Davison et al., The Human Cytomegalovirus Genome Revisited: Comparison With the Chimpanzee Cytomegalovirus Genome, (2003), J Gen Virol, 84: (Pt 1), 17-28.

Marchini et al., Human Cytomegalovirus With IE-2 (UL122) Deleted Fails to Express Early Lytic Genes, (2001), J Virol 75: 1870-8.

*Primary Examiner*—Bruce Campell
*Assistant Examiner*—Myron G Hill
(74) *Attorney, Agent, or Firm*—Bozicevic, Field & Francis LLP; Pamela J. Sherwood

(57) ABSTRACT

A global functional analysis of HCMV genes is performed by constructing virus gene-deletion mutants and examining their growth phenotypes in different natural HCMV host cells. This systematic analysis of the HCMV genome identified 45 viral ORFs essential for viral replication and characterizes of 115 growth-dispensable viral genes. Of particular interest is the finding that HCMV encodes genes (temperance factors) that repress its own replication on a cell type-specific basis. In addition to HCMV, pathogen temperance may be a strategy employed by other infectious agents to enhance their long-term survivability within their respective host population.

5 Claims, 4 Drawing Sheets

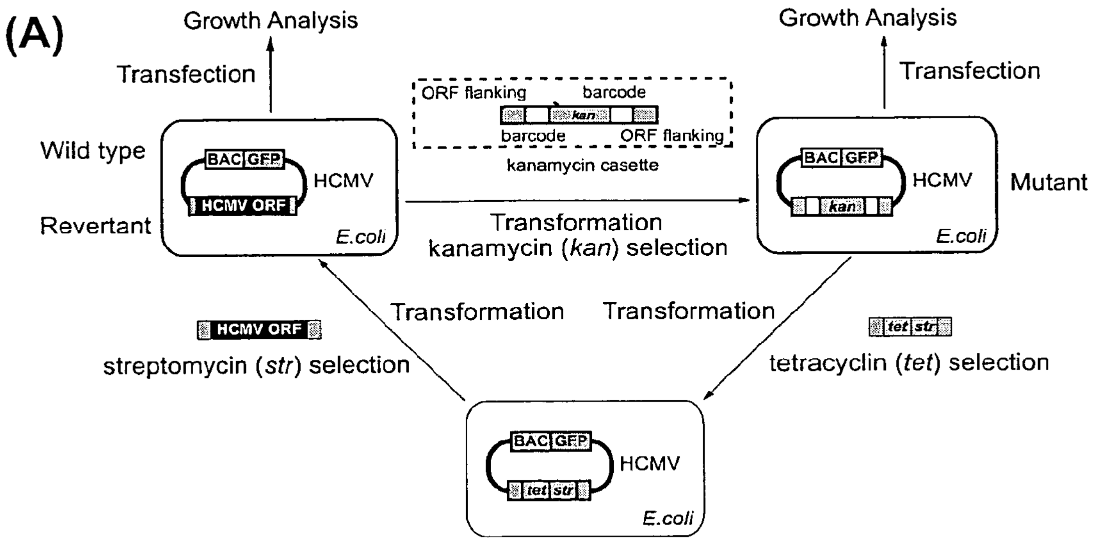
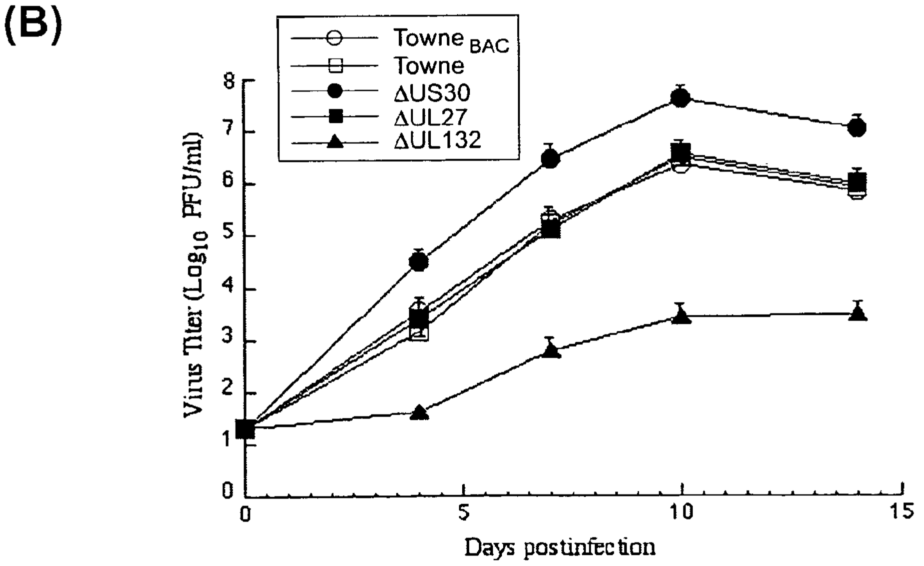
Dunn et al. Figure 2

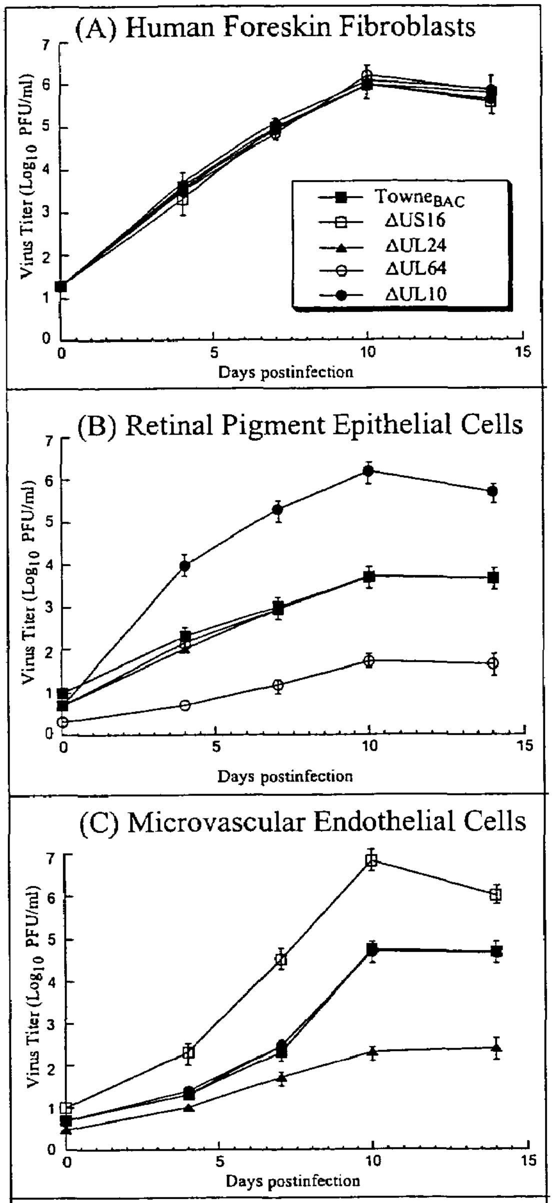
| Genes | Cells HFFs | RPE | HMVEC |
|---|---|---|---|
| $Towne_{BAC}$ | +++ | +++ | +++ |
| UL6 | +++ | +++ | +++ |
| UL7 | +++ | +++ | +++ |
| UL10 | +++ | +++++ | +++ |
| UL16 | +++ | +++++ | +++ |
| UL19 | +++ | +++ | +++ |
| UL24 | +++ | +++ | + |
| UL25 | +++ | +++ | +++ |
| UL64 | +++ | + | +++ |
| UL109 | +++ | +++ | +++ |
| UL116 | +++ | +++ | +++ |
| US16 | +++ | +++ | +++++ |
| US19 | +++ | +++ | +++++ |
| US22 | +++ | +++ | +++ |
| US29 | +++ | + | +++ |
| US32 | +++ | +++ | +++ |
Dunn et al., Figure 3

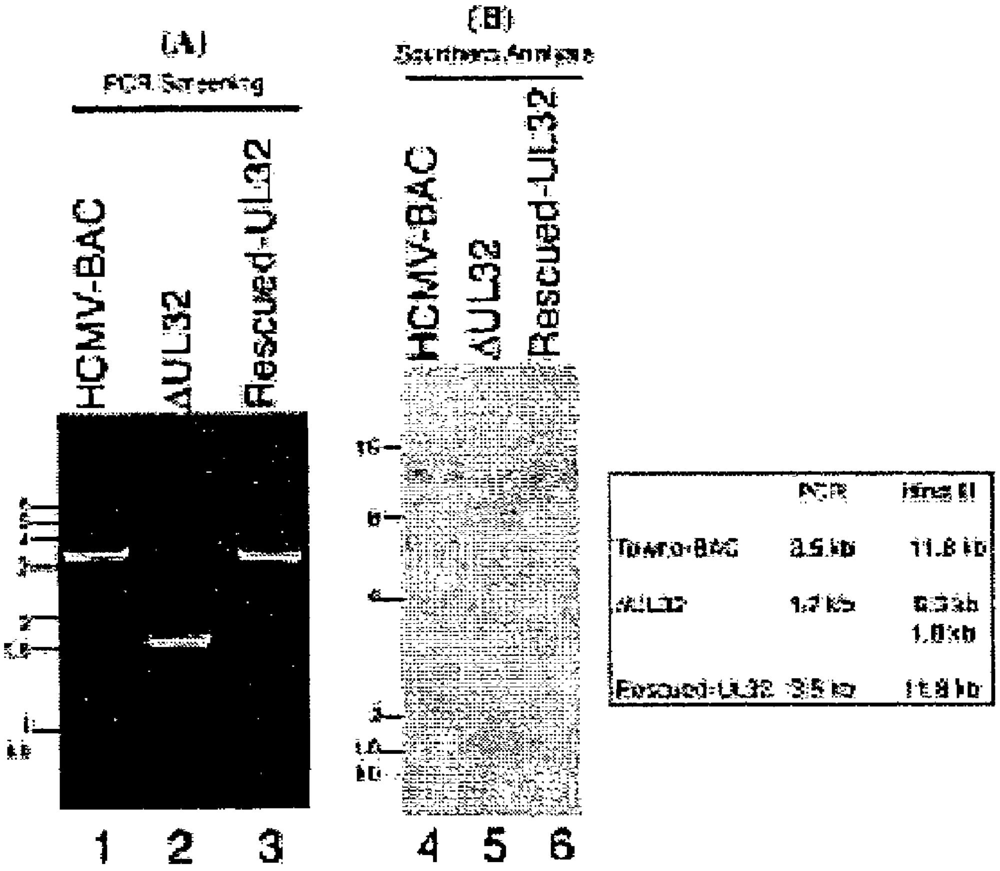
Dunn et al., Figure 4
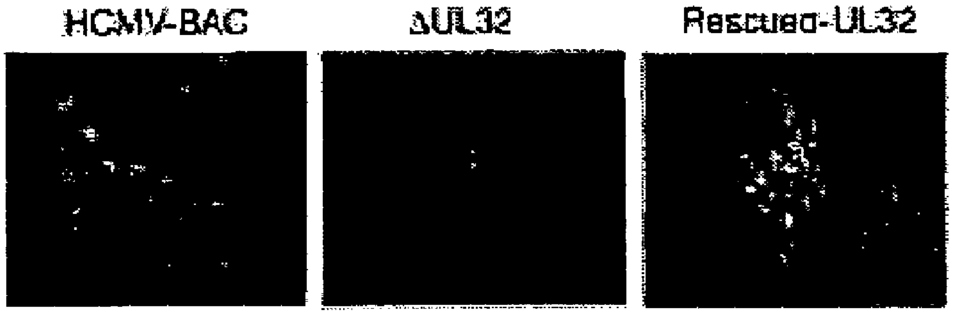
Dunn et al Figure 5

CYTOMEGALOVIRUS GENE FUNCTION AND METHODS FOR DEVELOPING ANTIVIRALS, ANTI-CMV VACCINES, AND CMV-BASED VECTORS

This application claims benefit of U.S. provisional application 60/490,200 filed 25 Jul. 2003.

Human cytomegalovirus (HCMV) is among the largest of the DNA viruses, with a genome of over 230 kb. This virus infects various tissue and cell types and, hence, is responsible for a myriad of complications including mental retardation, AIDS-associated retinitis, and vascular diseases. HCMV, is found universally throughout all geographic locations and socioeconomic groups, and infects between 50% and 85% of adults in the United States by 40 years of age. HCMV is also the virus most frequently transmitted to a developing child before birth. For most healthy persons who acquire CMV after birth there are few symptoms and no long-term health consequences, although there is usually a dormant virus infection for life.

However, HCMV infection is problematic for certain high-risk groups. Included among these are infection during pregnancy, and infection of immunocompromised individuals, such as organ transplant recipients and persons infected with human immunodeficiency virus (HIV). HCMV is a major cause of morbidity and mortality in AIDS patients with low CD4 counts, from either primary infection or reactivation of latent infection. Clinical illnesses in patients with HIV infection include chorioretinitis, pneumonia, esophagitis, colitis, encephalitis, polyradiculopathy, adrenalitis and hepatitis CMV also remains the most important cause of congenital viral infection in the United States. Generalized infection may occur in the infant if infected before birth, and symptoms may range from moderate enlargement of the liver and spleen (with jaundice) to fatal illness. With supportive treatment most infants with CMV disease usually survive. However, from 80% to 90% will have complications within the first few years of life that may include hearing loss, vision impairment, and varying degrees of mental retardation. Another 5% to 10% of infants who are infected but without symptoms at birth will subsequently have varying degrees of hearing and mental or coordination problems.

Although primary HCMV infection in an immunocompromised patient can cause serious disease, the more common problem is the reactivation of the dormant virus. Infection with CMV is a major cause of disease and death in immunocompromised patients, including organ transplant recipients, patients undergoing hemodialysis, patients with cancer, patients receiving immunosuppressive drugs, and HIV-infected patients. Pneumonia, retinitis (an infection of the eyes), and gastrointestinal disease are the common manifestations of disease. Because of this risk, exposing immunosuppressed patients to outside sources of CMV should be minimized. Whenever possible, patients without CMV infection should be given organs and/or blood products that are free of the virus.

Depending on the tissue type and the host's immune state, HCMV engages in three different modes of infection: acute infections with highly productive growth, persistent infections with low levels of replication, and latent infections where no viral progeny are produced. In different cell types, HCMV exhibits various growth rates, suggesting that its replication in a particular cell type is tightly regulated and thus, determines the outcome of diseases in specific tissues. Although there is evidence for a genetic basis of viral cell type-specific infection and growth regulation, many virus-encoded cell-tropism factors have not been identified, and their functional roles in viral replication are unclear.

Methods of controlling and preventing HCMV infection are of broad interest to the scientific community, pharmaceutical and biotech industry. The present invention addresses these issues.

Relevant Literature

The genomic sequence of human cytomegalovirus (AD169) has been deposited with Genbank; accession number NC_001347. The sequence information is reviewed by Davison et al. (2003) J. Gen. Virol. 84 (Pt 1), 17-28; Dargan et al. (1997) J. Virol. 71 (12), 9833-9836; and Chee et al. (1990) Curr. Top. Microbiol. Immunol. 154, 125-169.

SUMMARY OF THE INVENTION

A global functional analysis of HCMV genes was performed by constructing virus gene-deletion mutants and examining their growth phenotypes in different natural HCMV host cells. This systematic analysis of the HCMV genome identified 45 viral ORFs essential for viral replication and characterized 115 growth-dispensable viral genes. Of particular interest is the finding that HCMV encodes genes (herein termed temperance factors) that repress its own replication on a cell type-specific basis. In addition to HCMV, pathogen temperance may be a strategy employed by other infectious agents to enhance their long-term survivability within their respective host population.

Viral temperance factors, genes encoding such temperance factors, and viruses having mutations in temperance factors are provided. Viruses with deletions temperance factor genes exhibit enhanced growth phenotypes, as compared to the wild type virus. These repressors of growth facilitate pathogen temperance. The genetic sequence of such temperance factors in viruses are modified to modulate virus replication, e.g. in the development of vaccine strains, for research purposes, and the like. The temperance factor polypeptides are useful as targets for drug design, as targets for immunological agents, and the like. Drugs mimicking or activating growth inhibitors or temperance factors find use in therapies against infectious diseases. In vitro hyper-growth strains having diminished or absent temperance factors can be used for facile production of large quantity of subunit and attenuated live vaccines.

Genes essential, or dispensable, for replication of HCMV are also identified. The sequence of such essential or dispensable genes can be modified to modulate virus replication, e.g. in the development of vectors and vaccine strains, for research purposes, and the like. Protein products of these genes are useful as targets for drug design, as targets for immunological agents, and the like.

In another embodiment of the invention, methods and compositions for the functional analysis of cytomegalovirus are provided. Such methods include the construction of rescued mutants, and methods for tagging and introducing foreign genes into CMV genome. These approaches can be used for vector and vaccine development. A collection of mutant cytomegaloviruses is provided, where each virus contains a deletion corresponding to one open reading frame in the virus genome. The mutant HCMV are useful in a number of screening methods. Screening methods include the growth of HCMV in different human cell lines.

BRIEF DESCRIPTION OF THE DRAWINGS

FIG. 2. (A) Procedures for constructing deletion and rescued mutants, as described in Methods. (B) Multiple-step growth (multiplicity of infection [MOI]=0.05) of HCMV mutants in HFFs. Cells were infected with each virus and at different time points post-infection, cells and culture media were harvested and sonicated. The viral titers were determined by plaque assays on HFFs. The values of the viral titer represent the average obtained from triplicate experiments. The standard deviation is indicated by the error bars.

FIG. 3. Analysis of multiple-step growth of different mutants and $Towne_{BAC}$ in HFFs (A) (MOI=0.05), retinal pigment epithelial (RPE) cells (B) (MOI=0.25), and human microvascular endothelial cells (HMVEC) (C) (MOI=0.05). (D) Comparison of the growth properties of 15 mutants in these three cell types with those of $Towne_{BAC}$. +++, peak titer similar to that of $Towne_{BAC}$; +++++, peak titer at least 100 times higher than that of $Towne_{BAC}$; +, peak titer at least 100 times lower than that of $Towne_{BAC}$. The values of the viral titer represent the average obtained from triplicate experiments. The standard deviation is indicated by the error bars.

FIG. 4. Polymerase chain reaction (PCR) (lanes 1-3) and Southern analyses (lanes 4-6) of the DNAs of the deletion (ΔUL32) and rescued (Rescued-UL32) mutant, and $Towne_{BAC}$ that were isolated from *E.coli* (lanes 1-3) and human fibroblasts (lanes 4-6). In (A), PCR products were separated on 1% agarose gels and visualized using ethidium bromine staining. In (B), DNAs were digested with Hind III, separated on 0.8% agarose gels, transferred to membranes, and hybridized with a [$^{32}$P]-labeled probe containing both the KanMX4 and HCMV UL32 sequences. The numbers represent the size of either the PCR DNA products (PCR) or the DNA fragments (Hind III) of BAC-DNAs that were digested with Hind III and hybridized to the radiolabeled probe in Southern analysis.

FIG. 5. Microscopic images of green fluorescent protein (GFP) staining of human foreskin fibroblasts (HFFs) transfected with the DNAs (20 μg/$10^5$ cells) of $Towne_{BAC}$, ΔUL32, and rescued-UL32 at 10 days post-transfection. Viral infection can be visualized using GFP staining since all BAC-DNAs contain a GFP expression cassette.

DETAILED DESCRIPTION OF THE EMBODIMENTS

Figure 1:
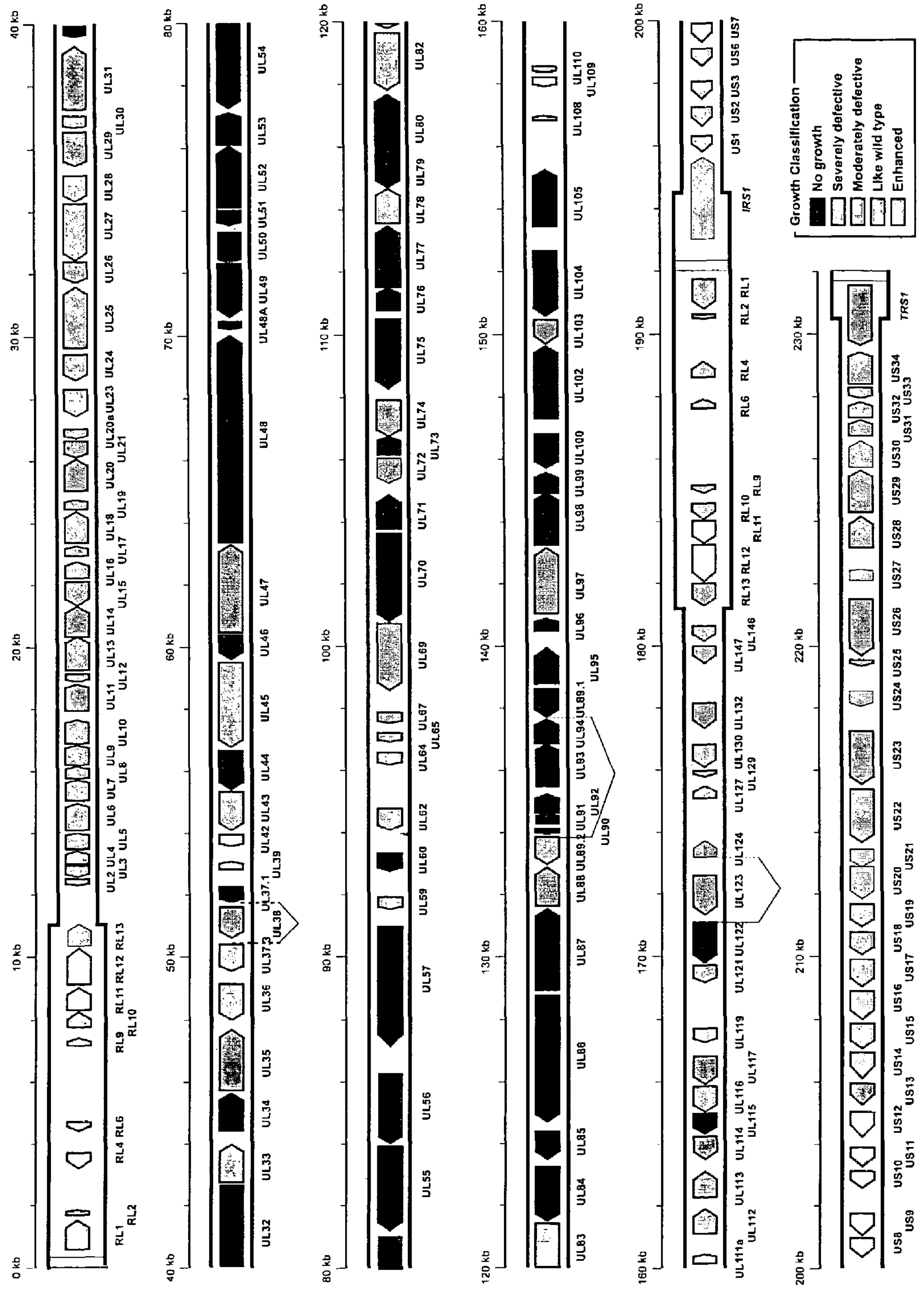
FIG. 1. Genome organization and genes of HCMV (Towne strain) based on the genome-wide shotgun sequencing of the viral sequence cloned in a BAC. Similar to the HCMV AD169 genome, the Towne genome is composed of a unique long (UL) region and a unique short (US) region, both flanked by inverted repeat regions (RL and RS). RL and RS are shown in a thicker format than UL and US. Each of the ORFs (RL1-RL13, UL2-UL147, IRS1, US1-US34, and TRS1) is color-coded according to the growth properties of their corresponding virus-deletion mutants in HFFs (see Table 6). The ORFs (RL11 and RL12), for which a deletion mutant was not generated, are shown in white. Repeated attempts to delete these two ORFs failed, possibly due to the presence of two copies of these genes at the inverted repeated regions. The vertical dashed lines represent the splicing junctions.

Using a bacterial artificial chromosome (BAC) engineering and RED recombinase technology in conjunction with growth curve analysis in human fibroblast cells in tissue culture, an open reading frame deletion library spanning the entire human cytomegalovirus genome was constructed. The complete sequence of HCMV Towne strain was determined, and is provided herein as SEQ ID NO:1. The BAC based ORF deletion constructs were then transfected into human fibroblast cells in tissue culture. Constructs with deletions in 45 separate and distinct ORFs in the HCMV genome did not yield any viral progeny upon transfection into the fibroblast cells, indicating that those regions of the genome are essential for viral growth. These essential genes are drug targets for anti CMV therapeutic applications.

In addition, the functional mapping of the genome identified regions in the viral genome dispensable for viral growth. All ORF deletion constructs that yielded viral progeny upon transfection were deemed dispensable for viral growth. Growth curve analyses were performed on the BAC derived mutant virus and ORF deletions categorized as either severe growth defect, moderate growth defect, growth like wild type, or enhanced growth. The identification of these non-essential genes identify which genes can be deleted to create an attenuated virus for use as a vaccine, which genes can be deleted to create a gene therapy vector so as to accommodate the delivery gene of interest without affecting viral propagation in vitro; etc. Further growth kinetic characterization of the constructed mutants were carried out on human retinal epithelial cells, human aortic smooth muscle cells, and human microvascular endothelial cells and compared to the results from the human foreskin fibroblast characterization. This comparative analysis identified open reading frame deletion viruses that replicated differentially, compared to the wild-type virus, in the cell types tested, indicating that these open reading frames encoded cell tropism important factors.

The various methods of the invention will be described below. Although particular methods of tumor suppression are exemplified in the discussion below, it is understood that any of a number of alternative methods, including those described above are equally applicable and suitable for use in practicing the invention. It will also be understood that an evaluation of the vectors and methods of the invention may be carried out using procedures standard in the art, including the diagnostic and assessment methods described above.

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture") (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Unless otherwise indicated, all terms used herein have the same meaning as they would to one skilled in the art and the practice of the present invention will employ, conventional techniques of microbiology and recombinant DNA technology, which are within the knowledge of those of skill of the art.

"Replication" and "propagation" are used interchangeably and refer to the ability of a virus or viral vector of the invention to reproduce or proliferate. These terms are well understood in the art. For purposes of this invention, replication involves production of viral proteins and is generally directed to reproduction of virus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "individual" is a vertebrate, preferably a mammal, more preferably a human. Mammals include, but are not limited to, farm animals, sport animals, rodents, primates, and pets. A "host cell" includes an individual cell or cell culture which can be or has been a recipient of an viral vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with an adenoviral vector of this invention.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "effective amount" is an amount sufficient to effect beneficial or desired clinical results. An effective amount can be administered in one or more administrations. For purposes of this invention, an effective amount of a temperance factor or temperance factor mimetic or temperance factor enhancer is an amount that is sufficient to palliate, ameliorate, stabilize, reverse, slow or delay the progression of the viral infection. An effective amount of a virus used in a vaccine is the amount that is sufficient to generate a virus specific immune response in the individual to which it is administered.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. "Palliating" a disease means that the extent and/or undesirable clinical manifestations of a disease state are lessened and/or time course of the progression is slowed or lengthened, as compared to not administering factors or compounds of the present invention.

The term "polynucleotide" as used herein refers to a polymeric form of nucleotides of any length, either ribonucleotides or deoxynucleotides. Thus, this term includes single-, double- and triple-stranded DNA, as well as single- and double-stranded RNA, RNA-DNA hybrids, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Mol. Immunol. 32: 1057-1064. Preferably, the polynucleotide is DNA. As used herein, "DNA" includes not only bases A, T. C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In addition, a double-stranded polynucleotide can be obtained from the single-stranded polynucleotide product of chemical synthesis either by synthesizing the complementary strand and annealing the strands under appropriate conditions, or by synthesizing the complementary strand de novo using a DNA polymerase with an appropriate primer.

The term "gene" is well understood in the art and is a polynucleotide encoding a polypeptide. In addition to the polypeptide coding regions, a gene includes non-coding regions including, but not limited to, introns, transcribed but untranslated segments, and regulatory elements upstream and downstream of the coding segments.

The term "virus target" is used to generally refer to a complete virus particle or virion, a nucleocapsid, capsid, or macromolecule from the virus, which may be a lipid, polysaccharide, protein, etc., usually an envelope or capsid protein. Viruses are infectious agents, usually comprising only one kind of nucleic acid as their genome. The nucleic acid is encased in a protein shell of capsid proteins, which forms the nucleocapsid particle. The nucleocapsid may be further surrounded by a lipid containing membrane, into which are typically inserted envelope proteins.

Viruses may be classified according to their genome composition. DNA viruses include parvoviruses, papovaviruses, adenoviruses, herpesviruses, poxviruses and hepanaviruses. RNA containing viruses include caliciviruses, reoviruses, arboviruses, togaviruses, flaviviruses, arenoviruses, coronaviruses, retroviruses, bunyaviruses, orthomyxoviruses, paramyxoviruses, and rhabdoviruses.

Herpesvirus is a class of viruses containing several important human pathogens. An important property of herpesviruses is their ability to establish life-long persistant infection of the host, and to undergo periodic reactivation. Their frequent reactivation in immunosuppressed patients frequently causes health problems. The reactivated infection may be clinically very different from the disease caused by primary infection.

There are eight herpesviruses known to infect humans: herpes simplex viruses 1 and 2; varicella-zoster virus, cytomegalovirus, Epstein-Barr virus, human herpesvirus 6 and 7, and Kaposi's Sarcoma associated herpesvirus (HHV-8). All herpesviruses have a core of double-stranded DNA surrounded by a protein coat having icosahedral symmetry. The nucleocapsid is surrounded by an envelope that is derived from the nuclear membrane of the host cell, and contains viral glycoprotein spikes.

The sub-family of β-herpesvirus include humanherpesvirus 5 (Human cytomegalovirus); muromegalovirus Murid (beta) herpesvirus 1 (Mouse cytomegalovirus); Suid herpesvirus 2 (Pig cytomegalovirus); Equid (beta) herpesvirus 2 (Equine cytomegalovirus); Porcine herpesvirus 2 (inclusion body rhinitis virus); Bovine herpesvirus 4 (bovine cytomegalovirus); Murid herpesvirus 2 (Rat cytomegalovirus); and Caviid herpesvirus 1 (guineapig cytomegalovirus). The sub-family of α-herpesvirus include the simplexviruses: Simplex-virus Human herpesvirus 1 (Herpes simplex virus 1); Human herpesvirus 2 (Herpes simplex virus 2); Bovine herpesvirus 1 (Bovine Mammilitis virus 1); and the Varicellovirus Herpesviridae: Duck Enteritis Virus (Duck enteritis herpesvirus (DEHV), Duck enteritis virus, Duck plague virus, Anatid Herpesvirus, Avian herpesvirus 2); Human herpesvirus 3 (Varicella-zoster virus); Suid herpesvirus 1 (Pseudorabies/Aujesky's disease virus); Bovine herpesvirus 1 (Infectious bovine rhinotracheitis virus); Equine herpesvirus 1 (Equine abortion virus); Equine herpesvirus 4 (Respiratory infection virus); Feline herpesvirus 1 (FHV-1); Canine herpesvirus (CHV) ("Fading puppy" syndrome virus); Equine herpesvirus 3 (Coital exanthema); and Avian herpesvirus (Infectious laryngotracheitis of chicken).

Characterization of HCMV Gene Sequences According to their Effect on Growth

The present invention provides for the classification of open reading frames (genes) in HCMV according to the effect that such sequences have on growth of the virus. Sequences are classified according to the effect on a virus when the sequence is deleted, and are: essential for growth, causing a severe growth deficit, causing a moderate growth deficit, having no effect on growth, and causing enhanced growth. In the tables setting forth the open reading frames in these categories, the sequences are referred to by the ORF, which are diagrammed in FIG. 1.

In order to unambiguously define the sequence of each ORF in the HCMV Towne strain, the genetic sequence of the HCMV is provided herein, as SEQ ID NO:1. Also provided are upstream primer sequences adjacent to the ATG start codon of each ORF; and downstream primers that are adjacent to the sequence 1 nt past the stop codon of each ORF. The sequence of the complete ORF can easily be determined by one of skill in the art, by using the primer sequences provided to delineate the ORF in SEQ ID NO:1. An ORF may thus be defined as the sequence of SEQ ID NO:1 that is bounded by the corresponding up and down primer. For example, the ORF of US26 comprises the sequence of SEQ ID NO:1 that is 3' of the upstream primer and 5', less 1 nucleotide, of the downstream primer.

The orientation of the primers (i.e. whether the primer is complementary or identical to the corresponding region of SEQ ID NO:1) with respect to SEQ ID NO:1 depends on the the orientation of the open reading frame in question. This can be determined by looking at the numerical identifers of the primers. These identifiers are three digit numbers followed by "Up2" and a letter, either "W" or "C" (eg. 006_Up2W or 453_Up2C). If the letter is a "W" then the upstream primer located is complementary to the SEQ ID NO:1 and the downstream primer is identical to the sequence in SEQ ID NO:1. If the letter is "C" then the upstream primer is identical to the sequence and the downstream primer is complementary. The 3' end of the upstream primers ends directly adjacent to the ATG start codon of the ORF. The 3' end of the downstream primers stop 1 nt. beyond the stop codon (i.e. there is a 1 nt. gap between the stop codon and the 3' end of the downstream primer).

| | | | | |
|---|---|---|---|---|
| 006_up2W | AAGAAACTCCATAAAATAGGCTGCCAAGTGCCGCTC CACGCCGCGGCACC | 006_down2W | TTTATTTGTATTCCTTTCCTGTTTTGTACTCGTAAA CTGTTGACGTTGTT | US 26 |
| 014_up2W | CCCCACTTGCCGCTGTACAACGAATTCACCAGCTTT CGCCTGCCCACCTC | 014_down2W | GTGCCACCGGTCCAGGTGAGAAAGAGAAGCCGCAAT CCGGGCGGCGGCAC | UL116 |
| 017_up2W | GCCGCCCGAGCTGAAGCAGACGCGCGTCAACCTGCC GGCTCACTCGCGCT | 017_down2W | TAGACATCACAGTTCACCACCTTGTCTCCCCGGTGT GTCTATTATCATCA | UL 114 |
| 019_up2W | CCGCACTCGGTCAGCACCCGCAGAATCCCGGGATCT CGGGCCCTGCGGCC | 019_down2W | AAAAGCACAGGGCCAGGAAAAGCAACCAGCCCCGCC ATCGCCGCCGCCGC | UL117 |
| 020_up2W | CGGCGCCAACTGGCTCCTTACCGTCACACTCTCATC GTGCCGCAGACTTG | 020_down2W | ACGCGAGCCTGCTCGTCGGGGGTTAACAGAGAGCCT TTATTATCAGCAAT | UL 115 |
| 024_up2W | CCGCCATGAAGGCAAGAGCAGCAGCAGCAACGACGT CACTACGATGATTG | 024_down2W | TGNGGCCTATAAGGTGTCTTCTATCACGGTGGCTTG TTCATCGCTTGGCG | UL109 |
| 036_up2W | CCTTCGTCCCAGACGGACGGCTATCGGTTCGCGCGC TCGTCTTTTCTTCG | 036_down2W | GCTGCTCTTGCCTTCATGGCGGTATTTCTCTTCCTC CCCCCTAACCCCAT | UL110 |
| 046_up2W | TCGCCCCGAGGCGCTGCTCTGAAGCCAAGTGCCGAC GGCGCTTTGGCTTT | 046_down2W | AGCGTCACAACTGACGTGGGTTGGGTACTGACGTGC AGGATATTACGCGA | US 33 |
| 064_up2W | GACGCCGCGCCGACGCTCAAGCTCTGGGACTGGACT TGGCCACGGTGGTG | 064_down2W | TGTGAAAAAGAATTCTCGTAAGCATGTTGACAACTG CAAAATAAAACCAT | TRS 1 |
| 070_up2W | ATTACTAATCCATAACATGGCTCTTTGCCACAACTA TCTCTATTGGCTAT | 070_down2W | GCACACTGGTGGTGGTGGGCATTGTGCTGTGCCTAA GTCTGGCCTCCACT | UL125 |

-continued

| | | | | |
|---|---|---|---|---|
| 073_up2W | AGAGTAAAGATTAACTCTTGCATGTGAGCGGGGCAT CGAGATAGCGATAA | 073_down2W | ACAATAGTGACGTGGGATCCATAACAGTAACTGATA TATATATACAATAG | UL 123 |
| 079_up2W | CGCGTCCTTTCAAGGTGATTATTAAACCGCCCGTGC CTCCCGCGCCTATC | 079_down2W | ACGGGGAATCACTATGTACAAGAGTCCATGTCTCTC TTTCCAGTTTTTCA | ul 122 |
| 083_up2W | CTGTTTAATAAAAGTAGCTTTTTTTATACATCTCCG TCTCTGGTCTCGTG | 083_down2W | TAGTTACCCTCTCGACGTCGCCGGCTGTCAATGACG TGCCTGCGTCAGTG | UL121 |
| 085_up2W | TCACCTATCCCATCTACGCCGTGTACGGGACTCGCT TGAACGCTACCACG | 085_down2W | GAAGTCAGCGAAATAAAGACAACACAGCAGCCGCTC CTCTCGTTTCTGGC | UL118 |
| 094_up2W | CTCGGCCAGGGGGTACCGAGGCGGTGCCCGCGACTC GCCCCTCCTCCAAG | 094_down2W | GTTGGGTGTGGCCGGAAGCGCTCGGGGTCGACGGTG GGCCGCCATGACAC | UL62 |
| 097_up2W | ATCAGCAGCTCGCACAGGCGCTGGGCTAGCTGCATC GTGCCGGCGCGACG | 097_down2W | AGATGAGACCGCTGCCGGGGGGCGGGTCACCGGCGC CGTGGAAAGTGAGG | UL70 |
| 098_up2W | CTATATATACATCAGCGTGCCCGAACGTGACCTTCC TAGCGACGACGGCC | 098_down2W | TAACGGGATAAGGGACAGCAATCATCACGCACAACA CCCTTCACTCTCTT | UL69 |
| 099_up2W | GCCGCCGCCGCGGTTGCTACTACTTTCTTAAGTGAT GCGAATTGGTGGCT | 099_down2W | ATAAACGTTCTCAACAGGTATGAAATGAACAAACTA GATGATGCTATAAC | UL67 |
| 100_up2W | CCAGTGTTCCTTGGAGAGACGAAAAGCGAGCGTGTT TCACGAGATGGCTG | 100_down2W | CAAATACGGTCGTGGCCGAGCGCAAAAAAACGCACC ATCGACACCACACC | UL65 |
| 110_up2W | GAGCCTGAGATGATGATGATGGCTACGAAGGACGGG CGGACGGGCAAACG | 110_down2W | TAATGACAGAATGAACTCCATGTTATACGCTCTTTA TATAGTTTCTCTGC | UL64 |
| 114_up2W | GATGCTTAGAGCGTGGAGATTGATGGTACTACTTGC CGCGTACTGTTATT | 114_down2W | TAAACACAATAGCTACAGCTGCGCGGTTCTGTGGAA CTTCACGTGCGATC | UL 4 |
| 115_up2W | TATTGTGTTTACGTTGCTTTTGAAATGTTAAGCGTC CCTACGGCGCTAAC | 115_down2W | ACAAATATGCAAAAGCAAAACACAACAAACTATACA CAGCTGGCTAACTA | UL5 |
| 116_up2W | TGGAAAGACAGTAAACAGTATGGACAAGTGTTCATG ACGGACACAGAACT | 116_down2W | TGAGCTGAAAAATAAACGTACATAGCTTTTAGTTTC CTCGACGGTGATTC | UL9 |
| 117_up2W | GTAAACATAATGACGTACATATACGTGGTTATACAA CAGGTGTTTGTGCT | 117_down2W | TATATTCAAACAGTGAGTTTGAAACCGGACATATCC GTCCGCTCACGATA | UL10 |
| 119_up2W | ACCGTGGCCTGTCCGCCCCGAGAACCCCCGCATCGT GCCCTGTTTCGTCT | 119_down2W | TTCCGTTTTCCTGCCGTGACTGCGAATCATCCGCTT CATGGCTCTCCTCG | UL14 |
| 121_up2W | CCCGTGGACGGGTCTCTTTGACACGAGCGCGGCACG CCGTTGCCACGAGC | 121_down2W | TTTGACCCCTCCTATCTTCTTTGATGATGTATCCTC TTAGCCGTGTGTTG | UL17 |
| 122_up2W | CTGAAAGTATATAACGCCGATCATGTCCGAGGAACT GTTAATAAAACGCC | 122_down2W | CGGGGGCACGCGGTAACCGACGTCGAAACAGCTCAT ACAGGGCGTTGATG | UL 18 |
| 129_up2W | AGTACTGTTTGAGCGTGACTGTTTCCAAATCGTACC GTGGTAAATAAATC | 129_down2W | CGGGCTAGTCATTGTGGGCACAAAACCTTCTCCCTG ATAAAAAGCACATT | UL7 |
| 130_up2W | CAGAATTATAGTAATGTGCTTTTTATCAGGGAGAAG GTTTTGTGCCCACA | 130_down2W | GTGTACAAAGAATGATTGTTATCCATCGAAGTAATA ACGCGTACCGGAAC | UL8 |
| 133_up2W | CCCTGATTCCCTTCATAAAGCTGTTGACCGGCCCTA GAAAGACCAAGAGC | 133_down2W | ACGCATAAGCGACCGGGGATGGGGGGAAATAAAGGA ATGGCTCGGTGTAT | UL13 |

-continued

| | | | | |
|---|---|---|---|---|
| 136_up2W | GGGCTCCATGCTGACGTAGGTACCGACTGGGGTCAA AAGCCTGGGTACTT | 136_down2W | GGCCTTCTTATAGCAGCGTGAACGTTGCACGTGGCC TTTGCGGTTATCCG | UL16 |
| 138_up2W | TGGAACGGTCTTTATATATACAAACGCCGTTATGCT CAGTGTCCGGCAAG | 138_down2W | TTATGGAAAATATGTAGTCCGTACCGCTTGGGGCTC AGAGTCCAAAGTCC | UL20 |
| 143_up2W | GAGAGTCTGAAACGGGGTGGGAGGGACTTTTGCGGG TAGTGCACGCTAAG | 143_down2W | TACCACGGTACGATTTGGAAACAGTCACGCTCAAAC AGTACTTTTTATTT | UL6 |
| 147_up2W | GGGACAGTCCCTACGGAACCTGAGAACATGTGGAAA TCACCTGTGGTAGA | 147_down2W | GGAGTTGGCGTTTCACAGTGATTTCATGCAATCATT TCCTACGCGACTTG | UL 11 UL13 |
| 153_up2W | TACCTACGTAACCTGGCCTTTGCGTGGCGCTATCGC AAGGTCCGGTCGTC | 153_down2W | ACGGACGTAGGTTATTTGAAAACCTACGTTAATCC TGAACGCGTTTCGT | UL19 |
| 179_up2W | CTCTCTAGGTAGGGGACTACCTCCTCGACGGTCCAT TCTAGCGGGACGAC | 179_down2W | GCATGGCCATCTTTCTCACGTTGTTGCTCATGCTCT CGGGTCCCCGTTGG | US 20 |
| 238_up2W | ATGGCTAATTGCCAATATTGATTCAATGTATAGATC GATATGCATTGGCC | 238_down2W | ATCAGTACCTGGAGAGCGTTAAGAAACACAAACGGC TGGATGTGTGCCGC | UL127 |
| 249_up2W | GAAAAGTAAAAGATGACCGCGCCCTCGGAGTCCTTT TTTCCTTTTCAATC | 249_down2W | GATACATTAATAAATATATTATATCTGGTGTATATA CTGAATGCTGCTGG | TRL7 |
| 250_up2W | GGGTACTAAAAAAGTGTTTAATATTGGGGTTTAATG ATAAAATCCAGGTT | 250_down2W | AGTCATCATCCTAAAATTCAGATATAAATGAACACA TGTCGTATGGGATT | TRL6 |
| 252_up2W | CCTTTTTATGTGAGTTTCTCTTCCGCGTCTCCCGGC CGTACCATCCACCC | 252_down2W | TGTGCAGGGCATGCGGGGAATCAGGACCGGACACGG GATAATTTCATCTA | TRL4 |
| 257_up2W | TGAGAGTCGATTCGATCGGTAAACATCGTAAGCATC GTGGCGGTGGTGTG | 257_down2W | ATGGAAACCTTACCCCGCCGGAACACCGCCGGGCTG TGAACCTGTCCACC | UL73 |
| 261_up2W | TCCCCGGAGAGGGTATATTCGTTCGGCGAGAGCGGG CGGCGGTGGTGGGT | 261_down2W | TGACGTAATTTATCTGCCACTTTTCTCCCCGCTGCC GTACAACGCCGCCG | UL78 |
| 263_up2W | GAGCTCAGCGGCTGTCCGCGCGACATCTTCTCGCTA ATCTGTAATATTAG | 263_down2W | TATCACGGTGTAGAAAAAAAAGAGAGGGAAGCCCTA AATATAGCGTCTCT | UL80 |
| 272_up2W | CCTTCTCCTGTTCCCTCCGCCCCCAAAACTGTCAGC GACGCTCAGACGTC | 272_down2W | TGGTCGAGCACCAGATGTAGAGGCAATTGCTCATCG TCAGCGAACCGCGC | UL92 |
| 276_up2W | GTGCTAGACCGTTGGAGTCGCGACCTGTCCCGCAAG ACGAACCTACCGAT | 276_down2W | GTGTCCCATTCCCGACTCGCGAATCGTACGCGAGAC CTGAAAGTTTATGG | UL 99 |
| 278_up2W | CATGGCGATAGCGGCGGCCCGCTCGCTCGGGAGGCG ATGGGGGCGCGCCG | 278_down2W | GCGGCGTAGCTGGCGCGATGCACAGCACGCACCTCA GCCGGCGGCAGACG | UL101 |
| 285_up2W | CGATGTCATTGGCCGCTGCGAAGGGAGAAGAGGGGA CACGCGAGTAAGTC | 285_down2W | GCGGTCGCCGCGTCAGACGGGGTGGCGGGTCCCGTG ATGGCATCGTGCCG | UL76 |
| 312_up2W | GTTGACGGCAGTTCTGAACCCACGTCGCCGCGAGCG CGGTTTGCATCACG | 312_down2W | CATGGCCACCTACCTGTGTGACGAGATACACGCCAT CCGTTTCAGGGTCA | UL88 |
| 316_up2W | GCGCGCCCATAAAAACGAAAGTGTCGTCGTCGCGAC CCGCCACAGCCGCC | 316_down2W | CGTAGAGCGAGTGTAACTGGATCTCCTCGGTAAACG CGTTCTGGACGTGC | UL91 UL92 |
| 317_up2W | TAGTCGTAAGAAGCGCGAGGACGCGCTTCTGAAACA GATGCGTTCCGAAT | 317_down2W | CGGTAGAGCAACAGCAACTGGCATAAGATACACGAG CTGTCGTCCTCCGG | UL93 |

-continued

| | | | |
|---|---|---|---|
| 320_up2W | TCGGTGTGGTAGCTAGTGCAGCTCTAGGAACAGGGAAGACTGTCGCCACT | 320_down2W | TACCTTCTCTGTCGCCTTTCCCCTCAGCAACCGTCACGTTCCGCGTCCCG UL97 |
| 321_up2W | AGAAGGTACAAACCCACCGGCGGGGAAAATACCGAGGCGCCGCCATCATC | 321_down2W | GAGGGATGTTGTCGTAGGAGCGTAGAGACACCTGGCGACCCAGAGCATCT UL 98 |
| 325_up2W | GTCGGCGAAAAAAGACCCCGCGGGCCTTCGCGACTCTCTTCTGTCCGAGG | 325_down2W | TTTTTACTAGTATCCACGTCACTTACCCACGTAGTTCCCCTACGTGACTC UL102 |
| 331_up2W | TTTCGACCTGTGTACCGATTCTGTTCTGGACTATCTGGGACGGCGTCAGG | 331_down2W | CCCTCTCCGGGGACGCTCGCCCTTTATGCAGCAAGCGACACGTGGTGGAA UL77 |
| 339_up2W | GGCGTGAGCGCGAGGCGTCGGAGCTCGGGGAAAGCAGCGCGACCCGGAGA | 339_down2W | TCGGACGCTCCTCCGGACGAAACGCCGCGGCGGCAGCGGCCGCGGCTTCC UL87 |
| 345_up2W | TTACTGGGTGCTGCCGGGCGGCTTTGCTGTGTTCTCGCGCGTCACTCTTC | 345_down2W | TCCTTTTTTTGTTGTTTCTTGTTTCTTCTCCCCGTGAACTGTCAGACCCC UL94 |
| 347_up2W | GCAGCTCCGCGTAGCGCTCCTGGATCTTGGCGGCCGAGTCTCCGCGCAAC | 347_down2W | GCTGACGCGCTCGTCTCGACCGCACAAGCGCCGGCCCCGCCGCCGCCACC UL95 |
| 348_up2W | TTGCTGGACGCCCTCTCGCTGAACGACGCGGGTCTCATCACGTTGAATCT | 348_down2W | TTTTTTTTTAATAAAATCTGAACAGAGGCGTGACGGGGATTGCTATACCT UL96 |
| 362_up2W | TATAAAATTCACTCAGTGGCGGCGTAGCCATTGTCTTCCGTTCATCCACC | 362_down2W | TGTTGCGATGCTCGTGGCTGCGGCGGCCGTTGTCGCGGCGTCTGCTGGCG UL 57 |
| 366_up2W | CAAGAGACCACGACGCGCCTCATCGCTGCTGGATTTGGCCCGCGACGAAC | 366_down2W | ATCACAAGTCTCTGTCACTTTTTTTGTCTAGTTTTTTTTTCTCCTCTTGG UL 55 |
| 378_up2W | TCACTTTATTGAAATCTACCTGATTTCTTTGTTATTTTCCTCGTAAACTT | 378_down2W | AAGACGCCCGGCGTCTAATAATACAGCCGCGCCGAGCCAGCGGGCCCCG UL 45 |
| 379_up2W | CTAGAGCGCGTGCCCGGGCACGCGGCCTGCGCGCACGGCGCGGTCCCGCG | 379_down2W | GACGGCGACGGTGGTAACTGTGGTGGAGACGGTACCGACGGCGTCCGCGG UL43 |
| 380_up2W | TCGGTACCGTCTCCACCACAGTTACCACCGTCGCCGTCACTGCCACCGAC | 380_down2W | TTATTCCGTAGCAGCAATGATGGTACAGTCAAGCACATGATCTATTTCCC UL42 |
| 382_up2W | GATGTACGTACCACGGTACGGACATTAACGTCACTTCCAACGCCACGAGT | 382_down2W | GAGAACTACGGCGCGGCGGCACGGCCTTTATAGACACTATCAGCGTTGAC UL37 |
| 384_up2W | GCTGTCAGGAATACCTGCACCCCTTTGGCTTCGTCGAGGGTCCGGGCTTT | 384_down2W | AAACATGCACATAAACAAACGGGACCACCGTGCTCGTCATCCTCTCCTCA UL36 |
| 388_up2W | CGGGCGCAGTCCGGGGCGACGACGCTTCCGGGTTCTGGAGAAAAGCCAGC | 388_down2W | TCACTATCCGATGGTTTCATTAAAAAGTACGTCTGCGTGTGTGTTTATTA UL32 |
| 393_up2W | GTTGAAAACGCGCATGATCTCGCGGAGCCATCTACGCGCCTGTCAGGGAG | 393_down2W | TCCACACGCTCAGCCGCGACTGAGCGCCGGGGCGCGCCGCTACTTGGGTT UL30 |
| 394_up2W | ACTGCTGCTTCTGCTTTTTTGTCTCCTGTGGATCGTCGCGGACTGCCGGC | 394_down2W | CGGTTATAAAAACACCGTCGCCCTATTTCTGGGCGTGTGTACACTGATGA UL29 |
| 397_up2W | GGGGCCCTCGGTGCGCTACCGGGCCCACATTCAAAAGTTTGAGCGTCTTC | 397_down2W | CTCTGTCTTCTCCGGGTTTTTTTTTCATGTTTTTTTTTCTTCCTATTTT UL26 |
| 398_up2W | AGAGGCCCCGCCTAGGTGGGCGGAGCGGTAATTTTCCACCGCCGCGGCCC | 398_down2W | AATCATCTCTGATGACGTAGCGAGCGAAGCGAGCTACGTCATCAGTCCGT UL60 |

-continued

| | | | | |
|---|---|---|---|---|
| 400_up2W | CACCGCCTCGCCGGCCACGGGGTTGATTCCTGTTCTTATGCCGACACCAG | 400_down2W | AAAGATCCGAACTTTAAAATTGTGTATTTTTATTTTCCCATCCCCCTCTT | UL59 |
| 407_up2W | ATTTGCTTTGTGATTTTGCTTCGTAAGCTGTCAGCCTCTCACGGTCCGCT | 407_down2W | AGTCTCAGCAGCATTATCACCGTCCCCAGTCACCACCGCCGCCGCTGTTT | UL 54 |
| 411_up2W | TACTCGGATTCATGGCGATCGGCGCCGCTGATTGAGGACGCGGAAAAAGA | 411_down2W | ATCCTGATGGAGAACCTTGTTCATCTCCATCGCACCGACGCCACCGCCGA | UL51 |
| 423_up2W | CCCGCAGCTGCTCTATCAACTTTTTGAAATCTACCGTGCGCCTCGCCATC | 423_down2W | TGTGTTTATTTTTTTCTTCTGTGTCTCCTCCCCGTATGCTGTCAGCGCCG | UL46 |
| 426_up2W | TTTCAAGACGACGTGAGACCCACACGCGGGTTTCACTTCTTTCTTTAATT | 426_down2W | AGTCCCTTCTTATACTATCCCGGAGTCTGTGGTTTTTTTGTTTACCCCTG | UL37 |
| 452_up2W | GGCCGGCGCCAGACCGGACGACAGCGTCTCGTACGTGAGCGAGTCGAGTC | 452_down2W | CCACGAGTAGAAGATGAGGAAACCGCAGCACCCAGACAGACGATACACAA | UL56 |
| 459_up2W | CCCGCTGGTGCTGGCTCTCCTGCTGGTGCTGGCTCTGCTGTGGCGCGGTC | 459_down2W | TGACGGTGTTTTTCGTCCCGCTTGTTGGCCACCGTGGGTCCCGGCGCGGT | UL49 |
| 471_up2W | TTTCGCTCGCTCGCGCCCGCTCCTTAGTCGAGACTTGCACGCTGTCCGGG | 471_down2W | TCCATCGCGGGACCGCGCCGTGCGCGCAGGCCGCGTGCCCGGGCACGCGC | UL44 |
| 472_up2W | AGAAGGGACTTTACCGCTATTGCTGCTATTCATAGAGAAGGATAGAAAGG | 472_down2W | ACTACAAAAAAAAAAAGCTGAACATGGTCATCTAGCAGCAAAGTTCTCCT | UL38 |
| 484_up2W | CCACGGCGGGTCGTTGGCTCCCGCTGTGCTGGCCGCCGCTGCACGGCATC | 484_down2W | GGCGGTAAAGCCAAACACCGGCTATATAGCTAGTCATCACAGTCTCCTCC | UL28 |
| 485_up2W | CCGCCGTCGCTCCGCGTCGCTTCGCCGCCACCTTCTTCTTCCTCTCAGTC | 485_down2W | GCGCCTCGTCGGTCGATGACCCCACGGTGCTTATAACGCGCCGCCACGGC | UL27 |
| 490_up2C | TTCAGAACGAGGTGCTCATCAACTACTGCGACATCGCCGACAACTGGGTC | 490_down2C | GTGGTTTTTACCCTGCTCAATAAAGTCACGTTTTCCTTACACGGTGTTGT | UL105 |
| 504_up2C | TCCAACGCGCCTGTGGAGGGCCAATCGGACCGCGGGAGCTCTCCAAGTGG | 504_down2C | AATACAAATAAAAAAAGACGCTGTGACACTTTGGCTCTTTCCTGTGCACC | US25 |
| 511_up2C | AGACGGTGCAGGAGTCCGAGGCGGCGGCGACGGCGGCGGCTGCGGGGTTA | 511_down2C | AATGTCCAAGCGCGTCCTGTTTCATAATTTTTCCGGTCTCGGCTCGGTTT | UL 113 |
| 520_up2C | GCTCCACGGCCTCCGACGAGCGTTGCGCTCGCGCTTTGCGCCGCCGCGTC | 520_down2C | CCACCAGCGCACCAACACCGCTCGCCTGCTCGCTCGTGCGCTACGGGGGG | UL 112 |
| 526_up2C | CTACCTGGGACGCGCAGTTGGGCGGCGGACTGGGGCGGCATGCTGCGGTG | 526_down2C | TCGAGCCACACGGAGTAGTCGTCCTCACGTTGCTACAAGAGGAAAACTAC | UL 111a |
| 530_up2C | TCTTTTTTCTTTTTAGTCGATGGAACTTTTCTTCGGTACGGGTTCTTGTT | 530_down2C | AAGGATCATATATATCTCGTCAGGGAAATACAAGTTAGACCATAATGTTG | UL108 |
| 542_up2C | CGACATCGGTGACACAGCTTCAGAAACAACGTGTGTGGCGCACGCTACTT | 542_down2C | AAAGACAAATGAGACGCTGAAGGCCGCGATCAGCCTCCCGTCTCTTTATT | US 30 |
| 543_up2C | GTCGGTGTCTCGTCGGTGAGACGAGGCCGCCGCCCGACAAGTTCGATCTC | 543_down2C | CCCCGCAGATATCCGGTTGATGTAGCCAGTCGCCTACACGCGACTTATCG | US31 |
| 544_up2C | CGTTGTCATCCGGCTTAGAGCAAACCGTCCTTTTATCATCTTCCGTCGCC | 544_down2C | CACACATCACACGGGGATTTACGCTATGTTGTTTATTGTCATGCCGTGTT | US 32 |

-continued

| | | | | |
|---|---|---|---|---|
| 546_up2C | CGCCGTCGGCACTTGGCTTCAGAGCAGCGCCTCGGG GCGATGCGACGGCG | 546_down2C | ATCGCGGCACAACGACTGGACGACGTCGTTTACGTA ATTTTAAGAAGAAT | US 34 |
| 557_up2C | GTGCGTGGACCAGACGGCGTCCATGCACCGAGGGCA GAACTGGTGCTATC | 557_down2C | AGAGGGGCGGACACGGGGTTTGTATGAAAAGGCCGA GGTAGCGCTTTTTT | US 28 |
| 558_up2C | CGGAAAAGTTTATGGGGAAAAAGACGTAGGAAAGGA TCATGTAGAAAAAC | 558_down2C | CGGCACTGTTCTCGAATGGACATGTTTCGTCCGACA TCGACAGTGCAGCC | US 29 |
| 582_up2C | CTTGGCAGAGGACTCCATCGTGTCAAGGACGGTGAC TGCAGAAAAGACCC | 582_down2C | TTTACAAATTCACATATACAACAACGCCGTCCCCCG TGCCCGCAGTTTTT | UL124 |
| 592_up2C | GGGAAGACGCAGTGATCCGTCGGTGTCTGCGAGAGT ACGTTGGCGACTAT | 592_down2C | GTACTCGTCGTGTCCGTGATCACGTACGTTTTCCAA AACGTGCCAGGCTG | UL71 |
| 626_up2C | TTTTTTCCGGATCGGCCCGATTTCTTTTTGTCCACC GACGCGCGACCGCG | 626_down2C | ATTTACAGGAACGGGGAAAAAAAAGGCACACGGTCC GTGGGAGACGCGGG | UL23 |
| 627_up2C | TTTTTAGAGCAGAACCTTACAGCTTTTTAATAAAAA ACAAGATAGTCAAC | 627_down2C | GCGCAGGTAAACAGGTAAGAAATACAAAAAATAACG TGATTGTGAACGCG | UL 20a |
| 639_up2C | AAAGAACAAAAAACACCCATCCCAGCGGTACCGTAC CTCGGCGACGCTCC | 639_down2C | CACGACCTGCGCCACTCGGACCGCTCCTGCGACCTA GCTTTCGGATCTCG | UL15 |
| 642_up2C | GCAGCGGGAGCAGATGATAACGCAAGAAGCGACCGC AGTGGGCCCACAGC | 642_down2C | TACCGCAAAAGCTGTGGCTGCTCTGGCAGCATGACA AGCACGGCATCGTG | UL12 |
| 650_up2C | TTTACCGTACCCAGACAACGGTGCTTTATAGACTCA TCACTTAAGGCGGG | 650_down2C | TACTGAGCGTGCGAACCGGGTAGGGTGCCGAACGAC GGGTATGCGTCGTC | UL3 |
| 653_up2C | GGATTCTTCTCAGGGCGGCCAGAGCGTGCCGGTATC TCAACGGATGGAAC | 653_down2C | CGTCGGTGTTTTATGCCCCAAGCAGCGTCGTCGTCA CTCGTGGCGTCACA | UL48 |
| 655_up2C | GCGTCTGGCTGTGTGCCGTTAAATACCTTGGGTGAC GACATCTCGAGGTC | 655_down2C | GATGTAAATAAAATGCTTTTATTTAAAACTGGTCCC AATGTTCTTCGGGA | UL21 |
| 666_up2C | GATTCCAAACCGGATACGCTACATACCTGCCACAGT GGGCAGCTTTTACC | 666_down2C | GCTATGTTACCACAGGAGATCACGGAACATAAATGT TTTCTGCGTATGTT | UL2 |
| 670_up2C | CGCTTTGTGTATTTAGACGAATCTCGGCGATAACCG CCGGCGTTGCCGCC | 670_down2C | ACAAGCGAGCGAGTGGGGCACGGTGACGTGGTCACG CCGCGGACACGTCG | US 21 |
| 676_up2C | CGGAACTGGTTTTCGGACAGAGCAGCCGTTTCCAGA GAACGCAGCGCACC | 676_down2C | TCTCCATGTCGGGACCGCAGCGCCCGGCGGCGTATC CGCAAGGTCTCGAA | US 15 |
| 679_up2C | TTTCGCGCAGCGCGCTTTATCCGACTCGCTGTCGAG ACGGCTCCGCCGGC | 679_down2C | TGCAGAATCATAAGTTTATGATGAATAAAAACGGGG AAAGGGAATCTGCT | US22 |
| 680_up2C | CGTGACCTCGGTGGTGTGCGATACGCAGGACATCCT GCACGACATCGAGT | 680_down2C | AGCATGGCGACAAGCGCGGCTGCTGTGAAAACGGGC GCGGTTTTATAGGC | US 20 |
| 681_up2C | GTTTTCACAGCAGCCGCGCTTGTCGCCATGCTTCAT GTCGTCCCGCTAGA | 681_down2C | CGTCTTATCAGCACCCGGTTACCGCGGATTTGATTG ACGTCACGAGTGTG | US 19 |
| 682_up2C | ACTGTTTCATCGACGCCTACCTTAGACCGACAGCGG TCGTAAGCGGCAGC | 682_down2C | GAAGGTGGGGAACGTTTAAGCGAGCAGGAGCGTGTC ATCTCCCCCATCTT | US 18 |
| 683_up2C | ACACTCTATAAACGGTTTTTCATACGCGCCTTTTGA TCGCCACCGCCGTC | 683_down2C | ATTGGTGGAGACGGCCGGCGCGGCGGGTGGGGGAAA CGACGAGTTTTTCC | US 17 US12 |

-continued

| | | | | |
|---|---|---|---|---|
| 684_up2C | CCCCACGGATCTCGCGCCTTAGACGCACGGTCATAT AGCCTCCGGCTGTC | 684_down2C | GCGTTCTCTGGAAACGGCTGCTCTGTCCGAAAACCA GTTCCGAACGAAAA | US 16 |
| 686_up2C | AAGACTCCACCGAGACGCTCACCCGTTCACTCGGGC GCATCACCCGCCTC | 686_down2C | GCTTCAGGTACCCGGCAAGTTTTATAGAGAAAGGGG GACGATGGGTGGTG | US 13 |
| 687_up2C | CTCTTTCTCTGCTTCTTTTCTGGGGTGTCTAGCTGG CGGCCTCTTTTGAC | 687_down2C | AGCAGCGTCAGACGAATCGCGGCTGGTGGCCCTGGG GGTGGGACGCGCCG | US 23 |
| 692_up2C | CTAATGCCTATAAAACCGCGCCCGTTTTCACAGCAG CCGCGCTTGTCGCC | 692_down2C | GACGTCACGAGTGTGGTCAAACCGTGGCGGCACCCT GTATCCGACCCGTC | US 19 US12 FAMILY |
| 696_up2C | CTGTAGCTTCGAGACCTTGCGGATACGCCGCCGGGC GCTGCGGTCCCGAC | 696_down 2C | CGAGTGAACGGGTGAGCGTCTCGGTGGAGTCTTCTT ATAAACCAGCGGAG | US 14 |
| 700_up2C | CCTCGCCTATTTAACCTCCACCCACTTCAACACACA CCTGCCGCACAATC | 700_down2C | GCGTGGCGGCGAAATACGCGATCCCTGGGCTGGTAG ATCCCCCTACCCCG | TRL1 |
| 710_up2C | GGACGAGGACGACGACGTCTGACAAGGAAGGCGAGA ACGTGTTTTGCACC | 710_down2C | TATTTGCGTATATGATGACTTGTTCCACCGTCGATG TTGTGTGCGCATCT | TRL 11 |
| 720_up2C | GGGGTGGCGGTAGTGGTGCTGCTGATGGTAGTCGGG ACGGAGGAGAGACG | 720_down2C | ATACCATGGGACCCCTTTTCGTCACACACGTCTTTC CGCTTACTCAACGC | TRL5 |
| 735_up2C | GAGTTCAGCGTGCGGCTCTTTGCCAACTAGCCTGCG TCACGGGAAATAAT | 735_down2C | GACCCAATAGCAGCCACAACGCCGTCAAGAACGGCG TCAGGTTTTTGGGA | UL130 |
| 738_up2C | CCATCCCGAGCACTCCACACGCTATAACAGACCACG GACACGGCAAATGC | 738_down2C | CAAACCTCGGTTTCTTCCTATTCTTAAGTTTTCCCT AGTATATTTGCCTC | TRL2 |
| 746_up2C | TGCGGCGGCGACGACGACAGCTGCGATTTGTCGGCC GACATGCCGATGGT | 746_down2C | AGGAAACTGGAGAGAGCCACAACAGAAACAGCGTGG GACTGTCCGCTGTT | TRL8 |
| 747_up2C | GTGGTGAAAGAAGAGCACCAGCAATCCCAGGAGGAG CAACAAGCCCTCAC | 747_down2C | CTGTCCATCTCCCTGTCTTTTCGCGCCGCCGGTCCC CCCCAAACCATGTC | TRL9 |
| 748_up2C | GTGCGGGGAGGATCGACGTGTGCGGTGCTTGTGGAA CACGGTGTTTTAAT | 748_down2C | AGGGGGGTGCTGTAGGTCTGCATGGTGCAAAACACG TTCTCGCCTTCCTT | TRL10 |
| 755_up2C | ACACGTCGTTCGCGGACATAACGAGAAATCCACGTC GCCACGTCTCAAGA | 755_down2C | CGAGGTGATGGGGCGGGGAAAGAGTTGGAACCGAAA GACAAAAAAAAAAG | UL132 |
| 758_up2C | TTGTGGCTGCTATTGGGTCACAGCCGCGTGCCGCGG GTGCGCGCAGAAGA | 758_down2C | CTGTAGCAGACTTCGCCGTCCGGACACCGCAGCCTG TGGATTCATGAAAA | UL129 |
| 773_up2C | TAGTGGCGTGCGCGACCCCCAGTCGGTTGAGTTCCG CCAGCAACGAGTTC | 773_down2C | TTGTCCTCGGATGCTCTGTGTAGAGAGGAGACAGAA AAGGGACTCTTATG | UL90 |
| 774_up2C | CCAGTGACGCCACGTGTTTCTTGACGCGCCTCAACA ATGCGCCCTTTGAC | 774_down2C | TTCTGCCGATGCCGGCGTCAGTCGCCGGCACCTGGT GGCTCTGCTGCGTG | UL89 |
| 778_up2C | CGCGCTGCTTTCCCCGAGCTCCGACGCCTCGCGCTC ACGCCGCCGCCGCG | 778_down2C | GGTGACTCGCCGCTAACCTGCGGTCGTCGCCGTCCT CCTCACCGGACGGC | UL 86 |
| 779_up2C | CGACGAGATCGCGCGGCTGTCGGCGCTTTTCGTCAT GCTGCGACAGCTGG | 779_down2C | CCGTATCGCGCGGACGCCTAGTGTCCGTTTCCCATC ACCAGGGTTCTCTG | UL 84 |

-continued

| | | | | |
|---|---|---|---|---|
| 780_up2C | GCCGCAGAGGGCGCGCCGCTCAGTCGCCTACACCCGTACGCGCAGGCAGC | 780_down2C | GTGGACGTGGGTTTTTATAGAGTCGTCCTAAGCGCGTGCGCGGCGGGTGG | UL 83 |
| 781_up2C | CCGTTCACCTTTGCGCATCCCCTGACCCCCCCCCTCATCCCGCCTTCGCG | 781_down2C | AAATACAGGGAATGGAAAAACACGCGGGGGGAAAACAAAGAAGTCTCTC | UL 82 |
| 783_up2C | TCGTCCATCGTCATTGTCGTCACCGTCGCTACCCGCTCACCGAGCGAACG | 781_down2C | GCGGCGTTGTACGGCAGCGGGGAGAAAAGTGGCAGATAAATTACGTCAGG | UL79 |
| 794_up2C | CGGTAGTTGCGGCAGAGGGGTTGTTATCTGTCGTTCGTTCAACGCGACTG | 794_down2C | CCGCGCACCGTAAAGTCGAGCACTTGCGGCTCCATGATCATCACATTCTG | UL104 |
| 819_up2C | GCCAACCACCACCTGGATCACGCCGCTGAACCCAGCGGCGCGGCCGCGCT | 819_down2C | ATGTCTTTAACTTTCTCTGTCCCTTTTCTCATAAACTGTCAGGTTCTACA | UL 75 |
| 823_up2C | CACGGCAGACGAGGAGCGGCGCGGCCCAGAGCGTGTCGGCCGATTTCGAA | 823_down2C | ACTACGTGTTGCGTGTTTTTTTTTCTATGATATGCGTGTCTAGTTCGCTT | UL103 |
| 827_up2C | CATCGGCGCGCCCCCATCGCCTCCCGAGCGAGCGGGCCGCCGCTATCGCC | 827_down2C | TGTCTCTTTTTTATGTCCATGTCTCCAAGTCTGGTGCGGGTGGCGGCGGG | UL 100 |
| 832_up2C | CCTCTCGCCGCTGCCGCCTAACCTCCGCTCGCACCACCGCCGCCGCCATC | 832_down2C | GTGTTCCTGTCCGGTGCTTAAGAACCTAGTGCACTAACGGGGTCTGACAG | UL89 |
| 839_up2C | GTTGTTCGTCTCCGCTTCTCCTCCGTCGCGGCCACGATTTCACCGCCGCT | 839_down2C | TTGGGGTCGGCGCGTGGCATGCTTGGTGTCTGCGGGCGCGAGAGGGCCGG | UL85 |
| 851_up2C | GCAAGCCAAACCACAAGGCAGACGGACGGTGCGGGGTCTCCTCCTCTGTC | 851_down2C | TTCTCATGGGAGTTTTTTGTATCGTACTACGACATTGCTGTTTCCAGAAC | UL74 |
| 852_up2C | CATGTATGCAGGTAAGCAACTGAGCCGAACGCACCTCAGCAGACGAGAGG | 852_down2C | TCCTGTGACTTTTTATCATAAACCGTTCCGCCCTGCTGCTTCGTTCCACC | UL25 |
| 857_up2C | CCGCCTAGAACCGCAGTACCAGTACTCCGCATGTCAACAGTACCTGTAAC | 857_down2C | GGGGAAATGGCGACGGGTTCTGGTGCTTTCTGAATAAAGTAACAGGAAAG | UL33 |
| 860_up2C | ACACACACCACACGTCACGACACCGATCGATTTTCTTTATTCTTAGTGTG | 860_down2C | GAAAGCGCTTTTGGGCTCACCCATCTGCAGTCCTGTTGCCTGAACGAGCA | UL39 |
| 868_up2C | ATCGACCCGCCCGCCGGCTCGACATCGGTGTCCCTGCCGCCGGCCTCGCC | 868_down2C | AAAAACGATAAAAAGCCTATTGTTTTTATTACCCGCTACTGTCAGTGTCG | UL48 |
| 896_up2C | GGCCCGCTCGCACGGACCTATACTATTACCGCCCCACCGCCGTCGTCGTC | 896_down2C | AAAACCAGAGCGGAACTTGAGAAATCAACGCTTTATTGTTCTCCAGTGAC | UL34 |
| 897_up2C | TTCTCAAGTTCCGCTCTGGTTTTGGTTTCGTTTTCAAAGGGAGCCCCATC | 897_down2C | TATCAACGTCTCGTCCTGAGACAGACACGTATAAAAAGAGGAAAACCGCG | UL35 |
| 911_up2C | TGTCCTCGTCGGCCGGGTCGCGCGGCCGTTTGGCCACCGCGCGCGCGTCC | 911_down2C | GCGCTCCAAAGCGAGCGATGTCGCCCTGGTGGCAGCTGGCCTGCGTGACT | UL47 |
| 918_up2C | TAGCCCAGGACATTCTTTTTCCGCGTCCTCAATCAGCGGCGCCGATCGCC | 918_down2C | AGGGAGCGCAAGGCTGAGCGTCGTTCGCGCGGCGTGCGCACGCCGCTCAC | UL52 |
| 950_up2C | AGTCGGCTACATGCGCCCTGGGTCTGACGCTCCAAAGCGTACGCAGTCTG | 950_down2C | TAATGAAACCATCGGATAGTGACGTGTCGGGAAAGGAGGACGGACGGAGG | UL31 |
| 986_up2C | GGAGAGTTGCGACATCAAGCTGGTGGACCCCACGTACGTGATAGACAAGT | 986_down2C | TGGTGCTGCCGCGGCGCTTGCACTTGGAGCCGGCTTTTCTGCCGTACAGT | UL53 |

Genes essential for replication of HCMV are identified. As set forth in Table 1, the ORFs essential for replication include the following ORFs:

TABLE 1

| ORF | Sequence Conservation | Gene Function |
|---|---|---|
| UL32 | β-herpes | Tegument |
| UL34 | CMV | Unknown (Transcription) |
| UL37.1 | β-herpes/CMV | Anti-Apoptotic |
| UL44 | Core | DNA replication |
| UL46 | Core | Capsid |
| UL48 | Core | Tegument |
| UL48.5 | Core | Capsid protein |
| UL49 | Core | Unknown |
| UL50 | Core | Egress |
| UL51 | Core | DNA packaging/cleavage |
| UL52 | Core | DNA packaging/cleavage |
| UL53 | Core | Egress |
| UL54 | Core | DNA polymerase |
| UL55 | Core | Glycoprotein B |
| UL56 | Core | DNA packaging/cleavage |
| UL57 | Core | ssDNA binding protein |
| UL60 | CMV | Unknown (OriLyt) |
| UL70 | Core | Helicase/primase |
| UL71 | Core | Unknown |
| UL73 | Core | Glycoprotein N |
| UL75 | Core | Glycoprotein H |
| UL76 | Core | Unknown |
| UL77 | Core | DNA packaging/cleavage |
| UL79 | Core | Unknown |
| UL80 | Core | Capsid assembly |
| UL84 | β-herpes | DNA replication |
| UL85 | Core | Capsid |
| UL86 | Core | Capsid |
| UL87 | Core | Unknown |
| UL89.1 | Core | DNA packaging/cleavage |
| UL90 | CMV | Unknown |
| UL91 | β-herpes | Unknown |
| UL92 | β-herpes | Unknown |
| UL93 | Core | Unknown |
| UL94 | Core | Unknown (Tegument) |
| UL95 | Core | Unknown |
| UL96 | β-herpes | Unknown |
| UL98 | Core | Alkaline nuclease |
| UL99 | Core | Tegument |
| UL100 | Core | Glycoprotein M |
| UL102 | Core | Helicase/Primase |
| UL104 | Core | DNA packaging/cleavage |
| UL105 | Core | Helicase/Primase |
| UL115 | Core | Glycoprotein L |
| UL122 | β-herpes | IE2 (transcription) |

The sequence conservation indicates whether an ORF is strongly conserved with the core group of herpesviruses, with the β-herpesviruses, or only with cytomegaloviruses. See Table 6 for genes previously identified as essential for replication.

In one embodiment of the invention, a cytomegalovirus comprising a deletion in one or more ORFs essential for replication is provided. As described below, libraries of such cytomegalovirus may also be provided.

In another embodiment of the invention, open reading frames essential for viral growth are targeted by ant-viral drugs designed to treat a cytomegalovirus infection in humans. Screening for such agents may involve contacting a polypeptide encoded by an ORF essential for replication with a candidate agent. Some types of therapeutic agents that may be developed against these identified viral genes may include, but are not limited to, polynucleotide based compounds that target the mRNA transcribed from these essential regions, small molecule compounds designed to inhibit or bind to the protein molecules coded by these essential genes, or recombinant protein based molecules such as monoclonal antibodies which may bind to the protein products encoded by these essential genes.

In one embodiment of the invention, a cytomegalovirus comprising a deletion in one or more ORFs designated as severe to moderate growth defects. Such viruses can be used to construct human cytomegalovirus vaccines. As described below, libraries of such cytomegalovirus may also be provided. The deletion of these genes results in attenuated viral growth in tissue culture ranging from 10-fold less than wild-type to severe growth defect compared to wild-type. These ORFs can be deleted to create an attenuated or weakened virus, which can then be used for vaccination for human cytomegalovirus infection.

Open reading frames identified as non-essential for growth, but which have a severe or moderate growth defect when deleted include the following ORFs:

TABLE 2

| SEVERE GROWTH DEFECT (12 mutants) | | |
|---|---|---|
| Genes | Conservation | Function |
| UL21 | CMV | Unknown |
| UL26 | CMV | Tegument (transcription) |
| UL28 | β-herpes | Unknown |
| UL30 | CMV | Unknown |
| UL69 | Core | Tegument (transcription) |
| UL82 | β-herpes | Tegument (transcription) |
| UL112 | β-herpes | Major early protein |
| UL113 | β-herpes | Major early protein |
| UL117 | β-herpes | Unknown |
| UL123 | CMV | IE1 |
| UL124 | CMV | Latent transcript(ORF 152) |
| Us26 | β-herpes | Unknown |

TABLE 3

| MODERATE GROWTH DEFECT (23 mutants) | | |
|---|---|---|
| Genes | Conservation | Function |
| UL2 | CMV | Unknown |
| UL11 | CMV | Glycoprotein |
| UL12 | CMV | Unknown |
| UL14 | CMV | Unknown |
| UL20 | CMV | TCR homolog |
| UL29 | β-herpes | Unknown |
| UL31 | β-herpes | Transcription |
| UL35 | β-herpes | Tegument/Transcription |
| UL38 | β-herpes | Unknown |
| UL47 | Core | Tegument-DNA release |
| UL65 | CMV | Unknown (pp67 virion protein) |
| UL72 | Core | dUTPase |
| UL74 | β-herpes | Glycoprotein O |
| UL88 | β-herpes | Tegument |
| UL97 | Core | Protein kinase |
| UL103 | Core | Unknown |
| UL108 | CMV | Unknown |
| UL114 | Core | Uracil DNA glycosylase |
| UL129 | CMV | Unknown |
| UL132 | CMV | Unknown |
| US13 | CMV | Unknown |
| US23 | β-herpes | Unknown |
| TRS1 | CMV | Transcription/egress |

In one embodiment of the invention, a cytomegalovirus comprising a deletion in one or more ORFs designated as severe to moderate growth defects. Such viruses can be used to construct human cytomegalovirus vaccines. As described below, libraries of such cytomegalovirus may also be provided. The deletion of these genes results in attenuated viral growth in tissue culture ranging from 10-fold less than wild-type to severe growth defect compared to wild-type. These ORFs can be deleted to create an attenuated or weakened virus, which can then be used for vaccination for human cytomegalovirus infection.

Open reading frames identified as lacking an effect on growth can be deleted for construction of gene therapy vectors. Deletion of growth like wide type genes results in no significant deviation of viral growth from that of wild-type levels. This indicates that these regions can be deleted from the viral genome without affecting viral growth in vitro. Deletion of these genes can make more space in the viral genome to accommodated foreign genes being expressed in a gene therapy procedure. Identification of these wild type-like growth genes presents an advantage over other attenuated dispensable genes in that high-titers of the gene therapy vector can be attained due to the conservation of near to wild-type like growth characteristics in tissue culture.

TABLE 4

GROWTH LIKE WILD TYPE (66 mutants, 76 ORFs)

| Genes | Conservation | Function |
|---|---|---|
| UL3 | CMV | Unknown |
| UL4 | CMV | Glycoprotein |
| UL5 | CMV | Unknown |
| UL6 | CMV | Unknown |
| UL7 | CMV | Unknown |
| UL8 | CMV | Unknown |
| UL10 | CMV | Unknown |
| UL13 | CMV | Unknown |
| UL15 | CMV | Unknown |
| UL16 | CMV | Immunomodulation |
| UL17 | CMV | Unknown |
| UL18 | CMV | MHC homolog |
| UL19 | CMV | Unknown |
| UL24 | β-herpes | Tegument |
| UL25 | β-herpes | Tegument |
| UL27 | β-herpes | Unknown |
| UL33 | β-herpes | G protein receptor |
| UL36 | β-herpes | Anti-apoptotic |
| UL37.3 | β-herpes | Unknown |
| UL39 | CMV | Unknown |
| UL42 | CMV | Unknown |
| UL43 | β-herpes t | Tegumen |
| UL45 | Core | Ribonucleotide reductase |
| UL59 | CMV | Unknown |
| UL62 | CMV | Unknown |
| UL64 | CMV | Unknown |
| UL67 | CMV | Unknown |
| UL78 | CMV | G protein receptor |
| UL83 | β-herpes | Tegument |
| UL89.2 | Core | DNA packaging/cleavage |
| UL109 | CMV | Unknown |
| UL110 | CMV | Unknown |
| UL111a | CMV | IL-10 homolog |
| UL116 | CMV | Unknown |
| UL119 | CMV | Fc receptor |
| UL121 | CMV | Unknown |
| UL127 | CMV | Unknown |
| UL130 | CMV | Unknown |
| UL146 | CMV | Chemokine |
| UL147 | CMV | Chemokine homolog |
| (US1) | CMV | Unknown |
| (US2) | CMV | Immunomodulation |
| (US3) | CMV | Immunomodulation |
| (US6) | CMV | Immunomodulation |
| (US7) | CMV | Unknown |
| (US8) | CMV | Immunomodulation |
| (US9) | CMV | Unknown |
| (US10) | CMV | Immunomodulation |
| (US11) | CMV | Immunomodulation |
| (US12) | CMV | Unknown |
| US14 | CMV | Unknown |
| US15 | CMV | Unknown |
| US16 | CMV | Unknown |
| US17 | CMV | Unknown |
| US18 | CMV | Unknown |

TABLE 4-continued

GROWTH LIKE WILD TYPE (66 mutants, 76 ORFs)

| Genes | Conservation | Function |
|---|---|---|
| US19 | CMV | Unknown |
| US20 | CMV | Unknown |
| US21 | CMV | Unknown |
| US22 | β-herpes | Unknown |
| US24 | CMV | Unknown |
| US25 | CMV | Unknown |
| US27 | CMV | G-protein receptor |
| US28 | β-herpes | G-protein receptor |
| US29 | CMV | Unknown |
| US31 | CMV | Unknown |
| US32 | CMV | Unknown |
| US33 | CMV | Unknown |
| US34 | CMV | Unknown |
| RL1 | CMV | Unknown |
| RL2 | CMV | Unknown |
| RL4 | CMV | Early protein |
| RL6 | CMV | Unknown |
| RL9 | CMV | Unknown |
| RL10 | CMV | Glycoprotein |
| RL13 | CMV | Unknown |

Virus encoded temperance factors that suppress viral replication are identified as follows:

TABLE 5

ENHANCED GROWTH (4 mutants)

| Genes | Conservation | Function |
|---|---|---|
| UL9 | CMV | Unknown |
| UL20a | CMV | Unknown |
| UL23 | β-herpes | Tegument |
| US30 | CMV | Unknown |

These ORFs encode repressors of growth that facilitate pathogen temperance. Counterparts of temperance factors can be found in related viruses. The genetic sequence of such temperance factors can be modified to modulate virus replication, e.g. in the development of vaccine strains, for research purposes, and the like. The temperance factor polypeptides are useful as targets for drug design, as targets for immunological agents, and the like. Drugs mimicking or activating growth inhibitors or temperance factors find use in therapies against infectious diseases. Temperance factors may also be cell type specific, affecting viral tropism.

Furthermore, ORFs identified as encoding cell tropism factors can also be deleted in vaccine constructs in order to prevent the vaccine strain from potentially causing disease in specific tissues. For example, ORFs encoding tropism factors for HCMV replication in human retinal epithelial cells can be deleted from the vaccine construct to prevent the possibility that the vaccine may cause HCMV retinitis.

Among the tropism factors are the following: The ORF UL24-deletion mutant grows normally in retinal epithelial cells and fibroblasts, but are significantly defective in growth in endothelial cells. The ORF UL64-deletion mutant grows normally in fibroblasts and endothelial cells, but is significantly growth defective in retinal epithelial cells. The ORF UL10 deletion mutant grows normally in fibroblasts and endothelial cells, but has increased growth relative to wild type in retinal epithelial cells. The ORF UL16 deletion mutant grows normally in retinal epithelial cells and fibroblasts, but has increased growth relative to wild type in endothelial cells.

UL10 and US16 encode cell-type specific functions for virus-growth inhibition. UL24 and UL64 encode cell-type specific functions for viral replication in HMVEC and RPE, respectively.

In one embodiment of the invention, a cytomegalovirus comprising a deletion in one or more ORFs designated as temperance factors. As described below, libraries of such cytomegalovirus may also be provided. In vitro hyper-growth strains having diminished or absent temperance factors can be used for facile production of large quantity of subunit and attenuated live vaccines.

Recombinant Cytomegalovirus

As described in the examples, a collection of viruses having a defined deletion in a single open reading frame are generated. It will be understood by those of skill in the art that various methods can be used to alter virus in a site specific manner. Such mutant viruses are useful in vaccine construction, in testing candidate drugs, investigating growth in different cell types, etc. The mutant virus also provides a basis for further genetic alteration, e.g. in deletion of a second ORF, to add back genetically engineered versions of the deleted ORF, and the like. Of particular interest are sequences of herpesviruses, e.g. alpha-herpesviruses, beta-herpesviruses, etc., particularly cytomegaloviruses, more particularly human cytomegaloviruses.

The panel of viruses may be provided in the form of isolated polynucleotides, in the form of viral particles, in the form of cells comprising the virus polynucleotides, and the like. Where the panel is provided with cells, there may be an array of different cells type, e.g. retinal epithelial cells, fibroblasts, endothelial cells, neural cells, hematopoietic cells, etc. Further, cells may be of one or more species, preferably including human cells.

In one embodiment, a set of recombinant viruses are provided, which set is useful in investigating the effects of drugs, growth conditions, cells, etc. on a variety of mutations. The following sets of viruses may be used individually, or may be combined, e.g. normal growth and enhanced growth, normal growth and growth essential, and the like. Sets of mutant viruses may comprise, without limitation, at least 2, at least 5, at least 10, at least 15, at least 20, at least 25, at least 30, at least 35, at least 40, up to 45 different viruses, each having deletions in unique growth essential genes, as described above. A set of mutant viruses may also comprise, without limitation, at least 2, at least 5, at least 10, at least 12 different viruses, each having deletions in unique severe growth defect genes, as described above. Another set of viruses may comprise, without limitation, at least 2, at least 5, at least 10, at least 15, at least 20, at least 23 different viruses, each having deletions in unique moderate growth defect genes, as described above.

Another virus collection of interest comprises the virus temperance factors, which may comprise 1, 2, 3, or 4 or more viruses having deletions in unique temperance factors. Such a virus collection may further comprise one or more viruses having deletions in unique tropism factors.

Another virus collection of interest includes viruses having deletions in the set of deletions resulting in normal growth. Sets of mutant viruses may comprise, without limitation, at least 2, at least 5, at least 10, at least 15, at least 20, at least 25, at least 30, at least 35, at least 40, at least 45, at least 50, at least 55, at least 60, at least 65, at least 70, at least 75 and up to 76 different viruses, each having deletions in unique genes that do not affect growth.

Recombinant viruses may be constructed according to the following methods. Two oligonucleotide primers are constructed to contain: sequences homologous to an antibiotic resistance cassette, a sequence providing a unique barcode tag, a common primer, and a region homologous to the sequence adjacent to either the start or stop codon of the ORF being targeted for deletion. By amplification reactions, a product is having the antibiotic resistance cassette, flanked by homologous sequences targeting the ORF to be deleted. Transformation of a host cell carrying a genetic construct of the CMV genome with the PCR product results in the replacement of the target gene upon selection for antibiotic resistance. The unique barcode sequences are covalently linked to the sequence that targeted them to the HCMV genome, creating a permanent association and genetic linkage between a particular deletion strain and the tag sequence. The ability of the genetically altered virus to cause disease may be tested in one or more experimental models, e.g. using a variety of human cell lines.

Nucleic Acids

The sequences of the provided HCMV Towne strain, the specific identified ORFs genes and recombinant viruses find use in research and therapeutic methods, for the recombinant production of the encoded polypeptide, and the like. The nucleic acids of the invention include nucleic acids having a high degree of sequence similarity or sequence identity to one of the sequences provided in Table 6. Of particular interest are sequences of other viruses, which may include, without limitation, other herpesviruses, e.g. alpha-herpesviruses, beta-herpesviruses, etc. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to one of the sequences provided in Table 1 under stringent hybridization conditions. Further specific guidance regarding the preparation of nucleic acids is provided by Fleury et al. (1997) *Nature Genetics* 15:269-272; Tartaglia et al., PCT Publication No. WO 96/05861; and Chen et al., PCT Publication No. WO 00/06087, each of which is incorporated herein in its entirety.

The sequences can be isolated from suitable sources, or a suitable nucleic acid can be chemically synthesized. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

Coding sequences of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5' may contains sequences required for expression.

Probes specific to the nucleic acid of the invention can be generated using the nucleic acid sequence disclosed in Table 1. The probes are preferably at least about 18 nt, 25 nt, 50 nt or more of the corresponding contiguous sequence of one of the sequences provided in Table 1, and are usually less than about 2, 1, or 0.5 kb in length. Preferably, probes are designed based on a contiguous sequence that remains unmasked following application of a masking program for masking low complexity. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention, including genomes of mutant HCMV, can be provided as a linear molecule or within a circular molecule, and can be provided within autonomously replicating molecules (vectors) or within molecules without replication sequences. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides

Polypeptides encoded by the ORFs identified herein are of interest for screening methods, as reagents to raise antibodies, as therapeutics, and the like. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by an ORF as provided in Table 1.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli,* other bacterial hosts, yeast, and various higher eukaryotic cells such as the COS, CHO and HeLa cells lines and myeloma cell lines. In mammalian host cells, a number of viral-based expression systems may be used, including retrovirus, lentivirus, adenovirus, adeno-associated virus, and the like.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines that stably express the differentially expressed or pathway gene protein may be engineered. Rather than using expression vectors that contain viral origins of replication, host cells can be transformed with DNA controlled by appropriate expression control elements, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the target protein. Such engineered cell lines may be particularly useful in screening and evaluation of compounds that affect the endogenous activity of the *** protein. A number of selection systems may be used, including but not limited to the herpes simplex virus thymidine kinase, kanamycin resistance, hypoxanthine-guanine phosphoribosyltransferase, and adenine phosphoribosyltransferase genes. Antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The polypeptide may be labeled, either directly or indirectly. Any of a variety of suitable labeling systems may be used, including but not limited to, radioisotopes such as $^{125}I$; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer—Verlag, N.Y. (1982), Deutscher, Methods in Enzymology Vol. 182: Guide to Protein Purification., Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a *** protein can be synthesized and then joined together. Methods for conducting such reactions are described by Grant (1992) Synthetic Peptides: A User Guide, W. H. Freeman and Co., N.Y.; and in "Principles of Peptide Synthesis," (Bodansky and Trost, ed.), Springer-Verlag, Inc. N.Y., (1993).

Compound Screening

Compound screening may be performed using an in vitro model, a cell infected with a mutant CMV as provided herein, or a panel of cells infected with individual mutant viruses as provided herein, or purified protein corresponding to any one of the provided ORFs. One can identify ligands or substrates that bind to, modulate or mimic the action of the encoded polypeptide.

The polypeptides include those encoded by the ORFs, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to the provided polypeptide sequence.

Compound screening identifies agents that modulate function of the HCMV polypeptides. Of particular interest are screening assays for agents that have a low toxicity for human cells. A wide variety of assays may be used for this purpose, e.g. binding assays of a compound to a polypeptide, effect of a compound on HCMV replication, effect on tissue specificity, and the like. Compounds may be assayed for inducing temperance of viral infection, for preventing infection, for preventing replication, etc.

The term "agent" as used herein describes any molecule, e.g. protein or pharmaceutical, with the capability of altering or mimicking the physiological function of an HCMV polypeptide according to any of the provided growth categories, e.g. growth essential, growth enhancing, and the like. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to the polypeptide. The binding assays usually involve contacting a polypeptide with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Active test agents identified by the screening methods described herein that affect polypeptide activity and/or virus growth can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (Cl) analysis, and normal mode dynamics analysis. Computer programs for implementing these techniques are available. See, e.g., Rein et al., (1989) Computer-Assisted Modeling of Receptor-Ligand Interactions (Alan Liss, New York).

Theraputic/Prophylactic Treatment Methods

Agents that modulate activity of the provided HCMV ORFs provide a point of therapeutic or prophylactic intervention, particularly agents that inhibit replication of the virus. Numerous agents are useful in modulating this activity, including agents that directly modulate expression, e.g. expression vectors, antisense specific for the targeted polypeptide; and agents that act on the protein, e.g. specific antibodies and analogs thereof, small organic molecules that block catalytic activity, etc.

Methods can be designed to selectively deliver nucleic acids to certain cells. When liposomes are utilized, substrates that bind to a cell-surface membrane protein associated with endocytosis can be attached to the liposome to target the liposome to targeted cells and to facilitate uptake.

Antisense molecules can be used to down-regulate expression in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Genetic manipulation to generate herpesvirus mutants has been possible through mutagenesis of the viral genome in human cells or maintained as a bacterial artificial chromosome (BAC). A construct, $Towne_{BAC}$, was produced by inserting a BAC sequence into the HCMV genome (Towne strain) and replacing the dispensable, 10 kb US1-US12 region (Marchini et al. (2001) *J Virol* 75, 1870-8). The $Towne_{BAC}$ DNA, while maintained as a BAC-based plasmid in *E. coli,* produces infectious progeny in human fibroblasts and retains wild type growth characteristic in vitro.

The cloned HCMV Towne sequence in the $Towne_{BAC}$ construct was determined (Genbank accession number AY315197) using the shotgun sequencing approach (Venter et al. (1998) *Science* 280, 1540-2). The Towne sequence present in the $Towne_{BAC}$ construct is predicted to encode 152 unique ORFs, with nine of these present in two copies in the RL elements (FIG. 1). Taking into account the 10 putative ORFs within the deleted US1-US12 region, the Towne strain potentially encodes at least 162 unique ORFs, many of which have homologues in the recently-reanalyzed HCMV AD169 strain genome (Davison et al. (2003) *J Gen Virol* 84, 17-28).

To systematically analyze the function of each ORF in viral replication, we employed a rapid bacterial homologous recombination system and generated a collection of mutants in *E. coli* by deleting each of the predicted ORFs from $Towne_{BAC}$ (Lee et al. (2001) *Genomics* 73, 56-65). Each gene was precisely deleted from the start to stop codons and replaced with a kanamycin resistance cassette (FIG. 2A). Each deletion was verified using PCR screening, restriction digest profiling, and Southern analysis (FIG. 4). In total, 150 of the 152 genes were deleted (Table 1).

The mutant BAC-DNAs were isolated from bacteria and transfected into cultured human foreskin fibroblasts (HFFs). Of the 150 constructed mutants, 105 produced viral progeny, indicating that the mutated genes are not essential for HCMV replication in HFFs. In contrast, 45 mutants did not yield infectious progeny even after repeated transfection and extensive incubation. To further confirm their non-growth phenotype, revertant BAC clones were constructed for several mutants (e.g. ΔUL32) by restoring the deletion with the intact ORF sequence (FIG. 2A, FIG. 4). The rescued mutant (e.g. rescued-UL32) produced progeny and grew as well as the $Towne_{BAC}$, thereby confirming that deleting the ORF sequence causes the no-growth phenotype (FIGS. 4-5).

Of the 45 essential ORFs in HFFs, 37 had not been previously reported, of which 15 had not even been suggested to be essential based on the studies of other herpesviruses (Table 6). Over 90% of the essential genes are conserved among all herpesviruses (core genes) or β-herpesviruses (Table 6). In contrast, about 70% of the non-essential genes are HCMV-specific and are not conserved among β-herpesviruses.

TABLE 6

A list of HCMV Towne strain genes categorized by the growth properties of their respective deletion mutants in cultured HFFs. Also shown are the sequence conservations of these ORFs with those in HCMV AD169 strain and other herpesviruses, the genome sequence of which are currently available[5-7,30], and their functions and the functions of their homologues in other herpesviruses that have been shown or implicated from previous studies. Although virus mutants with a deletion in each of the 10 ORFs in the US1-US12 region (marked with parentheses) were not individually constructed, these ORFs are listed as dispensable since they were collectively deleted and were not present in $Towne_{BAC}$. RL11 and RL12, for which a deletion mutant were not generated, are not included.

| Genes | Conservation | Function | Growth |
|---|---|---|---|
| | | NO GROWTH (45 mutants) | |
| UL32 | β-herpes | Tegument | ¶Essential |
| UL34 | CMV | Unknown (Transcription) | *Essential |
| UL37.1 | β-herpes/CMV | Anti-Apoptotic | *Essential |
| UL44 | Core | DNA replication | *Essential |
| UL46 | Core | Capsid | *Essential |
| UL48 | Core | Tegument | *Essential |
| UL48.5 | Core | Capsid protein | *Essential |
| UL49 | Core | Unknown | *Essential |
| UL50 | Core | Egress | *Essential |
| UL51 | Core | DNA packaging/cleavage | *Essential |
| UL52 | Core | DNA packaging/cleavage | *Essential |
| UL53 | Core | Egress | *Essential |
| UL54 | Core | DNA polymerase | *Essential |
| UL55 | Core | Glycoprotein B | ¶Essential |
| UL56 | Core | DNA packaging/cleavage | *Essential |
| UL57 | Core | ssDNA binding protein | *Essential |
| UL60 | CMV | Unknown (OriLyt ?) | *Essential |
| UL70 | Core | Helicase/primase | *Essential |
| UL71 | Core | Unknown | *Essential |
| UL73 | Core | Glycoprotein N | ¶Essential |
| UL75 | Core | Glycoprotein H | ¶Essential |
| UL76 | Core | Unknown | *Essential |
| UL77 | Core | DNA packaging/cleavage | *Essential |
| UL79 | Core | Unknown | *Essential |
| UL80 | Core | Capsid assembly | ¶Essential |
| UL84 | β-herpes | DNA replication | *Essential |
| UL85 | Core | Capsid | *Essential |
| UL86 | Core | Capsid | *Essential |
| UL87 | Core | Unknown | *Essential |
| UL89.1 | Core | DNA packaging/cleavage | *Essential |
| UL90 | CMV | Unknown | *Essential |
| UL91 | β-herpes | Unknown | *Essential |
| UL92 | β-herpes | Unknown | *Essential |
| UL93 | Core | Unknown | *Essential |
| UL94 | Core | Unknown(Tegument) | *Essential |
| UL95 | Core | Unknown | *Essential |
| UL96 | β-herpes | Unknown | *Essential |
| UL98 | Core | Akaline nuclease | *Essential |
| UL99 | Core | Tegument | *Essential |
| UL100 | Core | Glycoprotein M | ¶Essential |
| UL102 | Core | Helicase/Primase | *Essential |
| UL104 | Core | DNA packaging/cleavage | *Essential |
| UL105 | Core | Helicase/Primase | *Essential |
| UL115 | Core | Glycoprotein L | ¶Essential |
| UL122 | β-herpes | IE2(transcription) | ¶Essential |
| | | SEVERE GROWTH DEFECT (12 mutants) | |
| UL21 | CMV | Unknown | *$<2 \times 10^{-4}$ |
| UL26 | CMV | Tegument (transcription) | *$<2 \times 10^{-4}$ |
| UL28 | β-herpes | Unknown | *$<2 \times 10^{-4}$ |

TABLE 6-continued

A list of HCMV Towne strain genes categorized by the growth properties of their respective deletion mutants in cultured HFFs. Also shown are the sequence conservations of these ORFs with those in HCMV AD169 strain and other herpesviruses, the genome sequence of which are currently available[5-7,30], and their functions and the functions of their homologues in other herpesviruses that have been shown or implicated from previous studies. Although virus mutants with a deletion in each of the 10 ORFs in the US1-US12 region (marked with parentheses) were not individually constructed, these ORFs are listed as dispensable since they were collectively deleted and were not present in Towne$_{BAC}$. RL11 and RL12, for which a deletion mutant were not generated, are not included.

| Genes | Conservation | Function | Growth |
|---|---|---|---|
| UL30 | CMV | Unknown | *$<2 \times 10^{-4}$ |
| UL69 | Core | Tegument(transcription) | ¶$<2 \times 10^{-4}$ |
| UL82 | β-herpes | Tegument(transcription) | ¶$<2 \times 10^{-4}$ |
| UL112 | β-herpes | Major early protein | *$<2 \times 10^{-4}$ |
| UL113 | β-herpes | Major early protein | *$<2 \times 10^{-4}$ |
| UL117 | β-herpes | Unknown | *$<2 \times 10^{-4}$ |
| UL123 | CMV | IE1 | ¶$<2 \times 10^{-4}$ |
| UL124 | CMV | Latent transcript(ORF152) | †$<2 \times 10^{-4}$ |
| Us26 | β-herpes | Unknown | *$<2 \times 10^{-4}$ |
| MODERATE GROWTH DEFECT (23 mutants) | | | |
| UL2 | CMV | Unknown | ¶$10^{-1}$-$10^{-2}$ |
| UL11 | CMV | Glycoprotein | *$10^{-2}$-$10^{-3}$ |
| UL12 | CMV | Unknown | *$10^{-1}$-$10^{-2}$ |
| UL14 | CMV | Unknown | *$10^{-2}$-$10^{-3}$ |
| UL20 | CMV | TCR homolog | ¶$10^{-2}$-$10^{-3}$ |
| UL29 | β-herpes | Unknown | *$10^{-2}$-$10^{-3}$ |
| UL31 | β-herpes | Transcription | *$10^{-2}$-$10^{-3}$ |
| UL35 | β-herpes | Tegument/Transcription | *$10^{-2}$-$10^{-3}$ |
| UL38 | β-herpes | Unknown | *$10^{-2}$-$10^{-3}$ |
| UL47 | Core | Tegument-DNA release | ¶$10^{-3}$-$10^{-4}$ |
| UL65 | CMV | Unknown (pp67 virion protein) | *$10^{-2}$-$10^{-3}$ |
| UL72 | Core | dUTPase | *$10^{-3}$-$10^{-4}$ |
| UL74 | β-herpes | Glycoprotein O | ¶$10^{-3}$-$10^{-4}$ |
| UL88 | β-herpes | Tegument | *$10^{-2}$-$10^{-3}$ |
| UL97 | Core | Protein kinase | ¶$10^{-2}$-$10^{-3}$ |
| UL103 | Core | Unknown | *$10^{-2}$-$10^{-3}$ |
| UL108 | CMV | Unknown | *$10^{-2}$-$10^{-3}$ |
| UL114 | Core | Uracil DNA glycosylase | ¶$10^{-3}$-$10^{-4}$ |
| UL129 | CMV | Unknown | *$10^{-2}$-$10^{-3}$ |
| UL132 | CMV | Unknown | *$10^{-2}$-$10^{-3}$ |
| US13 | CMV | Unknown | †$10^{-1}$-$10^{-2}$ |
| US23 | β-herpes | Unknown | *$10^{-2}$-$10^{-3}$ |
| TRS1 | CMV | Transcription/egress | ¶$10^{-2}$-$10^{-3}$ |
| GROWTH LIKE WILD TYPE (66 mutants, 76 ORFs) | | | |
| UL3 | CMV | Unknown | ¶Dispensable |
| UL4 | CMV | Glycoprotein | ¶Dispensable |
| UL5 | CMV | Unknown | ¶Dispensable |
| UL6 | CMV | Unknown | ¶Dispensable |
| UL7 | CMV | Unknown | ¶Dispensable |
| UL8 | CMV | Unknown | ¶Dispensable |
| UL10 | CMV | Unknown | ¶Dispensable |
| UL13 | CMV | Unknown | *Dispensable |
| UL15 | CMV | Unknown | *Dispensable |
| UL16 | CMV | Immunomodulation | ¶Dispensable |
| UL17 | CMV | Unknown | *Dispensable |
| UL18 | CMV | MHC homolog | ¶Dispensable |
| UL19 | CMV | Unknown | *Dispensable |
| UL24 | β-herpes | Tegument | *Dispensable |
| UL25 | β-herpes | Tegument | *Dispensable |
| UL27 | β-herpes | Unknown | *Dispensable |
| UL33 | β-herpes | G protein receptor | ¶Dispensable |
| UL36 | β-herpes | Anti-apoptotic | ¶Dispensable |
| UL37.3 | β-herpes | Unknown | ¶Dispensable |
| UL39 | CMV | Unknown | *Dispensable |
| UL42 | CMV | Unknown | ¶Dispensable |
| UL43 | β-herpes | Tegument | ¶Dispensable |
| UL45 | Core | Ribonucleotide reductase | ¶Dispensable |
| UL59 | CMV | Unknown | *Dispensable |
| UL62 | CMV | Unknown | *Dispensable |
| UL64 | CMV | Unknown | *Dispensable |
| UL67 | CMV | Unknown | *Dispensable |
| UL78 | CMV | G protein receptor | ¶Dispensable |

TABLE 6-continued

A list of HCMV Towne strain genes categorized by the growth properties of their respective deletion mutants in cultured HFFs. Also shown are the sequence conservations of these ORFs with those in HCMV AD169 strain and other herpesviruses, the genome sequence of which are currently available[5-7,30], and their functions and the functions of their homologues in other herpesviruses that have been shown or implicated from previous studies. Although virus mutants with a deletion in each of the 10 ORFs in the US1-US12 region (marked with parentheses) were not individually constructed, these ORFs are listed as dispensable since they were collectively deleted and were not present in Towne$_{BAC}$. RL11 and RL12, for which a deletion mutant were not generated, are not included.

| Genes | Conservation | Function | Growth |
|---|---|---|---|
| UL83 | β-herpes | Tegument | ¶Dispensable |
| UL89.2 | Core | DNA packaging/cleavage | *Dispensable |
| UL109 | CMV | Unknown | *Dispensable |
| UL110 | CMV | Unknown | *Dispensable |
| UL111a | CMV | IL-10 homolog | *Dispensable |
| UL116 | CMV | Unknown | *Dispensable |
| UL119 | CMV | Fc receptor | *Dispensable |
| UL121 | CMV | Unknown | *Dispensable |
| UL127 | CMV | Unknown | ¶Dispensable |
| UL130 | CMV | Unknown | *Dispensable |
| UL146 | CMV | Chemokine | *Dispensable |
| UL147 | CMV | Chemokine homolog | *Dispensable |
| IRS | CMV | Transcription | ¶Dispensable |
| (US1) | CMV | Unknown | ¶Dispensable |
| (US2) | CMV | Immunomodulation | ¶Dispensable |
| (US3) | CMV | Immunomodulation | ¶Dispensable |
| (US6) | CMV | Immunomodulation | ¶Dispensable |
| (US7) | CMV | Unknown | ¶Dispensable |
| (US8) | CMV | Immunomodulation | ¶Dispensable |
| (US9) | CMV | Unknown | ¶Dispensable |
| (US10) | CMV | Immunomodulation | ¶Dispensable |
| (US11) | CMV | Immunomodulation | ¶Dispensable |
| (US12) | CMV | Unknown | ¶Dispensable |
| US14 | CMV | Unknown | ¶Dispensable |
| US15 | CMV | Unknown | *Dispensable |
| US16 | CMV | Unknown | *Dispensable |
| US17 | CMV | Unknown | *Dispensable |
| US18 | CMV | Unknown | *Dispensable |
| US19 | CMV | Unknown | *Dispensable |
| US20 | CMV | Unknown | *Dispensable |
| US21 | CMV | Unknown | *Dispensable |
| US22 | β-herpes | Unknown | *Dispensable |
| US24 | CMV | Unknown | *Dispensable |
| US25 | CMV | Unknown | *Dispensable |
| US27 | CMV | G-protein receptor | ¶Dispensable |
| US28 | β-herpes | G-protein receptor | ¶Dispensable |
| US29 | CMV | Unknown | *Dispensable |
| US31 | CMV | Unknown | *Dispensable |
| US32 | CMV | Unknown | *Dispensable |
| US33 | CMV | Unknown | *Dispensable |
| US34 | CMV | Unknown | *Dispensable |
| RL1 | CMV | Unknown | *Dispensable |
| RL2 | CMV | Unknown | *Dispensable |
| RL4 | CMV | Early protein | ¶Dispensable |
| RL6 | CMV | Unknown | ¶Dispensable |
| RL9 | CMV | Unknown | ¶Dispensable |
| RL10 | CMV | Glycoprotein | ¶Dispensable |
| RL13 | CMV | Unknown | ¶Dispensable |
| ENHANCED GROWTH (4 mutants) | | | |
| UL9 | CMV | Unknown | *$1 \times 10$ |
| UL20a | CMV | Unknown | *$1 \times 10$ |
| UL23 | β-herpes | Tegument | *$1 \times 10$ |
| US30 | CMV | Unknown | *$1 \times 10$ |

*Results from this study
¶Results in this study consistent with previous studies[4].
†Results in this study different from those in previous studies[4].

Based on their growth properties in fibroblasts, viral mutants carrying deletions in nonessential genes were further categorized into four groups: severe growth defect, moderate growth defect, growth like the wild type, and enhanced growth (Table 6). Twelve mutants were classified to have a severe growth defect in HFFs, thereby precluding the generation of sufficient titers for growth studies. Five of these ORFs have unknown functions, while the remaining seven genes are involved in regulating transcription or genome replication (Mocarski, E. S. & Courcelle, C. T. in *Fields Virology* (eds. Knipe, D. M. & Howley, P. M.) 2629-2673 (Lippincott-William & Wilkins, Philadelphia, Pa., 2001). "Moderate growth defect" mutants reached a peak titer of 10-10,000 times less than $Towne_{BAC}$ after 14 days in a multiple-step growth analysis (e.g. ΔUL132, FIG. 2B). This group contains 23 viral mutants of which 11 of the deleted ORFs have not been characterized, and their functions are currently unknown.

Sixty-six mutants retained growth properties that ranged from wild type levels to less than 10-fold fewer plaque-forming units at 14 days post-infection (e.g. ΔUL27, FIG. 2B). These "growth like wild type" mutants (Table 1) are considered to have deletions in dispensable genes, the majority of which are HCMV specific ORFs.

The mutant group that showed enhanced growth reached a 10-fold greater peak titer than the wild type virus during a 14-day infection (e.g. ΔUS30, FIG. 2B). We found it intriguing that these mutants were capable of reaching higher titers than the wild type virus. While their functions are currently unknown, recent bioinformatic analyses suggest that these ORFs are all either β-herpesvirus or HCMV-specific transmembrane proteins (Rigoutsos et al. (2003) *J Virol* 77, 4326-44).

Although 66 ORFs are found to be dispensable for viral replication in HFFs, it is possible that these ORFs encode important functions for HCMV infection in vivo, including those involved in immunomodulation. Due to the lack of an animal model for study of HCMV pathogenesis, cultured natural host cells have been used. In vivo, HCMV infects human retinal pigment epithelial (RPE) cells and microvascular endothelial cells (HMVEC), leading to viral-associated retinitis and vascular diseases, respectively. It is conceivable that some of the ORFs, while dispensable for HCMV growth in fibroblasts, are important for supporting viral replication in other cell types.

To test this hypothesis, HMVEC and RPE cells were individually infected with a collection of 15 viral mutants that grew as well as the wild type virus in HFFs. The growth of each virus in HMVEC and RPE cells was compared to the result found in HFFs. Diverse growth phenotypes of these mutants were observed in HMVEC and RPE cells (FIG. 3). For instance, the UL24-deletion mutant grew as well as the $Towne_{BAC}$ in HFFs and RPE cells, but was significantly defective in growth in HMVEC. Another mutant with a UL64 deletion replicated normally in HMVEC and HFFs, but barely produced viral progeny in RPE cells (FIG. 3). Our results suggest that UL24 and UL64 are important for viral replication in HMVEC and RPE, respectively. Interestingly, a UL10 deletion mutant grew normally in HFFs and HMVEC, but reached a 500-fold higher titer than $Towne_{BAC}$ in RPE cells, while a US16 deletion mutant replicated as well as the $Towne_{BAC}$ in HFFs and RPE cells but grew 100-fold better in HMVEC (FIG. 3). These observations imply that UL10 and US16 encode cell-type specific functions for virus-growth inhibition.

Research during the last two decades has collectively shown that the prototype herpesvirus, herpes simplex virus 1, encodes 37 essential genes and 48 nonessential genes. The majority (78%) of the 45 HCMV genes that are essential for replication in HFFs are highly conserved across all herpesviruses, suggesting that these core ORFs may represent the minimal ancestral genome of all herpesviruses. HCMV may have evolved from the progenitor genome through the acquisition of non-essential genes that are responsible for its infection and pathogenesis in various tissues. This hypothesis is supported by the identification of Epstein-Barr virus and Kaposi's sarcoma-associated herpesvirus-specific genes that are involved in their unique latent infections. The functional profiling of HCMV genes reported provides a step toward elucidating the role of each gene in viral infection.

Our analysis of the mutant library suggests the presence of viral encoded factors that regulate viral growth in different cell types. The discovery of HCMV encoded factors that repress viral replication on a cell type-specific basis represents a novel discovery in the field of animal viruses. Deletion of distinct ORFs resulted in mutant viruses with enhanced growth in specific cell types (e.g. ΔUS30 in HFFs, ΔUL10 in RPE cells, and ΔUS16 in HMVEC). While the mechanism by which these genes repress viral replication is currently unknown, we speculate that the genes may either directly block CMV growth or activate cellular antiviral machinery to suppress viral replication.

The presence of these growth-repressor factors may initially seem counterproductive from the perspective of the virus, however, their existence is consistent with the observations that HCMV exhibits different growth rates in various cell types. In vivo, these inhibitors may moderate viral loads to levels optimal for transmission, but prevent viral replication from reaching levels that can result in severe tissue damage or host death. Furthermore, they may suppress productive lytic replication to low levels or cease viral replication, thereby facilitating persistent and latent infections. Therefore, these repressor factors may have the effect of enhancing virus survival. This strategy of pathogen temperance may be a fundamental component in a pathogen's repertoire of factors that function to enhance its long term existence.

The presence of such temperance genes in viruses suggests that pathogen temperance is a prevalent survival strategy and present in other higher order organisms with greater genome content. This is consistent with recent observations in infectious organisms where deletion of certain pathogen-encoded factors resulted in a hypervirulent infection in the host (Parish et al. (2003) Infect Immun 71, 1134-40; Cunningham et al. (2001) Science 292, 285-7). Recognition of pathogen temperance may radically alter the way we perceive the emergence of hyper-growth virulent variants from benign pathogens. The underlying mechanism for hypervirulence may be the loss of these temperance factors, as opposed to the acquisition of virulence genes. Accordingly, drugs that mimic or activate temperance factors may lead to effective therapies against infectious diseases. Further studies of pathogen temperance will provide insight into the evolution of new and emerging virulent pathogens and facilitate the development of novel approaches for controlling future epidemics caused by these virulent strains.

Materials and Methods

Virus and cells. HCMV (Towne strain) (ATCC, Manassas, Va.) and human cells (Clonetics Inc. San Diego, Calif.) were propagated as described previously (Marchini et al. (2001) J Virol 75, 1870-8). The $Towne_{BAC}$, which contains a green fluorescence protein (GFP) expression cassette, was maintained in human cells and in bacterial strains DH10B and DY380 (Lee et al. (2001) Genomics 73, 56-65).

Genomic sequencing and bioinformatic analysis. $Towne_{BAC}$ DNAs were subjected to genome-wide shotgun sequencing analysis at MWG-Biotech, Inc. (High Point, N.C.). The sequence was determined to an average redundancy of more than 10-fold. The sequence database was manually reviewed before depositing it into Genbank (accession number AY315197). ORFs that potentially encode a protein greater than 100 amino acids were predicted using standard genetic codes, following the guidelines as previously described (Davison, supra.), or the manufacturer's suggestions (MWG-Biotech Inc., High Point, N.C.).

Construction of deletion and rescued mutants. To construct the deletion cassettes, two oligonucleotide primers (up1 and dn1) were constructed and contained the following components (from 3' to 5'): 18 or 19 homologous nucleotides to the antibiotic resistance cassette KanMX4, a 20 nucleotide unique barcode tag, a common 19 nucleotide primer, and a 25 nucleotide region homologous to the first 25 nucleotide adjacent to either the start or stop codon of the ORF being targeted for deletion. The up1 and dn1 primers were used to amplify the KanMX4 cassette, which contains the kanamycin resistance gene, nptl, fused with an efficient bacterial promoter. A second round of PCR using primers bearing 50 bases of homology to the region upstream and downstream of a particular HCMV ORF yielded a product in which the KanMX4 cassette was flanked by 50 nucleotide homologous sequences targeting the ORF to be deleted in the $Towne_{BAC}$. Transformation of the $Towne_{BAC}$-bearing DY380 strain with the PCR product resulted in the replacement of the target gene upon selection for kanamycin resistance. The unique 20-mer barcode sequences were covalently linked to the sequence that targeted them to the HCMV genome, creating a permanent association and genetic linkage between a particular deletion strain and the tag sequence.

All predicted ORFs that potentially encode proteins greater than 100 amino acids in size were initially selected for deletion. The deletion cassette was designed to remove the entire coding sequence for a given ORF. Although ~10% of HCMV ORFs overlapped with each other, the position of the deletions was not adjusted, nor were there any attempts made to avoid essential genes, genes in which a previous deletion had been constructed, or genes with a well-defined function.

To verify the correct integration of the deletion cassette, BAC-DNAs were prepared from kanamycin-resistant clones and subject to PCR screening using the primers for the corresponding deleted ORF. In restriction profiling and Southern analysis, BAC-DNAs were digested with restriction enzymes, separated on agarose gels, transferred onto membranes, and then probed with a [$^{32}$P]-labeled probe containing both the target ORF and KanMX4 sequence. Only clones with insertions of the cassette, as confirmed by PCR, restriction profiles, and Southern analysis, were further studied.

Construction of rescued BAC mutants was carried out by adapting a two-step homologous recombination approach in *E. coli* (FIG. 2A), first replacing the kanamycin cassette of the deletion mutants with a tetracycline and streptomycin (tet/str) cassette by selecting tetracycline-resistant clones, and then replacing the tet/str cassette with the intact ORF sequence by selecting streptomycin-susceptible clones. The latter selection takes advantage of the fact that only bacterial clones lacking the str cassette survive in the presence of streptomycin.

Growth analysis of viral mutants in cells. HFFs were electroporated with $Towne_{BAC}$ DNAs, then plated onto six-well plates, and observed for 3-15 weeks for GFP expression and cytopathic effect (CPE). No viral progeny were produced from $Towne_{BAC}$ DNAs containing deletions of essential genes. Mutants that did not reach more than 30% CPE after 15-weeks post-infection were considered to have severe growth defects, and their titers were not sufficient for the multiple-step growth analysis. Flasks of cells infected with mutants that exhibited moderate growth defects or growth like the wild type reached 30-100% CPE at 3-15 weeks post-infection and were used for the preparation of viral stocks.

In multiple-step growth analyses, $1\times10^5$ cells were infected in duplicate with different viruses at a multiplicity of infection (MOI) of either 0.05 plaque forming units (PFU) (for HFFs and HMVEC) or 0.25 PFU per cell (for RPE). The cells and medium were harvested at different times post-infection, and viral stocks were prepared by adding an equal volume of 10% skim milk followed by sonication. The titers of the viral stocks were determined in triplicate as described previously.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for identifying biologically active agents that modulate cytomegalovirus replication, the method comprising:

combining a candidate biologically active agent with a mutant virus comprising a defined deletion of a temperance factor open reading frame (ORF) selected from UL9, UL 20a, UL 23 and US 30;

determining the effect of said agent virus replication; and comparing the effect of said agent to that of a control.

2. The method according to claim 1, wherein said agent increases replication of said virus.

3. The method according to claim 1, wherein said agent decreases replication of said virus.

4. The method according to claim 1, wherein the mutant virus comprises a defined deletion of UL23 ORF.

5. The method of claim 4, wherein the candidate agent mimicks the activity of the UL 23 temperance factor.

* * * * *

UNITED STATES PATENT AND TRADEMARK OFFICE

CERTIFICATE OF CORRECTION

PATENT NO. : 7,407,744 B2
APPLICATION NO. : 10/897508
DATED : August 5, 2008
INVENTOR(S) : Liu et al.

It is certified that error appears in the above-identified patent and that said Letters Patent is hereby corrected as shown below:

In the specification:

The following text should be added between lines 7 and 8 of column 1:

--This invention was made with government support under contract/grant number AI041927 awarded by the National Institutes of Health. The government has certain rights in the invention.--

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 218802
<212> TYPE: DNA
<213> ORGANISM: cytomegalovirus
```

-continued

<220> FEATURE:
<221> NAME/KEY: misc_feature
<222> LOCATION: 19769
<223> OTHER INFORMATION: n = A,T,C or G

<400> SEQUENCE: 1

```
aagtggacgt tactgatgat tacgatatct gaaggttgca atgacacgtg ctcctgtccg     60
tgcaattgcc tttacctcca ccgcctccac tatcacaaat tcttctaact ctgtcaccga    120
tgctaacagc acttcagcta tcgcaaatgg aaccacgcac aaaccctcta ccgcttcttc    180
agtcgcatca gcaaccactt caacgctttc aaaatcatcg tcaagcgcta cgccaacatt    240
aacgttttct accattcata gtactactcc ctggttgaat accagcaaca taacttgcaa    300
tggcagtttg tacaccgttt ataaacactc taatttaaat tacgaagtaa ttaatgtaac    360
aggatatgtc ggtggatacg tcactttgaa aaactgcagt agaacggatg tatggcacga    420
tatagaatgg ataaaatatg gacctcgcgc acaccaactg tgcagcattg gacattatta    480
ttcaacttcc ccactgaacg gcatgtgttt agactgcaat aagacctctc tcactatata    540
caacgtaact accgaacacg ctggaaaata cgttttgcaa cgttacagtg acggtaaaaa    600
ggaaaactac tatttaaccg tgttatcagg aactgcaaca tcgtctccta tacctgataa    660
atgtaaaaca aaagaggaat cagaccagca taatagcaga acgtgggaca atgtaataaa    720
aactgtaaaa aacactaaca ttcccctggg aattcatgct gtatgggcgg gtatagtggt    780
atctgtggca cttatagcct tatacatggg tagccgtcgc gtccccagaa gaccgcgtta    840
tacaaaactt cccaaatacg acccagatga attttagact aaaacctaac atgcacatca    900
ataaactttt gtttttattt ttagccaata atgtctccgt gtggtttttg tgggttaagc    960
acttatggtg tgaagcagaa tattcatagt tattaaaaac atgggtatac aatgtaacac   1020
taaactactg ttactagccg cgctaatagc aactgcaacc attctaacta gcattttagt   1080
tccggtactt ttacatgaac aagaaaaaac attttaccgg cgattttta cgcaaagtca   1140
acatgtagaa agacccatca cggtaactca gggagataca gtttacctga acggtagtaa   1200
taatccctgc aactattcca gtttctggaa ctacggcagt tgcgaacttt gtggatggaa   1260
cggatacata cataaacagt accacgaaaa caaatcatgc tctccgcgat ttacatgttt   1320
taacgacaca aaaggtctca gacttaataa cgttacatct agcgattcag gaacatacac   1380
ggaatacgtg tatgaatgcg atttgccatg taatacaagt gactatgatg aatatgacat   1440
actaaactat cttgacaatt gtactactac cataaacagc accaattata ttattaccgt   1500
attgtctcca cgtcattcta aacacaccaa ttcccacata tccacgctgg ttggacagct   1560
gccgtggtga cggtaattat aatctgcgtt ttgacttact ttaacgttcc ggcaaccctg   1620
aaacgcaaac tacgaactag aaacaacgct acccacatac cgtgattaca aagtacccac   1680
actagttcat tcaggataaa tttgtgcttt gtgtagctct cagaaattgt acaaccccgc   1740
ttttccactc cgtcatgaaa gatcgtaata aactacttat atgtattatc tttattttca   1800
ccatgtgcct catctgtctt tactttaaac gccgttgtat tcctacccca tctccagaca   1860
aggcagatct gcgagtggaa tttccttcgt tatctccgtg tgtcggcata cagtgcgctc   1920
catgaaaaga cgcgtgatac atagcgtact ccaggacggt acagtttatg agaacataat   1980
tcaaggaaag tgcaggttcc tgttgctatg ttaccacagg agatcacgga acataaatgt   2040
tttctgcgta tgtttttata aaagagcgtc tcgaagcagt ttgagccaca ctacggtcca   2100
gatgacgagc gtaatcaaaa atatgccgcg tagtagtcga aagccgtact gagcgtgcga   2160
```

-continued

```
agcgggtagg gtgccgaacg acgggtatgc gtcgtcgtca tctttgacta taaggatcgc   2220

gaccgagttt tctggcatgg taaaagctgc ccactgtggc aggtatgtag cgtatccggt   2280

ttggaatcgt tcggctctgg tccgggggat agtgaggaat tctcagggga tgatatggga   2340

cccaatcact ggataagaca agggtttttc cccgtaagat gatcctcgta tcacatgagg   2400

tctggatatg tataaatgag gagtgaaata ggcacaggga atcagatgcc ggccttgtga   2460

tgcagccgct ggttctctcg gcgaaaaaac tgtcgtcttt gctgacttgc aaatacatcc   2520

cgccttaagt gatgagtcta taaagcaccg ttgtctgggt acggtaaaag tgactcggat   2580

tgtagcacgt catttttttt tgtttttgca tcgtttatcg tcaccactag tgcaatattt   2640

tgatcgtaag gctgaaagag tatcgttatg atgcttagag cgtggagatt gatggtacta   2700

cttgccgcgt actgttatta tgtttttgcg aattgttcaa tcagcacgac gactgctcct   2760

gtggaatgga agtctcccaa ccgtcagatt cccaagaata ttacttgcgc taattactca   2820

gggaccgtcg gcggtaacgt tacttttcag ggtctcaaga ataaaacgga agattttta   2880

tcttggctac tcgggtctgg ttataagtcc atttgctcgt tcttcccgca actccctggt   2940

gattctaatg agcagcatta cagatatgaa gtaaccaacc tcacgtacaa ttgcacctat   3000

gaccgcctga cgttactgaa tctgacaacg gaaaacagca ggaattacta tttcagaaga   3060

gaagatgcga attccacctt ctattactct tgttacaatc tgaccgtgtc ctaaagatcg   3120

cacgtgaagt tccacagaac cgcgcagctg tagctattgt gtttacgttg cttttgaaat   3180

gttaagcgtc cctacggcgc taacatgttt ctaggctact ctgactgtgt agatcccggc   3240

cttgctgcgt atcgtgtatc tagatcacgc ttaaagctcg tgttgtcttt tgtgtggttg   3300

atcggtttgc gtctccatga ttgtgccacg ttcgagtcct gctgttacga catcaccgag   3360

gcggagagta acaaggctat atcaagggac gaagcagcat tcacctccag cgtgagcact   3420

cgtacaccat ccctggcgat cgcgcctcct cctgaccgat cgatgctgtt gtcgcgggag   3480

gaagaactcg ttccgtggag tcgtctcatc atcactaagc agttctacgg aggcctgatt   3540

ttccacacca cctgggtcac cggcttcgtc ttgctaggac ttttgacgct tttcgccagc   3600

ctgtttcgcg taccacaatc catctgtcgt ttctgcatag accgtctccg ggacatcgcc   3660

cgtcctctga aataccgcta tcaacgtctc gtcgctaccg tgtagctagt tagccagctg   3720

tgtatagttt gttgtgtttt gcttttgcat atttgttttc agtcagagag tctgaaacgg   3780

ggtgggaggg acttttgcgg gtagtgcacg ctaagatgaa cgggtgggct ggggtgtgct   3840

tgataactca ctgtttgaat acgcgctcac gcacatatgt agcactcaac atgttagctt   3900

ttgcccgcac gccccggggc atgccgagct gccttttttaa taaagtctgg gtttccagat   3960

acgcgctggt tctgattttg atggtttgtg cctctgaagg ctcaacgaat tgggtcgtgg   4020

tttctcatag gctgcctaac tgtagcgcgg tatctacaac agtgggacaa aacgttgagt   4080

tatgcggctc ggcgtcatca ggttgtaaca taacccaatg gggacgttac cagaatggaa   4140

gtacgctggg gccatggtgt accctgtggg gaccatatac ccaagtctca ttaggacatc   4200

gtgtagcgtt cggctgttct tggacaacgt tttttatgta caacctttct caaaatcata   4260

gtggcactta ttatcgaaaa ggtgacaact gtaccgacaa acatataaca ctatcttgtt   4320

tcaacttgac ggtgcatccc aaggcggctc agagcacaac caccgtagtg acacccacgg   4380

tagttacaaa cgccacggcg aatgtgtcac ccattacgtc gactctagcg gtaaattcca   4440

gcgcgtttaa acacgttagt tatcaacggc aacagcgtgt cgaaaacagg acgtcatcca   4500

agaacataac taacttggca ttcacctatg gcagctgggg cgttgcgatg ctgctgttcg   4560
```

-continued

```
ccgccgtgat ggtgctcatt gatttgggtt tgcctcaatc ggcttggcgg cgctggcgaa   4620
tccacgtgga cgatgaagaa cgtggtctgt taacgtagga aataaaaagt actgtttgag   4680
cgtgactgtt tccaaatcgt accgtggtaa ataaatcatg gtttccggcg tgggttctca   4740
tcttatgacg gttccacgat tccgttggac agtgcatcat gtgtacaata aactattgat   4800
tttggcgttg tttgcccccg tgattttgga atccgtcatc tacgtgtatg cgccagaggg   4860
agggaacgtt accctggtat ctaacttcac ttcaaacatc agcgtacggt ggtttcgctg   4920
ggacggcaac cacagtgatc tcatctgttt ctacaagacc aaagaaggat tttcaacgcc   4980
ttatgtgggt ttaagtctaa gttgtgcggc tagccagatc accatcttca acctgacgtt   5040
gaacaactcg ggtcgttacg gagcagaagg tttcatgaaa agcggcgaaa atgaaacgtt   5100
cctgtggtac aacttaaccg tgacactgaa atctctgaaa actacctcag ctaataacgt   5160
aacaaccatc gttacaacga cgccgacggt gactggcgcg gagagtaacg ggactagaaa   5220
tgccatttta acaccacaac tacgtgctgt tgctggattc tccaatcaaa cgccctcgga   5280
aaacaacaca cacctggcct tggtaggtgt tgtcgtgttt ttgattctga tagttgtttg   5340
tattatgggg tggtggaaat tgttgtgtag taaatcagaa ttatagtaat gtgcttttta   5400
tcagggagaa ggttttgtgc ccacaatgac tagcccggga ctatctacgt cggaaaatta   5460
caacggaaat tatggactca cgaagaccgc caatacaacg cgtacaaata acagtgaccg   5520
gacaacgtta ggagccagtg cgtcgttgtt gggaagcacg gagactgcgg taaactttga   5580
caacgcgact acgattatcc cacaacgtgt ggaacacccg gttggggaaa tacaatatca   5640
gagaacgaca acacattatt cttggatgct aattattgtc atcattctca ttatttttat   5700
tatcatctgt ctgcgagcac ctcgaaaagt ttacgatcgc tggaaagaca gtaaacagta   5760
tggacaagtg ttcatgacgg acacagaact atgatgttcc ggtacgcgtt attacttcga   5820
tggataacaa tcattctttg tacacgaaaa tccaattatt ggaactacat atcaacgcca   5880
tgtacttcta tagttggcta cagtggccag aatatcagct tatctcccgt taacaaattg   5940
tcagtcaaag acgatgcttt tcaatggtat atagacaaac cgagagttac taacgcacta   6000
tgtatttatc aaaataacga gtgcagtgta caacccaatg agaacgctcc gaacattaag   6060
tggcaatgtg tacagaatca tacacttatt cttattaatt taacaactac atatagtaga   6120
aattactatt ttaattcttt tgaaaccctt ggagtaacaa tagcaaaata caataccctg   6180
tgttacaatg tcagtgtaca ttctgcctac caaacacact gttgtacaac cacgttatcc   6240
atgtattcac ccacacccgt acacaggtca tacacattaa cttcaaccaa cttcacacat   6300
gtcgcggtcc attataccgc cggtaacgtt gaagcacaac acgatactgc caccccacat   6360
acaatgtgga tcatacccct agttatcgtt ataacaatta tcgttttaat ttgtttcaaa   6420
tttccccaga aagcttggaa taaattcaca caataccgat acaacagtat gctcgccgcc   6480
acttaaagaa tcaccgtcga ggaaactaaa agctatgtac gtttattttt cagctcactg   6540
tttgaatacc gtaaacataa tgacgtacat atacgtggtt atacaacagg tgtttgtgct   6600
atgcggagac tgattaacca tatcgtgaac catgatcttt tccgatggtc tgtcgtgacc   6660
gcaatgatat tttacaggta ttccgaaacc tgtatggagg tcactgtcag agtaggtgat   6720
ccagttaccc tcggtagtgg acatggttat catccaggac aaaaagtaca ctggtataac   6780
cagtcatgcg tcggcatcag caacggcgaa aatacgcatc ctatctgcac ctacgaccct   6840
cctaaacctg gtagacaaaa gacaatgaaa accactccgt tgccatcacc actgttgtat   6900
```

-continued

```
gaatgtcaca attccacatt aagcattctt catgtaaacg tctcagatcc cagaaactat   6960
tgcaggcgaa aatgtccacc aaagggtaac tgtgagtttc ccacatgttt tacattatcg   7020
ctgatttcta gaacgacaac caccagaaga cccggacaaa aaactacgtt gtcgcgatta   7080
aaaaccacgc caaataaaca tacgcagcac aaaagatcca cgcgaggaac gtcacctaaa   7140
gattacaatg taacgggtct gccgaaaggc tttgcggact cgtttaccgg taacgtagag   7200
gcacatagag ccaaagatgc cgcacacagc gcatggattc tcattgtcat catcattatc   7260
atagtcgtca ttctgttttt cttcaagatt cctcaaagac tccgagagaa atgggacacc   7320
aagggatacc tttacaaagg gaccgatggc ctgcccacta cggactaatt atcgtgagcg   7380
gacggatatg tccggtttca aactcactgt ttgaatatag ggacagtccc tacggaacct   7440
gagaacatgt ggaaatcacc tgtggtagaa tgctgctcag gtacattacc tttcatcgcg   7500
aaaaggtact ttacctaacg gctgcatgca tctttggtgt ctacatcagc ctccatgatg   7560
cctgcatacc ggtggttggc aagataggta ccaacgttac gttgaacgcg gtagatgttc   7620
tccccccctcg cgatcaagtt cgttggtcat acggtccagg cgggcaaggc tacatgttat   7680
gcattttcac tggcacatca acaacaacgt ttaacagcac gcgctttaat ttttcatgtc   7740
tgagtaatta cagcctcctc ctcattaacg ttaccgcgca gtatagtact acctatcgta   7800
ctatgacatc gctagacgat tggcgtcacc aacaacataa ccatggtttt cgatggactt   7860
tagacacatg ttacaatctg acagtgaacg aaaacggtac attccccact accaccacca   7920
aaaagcccac tacgactacg agaacgacaa ctaccacaac acaaaaaaca accaccacga   7980
gaacaaccac caccgccaag aagacgacga taagcactac ccatcataaa cactccagtc   8040
ccaaaaaatc caccacccct aacagtcacg tagaacatca cgttggtttt gaagccacag   8100
cagcggaaac accgttacaa ccaagcccac agcaccaaca cgtggctaca cacgccctct   8160
gggttttagc ggtcgtaatc gttattatca tcattatcat tttctacttt cgaataccgc   8220
aaaagctgtg gctgctctgg cagcatgaca agcacggcat cgtgctcatc ccccaaaccg   8280
atctgtaagc aagtcgcgta ggaaatgatt gcatgaaatc actgtgaaac gccaactccg   8340
tgccagctgg cgcggcggac aggcctttga cgtatttgaa gccaggcgcg ctctcgatac   8400
cgaaaggatc caagggggct ttccaaagcc gacgtccctg attcccttca taaagctgtt   8460
gaccggccct agaaagacca agagcatgct gtgggcccac tgcggtcgct tcttgcgtta   8520
tcatctgctc ccgctgctac tgtgtagact gccattctta ctcttttttc agcggccgca   8580
gtgggcccac ggcttggaca ttgtcgagga ggacgagtgg ctacgggaaa tacaaggagc   8640
gacgtaccag ctgtccatag tgcgccaagc tatgcagcac gccggattcc aagtcagagc   8700
ggcgtcggtc atgatacggc gaaacgccgt tgacctggac cgaccgccgc tttggtcggg   8760
atcgctcccg catttgcccg tctacgatgt gcgttccccg cggccgttga gaccgccgtc   8820
atcacagcat cacgccgtat cacccgaact gccgtcgcga aacgggatac gttggcagta   8880
ccaagagctg cagtatctgg tggaagaaca acggcggcga aatcagtcgc gtaatgcgat   8940
tccgagaccc tcgttccccc ctccggatcc accatcgcag ccggcagagg atgcacgaga   9000
cgcggacgca gaacgtgccg aatcaccaca cagtgcagaa agcaccgtca gccacggcgc   9060
gagtgacaac gcagtgcggc gacggcacga aagacggcgc tataacgctc tgacggtccg   9120
cagcagggac tcgctgctcc tgacgcgaat acgcttctcc aaccaacggt gtttcggacg   9180
cgggcgtctg agacatcccg cgggaagcgg tcccaacacc ggcggaccgc gacccggcgg   9240
tgcgggactc cgtcaactac gccaacaact gacggtccgc tggcagctgt tccgcctacg   9300
```

-continued

```
gtgccacggt tggacacagc aagtctctag ccagatcaga acccgctggg aggaaagcaa   9360
cgtcgtgagc cagacggcca cgcgagtacg tacgtggttt gtgcaaagaa ccacgttgtg   9420
gcgtcgcacg tgggttccgg gacagaaccc ggcggccgaa gcgcaagaac tggccgtcat   9480
accgccggca cccacggtgc tccggcagaa cgaggaacca cgtcaacagc ttacgggaga   9540
ggagacaaga aattcaacgc acactcaacg tgaagaagtg gaggacgttt cgagagaggg   9600
cgcgagagaa gggaatgatg ggagccgagc aagtggaaac gacgagagaa ggaataatgc   9660
gggaagatat gatgatgatc atgaggttca agagccgcag gtcacttatc cagcgggaca   9720
aggagaactg aataggaggt cacaggagga gaacgaggaa ggtggaccgt gtgaatcgcc   9780
gccaatgacg acaaatacgc tgaccgtggc ctgtccgccc cgagaacccc cgcatcgtgc   9840
cctgtttcgt ctatgcttag gactgtgggt ctcgagctac ctggttcgac ggcccatgac   9900
gatttagaat acaccgagcc attcctttat ttccccccat ccccggtcgc ttatgcgtgt   9960
caaacactac caataaagat aatctgccaa tcgcacctta tatataatat gtggtcgcgt  10020
gtggtctttt taaggagctc tgaaacacag acaggtatgg gcggtggccg gctgccgccg  10080
ctgtggctgc cgctgctgat cgcctggagc gagtggggca actgctgcct cgatgcgcct  10140
ccggtggtgc gttcgccctg tctgcagccg gtgcgcgacc gcaaccgcga gcggaacccg  10200
ggctcaccgc agttgctgcc ttacggcgac cgtctggagg tggcctgcat cttccccgcg  10260
cacgactggc cagaggtctc tatccgagtc cacctctgct actggcccga gatcgtgcgt  10320
tcgctggtgg tggacgcacg cagcggtcag gtgttacaca acgacgccag ctgttacatc  10380
gccggcgggc gctggcgctt cgaggacggc ggcgcggcgc agcggctgag cctctcgttt  10440
cggcttatca ccgagaccgc gggcacctac acctgcgtgc tgggcaacga gacccacagc  10500
ctggcgaccg agaccacggc gctggtggcc gacgtgcacg acctgcgcca ctcggaccgc  10560
tcctgcgacc tagctttcgg atctcgctca cagacgcggt acctgtggac gcccgatccc  10620
tccaggttgc gcagtataaa ctgtggttgg gagggtgaac ggcaccgcgt ggtccactac  10680
atccccggca cctcgggtct gctgccctcg tgcgaggagg acgagcgcga actgtgcgtg  10740
cccttcatca gccagagcat cgcggacaac aactgcagcc accggcatcg ggtagacggc  10800
gctaggcggc gctatcatct gcggagggat tactggctga cggatccgaa gatcgggctg  10860
ctggccgcgg gatcggtggc cctgacctcc ctctgccacc tgctgtgcta ctggtgttcc  10920
gaatcgtacc ggcgtctgaa caccgaagag gaaaacgagg cggcagagga aactgccgcg  10980
ggagaagcct ctgcggtagc ggcggcggcc gtctctgagg aagagcagca gcgggagtaa  11040
acgaggagag ccatgaagcg gatgattcgc agtcacggca ggaaaacgga atgtcagatg  11100
acgggcgccg gcgagcgacg cggctctgcc gtcggtgcgc tcatctgcgg cagcggtacc  11160
cgacgcggca gcggcgccaa cgaacgccgc gactccgacg tcggtcccat cgcccacagt  11220
agcggtacca gacgcggttc ggcgaatgaa acgtccgcct gtacgcggac cgatcaccag  11280
aaggcggaca ttgggctgtg gttcatgttt ctggtttttg gactgtgttc gtggttggcg  11340
atgcggtatc gcgcacaata aattttgaat cgatgtcaag gaacgcgtgt tttgtatttt  11400
attgggaata ttggcgggga taaaccggtt tcggatgttt acccttaatc ttaccgggga  11460
cctcgttgtc ctctcctcct tcttcctcgg acacggggct ccatgctgac gtaggtaccg  11520
actggggtca aaagcctggg tacttatggg gagcgcgcac aaaggaccgt caggcgccgg  11580
catggagcgt cgccgaggta cggtaccgct gggatgggtg ttttttgttc tttgcttatc  11640
```

-continued

```
tgcctcttcc ccgtgtgctg ttgacctggg tagcaagtcc tccaactcga cctgccgctt  11700
gaatgtgact gagttggcct cgatccatcc tggggaaacg tggacgttac acgggatgtg  11760
tatttctatc tgctactacg agaatgtgac cgaagacgag atcatcggcg tggcttttac  11820
ttggcagcat aacgagtctg tggttgacct gtggttgtac cagaacgaca cggtgatccg  11880
caatttcagc gacatcacca ctaacatctt gcaagacgga ctgaaaatgc gaaccgtccc  11940
tgtgactaaa ctgtacacca gccgcatggt cactaatctt accgtgggcc gctatgactg  12000
tttacgctgc gagaacggta cgatgaaaat aatcgagcgc ctctacgtcc gattgggctc  12060
actatatccg agaccgcccg gatccgggct cgccaaacac cctccgtaa gcgccgacga  12120
ggaactgtcc gcgaccttgg cgagagacat cgtgttggtc tcggccatca ctctgttctt  12180
cttcttgttg gccctacgga tcccccagcg attgtgtcag cggctgcgca ttcgcctgcc  12240
gcatcgatac cagcggttac gcaccgagga ctgaacggat aaccgcaaag gccacgtgca  12300
acgttcacgc tgctataaga aggccatgtc ccccgtggac gggtctcttt gacacgagcg  12360
cggcacgccg ttgccacgag catggatcac gcgctcttca cacacttcgt cggccggccc  12420
cgtcactgtc ggttggaaat gttgattctg gacgaacagg tgtctaagag atcctgggac  12480
accacggttt accacaggcg ccgcagacat ctacctcgac gccgcgctcc gtgcggcccc  12540
cagaggcccg ccgagattcc caaaagaaga aaaaaggcgg ccgtccttct attttggcac  12600
gatttgtgct ggctgtttcg acgacttttc tttcctcggg aggactcgga gccactgatg  12660
tcggatccgg cacggtctcc cgaagaggag gagtaaacaa cacacggcta agaggataca  12720
tcatcaaaga agataggagg ggtcaaaacg cggactgaaa gtatataacg ccgatcatgt  12780
ccgaggaact gttaataaaa cgccatgatg acaacgtggt gtctgacgtt gtttgtgctg  12840
tggatgttga gagtggtggg aatgcacgtg ttgcgttacg ggtacacggg gattttcgat  12900
gatacatcgc atatgacgtt gaccgtcgtg gggatttttg acgggcaaca ctttttttacc  12960
tatcacgtta attccagcga tagaacgtca agtcgggcca acggtaccat ttcttggatg  13020
gccaacgtct cggcggccta ccccacctac ctagacgggg aaagagccaa aggtgacctt  13080
atttttaacc aaaccgagca aaacctgtta gagctggaaa ttgcgttggg ttaccggtca  13140
cagagcgtgc tgacgtggac gcacgagtgt aataccacgg aaaacggtag ttttgtagcc  13200
ggttacgagg gatttgggtg ggacggggaa actttaatgg agctcaagga taacctgaca  13260
ctatggacgg gccccaatta cgaaattagt tggttgaagc aaaacaaaac gtacatcgac  13320
ggtaaaatta aaaacatcag cgagggggat actacaatac aaaggaacta tctcaagggt  13380
aattgcactc aatggtccgt catttatagc gggtttcaaa cccccgtcac ccacccagtg  13440
gtaaagggcg gtgtccgaaa ccagaatgac aacagagctg aagcattctg tacatcttac  13500
gggttctttc caggggaaat taatattact tttattcatt acggtgataa ggtgcccgag  13560
gatagcgagc ctcaatgcaa tccgctactt cccaccttgg atgggacttt ccatcaggga  13620
tgttacgtag ccatcttttg caatcaaaac tacacctgcc gcgttacaca cggtaattgg  13680
acggtggaaa tccccatcag cgttacctca cctgacgaca gttcctcggg ggaggtcccc  13740
gatcacccga cagctaacaa acgctataac accatgacca tcagcagtgt cctcctagcc  13800
ctgcttttat gcgctttgct attcgcgttc ctgcactact ttaccacctt gaaacaatac  13860
ctacgtaacc tggcctttgc gtggcgctat cgcaaggtcc ggtcgtcatg accatcaacg  13920
ccctgtatga gctgtttcga cgtcggttac cgcgtgcccc cgtcaacacg gtcatgtttc  13980
tcacgcgacg cactcgtgat gggttctgcg gtcggttgac gtccatcgcc acgaattccc  14040
```

-continued

```
actacactat gttcgtgttg gatcacgggt ccgtgcgcat cgagcgaccg agtcagtcag  14100
aagtggattg cgccagttta atggaaacgc tgaagcggat tcggttacga aattcgtggg  14160
tagcgtcaga agacgagcta gatgtgagtc gcagggacgc gtgacacgaa acgcgttcag  14220
gattaacgta ggttttcaaa ataacctacg tccgtgagtg acgcggtttc gtgttgaaac  14280
ccgcgcccgg ttcccacggt ggtttatgat gaaaccggcg ttggggatct acgcgggttc  14340
ctcattcaac ctgcgaaaag aggaagttgc ggtaaaacca cgtcaataaa gacgtcaatg  14400
acacctcaat gttgcgttgg aacggtcttt atatatacaa acgccgttat gctcagtgtc  14460
cggcaagatg ctcgggatac gggctatgct ggtgatgctg gattactact ggatacagtt  14520
gacaacgctc aatggcaccc gaaccaacaa taccgatacc atctttgtgt ctctccttac  14580
cggtcccaac ggagttaccc gcacggccat cgggggtttg tattcaaact acactaattt  14640
aactggacca tttggcttca cttcaacaaa cgcatcaata accaactctt ccactgaggg  14700
taattggagc gtggctaatc tgacagagag ctgcatcaac cgcggtgagt cctatctgac  14760
taccctctgg cttctgaact gcactcaaaa caatacttat tggtattctg gaaatgctta  14820
caaccatacc aatagcacct gtgaaaatca agtttcgaaa tatctctttt ccggcatgtg  14880
ccagctatgg aaaaattgga tcaatattac ttttaataac actatcaaag tcgagttgct  14940
gggaaatgaa acacgctgca tgctgcttcc taaacagtat actctgaacg ctacggtaga  15000
atggtacaac aaatctgaag gtaacgtacc aaaagaattt atggactatg ttatcctgac  15060
ccccttggca gtgcttacat gtggacttca ggaagcttat atagtcgaca agggtcgtag  15120
atacatgtat ctgttctccg tgtcctgcgc gggaatcaca ggtaccgtat ctattatact  15180
cgtctcccta tcgctgctca tcctcatctg ttactatcgc tgtggccggc ttctgatatg  15240
cccacgcggc tttgaactct tgccagaatt cactgaggaa gaggaggaaa aagaaaaatt  15300
gttaacgcac aaggacattg aagtccaggt gcctatccgc acgcggcgac tgctcgtccc  15360
ttggatccgg gagagcaaaa tgtgggtact accacccccg ctgcctccac gacctcccca  15420
cttaatagaa ttcccgccgt ctcctccgcc atcgcctgga cccatgcaca tggtggtctg  15480
catgccagca tgacggactt tggactctga gccccaagcg gtacggacta catattttcc  15540
ataaatctac actgaacttg agcacaaaaa tactgacaat ggactggata tacagacttt  15600
tatatgatcc ctgtacagat gtaaataaaa tgcttttatt taaaactggt cccaatgttc  15660
ttcgggaatc atgggatggg gacgaggtac gcggtaggga gcaaaaccgg gcacatgggg  15720
gggaacatcg tccagcagta gcaccagcgg attgggcagg ggctgttgcg gaggtcggtc  15780
gatgacgatg tcgatctcca tcggcagatc cggtaacatc tcttcgtctc cctcaccgac  15840
cagcactcgg cgctgttctg gatgtatatg attctggaaa agcctccgac gagctcgcgg  15900
cgcgtagaaa gccaagcggc gcaagggccg gcgagcccga aagtccatgc gcacagatgg  15960
catgagtcct tgagtgacgg tggtgagctg gggaacaggg ctacctccca tcgcgacggt  16020
gacagtggat ccatgagaga ggcgccgcac gctgcatggc taaataccgt gaatcccctg  16080
acgtcgtctt tcgtcccgaa cgcgtcatgt tgggggcgag gcgtaaaccg tcgaggttga  16140
aaaaccgcgt atctgcggtt cgtccggact acgttgtttt tcagaagcgg ccacatgacc  16200
tcgagatgtc gtcacccaag gtatttaacg gcacacagcc agacgcgttc gtcagcagcg  16260
acgccgacaa gacctcagca tggctcggag gctatggata ctgagcttag ccgtgacctt  16320
gacggtggct ttggcggcac cttctcagaa atcgaagcgc aggtaaacag gtaagaaata  16380
```

-continued

```
caaaaaataa cgtgattgtg aacgcggtta tcgtgttttt gcagcgtgac ggtggaacaa  16440
cccagtacca gcactaactc cgatggtaat accaccccca gcaagaacgt aactctcagt  16500
cagggggat ccaccaccga cggaaacgaa gattactccg gggaagagta tgacgttttg  16560
attacagacg gagatggcag cgaacatcag caaccacaag agaagaccga cgaacacaag  16620
ggagaacaca ccaaagaaaa tgaaaagacc cagtagcagc agatcccaag ggttaaagac  16680
catgttgact atcttgtttt ttattaaaaa gctgtaaggt tctgctctaa aaacaccccg  16740
cctccggtct tttttctttt gtattcggca cgcgaaacat ggtttcttcc catagcctgt  16800
ctaactagcc ttcccgtgag agtttatgaa catgtatctc accagaatgc tagtttgtag  16860
aggctatgcg ggatgctgcg gcggcgcgac cttccctctc cacccagccc cgtcaaaaca  16920
cacgcgactc gagcggttcg tatgaaaaat aaaaaacagc tttttattta caggaacggg  16980
gaaaaaaaag gcacacggtc cgtgggagac gcgggttcac gcgtcgtcaa aaagttggtg  17040
gtccactccg taaggacagg taggcttatt tagcttccgc atgctcctgg ttccgtaata  17100
aatgccgttt tcgtggcagc gtgtcatgcc gcgagtcaca aactccatca aactgtcggc  17160
cacgatgcaa acgtgctgat tgttggcagc aaagacgcgc atacagtcgt ccacgaagag  17220
gttgatcacg tcgtaggggc ttaccaacca gcctaaaggt tccacgtggt tactgccgac  17280
catgaccctc cagtcgttaa tctcgctcca gtcgtacagc cgaatcgtgg agacgcgaat  17340
gacgctgtaa tcacccatga ccatgagtcg gccgcgatac gtagcacgcc actgcgcgaa  17400
cgcgtggatg tgcatgcagc cggccagcgc tctaagcgag gcggtgtgcg gcagctcctc  17460
tgggacggtg atgaagttgc agcgtcgcaa accgatgttg agaaattcag tgatgctctc  17520
ggccacaaag gtcaacgagt cagagtagat gtggtcggtc cacaggtaca tggcgcccga  17580
ggcgcccagg tacagttcag acggcacgtt gtgatcgccc ttgtgtttaa gaaagttgta  17640
ggtgcagatg ctgccgacga aacgcagcgg ctcggggcag cagaggtagc tggccagacg  17700
ctgtgcatcc cgtccttcgt cgcgcaccaa gcgccagcga cgccggataa cgaggcagcg  17760
gtctttgggc cagaccaggg ccacgcgttg cccgggtttc cacggtcgcg acgtcttagg  17820
aggcctccag cggtcgagca gattgagaaa acagtccttg attaccgaca tcgcggtcgc  17880
gcgtcggtgg acaaaaagaa atcgggccga tccggaaaaa aaaaaaaacg acggcaaaac  17940
accgccgtgc tcgagcgaag ggtggcggag ggccagaaga tgcggccttg acggcgttgg  18000
cagcgaaaaa attggcacgc gagtcaaacg ggaagtagcg tcggtgtttt atgccccaag  18060
cagcgtcgtc gtcactcgtg gcgtcacagt caacggtgct gacgtccttt ggggcagtcg  18120
ggcacgcgat cgtagatgcc gttgtggccg ctgaaacgtc ggttttcaaa cagcaggtta  18180
agtcccagac acatgaacgt gttgagatta tctcccaccc ggatgtagcg gtcgtcgcgc  18240
acgtcgcagg cgtagacggc cccggtatag gcgacgacga tggggataag gtcgacgggc  18300
cagcgcaagt gaggaaaggg cgcgttctcg cccttgaggc tgacggttcc caggccgaga  18360
acgcgcattc cgaaagcggt tttgatgttg cgcagcaagt gaccgccttc cacgctgttt  18420
tcgaaacacc tgaggttgca tagacgcagt tccgttcccg gcgggtacgt caacggcatg  18480
aactgcccgt ggtggcggat gatgaatcgc gccatggtat ccaaaccgag gctccaggcg  18540
cgcaacagcg ggcgaaagta gcgcttaacc aacgacgagg tcaggtagcg catgcagtgc  18600
agggtctcga cggcgcgcag cccgacgcgc gcaaactcca tgaggttgcg ggccaggtag  18660
tagacggcgg tgtcctcgcg tacatagcaa aaaacatagc cctcgtccga gatgaggcac  18720
acagcggtct tcttctgctg atccggcgac aacacgccct cgttcacgaa gcgacccacg  18780
```

-continued

```
aaggccaggc gcgtctggca acacaggtag tgactccaag ccttcacgtc ctccggtttg  18840
aagtcctcgt ccgtctcgat ctcctgcagc actaggttcc agcccggcgg ccagaccacg  18900
ggcaacacct ggcctgcgtt gatgcgcacg taagcttcca gacagcccag gccgaactcg  18960
gccgtgagcg ccaggctagc cagatcgctc atgtgacgcg ccgagtcagt gggcgagccc  19020
gggggcccgt cgcacaccac gctccgtctt cttgtcctca ccgcggccag cgtggcgagg  19080
acactttccg cgcccgaggc tgtatcttcg gtttgcccgc cggagccggc cctcactata  19140
taacgtcccg cccgggtctc ctccatgtat gcaggtaagc aactgagccg aacgcacctc  19200
agcagacgag aggatgtcgt cgcggcgtcg cagctcgtca cgtcgctctg gcgaaccctc  19260
gacggtgatt tatatcccct cgagcaacga ggacacgccg gcggatgagg aggcggagga  19320
cagcgttttc acgagcacgc gggcgcgcag cgccacggaa gatctggatc gcatggaggc  19380
cggtttgtcg ccctacagcg tctcctcgga cgctccgtcg tccttcgagc tcgtgcgcga  19440
gaccggcggc accggcgccg ccaagaaacc gagcgaaaag aaacgatcgt cgtcgcgtcg  19500
gcaaccgcag atcgcagcgg gcgcgcctcg gggctcgccg gcgacaccca aggccggcaa  19560
gtcgcctaaa gtctcgcgac cgcctagtgt gccctcgctg cccgagaacg gcgccggcgg  19620
cggtggcgac gaatacagca gcagcggcgg tagcagcagt cgcaccacca gtaacagtag  19680
cagaagtacc agtcccgtgg cgccaggtga gccgtccgct gccgagggcg atgagttttc  19740
cttctgcgac agcgacatcg aagacttgna gcgcgaatgt taccgggtca gcgtggccga  19800
caatctgggc ttcgagccca gcgtggtcgc gccgcagcac gtcgagtatc tcaaattcgt  19860
gctgcaagac tttgacgtgc agcacctccg ccgcctcaac gaatgcatac ccatgccggc  19920
cttcgcgctc accagcctcg tcgacccgt cttaaacaac gtagcgcctg gcgagcgcga  19980
tctcacgcgt cggataatca cgcacgcggt gatcatcaac tattactacg tggcgcaaaa  20040
gaaagcgcgc cacatggtgg aggccatacg gaccaccgtg cggggcgaca cggtacgcca  20100
ggtagccgcg caggtcaaca accagagccg ttcggggcgt gcggccgcgc tagcgcttca  20160
ctttctcacg tcacgaaaag gagtgacgga cggccagtac gccacgtctc tgcggcggct  20220
ggacgaagag ctgcggcatc gcggcacgcc cgaatcgccg cggctcaccg aggtctacca  20280
gacgctacgc gattacaacg tgctcttcta taccgcccac tacacctcgc gcggcgcgct  20340
ctacctctat cgacaaaacc tgcagcggct caacgagaac caccggggca tgctccggct  20400
gctttcggtc gaagagatat gcgaagagca cacgctcaac gatctggcgt tcctagtagg  20460
cgtcgagctt atgatcacgc actttcaacg caccattcgc gtgctgcgct gctatctcca  20520
gcaccagctg cagagcatct cggagctgtg ttacctcatc tatgtacaac tgccgtcgct  20580
gcgcgaagac tacgcgcagc tcagtgacgt gctctactgg gccgtcagtc aaaactacga  20640
ctacgcgctc tacgcgagca cgccggcgtt gtttgacttt ttacgcgtcg tgcgtcagca  20700
ggacgccttc atttgcaccg actacgtgta ttgcgccctg cgcctgctgg cctgtcccga  20760
ccgacctatt atcggtgaca ccggcggcag cagtagctcc caacgcctcg taggtgagtt  20820
tatggtgcgc gatccgctgt tgcgcgaccc gcgcgccacc cacctgcgcc agaaactcat  20880
cacccgagac atatgcgtgg cgcggttgca agcgcagccc tcgagtcgac acattccggt  20940
cgaacacacg ggtgtctcct ccgtcaccct gctcaaaatc tttagccagg tcccccccga  21000
cgaacgcgaa gaagacacgt tacgcgagat ggctcttaaa gcgtttatgg aagcgaacgg  21060
taatcacccc gaacaaatct gccgatcccc accaccccg ctgccgccgc gcgactatcc  21120
```

-continued

```
tcaacgcgac gagcgggacc gtcaccgtcg cgaccgccgc gacagcgggg aatactgttg  21180
ctgatggtgg aacgaagcag cagggcggaa cggtttatga taaaaagtca caggaaagta  21240
tgtgttgttt tttaatgtac caagaataaa aatgcgtct acgaccaaag cggtgtgtgg  21300
acgctcgtcc tctctgtctt ctccgggttt tttttttcat gtttttttt cttcctattt  21360
tgttacggca acagcgctga tggcacgttg ccggcttcga acatcgcgtc ggtgatttct  21420
tgcttgcccg gcgtcacacg gtgacgtagc agcgcgcggc tcacgtagca ggctgactcg  21480
cggatgacct ggccgtcggc gtcgcgtcgc aggcccgagc gtttgccgtg acgcagtctg  21540
ccctgcgcag cgcgctccac gtcttcaaag tagctgtgta gcaggccgcg ctccagcagc  21600
tgcggcagcg agtcggcggc gcgcaccaca aagttctcac ggctgatctc gtagcacagc  21660
acgctgccgt cggccgccac gccggccacg ctgcggtccc aactgaaaag gttggcgagt  21720
ccgatggtgc cgatgacgcg caactgaccc tgggtcacca ccagcagctt ccagtattct  21780
acgtcgcgcg gggtgaggat ggtctcctcc acgtcgcaga caaacagcgt gtagccgcgc  21840
ggatagggca gatccaggtg gcgaccgcgc tggcggcgca taaaatcgtc taaattcaaa  21900
ccgccgtcgg gtgcgcgcct gctcgtcatc gccgcgcctc gtcggtcgat gaccccacgg  21960
tgcttataac gcgccgccac ggcttcatgt ggcgtgacct ccgacctcgt gaggccgaaa  22020
acggcgtaca tgaagacgct caaacttttg aatgtgggcc cggtagcgca ccgagggccc  22080
cggggcggcg acgacggcgg gtccgagttc cagcggggcc ttgcggcggc agcggttagc  22140
ctggttgctc agctcggcgt ccgagagcgc cgagctgaac tgcggcagcc gcgtgcgatc  22200
ctgcggcgcg tccccgtgtc gcagcgagtg ccagagcagg cgctggacgc gcgccgtctc  22260
gggcgtcggc ggcgcgcgac agccccggcg cagcgtgaaa acgtgcaggc acaacagctc  22320
gcgcttgatg cgcagcgaca cgctgcggta gtcgggaatc cgctgcacca gctcgagaaa  22380
gtcgcagaag gtctccacga acgtgtcctc ggtgaagcga atgcgcttca gatcgtggac  22440
gtgtttgcga aaccgcgaca gttctcgacg ttgcacgggg ttctgagcga gtcccttgcg  22500
cagcagcgca gcctcgcctt taaacagcct gatgagccgc tgcacgtccc cgctcaacat  22560
acgtatacac gccgtgtact cgtgacgtat actggcgcgc agcagccgaa tgatacgcag  22620
ggccagcacg gcgttggagg ccaggtacat ggcgtagccg cgacgcgggt tggcacaggc  22680
ccagcccgcg gggagcagaa agtagtcgtc gaccagcgtc tgcgaccagt cggcgaagcc  22740
caggtcacgt gatacgctgt cctggacgcg ggccacgtcg ccggccgtga ggtggcggat  22800
cgccggcagg tgaaacgcgc ccaggtgtcg gttgcgctcc agtctcagct cggcgtgctc  22860
caaacgggaa tggtgggacg ccaccgcgga gggcgacaaa gaggagtggt cattgccgcc  22920
gtggttaccg ttgtggttac cgccgttgtc gcgcccgtcg ccgcactcgc aaaaggccgc  22980
gtagaggtcc ttcaacgccg cttcggctcg cgccataaac gtggcgtgga aaaaaacggc  23040
ggcgcggtgc gtccggtact tgacgggcaa cccgcggcac agggccgccg gcaggcagcg  23100
gccgatgagt tcgcgctcct cgggctccag aaacaggcac agggtgccgt ccaggcgcag  23160
gtacagctcc tcggtcatcg agcatagctg ccgcaaataa tgggtgcgcg tcccaaaggt  23220
cttgtaatcg agcaacgtgc acaccacgta ttgccccgtg gccacggcca gagcgatgcg  23280
tttggcggcg cgactgatct ctggcaagta ctgcgcctcg tgcaccagac ggcggaaagc  23340
gccggcgttg agccagcgaa aatgctgcgg atcgggcggc aagggcacgc ctcgaagcgc  23400
ggcccagacg gcgaggtccg actcgagcgt cagaccgcgg atgtcgtact tgccgtgcgc  23460
cgtagcgcag gccgaatgga ccagacagct gcggcgaatg tacaccatgg cgtgcttggg  23520
```

-continued

```
atgtttgggc gccggcgttt tctttttctg accgccggcg gccgccagat cctcgggcgt  23580
gcgacacaac aggccggcgc gcacagcctc ctgtcgatta cgaatcggcg tcaggtaggc  23640
gcgcaggaac tggtgacaaa actcctcatc atcacgacag tcgtcgagat actcgtacgt  23700
ggtgagcgga tcacgaaata ggcgctcgtc accgtcgtca tggtcttctt tagcctgctc  23760
ctccggctgc tgggttggca gtggaggcgg cggctgatcc acggggttca tgactgagag  23820
gaagaagaag gtggcggcga agcgacgcgg agcgacggcg gtaaagccaa acaccggcta  23880
tatagctagt catcacagtc tcctccttca cgacgccccc gtgccgctca cgctatccag  23940
cacgctacgg cccgaaaaca cgtactcgct gacgtcgtac gcgggcgatg tatggctgct  24000
caccggtttc gcggcgacgg ttgcgctcga gtccaacggc gagaagcaaa aacgccgtgg  24060
gcaacgaaac cagaaggagc cctgacggat aaaaccgcgc agcgtctcgg ccaacttaac  24120
cagcatcgta ccgtacagca gtacgtgaat gccgccgtgc gcgtccataa atacggcttt  24180
gttcacgggc tccatccatc cgatgactac aaagtgggcc tgttctagca cgccgatcac  24240
aaaattgttg gcctcgtcgg cctcggccac gttccacgag ccgaaagtga aagtacaagc  24300
gggcgagccg cccaggcgga tcttgctacc ggcgtggagc tgacatacgc gcagcagatt  24360
ggtgcggtcg tgcagtatct gggagagttc gtacatgccc gcaaaggtgt gcttaaacca  24420
cgcgccctct acgatttcat ccacgtagtc gcgctcaaag aagctgtaca cggcaaagag  24480
gccgttctca aaaaactcgc cgaacgagag ccccagtacg tacaccttgt cctcgccggg  24540
caggtacgca aaggcgtgcc cgtgcccgga gacccagatc tcgggcgccg tgtttgcgtc  24600
cggcacgcat tcgtacacac tgacgaggcc gataaagtac aagcggccag cctggcgcag  24660
gcacgagaag cgccggtagg tcttgtgatc gcgcaccacc ccaaagtact gagtgtcgcc  24720
cagcatgatg ccgtgcagcg gcggccagca cagcgggagc caacgacccg ccgtggcgcg  24780
cacgtagcgc tgcaggtgaa ccccgctcgc acgctcgcgc ggcttcgggc gcttgtgggt  24840
ccaggcatca cgcagaccgc gccagatgct gctgaacttg ggctgcccgc gcagatagag  24900
cgacgagagc gagtcaaagt agcccacgac gagcctgtcg ggagacacaa gagcgcgaaa  24960
atcaaaccta gagcgacgac ggtgaaaaaa ccgaccagaa gcgcgtgtct caaacacgct  25020
actttcggtt ataaaaacac cgtcgcccta tttctgggcg tgtgtacact gatgactcac  25080
ctacgctttt tgaacggcag tctcagctcg ggattggcct cgtacagcga gctgcggtcc  25140
acggggccga tactctcgta gcgaaagtcg tcgatgagca gcgccagccc cacgcgcacg  25200
aagcccctga ggtcgcgcgc cagccgcacc aacttatcct gccccaccag cgccgcgtac  25260
acggtgcccg tgtcgccgca gagaatccgc acgcggtgaa agaaggtctt gtcctcggcg  25320
ccctcaattt cgcccagcgg catgacgggc tcgcgcgtgt acaacgaacg ttgaaagcgg  25380
cgcagcatcg aggccgagag ccccagatcg cgcgccgtgc gcagcactag ggaatgcttc  25440
tcgggccaga tgagggtcag ttgcgcctcg cggtgcgcct ctacgtaggc gcagcgagcg  25500
gcggtgtcct cgcaggccag caactcgcgg aaagccagca acgaacgtag gtagcgaccg  25560
cgagcggagg cgcgcgagcg gcggcacagc tcggcccgat ggtcgggatg caccaagggc  25620
acgttgggtt gcagacgcgc gcagatggat tcgtgcaccg ggtcgcagcg gatcatgccc  25680
ttggcaaaaa atccggccag atccgaggcc aactcgtaca ggcagtcctc ttgcgcgtcg  25740
taggcgaaca cggcgccgta cgcgtccacg aacacctggt accggcaggt ggcgtgcgag  25800
accgtgccaa tgagatgcag agctcggaat tcgccgaaaa agtcgttctg gcagtgctcc  25860
```

-continued

```
agatcgatct cggtcagcga gtgcggcgaa tgctcgcccc cgaccacgta gatgcactgc  25920
gagggccagc ccagcgatac gcacgagccc tcgaagcgcc gcaaataacg ccgcaggccc  25980
tcatagtcgc gtcgcacgca cagatcggcc aagtcgcgcg tgcaaaagac ctcgggtacc  26040
aagcagcgtt tgcgacgcgg ccgacgcgcg tgcccgggca gaggaggaag gcgcgacggc  26100
ggcgacgacg aggaggaaga cgccgtggcc gccgagcagc ccttgcgacg gccggacatg  26160
ccggcagtcc gcgacgatcc acaggagaca aaaaagcaga agcagcagta gtctcggcga  26220
cccgctccac cccgtcctcc acacgctcag ccgcgactga gcgccggggc gcgccgctac  26280
ttgggttttt atagccatct gccccccgtc tcgggcaccc gggagcgatc tacggagacc  26340
tgacagcagt tgggcaacac aagacaggga aatacaaaga cacttttaat aaaaaacgag  26400
actactttgt gtgtgtgctc cgtaaactgt ttattctccc cctccgtctc gctctggatg  26460
ggctccgggt ccgtcaacac gcgacccgcg cggcaaaagg cacgctgttg acggcgcgag  26520
agcccgtcgt gatagtccat catgccccgg agatcgtgca caaagcagct gtcgccgcgc  26580
agaaaccgac gcagcgtctc cacgtgctgc agctgtcggc gcgtatcagg agccgtcatc  26640
gccgatgtcg tcatctccct gacaggcgcg tagatggctc cgcgagatca tgcgcgtttt  26700
caaccgccgt gacacatcag gtccatcttg agctggcgcc gggcctcgcg caggtctcgc  26760
acgcgttgtg agcgggaggc gagttcggct tcttgctcga actcctgctg ctcactgtcc  26820
gagagggtgc gataaaaggc ggcaaagtcc tccaagtcgg ctacatgcgc cctgggtctg  26880
acgctccaaa gcgtacgcag tctgatgaag cggacccatc gagcgtcacg gcacgccgtc  26940
ttgaacgcgg ggcccgggaa gaggttcttc tccccggcgc gctcgggccg gcgaggccga  27000
cgcggtttat atacaccgtc tcggacggcg ggacgccgag cccgcgccgc ggccgctcat  27060
ccggagacgg cggaaaccgc ggcgccggag gaaacgggga ccggcaacga cggcggcggc  27120
gaccagatta tgggggacaa gcccacgctt gtgaccctgt tgaccgtcgc cgtgtcgtcg  27180
ccgccaccgt cgtcgccgct gccgctcgtc agcttcacgg agctgctgtt accgccgccg  27240
tccgtcgccg ccgctgcggt ggcggcaaca gcgacgagcg aggtgggcga gaaaaccgcg  27300
gagcaagagg tagcggctgc gggtccggag accgggaatg agagaagaga aaacagggag  27360
gacgaaggag gggagacgag gacgacgggc accaccgcgg tcaaaaggtc gcacgacggt  27420
atccctcgcc aactggcaga gcgcctgcgg ctgtgccgcc acatggaccc cgagcaggac  27480
tatcgtctgc cggcgcagga cgtggtgacc tcgtggatcg aagcgctacg cgacgcggac  27540
cgcgacaact acggtcgctg cgtgcgccac gccaagattc accgttcggc ctcgcacctg  27600
acggcctacg agtcgtactt ggtgtccatc accgagcagt acaacacggc ctcgaacgtg  27660
acggagaaag cttcgtacgt gcagggctgc atctttctct cgtttcccgt catttacaac  27720
aacacgcagg gctgcggcta caagtacgac tggtccaacg tggtgacgcc caaggcggcg  27780
tacgccgagc tcttctttct gctctgctcc accagcgaga gttccgtggt gctgcaaccg  27840
ctcatcacca agggcgggct ctgctcgtcc atggcggttt acgacgagga aaccatgcgg  27900
cagtcgcagg cggtgcagat cggttttctg cacacacaac tggtcatggt gcccttcgtg  27960
ccgcacgcct gcccgcatta cgccgtgcct ttcacgacgc cgggaaagcc gggctgcggc  28020
ggtgctccga gcggcgttgc ggggttggag gaggcggcgc cctttggacg ggtcagcgtc  28080
acgcggcatg gcgcgacgct gctgtgtcgc gtggaccatc tgacctggat cagtaagcgc  28140
gtaaccacgt acggacacaa aaaaattacg cgctacctcg cgcagttccg cggcacgatg  28200
gacgacgacg aggcggcgct acccggcgag gacgaggcgt ggatcgcgtc caaaaacgtg  28260
```

-continued

```
cagtacgaat tcatgggtct cattttcacc gtcaacgtgg attcactatg cgtggacgcg  28320
gaacagcgcc aactgctggg caccgtggcc acctccttct gtcaccgcgt ctcggacaag  28380
atcacggcgc gcaacatgcc gcgcgccttt tccttctact tgctaacgag cgcgcagcgc  28440
gggtacgacc tgcgatttag ccgcaacccg tcactctttt ttagcggcga cgcgctcaac  28500
tgtccgcttc tcaacgagcc caacgtgttt tcgctcacgg tgcacgcgcc ttacgatatc  28560
cacttcgggg tgcaaccgcg gcagacggtg gagttggact tgcgctacgt gcagatcaca  28620
gaccggtgtt tcttggtggc caacttgcca cacgaggacg ccttttacac agggcttagc  28680
gtgtggcgcg gcggcgagcc gctcaaagtc acgctgtgga cgcgcacgcg ttccatcgtg  28740
atcccgcagg gcactcccat cgccacgttg tatcaaatca ccgagggcga cggtaacgtg  28800
tactcgtaca atcaccacac ggtgtttcgg cagatgcacg ccgccggagc aaccacgttc  28860
tttctgggcg acatgcaatt gcccgcggac aactttctca cgtctcccca tccctgaccc  28920
tccgtccgtc ctcctttccc gacacgtcac tatccgatgg tttcattaaa aagtacgtct  28980
gcgtgtgtgt ttattaacta ttcctccgtg ttcttaatct tctcgatctt ttggaggatg  29040
ttctgcacgg cgtccgacgg cgttttggcg ccccccatgc cggcagaacc cggttgcggc  29100
cccgtaccgc tcttctgggg cgacgatagg tcgaaagcca ccgttttcat gcccgtcgtg  29160
ctcttgacgg gggaacctac ggcggcggtc cccgtcgagc ggcgtgattg caaagccgcg  29220
ctcgcccccg gtttcaggat ggagggggag gccacaggcg gcgcattcga tacgctgctt  29280
ttggccgtag acgacggtgg gtaaacggtg gttaccgcgg gatacgtcgg cgtggtcgag  29340
gcggcccggc tggtgccgga caggcgaccc ggcgcgctac cgctcacggg gaccgagggc  29400
ggtcgaccta ccaccgcctt gccgcccaaa gtaggtttca aagaaggaac accgacgcgg  29460
ctgccccgac ctttcaccgg agacggaggg gcactcttgg ccggggacgg agaggctgac  29520
gaaagcatgg acagcggcga cgtgacgggg gacacgacat catcctccgt gggcgacaaa  29580
acggacgccg aggctgacgg ctgtcgagcc gaagcggaag aggttctcgc gccagaagtc  29640
acgttccttg atgacgttgt tttagacgaa gccggttgag gttgcaacag cgtggcgggt  29700
accgtcgacg gcgtgcccga tacctgtttc tctacccttc cctgaaccgg tgtcgacgtc  29760
accgtctgcg ctcgggcgga cgcgtgcggc gtcgcgactc gcttgcccag caccggtttc  29820
tggctcgtgg atgtcgtcgt cattggagac gataacttag ctttacgtat tctggacggc  29880
gtcgactgct cgggcgtctg actgggaggc gaaatgacgt cgttgtaatc ggacgacggt  29940
gttgtgtgtc ccaggctgac gacggagccg gtgtccgagg agtcgtcgtc ttcctcctcg  30000
ctgtcttcga ccggtgactc tgcagtttgg tcccttaaag cccaaacctc atcagcggcg  30060
ttctgagacg ctgtttgtgt caccgcggcg cgtggagtcg acggcctccg aggggtggtg  30120
gacacgttgt tttgagaagt cgtggaagtc gtaggcatcc tgaagggatt gtaagccagg  30180
tgaggattct tgagggccca cgcgcgttcg cgcggccagt tggcggggtt catatccccg  30240
ggcaacggcg ccgtcggagc ccagggcgag ttaccgttga ccggggtttg ggtacccgcg  30300
aaggtaggtg tcggggccgg agcgggggcc gtggaaggat tgacaggcgt cggcgtgagg  30360
atggcagcgc cggcgccagc agggacgtta actccggcgc cgaacgtcaa cgtcggttgc  30420
tcgaacttgt acgcggtggt gacgggcggt ttggcgctcg tctcggtatc cgtgatgtcc  30480
accggcgtgt cggtgaaacg cggatcttga cggttggggg gatagccatc cgagctgtcg  30540
gaatcctcgt cgcccgagaa aagatcccct cttgtctccg tgagcggcct cacgtcccac  30600
```

-continued

```
gcgctgtccc gacggaccct tcccgggctg gccttggtta cctgcgggga gacgagactg  30660
aaagccgcgt gacgctgttg ttgctgcggg atgttcaagg gaccgctggt cggtttctga  30720
ctgcccgagg ataacatgcc gctgaaaatg ctggaaacac cgttgccact agcggcgccc  30780
ttgccgctag ttcccggttt cttgatgggc gtaaagatgt ttttctcgtc atcatcatcg  30840
tcgtcgtcct catcggcact ggagccaaag agcctccggg aggcgcccgg tttacgtgtc  30900
gggggcggcg gttgctgctg acgttgctgc aggttctgct gcctctcctc ccaagccttc  30960
agctgctgtt tctcacgctg caccacctcg tcgtccaccc gtttctgccg ctcgcgacgc  31020
ttttcctctt cgtcgtaata gccgacggcc gccgaacggg cggcgtgggc gtcggcggcc  31080
ggtgccagag aaccatgggc ctcgaagcgg aacggtttgt gtcccttcca gggactggcg  31140
atccagctcc agccgtccag cggctgcgtg ggacatgtt tcttgggtac cgacgagaag  31200
gctgaaccgc cgccgagcga gaggagattg gcgtcatcgt caaactccaa cgacggcggg  31260
cgcgcgccca aaaaggtgtg cgccgactgc gggaagctgt ccacgtagat gtcaaagtcc  31320
tcgatgagca gctccagcag cgtgtcggcc gagtcaccgt tttccacggc gtgtttgagg  31380
atattgcgac agtagttgga atcaaaggaa aggcacatgc gcagctcctt gaccagcagc  31440
ttgcagcgct cctgaatgcg cgccagacat ttgcgctcca gctcctccca agacctgcgc  31500
acgttcatga tgagacggcc cgtgtacacg agcttgttga cggcgttgac cagcgccgtg  31560
ttggcgtgcc ggtccaggtt aaggtcgagc ggtttcacgc agaacatgtt acggcgcaca  31620
ccctccaggt tttcttcaat gcgctgcacc tccgtatcct tgaggtgcac aaaagcgatg  31680
ggttccgtct ggccgatggc tgtgaccagc gtctcgcgca ccgacatctt ggccagaatg  31740
accgcgctta cgagcgcgcg ctccacaatc tcagcatcgt ggcgtacgtc cgtatcgaat  31800
tcggtacggt ctagcacagc caggtggtca cgcgccttac cacgatcacc gaacgggtaa  31860
gtgtagccgc gacgcgccac ggccgcgcaa cgcacctcga actcctcgag aaccgaggag  31920
aggtcggggt tgtggaaacg cagctcgcgg tagtatccca accaaagcat gagctcgttg  31980
aacagcaccg tacgccggtg caggcgtttt tcgccacatt ttttcaggat cttggggtgt  32040
gcctcgagat ccacgtcggg cttttgcgtg agatggcgca gaaagttgac cagggccacc  32100
acatcgcgcc gctgtagacc gataaactgc aaactcatgc tggcttttct ccagaacccg  32160
gaagcgtcgt cgccccggac tgcgcccgcg gtctgctatt cgtccacgat ggacaccatc  32220
atccacaaca ccacggtgag cgccccacct agagggaggg ggggtagttt aatagcggag  32280
gcggatacgc ggttttcact ctggcaccgc tgacttgttt cttttgtttt ttgctccgtg  32340
tgcttgttcc gcctagaacc gcagtaccag tactccgcat gtcaacagta cctgtaacat  32400
gacggagacg ctatccgcca tccgcactac agaagccgtg atcaacacgt tcatcatttt  32460
cgtgggcggc ccgctcaatg ccatagtgtt ggtcacgcag ctgctcacga accgtgtatt  32520
gggctattcg acacccacca tctacatgac caacctctat tccactaatt ttctcacgct  32580
caccgtgctg cccttcatcg tgttgagcaa ccagtggcta ctacccgcta gcgtgacttc  32640
gtgcaaattc ttgtcggtaa tttattactc aagctgcaca gtgggctttg ccaccgtagc  32700
cctgatcgcc gccgaccgat accgtgttct tcataagcgt acctacgcgc ggcagtcgta  32760
tcgctctacc tatataattt tgctattgac ttggtttgcc gggctgatct tttccatgcc  32820
cgcggccgtt tacactacag tagtgataca taatggtaca gatgagaata ccaatgggca  32880
cgctacctgc gtactgtact tcatagccga cgaggtgtac acggtactac tctcgtggaa  32940
agtgctgctg acgctagtgt ggggcgccgc gcccgttatc atgatgacgt ggttctacgc  33000
```

-continued

```
cttcttctat tcaaccgtac agcgcgcatc tcagaaacaa aggagtcgca ctttaacctt  33060
cgtcagcgtg ttactcatct ccttcgtggc gctacagacg ccttacgtgt ccatcatgat  33120
tttcaacagt tacgccacgg ccgcatggcc catggactgc gaacacctga cactgcgacg  33180
caccattggc acgctgtcac gtctggtacc ccacctacac tgcctcatca atcccattct  33240
gtacgcgctg ctgggtcatg actttttgca gcgcatgcgg cagtgtttcc gcggccagtt  33300
gctggaccgc cgcgctttcc tgagatcgca gcagaatcag cgagctacag cggagacaaa  33360
tctagcggct ggcaacaatt cacaatcagt ggctacgtca ttagacacca atagcaaaaa  33420
ctgcaatcag cacgccaaac gaagcgtgtc tttcaatttt cccagcggta cgtggaaagg  33480
cggtcagaaa accgcgtcca acgacacatc cacaaaaatc ccccatcgac tctcacaatc  33540
gcatcataac ctcagcgggg tatgagcttt cctgttactt tattcagaaa gcaccagaac  33600
ccgtcgccat ttcccctcat atacggtaca cgtccccctg atctgtcatc acggtacaca  33660
gatttcgccc gactgcggac accgacggcc aatcgcgtgg cgtaggagtg gcgccccggc  33720
ttcattataa cgccacgtcg gagcccctgc gcgccacaac gccgtccggc gcaacttctg  33780
tctcggcacg gtacgataaa aacgacgtcc cccgtcgacg ttgttttctc cgagcggtga  33840
tcgttcccgt ccctctcctc cctccgcggc ccccacggcg gcggcccgct cgcacggacc  33900
tatactatta ccgccccacc gccgtcgtcg tcatgaactt catcatcacc acccgagact  33960
tctccaacga cgattcagtc ctgcgagccg ccgagatgcg tgacaacgtg gcaggctcga  34020
tttccaaagc gtacaagggt acggtacgcg ccgaaggcaa gaagaagctg ctgctgaagc  34080
acttgcccgt gccgcccggc ggctgctcgc gccgcaacag caacctcttc gttttctgca  34140
ccgagcgcga ctaccgcaag ttccaccagg gcatcgcaca gctcaagcgc gcgccggccg  34200
aactggaccc ccacgagatc cagcaagtca cggccagtat ccgctgccgc ctgcagccca  34260
gtctccgcga gccgcccacg ccggccgacg agctgcagac ggctgtgtcg cgcgtgtgcg  34320
cgctcttcaa ccagttggtt ttcacggccc agctgcgcca ctactgcgag caccaggaca  34380
aggtggtgag ctacgcgcgc gacgagctga ctaaacgctg cggcgaaaaa tcggcgctgg  34440
gcgtggaggt gcatcaactg gtagccctgc tgccacacga gcgccaccgc gaactgtgcc  34500
acgtcctcat cggcttgttg caccagacgc cgcacatgtg ggcgcgctcc atccgtctca  34560
tcggacacct gcgccactac ctgcagaaca gcttcctaca cctgttgatg aactcaggtt  34620
tggatatcgc gcaagtcttc gacggctgtt accacagcga ggcctaccgc atgctcttcc  34680
agatcggtca tacggactcg gtgtcggcgg ccctggaact ttcacacagc gcggcggccg  34740
ggccgcccga ggccgatgag aacaacgacg aaggagagga ggacgacgac gagctccgtc  34800
acagcgaccc ggcgccgctt cacgagtcca agaagccccg caacgcccgt cgtccccgca  34860
cacgcgtgcc gcctcacgag caaaagcccg aagaaaacga ggaggaagaa gaggagctgt  34920
ttccctcctg caaggcaacc gcagcattcc tgcgggcaga accctccgtc tccaacgacg  34980
acggcaacgg cggcgaacgc tgcgacacgc tagcgaccgc cctgcggcat tgcgccgacg  35040
aagaagacgg acctctagcc agccagaccg ctgtgcgggt cgccgcgacc ccctcacctt  35100
cagtcacccc agcccttacc cccgtcacgt cccccataac cccgttgtgt atttaacgtc  35160
actggagaac aataaagcgt tgatttctca agttccgctc tggttttggt ttcgttttca  35220
aagggagccc catcatggcc caaggatcgc gagccccatc gggcccgcca ctgcccgttc  35280
tccccgtgga cgactggctc aactttcggg ttgacctgtt tggggacgag caccggcgcc  35340
```

-continued

```
tgctgctcga aatgttgacc cagggctgct ccaactttgt ggggctgctc aactttggcg  35400
tgcccagccc cgtatacgcg ctggaggccc tggtggactt ccaggtgcgc aacgctttta  35460
tgaaggtaaa gcccgtggcc caggagatta tccgtatctg catcctcgct aaccactacc  35520
gcaacagccg cgatgtgttg cgggacctgc gcacgcagct cgacgtgctg tactcggagc  35580
cgcttaagac gcggctgctt agagggctca tccgactctg ccgcgctgcg caaaccggcg  35640
tcaagcccga ggacatcagc gtgcacctgg gcgccgacga tgtgacattc ggcgtgctaa  35700
aacgagcgct ggtccggttg caccgggtac gcgacgcgct ggggctgcgc gcgtctcccg  35760
aggccgaggc acgctatccg cgcctcacca cctataacct gctgttccac ccaccgccct  35820
tcaccacggt cgaggcggtg gatctgtgcg ccgagaacct gtccgacgta acacaacgtc  35880
gtaaccgacc gttgcgctgc ctcacctcca tcaaacgccc gggctcacgc accctggagg  35940
acgcgctaaa cgacatgtat ctgttgttga cgctgcgaca cttacagctg cgacacgcgc  36000
tggagctaca aatgatgcag gactgggtgg tggaacgctg caaccgtctt tgcgacgcgc  36060
tttactttttg ttacacgcaa gcccccgaaa cgcggcagac tttcgtcacg ctggtgcgtg  36120
ggctggaact tgcgcggcaa cacagcagtc cggccttcca gccgatgctg tacaatctgt  36180
tgcaactact gacgcagctg cacgaggcca acgtgtacct ctgcccggga tatttacatt  36240
tcagcgcgta caagctgcta aaaaagatcc aatcggtctc ggacgcccgc gagcgcggcg  36300
agttcgggga cgaggacgaa gagcaggaga acgacggcga gccgcgtgag gcccagctcg  36360
atctcgaagc cgatcccaca gcgcgcgagg gcgagctctt tttcttctcc aagaacctgt  36420
acggcaacgg cgaggttttc cgcgtgcccg agcaacccag ccgctacctg cgtcgacgta  36480
tgttcgtgga acggcctgaa accctgcaga tcttctataa cttccacgaa ggcaagatca  36540
ccaccgagac gtatcacctc cagcgcatct atagcatgat gatcgagggc gcctctcggc  36600
agacgggcct gacacccaag cgcttcatgg aactcattga cagagcacct ctgggccagg  36660
agtcggaacc cgagatcaca gaacatcgcg atttatttgc cgatgttttt cgccgtcctg  36720
tgaccgacgc agcttcttcg tcgtccgcgt cttcgtcgtc gtcctcagca tctccgaatt  36780
ctgtttcgct gccgtccgcc aggtcgtcat ccacacgaac caccacgccc gcgtccacgt  36840
acacctcggc cgggacttct accacgggcc tcttgctctc ctcttcttcc ttgtcggggt  36900
cgcacggcat tagctccgcg gacctggagc agccgccccg gcaacgacgc cgcatggtca  36960
gcgtaaccct cttttcgccc tactcggtag cctacagcca ccaccgacgt caccgaagac  37020
gacgcagccc gccacccgca ccccgagggc cggcccacac acgtttccag ggacccgaca  37080
gcatgccgag cactagctac ggcagcgacg tcgaagaccc gcgggacgat ttggccgaaa  37140
atctacggca tctctaaacg cggttttcct ctttttatac gtgtctgtct caggacgaga  37200
cgttgatatc aataaaaata ccgtcaacgt ggttttctaa cagtgtggtt ttctttattg  37260
accagcggag tacacagttt acgagtaaaa aagacaggga aaggttatat aaaatgctgt  37320
gttatataca aaaacatgca cataaacaaa cgggaccacc gtgctcgtca tcctctcctc  37380
aatcagttgt tcatgtaggc gtgtggcggg gtgaggggcg gcatgccgtt ggcggcgccg  37440
ggaataatgt gtcgtcgacc ggcgtcgcac accttgaaac gccgtcggcg cacgcagcgg  37500
tcgcaggacg ggatatccca gaggaagccc atataggtct cggggtcctc gtcgtgaaag  37560
cggtaagaga gttcaaggtg gtgcaatgag cccgtccgag ctcgcagctt ctggcgaaca  37620
ccctccacgt catcggtgca cagcgacagt gctgggctgt cacacagggc ctgaagctcc  37680
tgcggccaca ggtgcgtggc caggggcgag tccgtcgtca ccagtttgac gcagtgcatc  37740
```

-continued

```
aggttctcgg tgatggcgtc gtacaggcga ctctcagcct cctcgtgcgt catcacgttc  37800
cgaggcagcg acagctcgtc gtcgtcatcc tcgtcaaaca tgatcatggg gtcaggggtt  37860
tttttgggat gttgacaggt gggtgtcttt tccagacgca cgatggcctc acgccggctg  37920
ctgaaacggt ggtttcggtg tcccttcttt cccatgacgc aggtgaacat aaccacgtcc  37980
tcggccagac ggtagacggc gtccatggcg gggtcgtagc cgtagacgac gccgaaagtg  38040
tccaccaaga cgtactggcg tacgagaaac tctttgcgtt ctggcacctc gtggcccagc  38100
gcgcccaaca gctggtgata acaggtgatg cgcggcacgg tacggatcat gagctccatg  38160
gtctggatgc tgccgcccgc gcggacaacg ctgaaggatg tttccttgaa cttcataacc  38220
tctgtgttgt gggtccagaa ggcgaaatgg gtgtcgggac actcatcgaa agggtcgtcg  38280
atgctgtagg aagcgtagcc ccgcttggtc acctcggccg acaggctctc cacgtcaccg  38340
cggtagagca tgacggcgtt ccagtagtcg tcgtactgca ccatgggccg ctggtagtcg  38400
cgcatagtgt ggaagtggtc gcagtgacga aagccatgcc gcagaaagtc cttcatggtg  38460
gccgccagct cgtagacgca gtcacgcaga tcatcgtagc agtagatgcc gccgcgctgc  38520
ccgatgagca cgatgagttg gtagcgcata aagcccggac cctcgacgaa gccaaagggg  38580
tgcaggtatt cctgacagca gacgtaagca cctggtggag aaataagaaa aatccacaca  38640
cgttgaaaac acctggaaag aacgtgcccg agcgaacgtc ctctttccag gtgtcttcaa  38700
cgacgtgggg cttaccttgc gaacagacgg tgcccatctt gcccacgaag ggccccaggg  38760
cgctgcgcga acggagctgg atgaagcagc gttcgggcca ggccacgtgc agccgggtgc  38820
cgcattcctg ctccagaaag tcgttgagac cgttaaagtc cccggctcgg atggcgatgc  38880
agccgtaggc catcaacgtg tcccgtaggt cgtccatgac ggactcctct accttcgctc  38940
gccgacgctg cgcttctcca gccaccgctg cggtcgacag actcctccgt ccgccttcgg  39000
agaactacgg cgcggcggca cggcctttat agacactatc agcgttgacg tcagacgatc  39060
cgatgaacgt cgttttttgt gctggaactt ccctcgtccc gacaaatgta gcggaaatct  39120
tcaagcaaat cgcgacgaag tccgatgagg aggatgcaaa agaggctgag caacgcgatg  39180
ctgcccgccg ccacagtaca tatgctcaac aacgcccagt gtcccaacgc gcgacttttg  39240
gctcggagga gagccgaacg gcggtttttc cacatgatgg ataacgtagt ccaatacctc  39300
catccttcgc attccgatgt ccacatggga agcgatgtca tgttagttcc cgtaaacgtt  39360
gtgttttttt tattgttttt cgtaagctta acgctcctct tgagaaatcg cggacacatg  39420
tcttgtagaa aaatataatc actttccgca tataccgtta agattgacat cacagtgatg  39480
gtgttgtttt ctgaagaagt cacgttatcg gtgacgttgg tttcctccca atttacggat  39540
gactcaaacg gactcgtgcg cgccagtgct cgcaatacgt aactgcggcc ggtaaggtta  39600
agcgtcagct gtcccatggt aatattagtg tcatttgtaa aacacgcaac ctccccgtag  39660
acctcggtga cgttgatatc gcggctctcg ttcaggatgc gcaggggaaa ccagccttcc  39720
aggtggtact gaaaaccaaa cgtgagcatg acgctgtgcc actgccgacg tgattgccga  39780
aacgttacgt ttaaaggcag ttttgattcg gctccggcgc aggggccgtt gtagatttgc  39840
gtatgattgc acgtgcagtt taaccggcag ttcatactcg tggcgttgga agtgacgtta  39900
atgtccgtac cgtggtacgt acatcggaca gaaacaccgt atcccgtgct ccaaaacagc  39960
gtcaacaaca gccacacaga cacctacgtg gggacgacac gggacttttt attgacggag  40020
actcatgttt acaccctccc ctttcccata ggtaaaaacc cacgtttata acacacgttg  40080
```

-continued

```
tttttacctg aaacccgcgc ggcccgtgga cgcgacaaaa aaccgcggca ctagaaagaa  40140
aatgaaacaa gtatgtttat taagcagcat gtggggctaa tagggggggat aactgaggta  40200
tagcaactat taaaaaatac tacaaaaaaa aaaagctgaa catggtcatc tagcagcaaa  40260
gttctccttc tagaccacga ccaccatctg taccacgtcg ccctccccgg ccgtgtacat  40320
cacatccttc accacgaccg gcggcaacgg cggcgacgag gacaactcgc tctcgacgga  40380
ggccgggacg acagaggacg ggggggtggt ggcggcggag gacggagggg tggtgacggc  40440
agcggggtct tcttccgaca cgggcgacgg cagactcggc ggcgcggaca gcacccgttg  40500
cgccggagcg tgagaaggct gaaccccggt ggcctggatg tgggccaacg aattggctcg  40560
cagcgaatcg cgatccacga aggtcatagg aatcttccct tcgcggatcc gccgctcaga  40620
ttccaggatg gcgcgcacgt agctgttcac cgatttggca aaagtgcgcg gcccctccgt  40680
attcttgtcg cgacgcgctt ccaacacctg cttttcgtag tccagctggt ggaagaccat  40740
caccaggtcg tccatggtgt gcgcgtgctg acggacgtgg gagcgcacct ccaccgggaa  40800
cagagcgttc caatactcca gcactatggc accgtgccag aactgcgcca tgctgggagc  40860
caggaaaaac aggataccgg agtcgtaggc gaacacgtcc cacttgggcg tcatgaacaa  40920
caccagctga cgcgtgggcc gcctcgaagc ttcctcccag gcctcgatga ccccgaacat  40980
gatgagctcc tggtccaacg gggggcagtg tcgctccagc caactgatct tgctcaggtt  41040
catctgcaga aactcgtagg aggggtcgca gatgcacacg tagagacccg agtcgtgccg  41100
cagcctggct ccgcgcttca tcagtttcct caccgcgtag cgaagcgcca ccttgcccaa  41160
cgccgacgcc tggatcagtc cccccacgtc catctgcgtc tgtcgccact cggcctcgtc  41220
cagcaggctc atgatagcgg cggtgctatg cgtggtcgta gtcatccttt ctatccttct  41280
ctatgaatag cagcaatagc ggtaaagtcc cttcttatac tatcccggag tctgtggttt  41340
ttttgtttac ccctgcttac tggtgagact gctgggggcc gttgtgctgc agcagccgag  41400
cttgtcgccg ccgttgccac aggaaccggt gcctccgcag ggcctttttg agggcctcgc  41460
aggcttctcg cgcaagtcct gagaggccct cggcgtcgat ggggttcacc tcgggcgtcc  41520
gagcctcgtt ttcttcttct tcatcctccc tttcctcctc cgtgtcctcc cgctctgtgt  41580
cctccgttac gctctcctcc ccggcctcgg ccaagagcgc ggccaccaag tccacggacc  41640
gctcggtctc cgagttctca ccgtcaatga cgccatgttg gcggcgtaac cggtgccgag  41700
aacgccgggt gagcgcacat gctttttttct ttcttaacca aggcgggaga ggatcttcaa  41760
ggcgttttcg ctggatccag cggtagctaa agtaccaaaa ggccagcagg cccacgctac  41820
ctaacagatt cacgtagact ggagacataa ttaaagaaag aagtgaaacc cgcgtgtggg  41880
tctcacgtcg tcttgaaaca ccgtcttata tacatgaaga tgccggacat gacgcgccca  41940
agacacgtgg ggttttcccc ttaggcgacc cgatttctta agatgttttt catcttcgca  42000
cgcgatgtac tacatcaaag ggtcggctga ccgaccgcat tgacgcacag tttccgagta  42060
cgcgcgtctc ggagcacctg acggtgagcc acccagctca cgcggatagg gaacaacact  42120
gacgtgaggg gcaattcacg tcactgacgg ctgacgggaa taagacgggt gagggatttc  42180
cacctttttc ttaagtgtga ctgtccttac ggtaaatcgc acctgtgacc tcttaacccc  42240
tcctccctgg tacccgataa cagtgaaaaa cacacaccac acgtcacgac accgatcgat  42300
tttctttatt cttagtgtga tgataggtaa gggcactcgt gaggatgtgc agttatcatt  42360
atcaagcctt cttcaaggcg tagtgatgat cgttgggcag aacccccagg ctcctagcga  42420
tctgggaata gaaggaggag aacgagccca gggccagaat gcccacagtg tacatggccc  42480
```

-continued

```
aggtctccag accgaacgtg gcgggtcgca gcttcagatg gtaggccacc cgctccgaga  42540
gttgtgaatg ctcgttcagg caacaggact gcagatgggt gagcccaaaa gcgctttcgt  42600
ttacgccgcg cacgtgcacc gtctgggccg gacaatcctg gtgttgcgcg cgaaagtggt  42660
ccaggcagga gactccgtct gcgcggcgat gtgtgttgtt acccacttca atcaacagcg  42720
tgttaacggc aagatgacgc gagaacgcga cgacggtgtt gctggaggtc tggcggcagc  42780
agtacaaagg cgcccgtcat gaagacgtag gcaggggaat tcccatattt ttatggcttc  42840
ttttaaaagt ctgtgtccga ctccattcgg cgcttttccc aaaccgtggt ctcctcgtcg  42900
tccgactcgg tacccaggag atggtaagtc ttttgccgca cgtagaaagc tttcaacgtg  42960
gagcaaaaga tgagaataaa gaccccgaaa acgaaacaaa ccacgccgat catgccgatg  43020
cagacgttca tgtcgacgta gccggcggtg ctgttggcgg tgcggcaaaa gagtgtcatg  43080
tcgtacgtgc acaaaaaaca ccacacacca caggccaggt cgtagcgtag ttattattcc  43140
gtagcagcaa tgatggtaca gtcaagcaca tgatctattt cccgttatcc cgatgttgac  43200
accgtccccg ttgtattgga attgtcccgg ttaatcacca cggtgaacac cacggccaag  43260
aaaatgatcc ctaatatagc gaccactaag agagcaaaag tccatttcca gccgttgtca  43320
aagtacgccc ccgtggtggg atgcatggtg gcgggcattt ccatcatatc catgtcgaac  43380
gtgtgtcgcg gcgacggcga actaaccagg cagtacgggg gtcgataggg cggtgggctg  43440
cagtcaggtg gtggcggcgg tggcgtggaa accgtcgtcg ggcacagacc catggcctgc  43500
tcgtaggtgg ggggcgcgtc gtcgtgatcc cggtcgcgga gcatcggcgt gggctccatg  43560
tcggtggcag tgacggcgac ggtggtaact gtggtggaga cggtaccgac ggcgtccgcg  43620
gctcaccttc gagcaaagag ccccttcttt ttgcgcaaac gacggcaaaa cagttctctg  43680
ggacagccgg tggcgcggta agcgggtgcc acgctttcag ggtgtgtaaa acagtcgcgg  43740
gcgaagcagt agttgttgca gaaccgcaag aacccgacgc gaaagaagcc caggagtccg  43800
cgcgccagaa agtgcgcctg ccgcgtctcg ggatgcacgc cgaagacggc gccgctctcg  43860
ttcaccagta tggagatgtc caggcgctgc tgtgactcca ccggcacggc ccgcaccaca  43920
aatacctgca gcacgttcag cgagcacgtc tcttttaacc agttgccgtg ggccggatcc  43980
tcgtaagtct ggctcccgtt caagacgacc gtcgtcagcg cctcattacc gtctcgccag  44040
ctgaagatgg aaccctcgcg cttcatgcac aggcgccaca gggccagcag gtcgcgcgcc  44100
aacatgaact cgcgacccac gtcgccgccg gtctcgaagc ggacatagcc cagttcttcg  44160
cgcagcggcg cgtagttgcg caggccctcc tgcacgaagc cgcggaaacc ggaccgcgac  44220
accaggtaca gcgattccac cacgggcgag tagacgtaga cgcggccgcc ctcgccgatg  44280
agtatgggta gcggtgggcg gccgatggct tcgcaacgac tcacagtgcc caccggcagc  44340
aggaacttgt cgcagcacag gaaggtcttc tccaaacctt taatattgag atgtccaaag  44400
tagccaacgc gtaacaggtc gcagtaggtg aagaaccaac cgttcggcca gttgagacgc  44460
agcaccgtgc cactgacgcg acgaaccagc ttctgcaggt ccttgcgggc gtcggcggtg  44520
acagagcagc ggaaggtctc gttgaccagc tcgacagcca gcgcgtcctc cagcgtgcgt  44580
tccttcatct cgtcgttaat gctctggcgg cgccgccgga tttcgtcgaa acgggccgcg  44640
gaggcggcga ccgacgcgga ggtcgtccga acgccctctg tgacgctgtc gtccggccag  44700
tcaagaaagc taaggctggc gctgcgccgc ctaaagtgtc cgatccgcgc gggacgtcgc  44760
tgaggaacgg tggctggtct gctggggcgg gtacggccgc gggtgtccgc ggacacgtta  44820
```

-continued gttatacacg ggattgagtc acgtggcacg ttgccagctg aaaccgccgt cgtctccgcc 44880
ggcgttttct ccatcgcggg accgcgccgt gcgcgcaggc cgcgtgcccg ggcacgcgct 44940
ctagccgcac ttttgcttct tggtgttagg gacgaactcg aacgttacag aatcctcgct 45000
gtcgctctcc tctttcgcgt cgttgaagta attgccggag ttgcgatcca aaccgccgcc 45060
tcctcctcct ccgccgccgc ccgatccacc tttggacgtc aggtaactgg tgatcttgtg 45120
ctgctcgtat ttttccttgg aggaaagacc gtgatcgtga tcaccgccgc cgccaccgct 45180
gctcattttc cgcgtaccgg aaccaccgcc gccaccgcgg tcgtgcttct tgccgccacc 45240
gccgccacct cctcccagac cgccgagacc catgggctcg ttcatgagat cgttatccag 45300
acccgggccg tcgtcgtgca gaccgccggc attggccagc gaagagaggc tgccgccacc 45360
accgccgccg ccacgcgact tgccgctgtt cccgacgtaa tttttgtcga agggatcgcc 45420
acgctggaaa ggttcctcgg tgagaaagtt ctccacggcg aacagaccgt tgcggctggc 45480
cacgtacaac agcgtgtcgt gctccgtaac tatacgcagc gtgcacggta gtttggtgac 45540
ggcgcaattg agcagcgtct ggtagaagtt cttcagctgc acgttgatac gcatgttttt 45600
tacgccgtgg aaactgacgc ggttattggc cgtgaattcc agctcgctgc cgttggtcag 45660
gatgaacttg atggccggcg gaccggcgtg caccagaatc tgcacggtgc ccgtagggca 45720
gggcgctttt ttaacgttac gcttgacgcg ggtatgcggc ccgatccact taagcaggtc 45780
ggccaccacg ccgaaatcga gatccacgtg cacggccgaa ttctcgcttt cgcgcacaat 45840
gtcttgaccg tgcacgcagg ccgagctgaa ctccatattg aaatcgggcg cgcacatgga 45900
gatcttggcc gacaggtccg agatgtcctg cacgtagaac ttggtcaggt ccttgctgga 45960
ggtcaggtac ataaaattgc cgagcagcgg cgtggaattg ttaatggtct tgggctgaaa 46020
cgacttgtcg gtgatgtaga ggcatgagct gttaaaagtg atttttgaca cgcaatgact 46080
gcgtaccgtt tgcaagataa gcgacggcgt gggcaagaag gtaaccgtgg tgttctcctt 46140
gagcgcacgg atcacagatc gcagctgctg gatagccgtc ttgtacggct tcagccgcag 46200
cgccagcgtc ggtggctccg agaggcgcgt cttgcgatcc atcccggaca gcgtgcaagt 46260
ctcgactaag gagcgggcgc gagcgagcga aagttttata gagagcacac acgacgaccg 46320
ggaacgctgc gaagacgccc ggcgtctaat aatacagccg cgccgagcca gcgggccccc 46380
gactaagagg cacagtactt atatactccg accttaaagc gccagtggta ccacttgagc 46440
atcctggcca gaagcacgtc gggcgtcatc cccgagtcat agtagaaaac cagggccacg 46500
cactggtcca caaacacgct caggttcacg gccgccattt ccacgtcgtt ttggatcgcc 46560
ggcgccgcct ggaacagaca ctgcgtcgcc ttgccctcct cctggtgctg ctccaaccac 46620
gcgtaattca ccacgggcac gcgcagcggc ctccgcacca cagtggggaa gtaacactca 46680
cggttgggcg ggcacaatga ccacaccgtc tcctcctcga acacggtgcc gcgcgaagcc 46740
catactgacg gcgtcacgcc ccacagatgc gccacctcgt cgtcgggacc caccgccaga 46800
aactgacagt tgcgcaatcc gaactcgagc atgtcggcgc gcagcgcttc ccagcgcgcg 46860
ctggcgatgg agagccgcgg caaccgatac aattcgaaaa tgaatttgcc ctcttgatag 46920
atggtgcgtt cgaaccattc gcagcgtggc aaacccgact tgcacaaatc gacgctagcg 46980
cgcaccgcgg caaagtacat gtgctcaaag atgcgctcga tcaagtccca agaggcaaag 47040
tacgtaaacc ctaaccgcat aagcgcagtg tgcaggccag ccacgccgat gtgcagcgga 47100
cgcagttttt ccagcgcgct ctctacccac cattcggacg ccgacattag cgcgtccaag 47160
cgcgcgttgc cccaaaccac cgcctcggtc accaactcgc gcagcacgct caaatcaaag 47220

-continued

```
taacgtcgcg tgttccccaa aaccacgtcg ggtagatgca gcttctgctc gtcgctacgc  47280
gcaaacacgc agcgagccac gttcaccgtc agccgctgca ccggcatgtc acactcgcca  47340
aagtggcacg acgccatatc gggactcaag cacggcggca ggcacacgct gtcggccata  47400
atcgagtact tgactacgtg atggacaaag accaccgagg cacggccctt gagcgcgcac  47460
agcaacatct ttttcagaaa atcgtccgtg ttcacgacca ccttggggca cgattgctcg  47520
cagcgcgaat actctttctc gaaagccgac tcctgaccca gatccgagag ccgccgggag  47580
acaggccgcc cgaacagcga gtagcgctgc tcacgcgcac ggtagcgctt cattaacacg  47640
ctaggcacgt tgaaagcgta gcaaaccccc gtcaactccg acgtgctttc tttgagaata  47700
aagttaatca cgcggatagc ggccacgtcc cacatgtcca caaacacacg taccacgggt  47760
cgatgcacct ccttctcgcg tatcaaatcg cagtatcccc ccaggcaacg aatcacgctg  47820
ttcacatcgg cgttgagtcg cgttacgttc accgacacag aaacgccgca actcaaggta  47880
ctcatccact tgcacatggc cgcccaactg gcgtcacgcg agaaagggtc ggccgagatc  47940
agaaagtcgt actgcggcac gcgatcgaaa cccacggtag acatggtgaa ggtagacagc  48000
gacagctgcc catcgcgaca gcgcttcaac accgagtcca acacttcgcc ctcgaaacgc  48060
gcatccagat ggaaacgata gatgcgcgag tgcctactgt tctcgatagc ggccgtcaac  48120
gccacggcga tgcgcaaaaa cacgccgccc gggctctcgt cctgtccatg cagttggcga  48180
cacaccttat ccaaacacaa aatagccgcg tacaagcccc agcaaccggc caattccaca  48240
aaacgcgccg tctcctcggc cagcttgggt agatcctcca tgtgacgcag cacaaaacgg  48300
cgcaccgact catcgcacag ctccgaagcg taacacagtg gcgtgcggct ttcgcgcgcc  48360
cagttggctt tgaaataaaa gcgacccaac agcagatcgc aacgcggcga gtgacgaatc  48420
agacagggac cgtggcgcat gatgagctga aacagcctga aactgcccaa accggcactg  48480
tgtcgcgaca cggtgtccat ctcgcgccac agcgcgttcc tgtcggacgg cagctcccgc  48540
gccggctcct gtacgccaca aaagcgaaac ttgccccagt agccgtgaca atgacacttt  48600
ttgcccatca acatgcgcgt agcctgtatc ggcggcgata ctttgcagag tgaagccccg  48660
aaatcgtcct cctcctcgac actgtccagc tccatcctgg tcgcgccggc cggattgaag  48720
gtgctcagac cgctactcac acgtccaccg cgactgggca cggcgggacc gctgtcacgc  48780
gtcaacgaca gcacagacgg cgtgccgtcg ggagacggcg actcgggacg ccaactgacg  48840
acgccgccac cactcgtaaa acccgctaca cacgctacgc cgctcgatac gttggtattt  48900
ccagcggacg cttccttgtc acccccgggc agcggcccct cctcgagctc gctgtcatct  48960
cccccggtag tatcagcggc ggcctctgcc gacgattcct ccgtctcggt ttccgagccg  49020
cggcttggaa tcctacctgg ccggcaccga tgtgcgggca ccgaggacac ccgctgttcc  49080
tcgtccgcgt cagccggatt cataagttta cgaggaaaat aacaaagaaa tcaggtagat  49140
ttcaataaag tgagtctaga tggcgccgat aactacggtt tataaagtct gtgtgcgatg  49200
tgtttatttt tttcttctgt gtctcctccc cgtatgctgt cagcgccgct cagacgaatt  49260
ctcgaaagtc tcccaattcg acgctaaagt tgtccaaacg gacgacggac agtttgagtt  49320
ctttgtgtac caggaacgag gtgtgaatgt cgtcagccag gcaccagccc agcttttgta  49380
tgaccccggt acacagaggg atctggcgcg ggcgcgtgat gcgacggttg acaaagctac  49440
agcgctcgcg ggcgaacttt ccgcgtgcaa cgtcgaccag ggtctgccag tgtgcgatgc  49500
tggaggtgag cacgtagatg ccgggacgtg tttcgggccc gtcatagtca tagacgatga  49560
```

-continued

```
ttaaatacac gtattgcagc cgtccccggg tctcttccca cgtcaggtac atgtctttcg  49620
gtatcatcaa cgcgaacacc tccgttttga gcgtgttgta aaggtagccg cgcatgacgc  49680
aggtgagcaa cgaggtgatg cccagcgaga cggtcttaac gcagcccagc gtctcaaggc  49740
ggcggtgcag cagatgcggg cccaggtcca gccactgcag cgcggcgcgc gcggccgagg  49800
ccgtgtacac gctttcgagc aggcagcgcg tgctggccga gacgttggag gcgcgaatgc  49860
ctaacaggta gaggctgatg tagaggtgtc gcggcgagtc gcaacccgtc tccatgcgga  49920
tgagcagcgc gcccggctgc gcctcgaact ctaccaggcc ctcgggcacg aagaaacgcg  49980
ccgtgagcgc ctggtgatcg gcgtggtaga ggtagcgcac cgatatagta tttacctcgc  50040
gtttggcttt gagcgccgtc actagttcat tgtcctcgtc ggccgggtcg cgcggccgtt  50100
tggccaccgc gcgcgcgtcc atgatggcga ggcgcacggt agatttcaaa aagttgatag  50160
agcagctgcg ggcacgggcc acggacaaag cggaggcgtt aaataccgtg agccaattgg  50220
agatcggcgc ggtggatgcc caggacgtga ccgcgagcgc cgtgcgcgcc ttcgtgggtg  50280
cgttgccgag ctcgggctac cactttggct tcgtgcgtca gaacgtggtc ttttacctcc  50340
taagccacgc cacggtacag acggcgcgcg acccgctgta cgccgccgag cagttgcacg  50400
aacagctgga ccgcttcctg cgacaccagc acgacggcgg cggggacgag gaccggttgc  50460
cgttctacca caacggggcc acgctgacgg ctttccagaa gctgttgcag accctgcgcg  50520
agatccagac cgtaatagcc gaacagagcg gcggcaccgc ggcggcggcg gacttgatcg  50580
ccagtaacaa cgcgtcggcc gagcgccgcg gcaagaaggg cggttcgagt tccgggggcc  50640
agcagccgct ggtccgccgg gtgatcacgc agctggaaac ggctgccacg gaggcgcggc  50700
cctacgtcaa ttgtcgcgcc gtggccgaac tcctggacct gacctaccag cggctcatct  50760
actgggcctg cacgctcatg ccctacgtgt tgtttcggcg cgacaccgac accgaactgg  50820
acacggtgct tctgatgcat ttttttaca cacgctaccg ttcggttaac ggcgatttgg  50880
ccgtggagtt tcaaaactac gtcaagaaca gcgtgcggca catgagctct ttcgtcagtt  50940
ccgatatcga cggcgaccag aagcccggtg ccgaacacat gcgtgacgtc agctacaagc  51000
tgttcgtggg taatctgcag gcgcgtgacg ccagcggcct catgtttccc atcattagca  51060
cgcgcatctc caccgtgaac ctttacctgt cgcccgaacg tatgtttttc cacccgggtc  51120
tgatctcgcg tctgttgagt gaggaagttt cgccgcgcgc caacctagac gcttacgcgc  51180
gcgtgtgcga tcgcgtgctg gaagaccact tgcatacgcc gcgacgcgtg cagcggctac  51240
tggatctgac gcagatggta acgcgactgg tggaactggg tttcaatcac gatacctgcg  51300
cggcctacgc gcaaatggcg ctgatccagc cggccagtca gaagagctcg ctctttgtca  51360
gcgagattcg cgagaaactc atacagatca tctacaattt ttacacgttt ttcatgtgcc  51420
tctatgtgta cagccccacg ttcctgttcg accaccggcg gcggttgatt ttggagcagc  51480
atcgatccac gttgatcggc tccaaggagg aactacagca cgtctggagc aacgtgacac  51540
tgaacgtcaa tacgcacttt gcggttcagt acacggaaga agactttgag gcacatacga  51600
agggtgccac ggaggcagag cgcgagtacc tgtatcggga cctgcacagc aagtggggcg  51660
tgcacctgtt taccttgcgt ccgtctcgcg gcgcggccgg cgcggcctcg cctttgcctc  51720
cgcttgacgg cgtcacacgc tccgacatct tacgcgaatg cgcgctcgtt aatctgaacg  51780
aaggccgcgt caactacgcc tccctgctag ccttcagcca tcatcccgag ttccccagca  51840
tcttcgcgca gttggtggtg gtaactgaat tttcggagat ctttggtatc ccgcagggcc  51900
tgtttcaagc cgtgggttcg ccgcgtcttt tcgcgctcat tcagctgtgt cgtgtattgt  51960
```

-continued

```
tgcccgagca ggtgacgctg taccagaacc tggtctccat ttacaacctg accacctttg  52020
tcaagcacat cgacgccgcg gtttttaaga cggtacgcga ttgcgtcttc gacatcgcca  52080
cgaccctcga gcacctcagc ggtgtacccg tcacgcccaa tgtggacctg ctggccgagc  52140
tcatggcgcg ctccgtagcg cataacctgt acaccaccgt caacccgctg atcgaggacg  52200
tgatgcgcag cagcgccggc agtctgagaa actatctgcg acacacgcga ctctgtttcg  52260
gtctggcgcg cggccgggcg cgcctctcgg aggacggcgt gacggtgtac gtggaggtac  52320
agggtcagta cggactgcgc gtacctacca cgcgtttcgt agaacagttg cgcgaactgg  52380
ttcgccgcga tcggctgttg gccgagaatc tgcgcggctt aaacgagcgc ctgctgagtg  52440
ttcgcgtgcg cgtacgtcag atcagcagcg acacagagga agtaagccga cacgccaagg  52500
gtcaccgcac ggtggcccag atgagcaagg cgctcaaaaa gacggcctcc aaaatcaaag  52560
tgttggaaac acgcgtgaca ttggcgctcg agcaggcgca acgttccaat ggcgccgtcg  52620
ttaccgcggt gcaacgcgcg ctagccgtct ttgacgtact aagtcgcgag aacttggaac  52680
gccgcggcgc acagctctgt ctgacggaag cgacgagcct actgcaccga catcgcgcgc  52740
tagcgccgat gacctggccc gcgggcacgg gcgttgcggc ggcggccgaa gcggatcgcg  52800
ccttacgcga gttcttggag gcgccctggg aatcggcgcc ccaaccgccg cgactccgca  52860
tgacgcccga caccgatcac gaagaatcga cggcaggcgc gacgtccgta ccggaggtcc  52920
tgggtgcgcg ctacgaaccc gcacacctgg ccgcgagcga cctattaaac tggtacatcg  52980
tccccgtaag ccaggcgcag caggacatct tgtcttcgat cgacccgccc gccggctcga  53040
catcggtgtc cctgccgccg gcctcgccat gaaagtcacg caggccagct gccaccaggg  53100
cgacatcgct cgctttggag cgcgagcggg caatcaatgc gtctgcaacg gcatcatgtt  53160
cctacacgcc ttgcacctgg gtggaacgag cgccgtcctg cagaccgagg cgctggacgc  53220
catcatggaa gagggcgcgc gtctggacgc gcggctagag cgcgagttgc aaaagaagct  53280
gcccgccggc gggcggctgc cggtctaccg actgggcgac gaagtgccgc gccgcctgga  53340
gtcgcggttc ggccggaccg tgcacgcgct ctcgcggccc ttcaacggca ccaccgagac  53400
gtgcgacctg gacggctaca tgtgtccggg catcttcgac tttctgcggt acgcgcacgc  53460
caaaccgcgt cccacctacg tactcgtcac cgtcaactcg ttggcgcgcg ccgtggtctt  53520
caccgaggac cacatgttgg tctttgatcc gcacagctcc gcggaatgtc acaacgccgc  53580
cgtgtatcac tgcgagggtc tccatcaggt gctgatggtg ctcacgggct tcggcgtgca  53640
gctatcgccc gctttctact atgaggccct ttttctctac atgctggatg tggcgaccgt  53700
gccagaggct gagatcgccg cacgtttggt ctccacctat cgcgaccgcg atatcgacct  53760
caccggcgtc gtccgagaaa gcgcggacac ggcggcgaca acgaccaccg ccgcaccttc  53820
cttacctccg ctgcccgacc ccatcgtcga cccgggctgc cctcctggcg tggcgcccag  53880
cattcccgtc tacgatccct cgtcctcacc caaaaaaaca cccgagaaac gccgcaagga  53940
cctcagcggt agcaaacacg gaggcaaaaa gaaacccccg tccacgacgt ccaaaacact  54000
ggccaccgcc tcctcctcct cagcgatagc ggcggcctct tcttcgtccg cggtaccacc  54060
gtcctacagc tgcggcgaag ggccctgcc ggccctgggc cgctaccaac agctggtcga  54120
cgaggtagag caggagttga aggctctgac gctgccgccg ttgcctgcca acaccagcgc  54180
ctggacgttg cacgcggcgg gtaccgaaag cggcgctaac gcggcaacgg ccacggcgcc  54240
gtccttcgac gaagctttcc tcaccgatcg tctccagcag ctcatcatcc atgccgtcaa  54300
```

-continued

```
tcagcgctcg tgtctgcgcc gcccctgcgg tccgcaatcg gcggcgcagc aggcggtacg  54360
cgcctatctg ggcctatcca agaaattgga tgcctttctg ctcaactggc tgcaccacgg  54420
cctggatctg cggcgcatgc acgactacct gagccacaag accaccaaag gcacgtactc  54480
gacgctggat cgcgcactgc tggagaagat gcaagtcgtc ttcgatccct acggacgtca  54540
gcacggcccg gcgctcatcg cctgggtgga ggagatgcta cgctacgtgg aaagcaagcc  54600
cactaacgaa ctgtctcaac gactgcaacg tttcgtaacc aagcgaccga tgcccgttag  54660
cgacagcttc gtctgcctgc gacccgtaga ctttcagcgt ctgacgcagg tcatcgaaca  54720
gcgacgtcgg gtgttgcaac gtcaacgcga ggagtaccac ggcgtttacg agcacttggc  54780
cggcctcatc accagcatcg acattcacga cctagacgcc agcgatctga accgacgcga  54840
aattctgaaa gcgctgcagc cgttggacga caacgccaag caggaactct ttcgcctggg  54900
caacgccaaa atgctagagt tgcagatgga cctggaccgt ctgagcacgc agctgctaac  54960
gcgcgtgcac aatcacatcc tcaacggctt tttgccggta gaggacctga agcagatgga  55020
acgcgtcgtc gagcaggtac tgagactctt ttacgacctg cgcgacctga aactgtgtga  55080
cggcagctac gaagagggat ttgtcgtcat acgcgaacaa ctgagctacc tcatgacggg  55140
cactgtgcgc gacaacgtac cgctactgca agagatcctg cagctgcgac acgcgtacca  55200
gcaagccacg cagcaaaacg agggtcgcct cacgcagatt cacgacctgc ttcatgtcat  55260
cgagacgctg gtgcgcgacc cgggcagccg cggctcggcg ctgacactgg ccttggtaca  55320
ggagcagcta gctcagctgg aagcgctagg cggcctgcag ctacccgaag tgcagcagcg  55380
cctacagaac gcgcaactcg cgctaagccg cctctacgaa gaggaagagg aaacgcagcg  55440
tttcctcgac ggactctcgt acgacgatcc gcccaccgaa cagaccatca agcgacaccc  55500
acaattacgc gagatgttac gtcgcgacga acagacgcgt ctgcgactca tcaacgccgt  55560
actgagcatg ttccacacat tagtgatgcg actggcgcgc gacgagtcgc cgcgaccgac  55620
gttttttgac gccgtcagtt tgttgttgca gcaactgcca cccgactcgc atgaacgtga  55680
ggatctgcgt gccgccaacg ccacgtacgc gcagatggtc aagaaactgg agcagatcga  55740
gaaagccggt accggcgcat ccgaaaaacg cttccaagcg ttacgggagt tggtttactt  55800
tttccgtaat catgaatatt tctttcaaca tatggtcgga cgactgggcg tcggacctca  55860
ggtaacggaa ctctacgagc gatatcaaca cgagatggaa gaacagcacc tggaacggct  55920
ggaacgtgaa tggcaagaag aggccggcaa gctcacggta acttctgtgg aggacgtgca  55980
gcgtgtcttg gcccgggcac cgagccatcg tgtcatgcat caaatgcaac aaacgttaac  56040
caccaagatg caagactttt tagacaagga gaaacgtaaa caggaagaac agcaacggca  56100
gctactggac ggctaccaaa aaaaggtgca gcaggatttg caacgcgtgg tggacgccgt  56160
taagggcgag atgctctcca ccatcccgca ccaaccactg gaggccacac tcgagctgct  56220
cttgggccta gatcaacgcg cccaaccgct actagacaag ttcaaccagg acttgctgtc  56280
ggcgctgcag cagctgagca aaaaactaga cgggcgaatc aacgagtgtc tgcacggcgt  56340
gctgacgggt gatgtagagc ggcgctgtca cccgcaccga gaagcggcta tgcaaaccca  56400
agcctcgcta aaccacttgg accaaatttt gggtccgcaa cttctgatcc atgagacgca  56460
gcaggccctg caacacgccg tccatcaagc gcagttcatc gagaagtgtc aacagggcga  56520
tccaactaca gccatcacgg gcagcgagtt cgagggcgac tttgcacgct accgcagcag  56580
tcaacagaag atggaggaac aattacaaga gactagacaa cagatgaccg agactagcga  56640
gcggctagat cgctcgctgc gccaggatcc cgggagcagc tccgtcacgc gtgtacccga  56700
```

-continued

```
gaaacccttc aagggtcagg agctggcggg tcggatcacg cccccgcccg ccgacttcca  56760
gcggcccgtt ttcaaaacgc tgctagatca gcaggccgac gcggcccgga aagcgctcag  56820
cgacgaggcc gatctgctga atcagaaagt acagacgcag ttgcgacaac gcgacgagca  56880
gctgagcacg gcgcagaacc tgtggactga tctggtcacg cgccacaaaa tgagcggcgg  56940
actggacgtg accacccccg acgccaaggc gctgatggaa aagccgctgg agacacttcg  57000
cgagctgttg ggcaaagcca cgcaacaact gccgtacctg tcggcggagc gcacggtgcg  57060
ctggatgctg gcttttctgg aggaagccct tgcgcaaatc accacggacc ctacgcaccc  57120
gcatcacgga agcaggaccc actaccggaa cctgcaacag caagccgtcg agagcgccgt  57180
gacgctagcg catcaaatcg aacaaaacgc ggcctgtgaa aattttattg cacagcatca  57240
agaggcgact gccaacggcg cgtccacgcc gcgggtcgac atggtccagg cggtggaagc  57300
gatctggcag cgactggaac ccggacgcgt agccggcggc gccgcgcgtc atcaaaaagt  57360
gcaggaactg ttgcagcgct tgggtcagac gctaggcgac ctagaactgc aggaaacgtt  57420
ggcgacggaa tactttgcgc tgttacacgg catccagacc ttcagctacg ggctggactt  57480
tcggtcgcag ttggaaaaga tccgcgatct gcggactcgt tttgcggaac tggccaagcg  57540
acgcggtaca cgtctctcca acgagggagc cctgcccaac ccacggaaac cgcaggcgac  57600
gacttcgctg ggcgccttta cacgcgggtt gaacgcactg gaacgacacg tccagctggg  57660
tcaccagtat ctgctcaaca agctcaacgg ctcatcgcta gtctataggc tggaagacat  57720
tcctagcgtg cttccgccaa cacacgagac cgaccccgcg ctgataatgc gcgaccgcct  57780
gcgtcgtcta tgcttcgcgc gtcaccacga caccttcctt gaagtggtag acgtcttcgg  57840
catgcggcaa atcgtcacgc aggccggcga acccattcac ctggtcaccg attatggcaa  57900
cgtagccttt aagtacttgg cgctgcgaga cgatggccgg cccctggcat ggcggcgccg  57960
ctgtagcggc ggaggactca agaacgtcgt caccacacgt tataaagcca tcacggtagc  58020
cgtggccgtc tgtcagacat tgcgcacttt ctggccacag atctcgcagt acgacctacg  58080
accctacctc acgcagcatc agagccacac gcaccccgca gagactcaca cgttgcataa  58140
ccttaagctc ttttgttatc tggtgagcac cgcctggcac cagcgcatcg acacgcagca  58200
ggagctgacg gccgccgatc acgtaggcag cggcgagggt ggtgacgtag gggaacagag  58260
accgggccgc ggtaccgtgc tgcgcctgag tctgcaagag ttttgtgtac tcatagcagc  58320
tctgtacccc gagtacatct acaccgtcct caaatacccg gtgcagatgt cactaccctc  58380
cctcacaact cacctacatc aggatgtgat acacgcggta gtcaataaca cacacaaaat  58440
gccccccgac caccttcccg aacaggtcaa ggccttctgt atcacccccca cccaatggcc  58500
cgccatgcag ctcaataaac tgttttggga aaataaactg gtacagcaac tgtgccaggt  58560
aggcccgcaa aaaagcacac cgcctttagg caagctatgg ctctacgcca tggccacgct  58620
ggtctttcca caagacatgc tgcagtgtct gtggctagaa ctgaaacccc agtacgccga  58680
gacatacgcc tcggtgtccg aattggtaca gacattgttt cagattttca cgcaacaatg  58740
cgaaatggtg accgaggggt acacgcaacc gcagctcccc accggagagc cggtgcttca  58800
gatgatccgc gtgcgacgtc aggacacaac caccacagac acaaacacga ccacggagcc  58860
gggactttta gatgttttta ttcaaacaga aaccgcccta gactacgcgc tgggctcctg  58920
gcttttcggc atacccgtgt gtctcggcgt gcatgtagcc gacctgctga aaggccaacg  58980
tatactagta gcgcgccacc tcgaatacac gtcgcgagac cgcgacttcc tccgcatcca  59040
```

-continued

```
acgctcccgg gatctcaatc tcagtcaact gctccaggac acgtggaccg aaacgccgct  59100
ggagcactgc tggctacaag cccaaatcag acggctacgc gattacctgc gtttccccac  59160
ccgcttagag tttattcccc tagtcattta caacgcacag gaccacaccg tcgtacgcgt  59220
gctgcgaccg ccctccacgt tcgaacagga ccacagtcgg ctggtgttgg acgaggcctt  59280
ccccaccttc ccgctgtatg accaagatga taactcatcc gcggacaacg tcgctgcgtc  59340
tggcgccgct ccaacaccgc cggtaccttt caaccgcgtg ccagtcaata ttcagtttct  59400
gcgtgaaaac ccgccaccca tcgcgcgagt tcagcagccg ccgcgccgac atcgtcatcg  59460
agcggccgcg gccgcagacg acgacggaca gatagatcac gtacaagacg atacatcaag  59520
gacagccgac tctgcattag tctctaccgc ctttggcggg tccgtctttc aagaaaaccg  59580
attgggagaa acaccactat gccgagatga acttgtggcc gtggcgcccg gcgccgccag  59640
caccagtttc gcctcgccgc ctatcacggt gctcacgcag aacgtcctca gtgctctaga  59700
aatactgcgg ctagtgcgat tggacctgcg acaactggcg caatccgtac aggacactat  59760
tcaacacatg cggtttctct atcttttgta accgacactg acagtagcgg gtaataaaaa  59820
caataggctt tttatcgttt tttatgttac aaaacaacgt atcactttta cggtgattta  59880
ttcttgctat tctttttccc cttgggctgt cagcgccggg tgcgcgacac ggctaccatg  59940
cgcaacaggt ccagcttaaa ggcgcacttg tcattaaaca ggctggacat gcgcgtgtac  60000
ttgctcagca tggtggccaa caccgggtgg gtggcctctg atatctcggt cggcagctcc  60060
aaaacgacgt tgacgacgtg acggtgtttt tcgtcccgct tgttggccac cgtgggtccc  60120
ggcgcggtgt tagacatggg gcaggccgtg gggggaggac gaagaggaag ccgctgctaa  60180
accgccgcgc gcctgctgca caatgtggcc gccgacgtgg caggcggtct gtttaaccag  60240
cgcgcagccc cgacacagcg gggcgccgtc ttcgctttcc aaacagctgt cgcggtactc  60300
gcccgtctga cagcgcgcgc acagcaggcc gtgcccgtgc gaagtgaggc gcaggagacg  60360
cgggaccgtc acgccgcgta ccaccacagt ggagtcgcag gtgcgtgccg cgcagggcag  60420
aatgacgtcg aaagccagcc ggtgatcgta cacggcacaa gccgcgttga ggcccagcac  60480
ggctttccag cccacgcgta cgcagcgctg tccaaagagc gtctcggaga cgagctcgta  60540
gacgcgctgc cgcaccaccc gctgactgcc gcagagcgag cagtgcacga gctcggcgtg  60600
cgtgttgaag atgacgctct tttcttgacg gtcccgataa tagaacatcg agttgagcgg  60660
aaagttttgc tggcagtgta gcttttcctt acccaggttg aggcagtgtc cgcactgccg  60720
acagaccacg gccaccagcg agcgcgcgtc cagatggcgc tcgcacttga gtcgacacag  60780
acaccagagc ggcaggtcga tgacgctgcc gatgaggccg ccgcgcagcg cggcgctgag  60840
tgcaaagagg acgatcttgg tgggctctac gtgacgcgcc tgctgtccgg cgcccgcgtg  60900
tcctaccgcc gcagctgccg ccgtcgagcc tcctccgcgc gtctcgtcgt gcagacccag  60960
tgcccgcaac ggcaccaggt atcgcggaca cgtgtcgcaa aacgtctgca ccgcttgtcg  61020
ggccagtacg tagagcgggt ttccgcaggg taccttcccg gcgtgccggc gcaaggctgc  61080
gatgaggccc cgcagctgcg gcgaccgcgg ctgccgttgg tgacaccact ggttacggtg  61140
gtatacggcc aaatcagcgc gggcgtcgaa gcgcttggcg cgtagtagtg ctaggcacgg  61200
cgagctggtg gggtgaagca cgggcagccg aaggtccacc ccgaaaagga aacggtgaag  61260
gtcacctagc agcgaggagg tgacaccgtc caacaacgcg tgcagccgct cgggcgggta  61320
gagccgcaga cggcgcagca ggtagtcggt gtcgtagcgt tcgaaacgca gaaaggccat  61380
cgtgcggacg gccacggtgt gcagacagtc catgctgtag acgtaagcga gaaacacaaa  61440
```

-continued gtagggcttg gtcataacca tacgctgaaa aagcgccgtc accgcctccc gctcggcctg 61500
ccgacacacc agccattcgc gcaggaagcg ttggtagaga cggtcgccca gctcgcgatt 61560
cagaaagcgc ttatccgtca cgaagagatg aaggacgcaa gaacgtggca cgtgatgcac 61620
cagctgctgc tggaggaccg ccgacgtctg cgccgcaaac tgcgccggtg gctgcgacgt 61680
ttctaccgcc gcttcctccg gctgcagcgc accgcggccg atcaccagct gcacatggaa 61740
atggtcctcg tgaacgcaga ggggcgcgaa gagacggcgc agagcctggt ggaactcctc 61800
agtcgcggtg tgcggagcgt gtcggagacg gcgattggcc atgaccgcgc cacagcagag 61860
ccagcaccag caggagagcc agcaccagcg ggcccagagt cgcgaagcgc gcgggcagcc 61920
acggcccaga ctgcggtcgc gatggcccgg agcgcgctcg ccaccacgat gacggtgccc 61980
aacgataacc agtccgctcc aaggacggcg cgcacggcgg agacggcgga tgacggtgat 62040
gggtcgacac ccctcgccga cgactcacgt gctcctccag aggccgacgc gcggaccctc 62100
cgacatcctg gcccgccgct gccgctgccg ccttcccttc tcccgccaga gccagcaact 62160
cctcctcctc ttcatcagcg tctccctcgc ttgcgcatcc gcatcgtccc atacaggcct 62220
cacaacgaca cagccgccac gaccccgccg ccatgggtgg cggcggcggc cgaggcccgg 62280
cagcggcgcc gccagcggcg accatggtgg gagagcaact cggatgacga ggaggaggag 62340
gagggggaga tgcggtccga gaggaccgct ttcccgccgt tcgcgtgagc gcggccgaca 62400
tgcgggcgcg ccacagggac ggaccgctgc cgctgtgact gcttacggtg acgtggttcc 62460
ggaccgccaa cgacgtcgac gcggctttct tggcgtacag ctcgcgcagc agattctcgt 62520
actcgccctc gttttcgggt ccgaaggcga tgagctcgat gttgaagacc gacgccgaat 62580
tggatttgcg caccacgcac ttcgtcagca ctccgtaggc cgagggcttg atctcctcga 62640
tgtccttgag cgtgacgatg agcgactcgt tcaccttaag cacattgaac tcacctacgt 62700
ggcgcgccgg cgagacgagc ttgacgggcg ctcgcacaaa acagcagagg gagacggcac 62760
agccagtgtt tttaaagata aaacaaggca cgtggtctgt gcggctctcc cagtagctga 62820
gcagatactc gacacaatag accgtgtctg tcttgagcat ggcgtcgcac accgagtaat 62880
tggggttttt acagatgagg ccggcgtcgg tgacgcgcag ctcgctggga cccaacttga 62940
ggatacgccg cgtggcctgc accagatcct gatggagaac cttgttcatc tccatcgcac 63000
cgacgccacc gccgatttat ttacccggcg ccggctcgtc ttttccctcc aggattccgt 63060
taatgtccat gagcttgctg acgatcgccg ttaatagttg cgtcttctca cggaggatct 63120
ctccgtgact gcaggtcgcg cagtcgccgt gcacgtactt gaggaaggcg gcgtacttct 63180
gacccgcgtt cacgaaattt aagcgcgcgt ccagagaggg cagcaacaga tcgtagacgc 63240
gcggcagcat cggctcgaac tgtaatagca gatcgtcgtc aagatcgggt agcgcgtgcc 63300
cgtcttcacc gtcctcgtcg tcaccacctc cccctcgag cccaccgctc gtaccagccg 63360
cgggctccgc gtcctcgtcg atcaccagcg gtcgcgtcgg caccggagaa tccacgtcat 63420
cctgcacgtc gttttcctcc tctccgtcgt catcgtccag aaacggcacc cgctgcttag 63480
cccaggacat tctttttccg cgtcctcaat cagcggcgcc gatcgccatg aatccgagta 63540
cccacgtgag cagtaacggc ccaacgactc cccctcacgg gccccacacc acgtttcttc 63600
ccccgaccag cccggccccg tccaccagct ccgtcgccgc cgctaccttg tgcagtccgc 63660
aacgacaggc cgtttcacgt tacagcggct ggagcaccga gtacacccag tggcactcgg 63720
acttgacaac tgagctgcta tggcacgcgc acccacgtca agtacctatg gacgaagcgc 63780

-continued

```
tggccgccgc ggcggccgcc tcataccagg tgaatcctca acaccccgcc aaccgttacc  63840
gtcattacga attccagacg ctcagtctcg gcacctcgga ggtagacgaa ctgctcaact  63900
gctgtgcgga agaaaccacg tgcggcggca cgcaatccac cgtactcacc aatgcgacca  63960
acaccactaa ctgcggcgga gccgtcgccg gcagtagcaa cgcaggaccc gccggcgctt  64020
cggccgcctg cgacctagat gcagaactgg ccggcctcga aacctcggcg gccgactttg  64080
aacaactgcg gcgactgtgc gcgccgctgg ccatcgacac acgctgtaac ctatgcgcca  64140
tcatcagcat ctgcctcaaa caagactgcg accagagctg gctcctcgag tacagcttgc  64200
tgtgcttcaa atgcagttac gcgccccgtg cggcgctcag cacgctcatc atcatgtccg  64260
agtttacgca tctgctgcag cagcactttt ccgatctgcg catcgacgac ctgttccgac  64320
accacgttct cacggtcttc gatttccacc tgcacttctt cataaatcgt tgctttgaaa  64380
aacaagtggg cgacgcggtt gataacgaga atgtcaccct gaaccatctg gccgtggtgc  64440
gggccatggt catgggcgaa gacacggtgc cttacaacaa gcctcggcgc cacccgcaac  64500
agaagcaaaa aaccaaccct tatcacgtcg aagtgccgca agaactgatc gacaactttc  64560
tagaacacag ctcacctagc cgcgaccgct tcgtgcagct gcttttctat atgtgggccg  64620
gcaccggcgt catgagcacc acgccactca cggaactcac gcacactaag ttcgcgcgac  64680
tagacgcgtt atccacgacc tcggaaagag aagacgcaag gatgatgatg gaagaagagg  64740
aagatgaaga aggaggagaa aaaggaggag acgatccggg ccgtcacaac ggcggtggca  64800
ccagcggggg gttcagcgag agcacgctaa aaaagaacgt gggtcccatt tacctatgtc  64860
ccgtacccgc ctttttttacc aagaaccaaa ccagtaccgt gtgtctgctg tgcgaactca  64920
tggcctgctc ctattacgat aacgtcgtcc tgcgcgaact gtaccgtcgc gtcgtctcgt  64980
actgtcagaa caatgtgaag atggtggacc gcattcagct ggtattggcc gacctgttgc  65040
gcgaatgcac gtcgccgctc ggcgcggcgc acgaggacgt ggcgcgctgt ggactcgaag  65100
cgcccacctc gcccggaggc gactcggact atcacggcct gagcggcgtc gacggcgcac  65160
tggcgcgacc cgacccggta ttttgccacg tcctgcgtca agcgggcgtc acgggcatct  65220
acaagcactt tttctgtgac ccgcagtgcg ccggcaacat ccgcgtcacc aacgaggccg  65280
tgctcttcgg acgcctgcac ccccaccacg tccaggaggt gaaactggcc atctgtcacg  65340
acaattacta tataagtcga cttccgcgac gtgtgtggct ctgcatcaca ctcttcaagg  65400
cctttcagat tacaaaacgc acctacaaag gcaaagtgca cctggcggac tttatgcgcg  65460
atttcacgca gctgttggag agttgcgaca tcaagctggt ggaccccacg tacgtgatag  65520
acaagtatgt ctagcgtgag cggcgtgcgc acgccgcgcg aacgacgctc agccttgcgc  65580
tccctgctcc gcaagcgccg ccaacgcgag ctggccagta aagtggcgtc aacggtgaac  65640
ggcgctacgt cggccaacaa ccacggcgaa ccgccgtcgc cggccgacgc gcgcccgcgc  65700
ctcacgctgc acgacctgca cgacatcttc cgcgagcacc ccgaactgga gctcaagtac  65760
ctcaacatga tgaagatggc cattacgggc aaagagtcca tctgcttacc cttcaatttc  65820
cactcgcacc ggcagcacac ctgcctcgac atctcgccgt acggcaacga gcaggtctcg  65880
cgcatcgcct gcacctcgtg cgaggacaac cgcatcctgc ccaccgcctc cgacgccatg  65940
gtggccttca tcaatcagac gtccaacatc atgaaaaata gaaactttta ttacgggttc  66000
tgtaagagca gcgagctact caagctctcc accaaccagc cgcccatctt ccaaatttat  66060
tacctgctgc acgccgctaa ccacgacatc gtgcccttta tgcacgccga ggacggccgg  66120
ttgcacatgc acgtcatctt cgaaaacccc gacgtgcaca tcccctgcga ctgcatcacg  66180
```

-continued

```
cagatgctca cggcggcgcg cgaagactac agcgtcacgc tcaacatcgt gcgcgaccac  66240
gtcgttatca gcgtgctgtg tcacgccgtc tcggccagca gcgtcaagat cgacgtgact  66300
attttgcaac gcaagattga cgagatggac attcccaacg acgtgagcga gtcctttgag  66360
cgctacaaag agctcattca ggagctgtgt cagtccagcg gcagcaacct atacgaggag  66420
gccacgtcgt cctacgcgat acggtctccc ttaaccgcgt cgccgttgca cgtaacttcc  66480
accaacggct gcggcccctc ctcctcgtcc cagtccacgc cgcctcatct ccatccgccg  66540
tcgcaggcga cgcagcccca ccactactct caccaccagc ctcagtctca gcagcattat  66600
caccgtcccc agtcaccacc gccgccgctg tttctcaaca gcattcgtgc gccttgacac  66660
tgtacggcag aaaagccggc tccaagtgca agcgccgcgg cagcaccatg tgcaaaaact  66720
tgtccttgcg cgcggtttcg ccgccgggaa agacgggcga cagcacgttg gttacagcct  66780
tgagaacctg ctcaaagtac ttgtcggcgt gaatgggcac gccgtgctcg cgcacgtagc  66840
tcggatcttc ggctacctcg tagttgcaca cggccgacgg tggtttccgc gccctcttct  66900
ttggcggctc tcctcctctc ctgttgctct cctctacccc gccgccgtca gcgtcgtcgt  66960
ccgtgccatc aatcgcgtcc gaccgggaaa ccacgccggt ggttacagaa tcaccgttgt  67020
cagaggaacc ctgcggcgcc gtccggacac cgggcgccgt cagtacgtaa aagacccgat  67080
ccccgaccga gggtagctcc tcagaacggg ccgccagtcg cttaatgacg gcaatgtgcg  67140
gcaggttaga ttgacggtac aacgagatgt ccttagaaag caccgacgaa agcaccaggt  67200
cctcgacacg cacacggtgc aggtacagat cgtcgcgggc ctgcaccagg cggcgcaaga  67260
tacgccagaa accgcgtggc acgccgtatt tcttgacttc atcgagtgag aggcgcgaca  67320
ggcgcacggc tgcttccgag acctcgcgat cctcaaagag cagcgagagg acgtcacgcg  67380
taacgccctt gacgaactcg caagccgtct tgcgcaccag atccacgccc ttcatgctca  67440
gacccgaggc gccctccact ttgccgatgt aacgtttctt gcagatcatc ataagagaga  67500
cgaagacctt ttcaaactcc agcttgacgg gctccacaaa aagacaggcc gtcacgtagt  67560
gcgccaggct gggcccacgc gccaccagag cctgcggcgt cagaccacga aagcggacaa  67620
acacgctgtc cgtgtccccg tagatgaccc gcgcctccac ccgccgttcg tccgagcccc  67680
ctgacgatgt ttcgagcccc tccggtaacg tgctgctctc ctccgaatcc ccctcccgcg  67740
ttcccaccac ataatcttct tgattaaaaa aattgtgcaa aaaacacggc tctgaaaagt  67800
tgtctttgat gaaccgcgcc gtgcgctcta gcatgtcgcg accgatgcgc gtgatgctgg  67860
cggcgatggg cagacacggc atcatgccgt tgaccacgcc ggtaaaaccg tagaaagcgt  67920
tgcacgttac tttgagcgcc atctgttcct tgtcgagcaa catacgacgc acagggtctt  67980
gacactcgcg catgcattcg cgcacggcac gccgctgcga aacccacttg ttgagcagtt  68040
ccgaaagcac cgagacgcgc accgaagcgc gcacaaagcg gtgggtcacg ccgttctcta  68100
gcgtgacgct gtatacgtcg gcagggtcca cggggtactc gccacccggc accaacaggg  68160
tggagtagca gaggttgtgg gccatgatga tggaagggta gaggctggca aaatcgaaca  68220
cggccacggg gtcgttgtag taacccacct cgggctcaaa caccgtggca ccttggtacg  68280
aaaccgccgc ggtaccgccg gcgccgtgac tgtcgttgga aacgccgacg ccgccactac  68340
tgccggagcc gacgctgaaa acgccgacgc tgctactact gttactacca gagccgggtg  68400
aaacgccgtc ctgactcgac ggcgcagatt gcaagggcgg cgacatctga aacatagccg  68460
ccacagaacc cgcgtcgccg ggcacggcgg cggtagagat gatagcggcg ttaggtgaca  68520
```

-continued

```
cggcaacgct attcgtttcg ggcaccgtcg tacctttgct gtagtggttg ggcaagataa  68580
aatcgcggca ggcgcactcg tctagcagcg aggtgtagat acggatctgc tgtccgtcaa  68640
agatgacacg ccgcaacgga attttagcca gccgcgcgat ggccccggcc tcgtagtgaa  68700
aattaatggt gttgaacaga tcgcgcacca atacggcgtc ctgcagacag taacggccta  68760
cctgggcgcg gccctcggca ttagccacga aacaacgcgg gatgtccttg taggacaggt  68820
catccttgcg ttgccgcagg taaagctcgg ccatagtgtt gagcttatag ttgggcgagt  68880
tagtcttggc catgcatacg gggtacatgt cgataaccac cgaacccgca atatacacct  68940
tggtggcggc cgtgctggcc ggattattgt gagaagccga gggaaaggcg gcggcgtact  69000
gccgcttaaa acccacggcg gggctgtgta aaaaaaaacg gccgccctgc gccgtgggca  69060
acttgcagaa gcgctgcgag tccaccttat acaggtactc gaggcgcgtg aggatgtact  69120
tcaagtcaaa agagttgatg ttgtaaccgg tcacaaaggc cggcgcgtac cgttgaaaga  69180
aaagcataaa gcccagcagc agctcgtatt cggaagggaa ctcgtagacg tctacgtctg  69240
ggcccacctg cccgcaggtg ccgatcgtaa agagatgaag acccgagtgc ccaaagatca  69300
cgccctccga ggtgcagccc cgaccatcgt tcccgtttgg gattccctga tccacggcgg  69360
tgtttcctcc cgtctcgtag cacacgcacg agatctgaat gacaatgtca tcagacttct  69420
cggcgcaggg aaaaccaccc tcgccgctca tgcactcgat atcgaaggac aggcaccgat  69480
aacgcggcca cgagctgtcg tcgggcacgg ccaccaggtc ggagacatcg cagtcgacct  69540
cgatatcaca agtcgacgcg cgaccctgct gccgccagtc gtaacgattc acggaacacc  69600
agccgaacgt ggtgatccgc cgatcgatga ccaaacgcgt cagcggatcc acacggacct  69660
cgtacacggg aaaaccctgc tccagcagat actcgccgat ctttctagcc atggtccagt  69720
tgctgataga cacacactgc aaatcgggca cgggtcgcgt cccgtacccg tagatggagg  69780
tcttggtggc cggcgtgaca gacacggcgt atggcgtccg cggttcgggc actagttcgc  69840
ccacgctggc aatgacctca cgcagcctat cggtgtcgct gtactcacag taaaagtagc  69900
tgcgctgccc gaaaacgttg acgcagatac tgtagccgtg ttctgtggcc ccgaagaaac  69960
gcaacacgtt ccccgaaggc accagatgct gacgatagcg cggcgacacg ttttcgggcg  70020
agtcgaagaa gagcacggcg tccgtttgat cgtaggtgtg aaaacgaata ggtcccacca  70080
cgcgacccac cagggtctcg cgccaaggac acggccaaac catgtcatga ctcaacaaat  70140
gtttaatctc tcgatagaac atgagaggca accgtcccgt cttatgcttg atcaaccccg  70200
tctgaccgtc gaacatgacg cctcgcggca cgatctgcaa aaactgtttc tgtggcggcc  70260
gcttgcccga gccctgcgcg gagccgggct gcgaacgctg acgccggcca cccgcaaccg  70320
caccgccggt cacgccgccg ctcagatacg ggttgaaaaa catagcggac cgtgagaggc  70380
tgacagctta cgaagcaaaa tcacaaagca aatacacatg cagcacctag atgtccagtt  70440
taaccccgta tatcacaagt ctctgtcact ttttttgtct agtttttttt tctcctcttg  70500
gttcagacgt tctcttcttc gtcggagtct ttcaagtgtc ggtagccgtt tttgcggtgt  70560
cgcagtcggt ctagcaggtt gggcttctgt cccttgtcct gcgtgccagt ctgtccgtcc  70620
aaagaatctg taccgttctg ctgcgctcgc tgctctgcgt ccagacggac cagggccaga  70680
agcatctggt aagcctgctc gttggtgtaa ggcggagccg ccgtggatgc atcagacgac  70740
ggtggtcccg gtcctttgcg accagaatta taaacacttt cctcgtagga aggcggagcc  70800
tgtaacgacg tgtctttggt gttgcccgac gtcacggtgg tcccgtcggc ggacaccaga  70860
tagggaaaga ggttctgcag cggctgcatg cagagacgcc gctgtcgagt atagatcaaa  70920
```

-continued

```
taaatgataa tgacgacggc tatggccacg aggatgatgg tgaaggctcc gaaggggttt  70980
ttgaggaagg tggcaacgcc ttcgaccacg gaggccaccg cgccacccac ggccccaatg  71040
gctacgccaa cggcctttcc cgcggcgccc aggccgctca tgaggtcgtc cagacccttg  71100
aggtagggcg gcagcgggtc gactaccttg tcctccacgt actttacccg ctgcttatac  71160
gaattgaact cgcgcatgat ctcctcgaga tcaaaaacgt tgctggaacg caattctttc  71220
tgcgagtaaa gttccagtac cctgaagtcg gtgttttcca gcgggtcgat gtctagggcg  71280
atcatgctgt cgacggtgga gatgctgctg aggtcaatca tgcgtttgaa gaggtagtcc  71340
acgtactcgt aggccgagtt gccggcgatg aagatcttga ggctgggaag ctgacattcc  71400
tcagtgcggt ggttgcccaa caggatttcg ttatcctcgc ccagttgacc gtactgcacg  71460
tacgagctgt tggcgaaatt aaagatgacc actggtcgtg agtagcagcg tcctggcgat  71520
tccttcacat tcatatcacg cagcaccttg acgctggttt ggttaatggt cacgcagctg  71580
gccagaccca ggacatcacc catgaaacgc gcggcaatcg gtttgttgta gatggccgag  71640
agaatagctg acgggttgat cttgctaagt tccttgaaga cctctagggt gcgccgttga  71700
tccacacacc aggcttctgc gatttgcgcc agcgcccggt tgatgtaacc gcgcaacgtg  71760
tcataggtga actgcagctg ggcgtagacc agattgtgca ccgactccat gttggataaa  71820
tgagttgcat tgttgccatc tgtacttctt ttggttctat tatgagtaag attcagactg  71880
gagcggttgg ccaaacgttc gagttccacc agagattttt gcttgatacc ttgccagaac  71940
accaccaaac caccagtggt ttcaaagacg gacacgtttc catatttttc atatgtttga  72000
ttgtatgaag tattgaaaat ctgctgtaac ttatttatgg cctcatcacg tacacagtcc  72060
agcgcagagt cggacatgtt cacctcttgc ttcttagata agaaagtggc ggtcattttg  72120
gcagaagaaa agtgatacga gtcctcggct tcggaacgaa tggtgcgttc cgaggcttcc  72180
cagaaagtga gttgacaagt aacattcttc tcgtcctgta tatcccagga gatcactgag  72240
tccgcacgtt caagaaaagc caccaacctg tgggtctcta acgcagaatt cggtcttcca  72300
aagtcggaga cgatagtgta gttcggaaaa atgaaaaact tgtcggcgtt ttctccaaaa  72360
tagctggcat tgcgattagt tccgttgtag aaaggagaaa tgtcaaccac atcacccgtg  72420
gaagttgcga aaaaatgata gggatacttg gagcgcgcag tagtgatggt caccatacaa  72480
ttcagattac aggtctcacg atagagccag gtgctgccgc ggctgtgcca ttgatccttg  72540
accgtcacgt aacgggtact gtgggtgttg gaataatcgt cgggcattaa ttgcatggtt  72600
ttgttttcat agctgtccct atgataagcc acgaaaaccg tgcctgctat aacgcggctg  72660
taggaactgt agcactgact gtgactgttg atatgatgaa tctcccacat aggaggcgcc  72720
acgtattccg tgttgctgcc cagcagataa gtggtgtgga tgtaagcgta gctacgacga  72780
aacgtcaaaa ccttctggta gactcgtacc ttaaaggtgt gcgcgacgat gttgcgtttg  72840
tagaccacca tgatgccctc gtccaggtct tcattgatgg gcttcatcga ggtgcagacg  72900
atattacgtt caaagcgaat aagatccgta ccctgtgcca tagaacacac gcgatagggg  72960
tacttggtgg tgttgacccc caccacatct ccgtacttga gggtagtgtt gtagatggtc  73020
tcgttaacac catggctgac cgtttgggaa gaagttacgc gttgagagac tgaaccggat  73080
cgagaatgag cagcagacgt cgtatgagag gaatggtgac tgtgagtagc agaagttcca  73140
cgagtagaag atgaggaaac cgcagcaccc agacagacga tacacaagtt aacgcagact  73200
accaggcacc agatcctgga ttccatgttc gtcgcgggcc aaatccagca gcgatgaggc  73260
```

-continued

```
gcgtcgtggt ctcttgcgtg ttgcgcggac cctccgggaa acgcccgcgg tcgaggagga  73320
ggggtacgga cttggcagcc aaggtcggtc cggctccctg aaggcacccg agacggccgc  73380
ggcggccgtc agggtggagg gcttggccgc gggagctgtt ggcacgtcgc cactctcatc  73440
cggtctggac agatgcctgt agaggaggag atatagatct ttggacttat aaagacttcc  73500
ttcgtgacga agcagcagcg gccactcttt gttatacgtg agaatcacat ctctgtccgg  73560
gtgcagttcg tcgcgcaggc acgcgatcga gagttgtttc ccgaaagttt cattatatag  73620
tgcgacggag agcacgagct cccgcacgtg catccacatc tccttctgca gcacgtttag  73680
atcctgacag tccgaaaaat tgaaaaaacc catgtacttc accaccatcc actcactggg  73740
atacacggta ccttccgcgc atttgaccaa atcgtccttg acgtggggta gtacgcccgc  73800
gttgtcgcag gcataggcca tgtccacatt gtgagagagg ggatagcgat cggtgcagtg  73860
tgtgaagagg ggcccgttac acaactcgta gatctgctga cccagtagcg ggagggattc  73920
cacaggcaga ctcttgtgga tcaggttatt gaccacatac aggtgctcat cgtacgtgaa  73980
ctgatccccc acgtccacca cgtcttggtc ctggtggtat tggctgcggt atagaaaccc  74040
attcatgagc ttagagataa agtccagaca caagggcccc actaggttga catcgatgag  74100
tttgctagtc agacgctcct gcgttttgat gcaacggatc accttgccat agcccacctc  74160
cgaaaccttc tgcaggtagg cgcgtttgcg cacgttcacc tcgcgggtga cgttgtggat  74220
gcgggaacgc gcgtccacca agtcgagagc ctcgtgttcg tcgcagttgc gcacccgtaa  74280
gccgttctcg ctgccgtcgc cgtcctgccc attcgcccct cccccaccg ctttcttgcc  74340
tcctccacgg gcccggccgc cgccaccgtt attcctctga ctgtgagtac tgctgttgct  74400
gctgttgctg gccgtcatca aagtcgtacc cgtccccgac atcgcctccc gtccacgcag  74460
gtgaatagcc tcgccctcgg ggccgtcgcc ccccgtgcca tcgggcagcg gacgtcgaat  74520
ctcctcgaga atatgcttga ttttggtgta catctcgttg ctttcgtgga gcttgttgaa  74580
caccgggttg tcctcgaaag cttgaatgct gagggatgtg atgaggtcga tgatcctgtt  74640
gggggcggca aagaccgacc ccacgaacat gcgctcctcc ccgtccaacg cctttcccc  74700
gagcacgaag atgtcctcca cgtcctcccc gtacagatgg cgactgatgc cgttcatgag  74760
cgcccggcac agctggtgat acacatttag ctgctggatg gtgatgccca cccgcttgac  74820
gataacctcc gaggtacggg accagtaggt aaaatccgac aaggaatata ttcgttccgg  74880
tatatccgta aacaggttgt actccctcag cgcctcctcc gcctcctgga tgtagctgtg  74940
gtaggccgat gaagaagaga ataggctttt gagggccgaa aggactccag ccaagtgggg  75000
gatgcgcgtt gtcaggtcca gcaggtcctg ctccaccgtc tggatattca catcggactg  75060
gcttgacgga cggtggaccg ctatatggtt gcacagcaag ccctgcagcc gcttgttcaa  75120
cgagcggccc tgattcggga tgatggtcag ctcctcgtag cattgggcgc atgtcgtccc  75180
ttcgacgtac acttcctgac gcgccaccgg cgagatgccg cataggcgac ggagaagctc  75240
cagcagctgc gcgcagacct ccaggccggc ctccggcgcc aggatcccgt acacgtagtt  75300
catcttgcac aggaagcgct cgatgtcgtt gagtgtggcc agactgacgc tgaaacggac  75360
gttgtccgta aactggagct ccacggtgtg atggcgatcg cagcgatcca aacggaggac  75420
ggtacggtag aaggccgccc ggtccggctg gcgcgagtag gccatcagcg cccggtccag  75480
caaagccgta tcctcgtgca gcgccttcag cagcatctcc agatagagcg tcagcagcga  75540
actctgcgta cgattctgcg ccaccacctc cgggtagatc ttccggtaca gatacactat  75600
agccgccgcg tttctcttga acggcgtgga ctccgccagt aacacgttcg gatcgcagta  75660
```

-continued

```
ctttagacac tccagctcca tggcgtattc gttgcatttc gaacacacta cgcatagttt  75720
ctgtaacaaa ttcatctcca tgactcgact cgctcacgta cgagacgctg tcgtccggtc  75780
tggcgccggc cagagacatg gagtcggtgc acaaataact cgcgggccgc tcgctatgcc  75840
gactgacgtt gacgttaata tataacgacg tcgtcgacga cgcgggttct gctcccgacg  75900
ctgttgccgc cgcctgcggc gcaacctcct ccaccaccgc cgccgccggc tcctccgcct  75960
cgggcgacgg gggctcggag atgaccggct gtgtctgaca ctcctcccct tcctcaggcg  76020
gcccgggcgc cgacgcgaat gtcggagctt gccagcgcgg cggcggtctc tgtctctggt  76080
gccgcggcgc caaccttcgg ggctgttgct gctgctgatg atgcgacgcc gtctgtcgcc  76140
gctgttgcgg cggtagctga tacggtgtcg cctggtgctg ctgtgtcggt ggctgctgtt  76200
gttgctgctg ttgttgcggt ctgaaaagcg gccacggggg ctgcgactgt tgctgctgtt  76260
gttgcgatgc tcgtggctgc ggcggccgtt gtcgcggcgt ctgctggcgg ttacaaccgg  76320
ctgcgtttgg ccggcaataa cccgctgccc ccgccgcccc cgctgctccc gccgacgccg  76380
ccagcctcgt cttcgccggc gttcacgaga aagcagccac ctcccgtctc gccgggcacg  76440
ccgaagcaaa tggagttgcc cgtgacggac tcgccgagaa gaagaccgcc acccccgacg  76500
ccggacgccg cgccgacgcc actgggcgcg aagagcgccg acaggtcgtg cacctccccc  76560
ccagcggcgt ccgtcaatcg ctgggcgtcg gcgtccagca cgcgtcgcaa gttctccagc  76620
gaaaagtcct ccacgccctg ctcctgcaac gcggcaaact tgtccatcag cgacgcggcc  76680
agcgcctcgc agccatccac gaagaagagc acatcgtcgg acgcggggat ctcctcgcgc  76740
acgctcagaa tctcgtacac ggccattact tcggggtcgc aatccaagtt ctcggcgtcc  76800
agcgccagca tgacgcggtt ttttataaga tccgcgtcaa aaagcacgtt ctcgcggcgc  76860
gagcgtttaa tgagcacgtc ggccagacgc gtagccaaga ggtagcgctg gcgcatgaaa  76920
cgataatctt ggccgctcat agagctcacg ttaaggctgc gttccacacc gttgcccgaa  76980
aagtagccga tctgcccaaa ctgatagatc tccttgctgt tgttgatacc cgcatatttt  77040
tccacgctca cgggcacggt caccaaggaa cgatgctcaa aaacgctccg tactaacgat  77100
tcacgcgcca cagtggcggc catgggcgcc ggcacgcctg cggtcttcaa gcccttgaca  77160
tgcaacgcaa attcggcggg cgacgagaaa cgcggactag cacctaacac gtgaggaaac  77220
tgcgcgtggt tctgcgtcgt taagcgcgtc gttaacccgt gcagcgagcc gatgtagtct  77280
ttgaagccgt agtagcagag gaatttgtta tggaaacggc tttccacgta actcagcaca  77340
cagtctggcg ccacatccag cagatcgtgc tcctgatagt cagccgtcac agccaccaga  77400
aatttgacga aagcattgaa ctcgcccatg tcacctatgg gcacattctt gggcaacgcg  77460
ttggaacaga ccttctgcca aaactgtaag caggggagac cacattcagg aaagagtcgc  77520
tcgtgatgtc gatacagcag aaatcccaag cagcccttag ccggattacg acgcggaacg  77580
tgatcgcggc gaaaaaacac gctacccgcg ttgcccttgc ccgcgcggta gatgggtcgg  77640
tttttcaccc gcaccatgat caacgtgggt accgacagcc gcgagagctt gatctccatg  77700
ggcaccacgg cgtacgtgcc ctgcgcgtac agcctaaagt ccagcaggcg gtcgtgatcc  77760
gaattcttgg acgacttgat ctgcttggtg aagagaaagc ccttgcgcga cgacgtggta  77820
gagaacgcgc cgtggatgga ttgaaagtgc tgcgtcatcc atttggatac caagttggtg  77880
gtcaacggat tgtccacaat gtacgaggta gcggtaataa gcgccacgtt ctggatcacg  77940
taaaagacgg atctgaaata ggcgtaggcc agcagcggct ggaaggccac ggcgtaggga  78000
```

-continued

```
ttcagatcca ggttgaaggc ctgcgtggcg cccgccacct cgtcgcggct gctcttgagg  78060
cgcacctccg aaacgaaacc cagggcctcg tcgtccacaa acttgttgag cgccgaaaag  78120
acggccacaa agtcgctttt gccgtgcgcg ctaaaggtat cctcgcccgt cacggggtcg  78180
atgagccgca tcttgcggca gtaatccaag atgcgattga gccgataggt acggtccacg  78240
ctagcgccca gcatgcgacc gccgcgcccc atcattcccc cggaatcccc gccaccccca  78300
ccaccacgac cgccgcccag accgtcgctc gggcccccgc tcacgtctcg tccaccaccc  78360
ccgccagcac cgccgcccgg agccccgtcg tcacctttgc cgtccaaacc cccgtccttg  78420
gcgtcgacgt tgtaacgccg accgaagctg cccaaaatat ccacgtcgtt gagaaaacgc  78480
gactgcacgg tgatcacgca gggctccttc ttgggctgct tgggcaccac gggcaagcgg  78540
gtgcgcaccc gcacgaaggc cgtctgataa cacgtgtggc aacaagtacc cccacaggcc  78600
tcgcacaacc ccgcggcgca gcccaccagg tgattcgtga gcgtcgacga acccgacaag  78660
cccgtgttat acaccgagac acgatttaga taccagacga agcccgaaac tagctgcgga  78720
cacgtgccac acaccaacgc caaatgctgc ggcccatagc gttcgtcctt gagcggcgcg  78780
ccttgaaact tgagcacctt gcgcgcgtcg ttgtagacgt cttcgcaggc cgccgacaac  78840
ccgttggtga actgaatagc cttgagcaac gtctcctgac tggccgtacc gccggcgctg  78900
ggatgccgcg ccgacgactg gagatacacc agcctgtgct ggtagagcac cgaattagcg  78960
ctgaagacca aggcggccac gtgcgtcgag agatgcaact tgagctcggt cagcgcgcgg  79020
atcagatcgc ggtgatcggt tgcgttggtc actaaaggcc actcggaaaa gagcatagac  79080
tcggcaggtt ggtaggccga atcgaaaaat accgaggcaa aactgaaggc caactcgcaa  79140
accaccgcgt cactcagcat cagatgatcc ttttccagac tgctgagtcg ctggctcatg  79200
taccccaagt agcgcttatg tggcgccagc ttcaccgact gctgactgtc gtgcacaaac  79260
tgccgcaacg ccgcctcgat cagcacacgc ggctccgaga agcgcagcga ttgacaccat  79320
gacgtgtaca cgtagtagaa aagcgtctcg cttacggccg gcacgtagag ccctcgcgcc  79380
tccacaaaag cgctgcgcgc atccagcgag acctcgtcgg cttcggcgtc aagctgcagc  79440
gaattaaaga gcgtaggcgg gtacaacggc acgcgcaccg cctcgccgcc gtgcagtcgc  79500
accgtggtcg cctcctccac gcatggaatc agctgaccgg caaagagaaa ctccttcaag  79560
ccgttgccca ccaccacgtg cacagtcgtc tcggacgcct gacagcccac cgccgcgcac  79620
aacgccgcca gatcggtagg cacgcgatcc gcctcgggcg tgtaggcctc caacgcgtac  79680
ttctggcggg cgtcctcgca cagccgatgc acgtctccgt gatcctcggt aaaagccacg  79740
atgccttgcg tatgatgaaa gtagagcgca aaaggacaga aggacgtgac tttcgtgagc  79800
accccgccgt cgtaacaaag cacaggcgta cgcacagaga cgccgaaatc cgcctccacc  79860
gtgagccccg ccaacagagg agcgatcacc acgctcgagg aacggtcgca taacgagaga  79920
gtggccagaa tctcctgcgt ttctgcgttc aacctgctga agtagagaaa agccgcgggc  79980
cccaccggcg ctagcgcggt tagttcctcg tggctcatgg tggatgaacg gaagacaatg  80040
gctacgccgc cactgagtga attttatacc aaggaaaagt tcagcacgtc atgtttgacg  80100
cacgacgtct gagacaccac cgtggccacc actgcggtct ggctgcggtt gcggaccacc  80160
aaaggcgaca accgcaacga tcccagcaat tcgtaagaaa agctaaccgc tacggtcggg  80220
tagcctctcg cagccagacc gctagccgac gcacccgccc gcgaaaatag cgtgatgttc  80280
gggacggctt tgcgtcaccg ccaactaacg tcggtagtcg agcacgtcgt ttatcctcag  80340
cacaccgtcc gatcacaatc cgttttccca ctcagtcgca caagcagcac ataaaaaccc  80400
```

-continued

```
cacacagggc acgtgaaaac accgtcccta gaaaacggtg ttttctgtcc taccgtcacc  80460
ggtatacaca ggcaaatccc aagcccgatc cccgaaaaca ccgtacggtg tttgtgacct  80520
ccaaaatcac atcagctaac aaaccgtgaa aagtcacgtt tcacgaacac ggtgttttta  80580
aatcacaaag aaccgcctga cggtttacaa gcagaaacac cgcaccacgg tggtacaagc  80640
gcgatgaatc tggtctcgca acctcaatcg ccgctatcac caccgatttt cgctgcgctc  80700
cgccgacaaa acgccgtaca agctacacac cccaaaaacc cgcgcgccta cgggcgccaa  80760
acctgtgtat tatcccaacg tcacaacacg acacaaaccg cgtaacgtgg tttcccgaac  80820
acgtacgcgg cacagacccc cgacacgtac tcgaagacct tacagtttac gagtcaataa  80880
aacaggaaaa gatccgaact ttaaaattgt gtatttttat tttcccatcc ccctcttttt  80940
accaaaaaac acatttttcg tcttgtaaaa agtaactttc gcccattgcc atgaaacacc  81000
gtgatgggga acggtgttgt gtgtcgactg acgtcactac ggcgatcagt atcgacgtcg  81060
tgtatacata acggtgcccg gtgtttttat tcggggcgtt gtcgcgtctt gatgtaatgt  81120
aacctgaaac cgccgtgccc aagaatgcgg aagccagcgt gtactcataa cggggttttg  81180
ggtacaatct gacgacatct ggcggcgagc gtacaccatc gaatgtggcg atcgccggct  81240
ctacgtcaca atgacgcaaa aacacactgt aaaacccgcg tagacagctt tcctggtcaa  81300
cgagcgccat ctggtgtcgg cataagaaca ggaatcaacc ccgtggccgg cgaggcggtg  81360
agcacttttc ctggtcacgt gaccatcagc gcaggaagcg aggcccgtag aaccgcccaa  81420
gaggcggtgc cagatgccaa cgtcataatc acaaggtgat ttgttacgtc acgcgtgtgc  81480
gcacgcacgc gcgcacgcgc gcggtagaat acagcgatcc ctagtgaagc cacacccatt  81540
acgtgtagcc atatccgctt acgtatacag ccacacccct aggtacgcca ccttatctac  81600
caatcacaga aacggatata caatgacccc tccctagact ccaccccttg tacggaaatt  81660
tcagataggt ggaacccgtt agggttccac cgtcctcggt gtacgtacag gcttctccgt  81720
ctaccggaaa tatacacctg ctgacgtaga cgctactccc ggatacgcgt cataagctac  81780
tggaccctag ggggggagtg tctacagggc tacgtgcacg ccccccttacc tagggtatcc  81840
gccccccttcc tctgttttga cctagtaaac ttaacgccgc cgcttctcac gtgacccctg  81900
acaagcctac gtcacactcg tcgtaaccac acccattccg gatatacgtc atcctgtgga  81960
attccggaca tacggtgacg tagcgagcgt agcgagctac gtcacgtatg cgtgcgtcac  82020
ctccggcgga aatcatctct gatgacgtag cgagcgaagc gagctacgtc atcagtccgt  82080
tctacgtata ccggatgcta ggcgacgccc cgtaggggcg gagcctagct tccacccccta  82140
ggatgcatac cctatatagc ataattcttc taacgaaacg ttctacgaaa acggactggc  82200
ggaacgggaa ccaccgtaac ccccccccct cacccccccc cttctcctcc ggaaccgggg  82260
ggggcaaatt tttaccaaat ttgggcaacc atgatttcca atgggacggc gtttccgtgc  82320
gcatgcgcag tcggggcgaa ttttcggtta ccagggcgtt accacgcgga ttatgggatg  82380
gggactcgag tgcgcatgcg ccggggatgc cgtatggaga gcctatatat aaagaggggt  82440
gaaccagggg ccccggtgcg catgcgcggg tcctggtccg cgggagggtc gtcctgcgca  82500
tgcgccggta aaattccact gggtgtgtgt cgtgcgcatg cgccagtatt tttccactgg  82560
aggcggtcag tgcgcatgcg tcggtaaatt tccattggat gcgcgtcgtg cgcatgcgcc  82620
ggtatttttc cactgggcgg ccgcacctag ggagcgcgag ccccgtgccg ggcatgggcc  82680
gcggcggtgg aaaattaccg ctccgcccac ctaggcgggg cctctgaaaa cctataaaac  82740
```

-continued

```
ccggcgtgcc cgtcgccccc cggcgcagtc cgcggcaggg ttccggccgt gctgcggtcc  82800
gcacgctgcg cccgctcccg cctgcctccc gccctacccc ccaccctccc cggccgaggc  82860
ccggcgccgg tccgtccgcg ggcccgtccc accgccctgg agcaccatcc ggggccgtgg  82920
gccgggcacc gggcgcggcc cgctccggac ctcggccggg ggtccctccc ctccccccgc  82980
tcgaccccc catccgacgg cccggccggg ctgggacccc cgcaccgggg tcccggttcc  83040
cgtccgtggc ccggggggac ccgagcgggg gcttcccacc cccaccccgc tcctccccgg  83100
gctccggccc gggatccctc gctgctcccg gcgacctccg ccggcttccc ggtccacccg  83160
ccgcggaatg gacgggaccc ggggtccgcg cccttcccct ccccccacgg ggggctgggt  83220
cgcggacccc ggttcctagg ctcgttccgc ggtgggcgac cggggatccc ccacccagct  83280
cccttcccg gcccgccttg ctggcttttg ggcccctgcg ggcttttttt ttccggctgg  83340
gggtcgcggc ggtcggccga cgttaaagct gattgatctc acggtggtgt ggacgggcga  83400
acccccggct cgacggcagt cggcccccgga gggttggggg ctgggggccc ggtcaggagc  83460
tccgggagcg gggtcgaccg cgacggcttc cgggtctcgc ggcggctccc tctcggcggc  83520
tccggttggg ctcccctccc ccctctcgag ggtccggtcg ccggttgtgg tcgggggtcc  83580
ctcggcctag ccgccggctc tcggtccgcc ttaccctggg cgttggccgg tcccgtgacg  83640
ctcccctccc ccgctgctcc ccaaaaactc cgcccgaacc gtcgcggttt gctggccctg  83700
ggcgtggtct ccccactccc ctccccccat cggccgccca gccggggtcg gcgcctcgga  83760
ccccaccagg ctgtggcgtg tgtgctggcc gatgcggcgg cgaggttggg tgtggccgga  83820
agcgctcggg gtcgacggtg ggccgccatg acacctcaat tgccgtcagt acgcccctcc  83880
acaatcaccg tccccacacg atgggcccgg cagttcaccc aacgttggtt caggcccagt  83940
cgggtttttc cccggtacga acgcacgtcc ccgtgggctc cacgcgtttt ccaccctttc  84000
ctggaggggt ccggaacacc gtgaatccac ggggagggtc ccggcacggg ccgaggagac  84060
cacgaccgtc ccacccggcg tgtcgactcg tccgagaccc gggaagggaa caggccccac  84120
cttttttccc ttctccgatt tgccgtggaa aacccgtgaa ccgatacggg tgcagacggc  84180
cgaaaaaatt cgagacggca atacgacggc agggcgtgat tttctccccc acccgacaaa  84240
accgtgtccc tcaaaattcc ccacctttct ctgttcaaat ggccccgaaa ctgtaaaaca  84300
ccgtttgacc gcaccccaac cggcgccatc ttggtgacct tctcgacggt tctctcgctc  84360
gtcatgccgt tctgagctcc gacatggcgg acgagagaaa atggcgtcga gagccgagga  84420
gcgttttcgc tccaggcggg taaaaaaata gcacgataac ttttctgtgc tttttttgaga  84480
cgtttttgaa gagctttttt tctgctcaga gcgaaaaaat gatagccctg aaaatctcga  84540
cgagtctggc cgagcggcgc catcttggag gaggggcgag tcgcgggcac cgcctcggta  84600
ccccctggcc gaggcgagtc cgcggtcgcc gcctgttccg tgatgctacc tagagggcgc  84660
cgtcgaggcg actcttcctg ttttcgccct gagggctaac ggtcgctgac gtcaaaccat  84720
ctcgtgctcg ctgagtcaca tccggttgtt gacaagcgat ggaggaccgc acccaaagtg  84780
cgccctctag tcatcgcgcc tgaccccttt tataaactgc tcgaagaaaa gaacacctta  84840
tgtgaaaaaa tacagaatga tgacaagttc attcaacaca accgctcaac aacgccatat  84900
ctatcagtgt ccaaaaacta tcttctatcc tttgaaacta taaatgctgc ctatatacat  84960
atttagtatc caagactctt accacgtaga cgaaaagaag tgatacaatg atcttgacgt  85020
gtatcgtcta tatcgtgcta gatatattca gataagacgc gcaaaccata gatttctcat  85080
cagtatcatg aaagacctat agctctatat acgaacctag tcattttagg acagccgccg  85140
```

-continued

```
gagaagccga cgagggatcg ggcgggtgca gccagaacct cacgcccgat cccgcctccg  85200
gtaggcgatt tgcatctgtt tggtaaaaag ctcataagtc tgtatgtgac ctatatatat  85260
attatacgct atgtacaccg aactgtcgct gttgtataag aagaaaaaac tctccatatt  85320
tatatcgtct gaatttttgc ttgatagaca cgtgtttgga actctgtccc cccacgtttt  85380
cactgtgtat aacaaaaata tgtgtttctc aaaagatctt gaggtgtttg aaaacggggg  85440
aaacctgcgt ttgggtgcgc taagccccgg actgggacgt agccggcgtc cggcacctat  85500
atttttctat ttttttttta caaaatatat gatgaaccaa gaataaaact ctagctctcg  85560
tctattttta atatgctcta cttagaacct ttttaatgac agaatgaact ccatgttata  85620
cgctctttat atagtttctc tgcactaacc tttaaaaccg tatccttccc tgttgtacaa  85680
atcatctttt gatacacaat gatgacctga tatccctcca tatatatgat cggatattat  85740
tccgttagac ttgtcctcct tttttttcct catctcctgt atctggagat atatgttgac  85800
caccaccgcc atgaccacca aaaagctagc cgtcacgact agaaatgtgt aggattcgga  85860
ctttccgttt gagaagaaag agaccgcgtc tctggacgct ctttttgtcg gtctgaatcg  85920
acccgggata cgtaagagag cggccctaca tcggggggcg ctcgagaccg acgacgttcc  85980
atctgaccag aaaaaaaaag gcacccctcg gtggcgacct ctcaccatcg tttgcccgtc  86040
cgcccgtcct tcgtagccat catcatcatc tcaggctcta tcggtaccat cgttgtcatc  86100
tgaaaaaaaa aactgcctca cccacctgcg taaaaacacc atctttccgg aggtgcggta  86160
agacgggcaa atacggtcgt gccgaggcaa aaaaacgcac catcgacacc acaccctcat  86220
gagcaccacc tgtcggtgtt ggtcgtcctc catcgttctc tacgaacatc tcgacgcccg  86280
ggtgacggac gacggcaaga cgtcccggag aagacggtgt tctctcgggc ggtacgctct  86340
ctggatctat aatatctata gtagctaaac gagactgtga gtacgacgaa ccacatcatc  86400
tttttttat gttgcttctt tagaaaatga cttatgtcga cgacactcgg catcagccat  86460
ctcgtgaaac acgctcgctt ttcgtctctc caaggaacac tgggtccgct gaaagggacc  86520
gtgtaccgac caaagcaaaa aacacacacg tagtaacatg atcaaccacg tctgaatgac  86580
acgaaaacac aatcgtataa cgctctattc atggaacgaa cttggaataa aaaaaccatc  86640
gcaggccaga ggctaagccg aaaccgtccg gggaagcggg cgcgagtttt ccgacttagt  86700
ctctggtgct cgttgagcct cttttttttt tcctgattct ctgaagaatc accgtcacag  86760
ccctatgacg cgaaatcaat tgctagaaca taaacgttct caacaggtat gaaatgaaca  86820
aactagatga tgctataacc ttatattgtg tgtatataga taggtgtgaa atttgtagga  86880
taaaaagtgt cgttgtatga tgcacaacga tcgtgaaact ggagactgta gctctctacc  86940
gaatgcaaat acacaaatga catcgattcc cgtccccaca taaagaaatg tgctttactg  87000
tgaaagaatg aagaagattc ttgttcctcg tacgacgggg ccctcgctcg tcgtgcctct  87060
tccccccctcc gggagagggg acgtcggggc cctccgtcgc accgggccga agccagtgaa  87120
atgtttacta cactgtcatc agaatatatg atgtatatta tttcctccaa actcctcacc  87180
atagccacca attcgcatca cttaagaaag tagtagcaac cgcggcggcg gcgaccggcc  87240
ggtcgtcgtc tcctcgtcct caaatgttgt acatgtgcag aaaaatgtgt aaatacgtgt  87300
tatttatccc atgcgtcttg tacatagata tatgttttta tatacgctat ttatacttta  87360
tatatccttt tgcataacca tagacagtca aggattttaa tgatttgctc atccgccttt  87420
gagccatcgc ttaggagtta gttcctctat gttctcggcc caccttttcg actacagtag  87480
```

-continued

```
caaacccttg tactaccacc ccgataaaaa ccacatcatc atcgtcacca cgacctggaa  87540
acgacacacg ttcccccca atcttgggca tgtgtatata taaaaagaat gggagggaga  87600
ggacgtgggg ctcgagaaga aataaacgcc aagctcgatt cgaaccaaaa aaccacatgt  87660
gtattgtgct ttttttttt tttacggtgg gggaaaagga gggggccgtc attaacggaa  87720
accgtgtatg gggtccggac acgaacagta cacagcttat ggggaaaaaa gctcacagag  87780
agaaaaaaac accaagctca ggcacgcgta catcattatc atcatcggat atctcaccac  87840
gggtcatagt agtaccaagg agtgtgtaac accatttttt cttttctttg taacgggata  87900
agggacagca atcatcacgc acaacaccct tcactctctt tttagtcatc catatcatcg  87960
ctgtaacaca gcatgtcctc gtaatcgggc gtctggcagc gcattaccac cgagtcgtct  88020
tcttgcggta ccggtggtgg tggcggcggc ggctgctgct gctgggttgc cgtcgtactg  88080
tgattaccgt tggcggactg cacagggatg atgggctgct tgtggggaac ctggggtgga  88140
ctgccgccgt gagaaggcga cggcgtcatc aagttaagat caccacggtg actccggaca  88200
ccggcgaggg gcgccggggg actgggaggg accgcggtcg tcttgtagac gacggtgtcc  88260
ccgtgtcgat ccgtggctcg taccagatct tgactgctag cgtcgtcact gtcttcgtcc  88320
tcttccagct cgccctcaga gtagtgctgc tgtggttgcg acggtggctg ggcgggagga  88380
gcggcggcgg cgatcattgg agagggatgt cgatgactcc cttctctgtc tttttatcg  88440
taggctgtca gcgttgctgg gtccgtcctg ctttccatat ttgtgtattg ctcatcggtg  88500
ggatgaattt ggtctcctcc ccgctgttgt ccgccggcag tggcatggtt gctggcggtt  88560
gtcgttgtcg taccggcaaa gacggtgaga tccaatagcg actgctcgtc gaagggacag  88620
tacgctatca tgaaacgata gggtgccaac gcgcgttgga tgcgcagttc gcacatctcg  88680
ttctgacact cgtggcactg cagggcgcct aggatcaggt ccgagacagc gccgcagcgg  88740
taggtaccca tggcgttgtt agtatcgaac tggtcaaaaa attggggcgt accggtgact  88800
tgcaacgcgc gacggcgtag cgagacggcc acgcgcgaga aagagcacac gtaggccatg  88860
gcgcggtgca tgggttgcga gaaggtctcg ggcggacgct tctgcagatc gcagacgtcg  88920
tcgcgtagcc aggcgctcat ttgaccgggc ttcttgacta accgtttgag cgtgctgcaa  88980
tggtcgcccc agccgtcctg gtggtccagg atgcagccca ggtccaggtt gttgagtttg  89040
ttgaagagca gctgacgcat gccgcccacc gtctccagat agggatcgtg cgggttgacg  89100
ggtagcccgt gcaggtggtg gtacttcatg tagctgagcg tttcgtcgat gatggccagc  89160
aatgtgtgta agttgggagc gttgtacacg gcgaagatct tttccaccac cagcttgcgc  89220
agcaacggtt cctccagcca atcgaactgt tgacggatgt gcaacaggta gtcggtgtgc  89280
atgagctcgt cgtgtgacag caggatgcga ccgcgcggct gatgatcttg cgggaaggcg  89340
gtggggacct tgagatcggc ggggtagggt gccagacgta gactctcggc cgtgtagcgc  89400
tgaaggtcgt agacgggcga ggtagaactc ggtgaggtac ccgacgaggc ggcgccgcgc  89460
tgcagacgcg ctcttttttt cttttcgatc aaacggctga gttgctgtag ttcgtcctcg  89520
tccatggcgt ccagttcgtc gtcaataagc gccagcatct gttgttgttg cggtccggcg  89580
gacgatccgt gatgattatt ggctgaggag gggtgagaag aaccgaaagt cgtaggacaa  89640
ctgggaactc ggcgacgaag atgcgtcgaa tcgccgccgt gatggtgcgg ttcgccgtca  89700
tcgttgtcgt aagacttacc gtagtggggg ttaaggggca ccgaggcgga cgcggccacg  89760
cgtcgcttga aagaggagga cgccctatgt ccgccacgga agcccgcggt gcccatgatg  89820
atgtgtccgc cggtgccccc gagtgcgtgg cgggaggagg gtggaagggg aggaggatag  89880
```

-continued

```
tggtccggat cgccttcggt atcatcgtct ttgctgtagc ggggtcgtcg tgcggggacg  89940
cagggtcggt gatgatgcga ggcggcgccg acggtatctt ccgcgagatg gtattcgctg  90000
gcggctgctc cgttccgtgt cgacggcgag gttggacttc gctcgcgtcg gaacttccgt  90060
ggcacgggtt cgtaatccag acagaagcgc cgtgcgcgac gggcgcggcg ttcgcgctcg  90120
ctcagggaag ataacgacgg agcgtcgtga cggccgcgtg agtgcagctc catggccgtc  90180
gtcgctagga aggtcacgtt cgggcacgct gatgtatata tagatgagac cgctgccggg  90240
gggcgggtca ccggcgccgt ggaaagtgag gctcagacgg cggtcgccgg cggcatgggc  90300
gcgtcgggcg gtctgatttt gatggaaatg tggacgtttt tggcgttgga gtgacacttt  90360
ttggtgaaac agcggctcca gaggctggcc cagagcgcgt agctgtgctc ggtgcgcagg  90420
tcgatgaaca cctgcacggt ctcttgcggg ttgcggtgcg tgtagttgag acagcgaaaa  90480
tcccgcgtgc gcgcgccgtc gcgccgcttg acggccacgc agcaggcgcc gtggggctga  90540
aagaggagga cgtggggcgc ggtaaactgc tcgctgacgt gcggttcgta gtgttgcgtg  90600
aggtgctcga gcagcggcgg ccacacgcgg gtgacgacga gccgctgcaa gtccgtgtcg  90660
gaaatcgcag cggcagtggc gccgtcgcca ccgtacaggt gataggcgag cacctcggtg  90720
agaccgcggc gtcgataacg cgtcacgtta agcgagcgcg tttcgatgaa gttggcttcg  90780
gtcgaggggc agattttgtc gcgcacgctg agaatgacgc gcggcggcgg cgacaggggc  90840
aacgcgggca ggtcgtgcgg cgggtggtgg tgaagcaggt tacgcaggtc cagttgggcg  90900
cgcacaaagc ctagcgggtg ttcgcggtag gcgtcgggca cgatgaacag cggcaacaga  90960
cggcgatgca tgaaatagcc gtcgtcttgg tccattttat acatgtaggg cagacgtaca  91020
gagcgtccat ggtggtagat gcctgtgtct aggctgctct cgggatgcga gatggggtcc  91080
agcagcgtgt gcagttcggc gtcgagacag acggcgtgat tgagcacctg cgccacggcg  91140
cgtaaaacgc tggggtgtac ggcgacggtg caggcgggga acggcgtgat gatgcgcagc  91200
cccagtttgc ccttgcagcg gcagtaaggg ggtgacgtgt caacggagga cgttgttttt  91260
tgaaaaacgc cgttatccgg gacgttattt ttattctctt tcccgtcttc gtcttcctct  91320
gtgtcgcgct cgtcccggta atcgagatag tcgtcgtcat cgaaaggcgc gccggccgcg  91380
tctacgggca cgctgttggg tgggcacgcg cttttgaaga aatagaccgg gtgccggtcg  91440
gggtgcgtgt agccaaagag gctcgcccat acggtcatcc agacgcgtcg tagtccgcga  91500
cataactcaa agacggtgtg tcgcgccaga ccggagacgc cgtcgcgcag ccgtaaatca  91560
aagtcggcca caaaattgaa gacgggcaga cgttcgttga agacttcgtg tcgcgtgtag  91620
tagaactgtg tctcggggct ggtgctggcc acgtcgtcgt cgtgtagcca cacggtctcg  91680
gtcagggcct catccgagaa acggctgtcg ggtacgtgac ggagcaggtc gcgcggaaag  91740
aggctgcgat gccaggtttc ggaggccacg gcgcagaaga cgtgctggtc attgggcagg  91800
tgtacgcggt agacgggcag cggtcgctcc agcagcggtg ccagcgcggg ctcgggtagc  91860
aggtagcgac gttgcgagta acgcgttagc gtgccggtgg tgtaggtctg ggctgtgcgt  91920
agcgaggcgc atagacgtaa caaaccggac agggagcgtt ccagcgggga gaagacagac  91980
tcggaaagcg tgttgatgcg ttcgagctgg cgcgccagct gcgtggaggt gccgaagaag  92040
cccgccaggt gcgtgccgtc gatgcggccg ccgtagccgg ccagccccag gccgtgcggg  92100
ctggtcgccg agtgggggga ttcgtcgagg cgcagtaggt gcgtctccac gtagtcgtgt  92160
agaaagttgt cgagcgagaa gtatttttgc atgacgtcca gcagctcggt ggaaagccgg  92220
```

-continued

```
cggcccagaa aacccggttc gcgcgtgcac tgcgcttcgg gcgccgcgtc agcgtcgtaa  92280
gccaccacgc gccggtactc gagcaaccgc gcgcgtgcca gcgccgtgcg gtaggccagg  92340
tagacgtagt gcacgcagac cgtgtcgggc agacgcgcac gttcgcggaa cgcgttgatc  92400
tgcgtgtcca cctgctctag ctcggtgtag tcgcggcggt tgcgcgccac ggcgtacgcc  92460
acgaaagcgg acacgcgctg acggaagggc gagcccagta gcagacgcgc gaactcgccc  92520
atggaggcgt gcgtggggat gatggtgccc aggtcgcgcg tgcagaagct gcgcacgtac  92580
tcctccacgg tggagatggt gctgtactgg ccctcgaata ggtagtaggc catggtcagc  92640
agcacctggc cctcggtgtg cccgaagacg ctgatgaacc acgagggcga ggtggggcag  92700
aggaagacct ggttgagatg acgtagcacg gccgcgtggt gaaagtacac caggtgcttg  92760
aattcgcgca cctcgccgcc gtgttcgggc gagagcacgg gcgtgcggaa gagatgccgg  92820
tagagcggct gcgtctcggc ctcgtccaga ctggcgataa gcgccgagag ggggatgggc  92880
tggcgcgcgg ccaggtagcg cgagagctgc agcgtttcgt tgttcacggc gaagacgggc  92940
gccacccgcc gcgagtccga gcacttttgt gtctgtaggc agaaataaac acgtcgcgag  93000
acctggtgtt tgaccagcag ggggaagacg cagtgatccg tcggtgtctg cgagagtacg  93060
ttggcgacta tatgagcaga atcatactct gttgcgaaca gaacgagcgt catcgtcgcg  93120
ccggcacgat gcagctagcc cagcgcctgt gcgagctgct gatgtgccgt cgcaaagccg  93180
cgcctgtggc cgattacgtg ctgctgcagc ctagcgagga cgtggagctg cgcgagctgc  93240
aggcgtttct ggacgagaac tttaagcagc tggagatcac cccggccgac ctgcgaacct  93300
tttctcgcga cacggacgtg gtgaaccacc tgctgaagct gctgccgctc tataggcaat  93360
gccagagcaa gtgcgcgttc ctcaagggct atctctcgga gggctgtttg cctcacacgc  93420
ggccggcggc cgaggtggag tgcaagaaat cgcagcgcat cctggaggcc ctggacattc  93480
tcatcctcaa actggtggtg ggcgagtttg ccatgtccga ggccgacagc ctggagatgt  93540
tgctggataa gttctccacg gatcaggcct cgctggtgga ggtgcagcgc gttatgggcc  93600
tggtggacat ggactgcgag aaaagcgcgt acatgctcga ggccggcgtg gctgcgacgg  93660
ttgcaccacc gacgccaccg gcggtcgttc agggggaaag cggcgtccgc gaggacgggg  93720
aaacggtcgc cgccgtgtcg gcctttgcct gtccctcggt ttcggactcg ctgatccccg  93780
aggaaacggg ggtcacgcgt cctatgatga gtttggctca cattaacacc gtctcctgtc  93840
ccaccgttat gaggttcgac cagcggctgc tggaagaggg cgacgaggag gatgaagtga  93900
ccgtaatgtc gccgtcaccc gagcccgtgc aacagcagcc gccggtcgag cccgtgcagc  93960
agcagcccca gggacgtggg tctcaccgtc ggcgctacaa ggagtcggcg ccgcaggaga  94020
cgctgcctac gaatcacgaa cgcgagattt tggatctcat gcgacacagc cccgacgtgc  94080
ctcgggaagc ggtgatgtca ccgaccatgg tcaccatacc tcctccccag ataccctttg  94140
tgggttccgc gcgtgaactc aggggcgtga agaaaaagaa acccacggcg gcggccttgc  94200
tgtcctccgt gtgaacagcc tggcacgttt tggaaaacgt acgtgatcac ggacacgacg  94260
agtacggggt ttctcataga cgtactttat taggtcaggg atgacgggga ggtttcgggc  94320
cgacgtcaaa aataacgtca ctcgtgttga cagggctttc tgcgtcggag ctcttttcat  94380
cttcttctgt ctcgtcgacg tcatcgtcta ccggcgaggg tgtccgttgc aacaacgcgt  94440
gctcgggcgt gtgggtgaaa ccgatgtcgg gggtgggcgg cacgatcatc tgtcctaggg  94500
ggtgactgcc caccggcaga taggtaaagc ggtgggtggt aaaaaccgct ttggctacgg  94560
tggtgtgtgg ggagatgcag acggtggtgt gcgaagtgtt gaccaccgtc acgccggccg  94620
```

-continued

```
cggtacccgg gagccagatg gtgggtcgga tgatgagatc cgactgacta aactggcgca  94680
cgcccactat gagggcgcag ataccgggcg cgtgcacgta ggccgcgtca aaatagacgg  94740
tttgcgtgtg acccggaccg atcaccagcg tctgacgggt acgtaatgaa aagaaacggt  94800
gttcgttggg cggcggcaag ttcatgagct gccaaggttc tggcacaaaa caggggaaaa  94860
cgccgatatc gccttcgatg gtgcctggaa agatggactg aaaagtgtcg ttgaggttga  94920
caacatccaa ctgcgggact tgcagcccgg attccagcag ctcgggcatg caaacgaatt  94980
gcgcgtccag gcatttgtaa aaggtaatgc cgaaaaaacc ttcggggata tagaggctga  95040
cgcccagcga ggtgggcact ttgcgctcgc gtgatagcca aatgatgtgt ttattgtaaa  95100
aggccagctg cgtgtggcat tgtttgacga tgaaactgga aggcatccac ttgtagggaa  95160
ctttgagcgg cgacggtaat ggcgacgacg cttcatcttc tcccggatgc tgctctttgt  95220
cgtatttctc ctcggtcgat tggggcagcg taaatgtggt ttgaaaatcg ctatcgctag  95280
cgaaacgtac gcagtaacgc atgttgacgg atttctcggc taggatgatg gagcctgatg  95340
acggtgcgga ctcttccttc attattaacg taggggtctc ccagaatcgc tgaaaacggg  95400
agcgcggcag ccgcgacagt accagttgag agtcgattcg atcggtaaac atcgtaagca  95460
tcgtggcggt ggtgtgatgg agtggaacac actagtacta ggtcttttgg ttttatcggt  95520
agcggcaagt tccaaccata cgtcgactgc tagcacaccg agtccctcta gctctactca  95580
cacctcaacg accgtgaagg caacgactac tgcgacaact agtacaacta cggtgacaag  95640
tacgacttca tcaacgacta gtaccaaacc cggttccacc actcacgacc ccaatgtgat  95700
gagaccacat gctcacaatg atttttacaa ggcgcattgt acatcgcata tgtatgaact  95760
ttctctgtcc agctttgcgg cctggtggac tatgcttaat gctctcattc tcatgggagt  95820
tttttgtatc gtactacgac attgctgttt ccagaacttt actgcaacca ccaccaaagg  95880
ctattgaggg tggacaggtt cacagcccgg cggtgttccg gcggggtaag gtttccatat  95940
gtggacgact gtaggctgaa gttacggatt tcacttaaaa acagcagcga gtctagataa  96000
tcccacatgg gatctataaa cgttctctga aacctcgtcg atggtgacgt aggtgtagtt  96060
ttgttattat cggaagccgt ttcgttttcc acgggcatgg tgtcgttgta atataaggag  96120
ctcatgtcaa gagtaccgta aatagtgtac ggtgtttcgt tgcgaatcaa tacgtgcgta  96180
tttttcataa attctgatac ggcggtccgg ttacggtttg gtttacaaaa aggttcatct  96240
cgatagcgca gagtagtata cacccacgtc gctagatctt ttaactgcgt ggtcagaatg  96300
gatttcataa agttttcgtc aggacgataa ccaattgtag atgtgggaat ccgagttggg  96360
acaataggac tataagttac attagtactg acgttaaaaa tagttgacgt gtaggaagaa  96420
tatggtgtgg tggtgctaac acgacttttc ttactgatcg atttgacagg cgcttgttta  96480
cgtttaagct ttcgcatagt gttcttcagc ttggtgctgt taatatactt gggaacgcgg  96540
aatatattcc ggctcatggc gttaaccagg tagaagctgc gtgtacagtt acgttgcgcg  96600
taacgtagaa gcagggcggc taaacctaaa aaataaattg tttggctatc cacattgact  96660
ttactcggac ccacgtacag tttggtgttc caacgtggta cgttaaaaaa cataggatta  96720
aatgtggtaa aattgccaca gttttcctcc ccggtgttgt tacgccggga tacatttagc  96780
atttcagaaa ggcaagtcat ggaaggtatc gtaccacagg atgggggtcg aaatgttatt  96840
ttttgccctg tatgattata ttccgaatac acatatttgg ccggtttacg gagttgggtc  96900
gtgtgaaaat cgaaccagag gtgggtaatg ctatgattac gaataggtcc tgctaaaatg  96960
```

-continued

```
gaattcgggg gaaactgttt catttctaca gttatgttat acaacttttg ctgactagga  97020
aatgtgaaaa acttgtaata atcacctgtt tttgacgcta gttcttgcag tatacgtaat  97080
tttagttgcc tctcttcctc ttttgctttc tgactcttta ctcgaaaacg cgctaccgtg  97140
atcttacagt ttatgaaaga gaatagcagg aaagttagcg acataaggaa aaataaatta  97200
aaaacacctc tcatctctcc ctttctcccc atgacagagg aggagacccc gcaccgtccg  97260
tctgccttgt ggtttggctt gcctgcgtgt actcactgct gattctggtc gttttgctgc  97320
tcatctaccg ttgttgcatc ggcttccaag acgacctagt ctcccgcacc ttggctgtgt  97380
accgagcttg tatccaaggc ccgatatgta accagaccca caacagtacc tcgtaaataa  97440
agacgcacag acctcacaca tatagtacca tcacaccgtg tggcgtgtac tttattacaa  97500
cgagcaagag tgcccctaag tattggggcc cgtaccgttt tagaagattt tgtgtgaatg  97560
tctttaactt tctctgtccc ttttctcata aactgtcagg ttctacagtc agcatgtctt  97620
gagcatgcgg tagagcagat agatgccgat gatggccgat agcgcgtaga cggacatcat  97680
gaggagacga ctgtcggtag cgtccacgac gacgtcagtt acttctagga ccgtaccgtt  97740
tttcaaaagc atgaggtagt gagttcgcgg agatgagacc accacttcgt tgtagggatc  97800
cagggcgaaa aggacgtcgt ccgagtcgtg catgtacatg atgttgatga cgccttgcgt  97860
gtcgtcgtat tctagtaggg cgctttggca aaaggcgcag ttttctaggg aaatgttgag  97920
cgccgctgtg atgctgtgtg tggtatgcat gttgcgcgtc agttcgcatt tagtttgact  97980
gtccgtctgg gtgatgatga ggctctggcc tacgacggtg gtggagacag ggtaggagat  98040
acctttgatc aggtactggt ttgttacgac ataactgacg tgttcggaga cggtcagcgc  98100
ggagaaggat tcgccgagcg gcagacaaaa caggtcgggg aaggtttcta gcgtgcttgg  98160
ttgcatggta gataggatgg agagggcggc gggaacggta gtggggacgg tggcatcggg  98220
gaagagacgt gtgaggcgtt cgagcgagtg atcgcgtcgc ccgctactgg aacagggtgt  98280
gtacaggtcg ctgaggtatt cgtggtgcgg atgagctagc aactgcgtaa agtgtgatag  98340
ctcggctaat gaacagaggc ccgtttctac gatgaagatt tcgcgtctct ccgtcgtatg  98400
tactagcatg gagtggacga ggctgcccat gaggtagagt tcttgacgcg cgaaggctga  98460
aagaaaagag gccaggtgcg ttttgtgtag ttttagggca aagtcggcga tctgtcgtag  98520
tgcccactgg gggatgagat gttgctgatt ctgtttagag agtatgtaga ccaggcgtac  98580
gaggctggtg atgtcggtga tctgattcgg tgtccaaagg gctcgtttgg ccaggtccac  98640
ggccgtggga tacagcagca acgtggtgcg tggtggtgtt tgtgagaggc aggtgatcat  98700
aaattcttgt atttgtaaga gtgcggcctg gcggtctagg gcccgtggga cggagacttg  98760
ggcgccggcc tcttcttgtc gggctgctgc gaacagtgct aatgcgtagg cgaaggccat  98820
ttctaccgtg cggcggtcca gcatctgaca tcgaccgctt ttgagtacat ccacggcgta  98880
acggtgaaag ctgttacgta gtagtgcgct gaggtccagg tagttgaagt caagtgcggc  98940
gtcaagaaag tccgggtctt tgagataaga gtgacggttc agttgatctt tcttaactag  99000
caccaggagc tcgtgttttt cagtttgtcg tagtataaag ttgtcgcgtt gatagggcgc  99060
tttaaagagt acgcgtggaa gatggccgaa gataagcagc atgggtgtgt cgtcgtctat  99120
ggacaccgta actacgaaga agtcctcggt cagtgttatt ttaacgtaac gtagttcgtc  99180
gatgaggtaa aagccttggt gcaaacaagg tgtgacggtg ctgaatagta gatcgtgtcc  99240
atcaaagagg atacaggtct ggttaaagtg tggtcggtgt agtcctgagg tggtatgtga  99300
ttctgtccag ccgtgtggag tggtttgcgg tggcatccaa acgtgaggta ttgacaggtc  99360
```

-continued

```
aatgggtggt ggcacagtgg tgggctgttc acctaggctg tcctgtgcct ttagctgctg  99420
cgaaaaagat cggtagctgg ccaggtcttt ggataccagc gcgtaagtgt taagtctctg  99480
ttggtatctt tccagggttt cggtcagatc tacctggttc agaaactgct ccgccagagg  99540
acccgcaaaa agacatcgag gcatatggaa tacatagtat tgattatagc tttggaaaaa  99600
gttgaaactg atggcgtttt ccctgacgac cgtgctgtta cggaggctgc tattgtaggt  99660
acactgggtg gtgttttcac gcaggaagcg gatgggtctc ccgtaggtgt tgagcagtag  99720
gtgaaacgct ttgtccagcg gttcggatat ggcttctgcg ccatatcgtg acgaaagtag  99780
gtggctgagg agacagacgg cgaggacgat gaggtaggag gggaggcctg gccgcatagc  99840
gcggccgcgc cgctgggttc agcggcgtga tccaggtggt ggttggcgtt acacccgaga  99900
gaaggagaga aaggatccca ggaaggagca cccgggtgcg gcgctacggg ttacaaaagt  99960
cgcgtctccg tctatttaat acgatgtcat tggccgctgc gaagggagaa gaggggacac 100020
gcgagtaagt catgccgtcc gggtgtgggg acgacgctga ttcgaagggg aacgctctgc 100080
ggagattgcc tcacgtgcgt aagcggatcg gtaagcgcaa gcacctggac atctaccgtc 100140
gcctgctgcg ggtctttccc tcatttgtgg cgctcaaccg cctgttggga ggccttttcc 100200
cacccgagtt gcaaaagtac cgtcgccgtc ttttcatcga agtacgatta agtcggcgga 100260
ttcccgactg cgtgttggtg tttttaccgc cggactctgg gtcgcgcggc atcgtgtatt 100320
gctacgtgat tgagttcaaa actacgtact cagacgccga cgatcagtcc gtgcggtggc 100380
acgccaccca cagcctgcag tacgccgagg gcctgcgcca gctcaagggc gccttggtgg 100440
actttgattt tctgcgtctg ccgcgcggtg gcggtcaagt ctggagcgta gtgcccagtc 100500
tggttttttt tcagcaaaag gccgatcgcc catcttttta ccgggctttt cgttcgggcc 100560
gtttcgacct gtgtaccgat tctgttctgg actatctggg acggcgtcag gatgagtctg 100620
ttgcacacct tttggcggct acccgtcgcc gtcttcttcg agccgcacga ggaaaacgtg 100680
ctgcgctgcc ccgagcgcgt gcttcggcgg ttgttggagg acgcggcggt ggcaatgcgc 100740
ggcgggggct ggcgcgagga cgtgctcatg gaccgggtgc gcaaacggta tctgcgtcag 100800
gagctgaggg atctgggtca cagggtgcag acttactgcg aggatctcga agggcgcgtg 100860
tccgaggcgg aggcgctgtt gaaccagcag tgcgagctcg acgaaggacc gtcgccgcgg 100920
acgctgctac aaccaccgtg tcgtccgcgt tcgtcgtccc cagggaccgg cgtggcagga 100980
gcttccgccg tcccacacgg tctttatagt cggcacgatg ccatcacggg acccgccacc 101040
ccgtctgacg cggcgaccgc gtcagcggcc gccggtgctt cttctacctg gctggcgcag 101100
tgcgccgagc ggccgttgcc cgggaacgta cctagctact ttggaatcac gcagaacgat 101160
ccctttatcc gctttcacac cgattttcgc ggcgaggtgg tcaacaccat gttcgagaac 101220
gcctctactt ggactttctc ctttggtatc tggtactatc ggctcaagcg ggggttgtac 101280
acgcaaccac ggtggaaacg agtgtaccat ctggcgcaga tggacaactt ttccatttcg 101340
caggagctgc tgctcggcgt ggtcaacgct ttggaaaacg tgacggtgta tccgacgtac 101400
gactgcgtac tctccgattt ggaagccgcc gcctgtctgc tggccgccta cggacacgcg 101460
ctttgggagg gccgcgatcc gccggactcc gtggcgacgg tgttgggtga gctccctcag 101520
ctgttgccgc gtctggccga cgacgtaagt cgtgagattg ccgcttggga aggccctgtc 101580
gccgcgggta acaactatta cgcgtatcgc gactcgcccg atctacgtta ctacatgccc 101640
ctaagtggtg ggcgccacta tcacccgggc acttttgatc gtcacgtgct ggtgcggctt 101700
```

-continued

```
ttccacaaac gcggcgttat tcagcatttg ccgggctacg ggacgataac ggaggagctg 101760
gtgcaagagc gtctgtcggg ccaggtgcgc gacgacgtgc tttccctctg gagtcgacgt 101820
ctgctggtcg gcaagctggg tcgcgacgtg cccgtctttg tgcacgaaca gcaatatctg 101880
cgttcaggcc tgacctgcct ggctggcctg ctgttgttgt ggaaggtgac caacgcggat 101940
agcgtcttcg ctccgcgcac gggcaaattt acgttggccg acctgctggg ttcggatgcc 102000
gtagccggcg gcgggttgcc tggggggcgc gcgggcggcg aagaggaggg ctacgggggg 102060
cggcacgggc gggtacgtaa ctttgagttt ctcgtgcagt actacatcgg gccatggtac 102120
gcgcgcgacc ccgcggtcac gctgtcgcag ctctttcccg gcctggctct gttggccgtg 102180
accgagagcg tgcgcagcgg ttgggatccc tcacgtcgcg aggacagcgc cggaggtggc 102240
gacggcggcg gcgccgtgct catgcagctc agcaagagca accccgtggc cgactacatg 102300
ttcgcgcaga gctccaaaca gtacggcgat ttacgtcgct tggaagtaca cgacgccctg 102360
ctctttcact acgaacacgg gctagggcgg ctgttgtcag tgaccctgcc gcgtcatcgt 102420
gtgtccactt tgggctcgtc cctctttaac gtcaacgata tttacgaact gttgtacttt 102480
ttagtgttgg gttttcttcc gagcgtggcg gtgttgtaat ttccaccacg tgtcgcttgc 102540
tgcataaagg gcgagcgtcc ccggagaggg tatattcgtt cggcgagagc gggcggcggt 102600
ggtgggtatg tcctcttctg cggagaagac tacctcagtt accgattcca tcatgctcgc 102660
tatcgtgaat ttcaaataca tgggcccgtt cgaaggctac tctatgtcgg ccgatcgcgc 102720
cgcttcggac ctgctcatcg gcatgtttgg ctccgttagc ctggtcaacc tgctgaccat 102780
catcggttgc ctctgggtgt tgcgtgttac gcggccgccc gtgtccgtaa tgatttttac 102840
ttggaatcta gtacttagtc agttttttttc catcgtggcc accatgttgt ccaagggtat 102900
catgctgcgt ggcgctctaa atctcagctt ctgtcgctta gtactctttg tcgacgacgt 102960
gggcctatat tcgacggcgt tgtttttcct ctttctgata ctggatcgtc tgtcggccat 103020
ctcttatggt cgtgatctct ggcatcatga gacgcgcgaa aacgccggcg tggcgctcta 103080
cgcggtcgcc tttgcctggg ttctttccat cgtagccgct gtgcccaccg ccgctacggg 103140
ttcactggac taccgttggc taggctgtca aatccctata cagtatgctg cggtggacct 103200
caccatcaag atgtggtttt tgctgggggc gcccatgatc gccgtactgg ctaacgtggt 103260
agagttggcc tacagcgatc ggcgcgacca cgtctggtcc tacgtgggtc gtgtctgcac 103320
cttctacgtg acgtgtctca tgctttttgt gccctactac tgcttcagag tcctacgcgg 103380
tgtactgcag cccgctagcg cggccggcac cggtttcggc attatggatt acgtggaatt 103440
ggctacgcgt acccttctca ccatgcgtct tggcattctg ccgctcttta tcattgcgtt 103500
cttctcccgc gagcccacca aggatctgga tgactccttt gattatctgg tcgagagatg 103560
tcagcaaagc tgccacggtc atttcgtacg tcggttggtg caggcgttga agcgggctat 103620
gtatagcgtg gagctggccg tgtgttactt ttctacgtcc gtccgagacg tcgccgaggc 103680
ggtgaaaaag tcctccagcc gttgttacgc tgacgcgacg tcggcggccg ttgtggtaac 103740
gacgaccacg tcggagaaag ccacgttggt agagcacgcg gaaggcatgg cttccgaaat 103800
gtgtcctggg actacgatcg acgtttcggc cgagagttcc tccgtcctct gcaccgacgg 103860
cgaaaacacc gtcgcgacgg acgcgacggt aacggcatta tgagcggcgg cgttgtacgg 103920
cagcggggag aaaagtggca gataaattac gtcaggttca cacgtcgtta gccagcgtcg 103980
gcatatgaag ggcgcgggcg gccagtacgg cctctgggtt gagacaggac gaggcagggt 104040
gagaaagagg aggatggggg ggaccggggt ggtggtgctg ctgctgttgt gggtgcggac 104100
```

-continued ggtgcgggtg ccgggacagc gtgccggcga acgttctgta atcttccata ataaaggtaa 104160
aaatgcccgt ttcgtgtcga ctccgctgga tctcgaaggc gtcgggggta atgcgcatct 104220
tgccggtgcc gatgagataa aagtaccaca ttttttgaca gatgatgcga atcaagggtt 104280
cgtacgcttc ggcaccccag tggcgtgtga agaaggccgc cagacgaaac aggcggtgtc 104340
cgtagagcgt gcctagggag aagaggatgt tgccgttgcg cgccaggtct tcggggaaaa 104400
cgaccggcag gccggtgtgg cgctgcacaa agcgcgtcag cagtccgccg ctcaagcgcg 104460
ggtgacacag gcgctggctg agacgggcgg cgcgtgtttc atcgaacacg gccgcctcaa 104520
agtccagccc cgggaaggcc tggcgcagtt cgcggtacag atgaggccag tagggttgcg 104580
gcgtcttgcg gctaagcacg gcgtggtccg agacacccag gttgttcata gtttcgcgca 104640
gtagcagcgt ttcgagaccg cggtgaaaga ggaggacgca gatgaggcgt acgattttga 104700
gttcttccaa acgcagcgag ctcagcggct gtccgcgcga catcttctcg ctaatctgta 104760
atattagatg attggcgcaa gtaaaggaga atttgcctgt gcggacccgc gggacggcgg 104820
ggttctcttc gtcgcgggcc atcatcgttc gctcggtgag cgggtagcga cggtgacgac 104880
aatgacgatg gacgagcagc agccgcaggc tgtgacgccg gtctacgtgg gcggctttct 104940
cgcccgttac gaccagtctc cggacgaggc cgaattgctg ttgccgcggg acgtagtgga 105000
gcactggttg cacgcgcagg gccagggaca gccttcgttg tcggtcgcgc tcccgctcaa 105060
catcaaccac gacgacacgg ccgttgtagg acacgttgcg gcgatgcaga gcgttcgcga 105120
cggtcttttt tgtctaggtt gcgtcacttc gcccaggttt ctggagattg tgcgccgcgc 105180
ttcggaaaag tccgagctgg tttcgcgcgg gcccgtcagt ccgctgcagc cggacaaggt 105240
ggtggagttt ctcagcggca gctacgccgg cctctcgctc tccagccggc gctgcgacga 105300
cgtggaggcc gcgacgtcgc tttcgggctc ggaaaccacg ccgttcaaac acgtggcttt 105360
gtgcagcgtg ggtcggcgtc gcggtacgtt ggctgtgtac ggacgcgatc ccgagtgggt 105420
tacccagcgg tttccagacc tcacggcggc cgaccgcgac gggctacgtg cacagtggca 105480
gcgctgcggc agcactgctg tcgacgcgtc gggcgatccc tttcgctcag acagctacgg 105540
cctgttgggc aacagcgtgg acgcgctcta catccgtgag cgactgccca agctgcgcta 105600
cgacaagcaa ctagtcggcg tgacggagcg cgagtcgtac gtcaaggcga gcgtttcgcc 105660
tgaggcggcg tgcgatatta aagcggcgtc cgccgagcgt tcgggcgaca gccgcagtca 105720
ggccgccacg ccggcggctg gggcgcgtgt tccctcttca tccccgtcgc ctccagtcga 105780
accgccatct cctgtccagc cgcctgcgct tccagcgtcg ccgtccgttc tccccgcgga 105840
atcatcgccg tcgctttctc cttcggagcc ggcagaggcg gcgtccatgt cgcaccctct 105900
gagtgctgcg gttaccgccg ctacggctcc tccaggtgct accgtggcag gtgcgtcgcc 105960
ggctgtgccg tctttagcgt ggcctcacga cggagtttat ttacccaaag acgctttttt 106020
ctcgctactt ggggccagtc gctcggcagc gcccgtcatg tatcccggcg ccgtagcggc 106080
ccctccttct gcttcgccag caccgctgcc tttgccgtct tatcccgcgt cctacggcgc 106140
ccccgtcgtg ggttacgacc agttggcggc acgtcacttt gcggactacg tggatcccca 106200
ttatcccggg tggggtcggc gttacgagcc cgcgccgtct ttgcatccgt cttatcccgt 106260
gccgccgcca ccatcaccgg cctattaccg tcggcgcgac tctccgggcg gtatggatga 106320
accaccgtcc ggatgggagc gttacgacgg tagtcaccgt ggtcagtcgc agaagcagca 106380
ccgtcacggg ggcagcggcg gacacaacaa acgccgtaag gaagccgcgg cggcgtcgtc 106440

-continued gtcctcggac gaagacttga gtttccccgg cgaggccgag cacggccggg cgcgaaagcg 106500
tctaaaaagt cacgtcaata gcgacggtgg aagtggcggg cacgcgggtt ccaatcagca 106560
gcagcaacaa cgttacgatg aactgcggga tgccattcac gagctgaaac gcgatctgtt 106620
tgccgcgcgg cagagttcta cgttactttc ggcggctctc cccgctgcgg cctcttcctc 106680
cccgactact actaccgtgt gtactcccac cggcgatctg acgagcggcg gaggagaaac 106740
accgacggca cttctatcag gaggtgccaa ggtagctgag cgcgctcagg ccggtgtggt 106800
gaacgccagt tgccgcctcg ctaccgcgtc gggttctgag gcggcaacgg cagggccttc 106860
gacggcgggt tcttcttcct gcccggctag tgtcgtgtta gccgccgctg ctgcccaagc 106920
cgccgcagct tcccagagcc cgcccaaaga catggtggat ctgaatcggc ggatttttgt 106980
ggctgcgctc aataagctcg agtaagagag acgctatatt tagggcttcc ctctcttttt 107040
tttctacacc gtgataccct aataaagcac accgcggtta ttatcaacgt ctctgttttt 107100
attatttaga aataaataca gggaatggga aaaacacgcg gggggaaaac aaagaagtct 107160
ctctctagat gcggggtcga ctgcgtgggg tgctggaagt ggaagcggtg ctgatgggcg 107220
agggtcgtgg cgcgggcacg gaccgcaacg tgctgctgat gtctgctgcg gtacgcacgt 107280
cgccgtccat gtcgctgcgc agataagagg taggtcgtag tgcggcgtgc tgcacgctca 107340
ccgttaatgg taccaggtcg tccaagctcg caaagacgtg ccacgagggg atgacgagcg 107400
tgagagcccc gttgttaccg cttcggcgtc tttgtccggt caggatcagt gcccgggaca 107460
gtccggcttg ggtgtccgag tcctcgtcgc cgctggcctc ctcgaagccg gcaaacatgg 107520
cctcggacag gggggtcggt gtcggtgtgg aggagaggtc atcttcgtcg tcctcttcct 107580
cttcttcctc ctcttcctcg gtgggtggta atcctggcga ttgcgggaga aactcggaga 107640
cggcgccgcg catgacgttg ctccgtggaa agagaccggc gcgcagctgc acctggggac 107700
gcttgatctt gtccggttta ccgggtgtga gagtccaaaa cccacggcgg aaaaagtgga 107760
tgcggcctag cggctgtcgg tgttccaaat gaacggcctg atcgccggtc agcgtgacgc 107820
ggagggtgat tcgcacacga tcgggtagcg ggccggcttc tatggagacg cccgggatgt 107880
tttccgggaa aaaaatggtg tcgtgagtct gattggtctc gaaagcattc tggatctgca 107940
cgatgtactc gggatgtatg cgcgttagcg taaaactttt gggaatcaac agctggaagc 108000
cgttgtccgg caagcgtcgt aggtgcgggt acggattgtg tcgcgccacc acctcggcgc 108060
gatgcgtgta aaccgaaaag tgcagaaaca cgctggtcgg cgggtgcggt gagtcgtgat 108120
gcagaaacag catgatccat tggcctcgct cgtccgtctc cgttttgtgg atgtacgtgt 108180
tagggtccga acaggccagc tgctccaggg cgtctaccag cgtcagcggg atagcgccgg 108240
cgcgaaaggc gaactggctg acaaagatct ggccggcctc caagctgctg tcggttctgc 108300
ggcgccagtt cggcgttacg gtcagtcgca cggcccagta gtgagccgtg cggcggatga 108360
tggcgcgcgc ctccactcgc ggccgatttt cttcgccgcc gcgccgctgg ctctgaaaga 108420
ggtgcagtcc gctaacgggc acgcggtcca gcggcagtgc aaaggccagt accgagaccg 108480
tgttgttttc tgagcctggc gtcaggcgtc gtgggccaaa gttgttgagg tccaccagca 108540
gtcggtcctg ttcgcccacc acgcagcggc ccttgatgtt taggtcggtc aggtctacgg 108600
tgtcgtgcgg agatttgttc tcctgaaaac agcagagaac cgagggccgg ctcacctcta 108660
tgttggtacg caggtccagg agtcgcagac gaccggcttc cagcgagccg ccttccacgt 108720
tggtgatgag ccgaagcacc tggcagtgca ggcgaccaaa gcttccgctg gcggcttcgg 108780
cctcgctgat cgcggccgct tccgacgagg gtccctcacc gggcgaggac gatgcctgag 108840

-continued acatcgcgaa ggcgggatga gggggggggt caggggatgc gcaaaggtga acgggtcttc 108900
gtgggaggtc gggaagggtt ccggcaactg tcgcaaatat agcagcggcg acaggtgtgg 108960
cggccaaaag tcgcgtgtct gagtggacgt gggtttttat agagtcgtcc taagcgcgtg 109020
cgcggcgggt ggctcaacct cggtgctttt tgggcgtcga ggcgatgcat ggcccgggca 109080
aggcgtcttg ccggtggcgg cgacgtttgg gttgcgcagc gggctgccat acgccttcca 109140
attcggcgaa gatgcggtag atgtcgttgg cgtcccagaa gaactcctgg tacttcagat 109200
tctgaccctg aaccgtagcc accatgggca ccaggttgcg ggccaggatg ccggcctgcc 109260
agggcggcca ggtgaacacg gccggattgt ggatttcgtt gtcggaatcc tcgtcggtgt 109320
cctcttcggg cgcgacggtg gactcggcct taaggcggcc gcgtgtcata acgcccgccg 109380
tgcacgccgt cgccgaggat gctgatttgc gtttgcggcc cgcggaagtg gaggcgcccg 109440
ccatggcgcc gccgccggta acgcggggcg tcttgcgctc ggtggttacg agttcctcgt 109500
cggagtccga tccgctggtc cagacgtcgt cgtcgccctg ggcggcaccc tcgtcgtgcc 109560
ggtcccaggt gtgtcggtac tcaagcttgc cctggatgcg atactggctg gtgaaggtgg 109620
ggtgttcgct gtactgaggc ccgcgctgca gcagcaagtc gatatcgaaa aagaagagcg 109680
cagccacggg atcgtactga cgcagttcca cggtctcgcg tatcgcttgc acctccagga 109740
agatctgctg cccgttcatc aataggttac ctgagatgct caggcccggg atgctcttgg 109800
gacacagcag cccaaaatgc tcgtgtgagg taaaagccac atccagcatg atgtgcgaga 109860
tcttgcccgg tttgattatc atatttttgg gacacaacac cgtaaagccg ttgcgctcgt 109920
gggggcgcat gaagggttgc gggttgcggg tcatcgtcag gtcctcttcc acgtcagagc 109980
ccagcgtgac gtgcataaag agcttgccgg agggcacgtc ctcgcagaag gactccaggt 110040
acaccttgac gtactggtca cctatcacct gcatcttggt tgcgcgcgtg ttctccatgg 110100
agcaaaccag ctcgtgcgcg cacaccacgt gccgcagtgc cacgtccttg gtgggaaaca 110160
cgaacgctga cgtgtagtag acgtcgggct ctttccactg gttctgctga cgcgtccagg 110220
ccagtcccga gaccgtgaga cgcgcctgcc acatctgctt gcccgacgcg tgaatcacag 110280
cgtcagctac gggcaggtgt cggtgtttgc gctcggccgc cgacgggtag tggtgcacgt 110340
tgatgctggg gatgttcagc atcttgagcg gcagcgcgta cacatagatc gacatgggct 110400
cttggctggg gcagatgctc cggcccgtgg ggttgtgcac gttgaccgac acgttctcca 110460
cctcgctgcc cgtaaagtac gtgtgctgca cctgcagctg attgtcgccg cggtggcatg 110520
gcgtcgagtc gggcgtgtac tgcgacacca ggatcagcga gggctggctc acgcgcacgt 110580
ggatacccgt ctgcaggagt cgcgtctcgt gcggcagcac cggcgtgtcg ccgcgactaa 110640
acacggcttt cagcacgtgc cccgaaatgg gacccagtac ggatatcatt tcgggacaac 110700
ggcgaccgcg cgactccatg ctgcctgcgc gtacgggtgt aggcgactga gcggcgcgcc 110760
ctctgcggcc gccgccttac ataggcaggc gaccagacgc ggaacccgaa ataaaaacgt 110820
tctacacaga gacaaccgcg gattattgag tgtctttttt tattaaaaaa aagaggcaaa 110880
gccccaccgt caccacaccc catcacacac caccaccgat ttttttgttt taaccccgta 110940
tcgcgcggac gcctagtgtc cgtttcccat caccagggtt ctctgtttag agatcgccgc 111000
agaccatggc taaagtgaca ggactcgttt tctctgtcgt attttccgta agcttacagt 111060
cttgcggttc cgtctccggg gacgccagcc gcatgggcag caggtcctcc aacgcgatgg 111120
aagcgcccag caccgagagc tgctgttgcg acggcgaatg ggacgtggac cgcgagtgta 111180

-continued gcgtggattt gacttggtgc gtcattgctg acaggcaacc gcgattcagc gtatgctttg 111240
acgagataaa atagaggcgt cccaggagcg cgtcccgtgg gaacgtggcg ccattctcgt 111300
cgctcaccag tacggttaat tccaaccagg agcgcggtag ccagaccgta acgggcattt 111360
tgagtccctg acggttgtgt ggtacaaaaa cacccagata aggcccgtaa aagcggcggt 111420
agatacgtaa cgtgtgcgag ttcttcagcg tcaattcgta agggacgcgc acctccagtc 111480
cctcgtccgc cgcgccagag cgtggcggta caaagtaagg cagtggcgcg tccgaaaaga 111540
agggtcgtcg caccgtttcg cgtcgcagcc gcaggcgaaa cgccactggg tcggctggcg 111600
cctcggtgcg gtcgcaggtc acgttgaaac gtaacatgcc gtcttggtat agcgtgagtg 111660
acgacagcgt caggtccggc ggtgattcgt tcgggtctag ctccaatcgt ccaaagacgg 111720
agggtcccaa tgtcttggcc gtggtttccg agaggcgcgc cgagatacgg ctggtgagtc 111780
cacgcggccc cgagatgccg ccttccactc gatgccagca cagcgcgtgt cgtacgcgca 111840
ccgtcagcgt gggcgtcaga tccgcgtccg ttgactccgc ggcatcggcg acggaagccg 111900
cgttctccgt tacgttgttt atatccagcg tcgactcgaa cgtgagttct ggcagatgca 111960
gcgccagaca gtcgtgtaac gccgtgtgat gcgcggcttt acgtcgtagc ggtagccgtt 112020
tcagcagcgg cgtgatgata cggagcgcga agagattgag tgataagcgc acgatggcca 112080
tgcgcgtcag ttgttggtcg attaccgagc gcaggatatg gcagcctggg cgtgcgggaa 112140
agagagagaa ggccgggcgc acgtcagaat cctcgttgga gaccacgcat agaatgccgc 112200
gttcacgatc gtcgttgcgg tcatcctcgt cctcttcttc tttcttctct tctttttcct 112260
tttttttctc gagctcgtgg gaagccgccg tttcttcttc ttgcgacgtc gcgggggcgg 112320
tttgagactc gccgttcgct tcccccaatt gcagcggcgt agagagcaga atctggaagg 112380
gatcccgcaa ttcttcgggt cggaggtcga ggtgcaactg gattagatgg taagttccgc 112440
ggtgcacccg aggctgacgg atgtcgtgtt tatccgtcaa tgtaaggatg gtctgcggcg 112500
agccgctgtg cttgtccagc tcgtccggcg ttttcaggag gaggctgtcg tcgtcggtac 112560
tggcgacgcc catcatggtc gtggtggtag tggtggcgag gaaagtgagc ggcggcgccg 112620
acagagctcg gcgttggcgg cggcatttgc cgctgtgtcg gctgctattg ctgccaacgc 112680
caccgccgcc gcctcgtctg gctcgtggcc ggcgggcccg attccgaagg ttggggtcgg 112740
cgcgtggcat gcttggtgtc tgcgggcgcg agagggccgg ctcagccttt aaatatgcag 112800
gtcgcggatt tgttatcggg tgaaacgtca cacaccgtga agacgacctg ttcgcggatg 112860
aggtcatcca gctgtcgcag catgacgaaa agcgccgaca gccgcgcgat ctcgtcgtcg 112920
ggcgacacgt gctgcggccg cgcgggcgtg cgcggctcgc cgacgctgcg ctcgcggtcc 112980
agccgcatca gcagctcctg gcacttgacg agcagcatgg agctgtcctc tagcgccaac 113040
ttgcgcacgt aggtcatggt cagctctgag gctagattgg ccaccatgga catggagagg 113100
caggcggtct tcatgtcgat cagcaggtgc tggtcgatga ccggatcggg gatggtgaag 113160
gtggcgtcgc gaaaagtaat ggtctgcagc tgctgcacgg cagcctttac ctcctcgtac 113220
gaacggtcga gcgagaagag gcccatgatg agtagtcgct ggttgatttc cagcgccagt 113280
ggcatgggca cgatccaggg cagcaccagc tcccactggc ccagcgtcag caggttctcg 113340
cgcgccagcg gtccgtggaa gagcggcggc agcacgcata gcgcgtcgcc cttctcccaa 113400
gtcacgggtc ccgtgttgag gacggtgtag agcagtccgt gcgtcggtac gtgtaggagg 113460
atctggttgc cttctacgcg ccgcatcaac gtcagcgtca tattgcgcag caggccgcgc 113520
agtcgcacgt agccgcgggt gtgatctacg aactggtgta ggcccagctg gtagtgcttg 113580

-continued atgagatgta gacgctgcgg aatgggcacg actgccgcta ctagcttggt cagtttgcct 113640
acgtcggcga tgctgagctt gtggtcgaaa gtgcagaaga tgttggcctc catggccgcc 113700
atagcggcgg tgaaatcgtg gccgcgacgg aggagaagcg gagacgaaca acgtctgcac 113760
cgggcgcggc gtcagagcga gcgtggcgcg tccgggcccg cgtttgcgtc taggtgactc 113820
gccgctaacc tgcggtcgtc gccgtcctcc tcaccggacg gcctcacgag ttaaataaca 113880
tggattgctg cagcgggatg atttcgccta cgacgtagtt accaaagtgc gtctcggacg 113940
tggcgaaagc cccggcgcca cccttgagtt tggtctccat cagcgccagc gtggtggtgc 114000
tgagaatcgg caacgcttcc tgcgtcaggc ggcacgggtt ttcgatgagt tgttccgtgc 114060
cttcgacgca gacgtactgc gtgtccgtgt cgccgcggat gcagtccttg gcgcgtagta 114120
ggtactcgtc gatggttttg aagagcgttt tgttggccgc gataatctct tctgtgttaa 114180
agtactgcgc acaggggctg tagaatttgg agttgtagcc caaacgttcg cgatgtcggg 114240
tgttgtacag tacgtcgctt agacagccgg cttgcgaggc ccaggggttg tgtgtggccg 114300
cgaaagtctg tgcgtcagct tcgcgatgat cgtagatggc cttggtggcg gcctccgtgt 114360
cgtacggatc gacgcccagc atgcaggagg cgcgtccgcg cgggttgttg gtgattttga 114420
agtaattaac gtccatcgtt accggcgtga ggatgagttc gcacacggcc ttttgtccgt 114480
gcaccgtggc ggcggcgttg cgctcggaca tgctgccgaa cgtcagcatg gagatggtct 114540
ccgtatctaa cagttgcggc cgttccacgc cggccgcgtg ccggatccag cggtccacct 114600
cgtcgtggcg gtacacgttc atagggaaga cgcgaaagag gtcttgcacg cggacgccca 114660
tgtcggtccg cacgcggttt acgtaggcta cgcaggtatt tgacgtgtaa cccagaccca 114720
tgtctacggt gttaatgttc tgcgtgacgt ggtacgtggt gctgatgtcg cgttcctcct 114780
tggtcacgat gggattgttg atgataactg acgtgcatga tttgccgctg tagagcagca 114840
tgtccacctc gaaggtgtcg gtgcgtacgg ccgtgagtgc gaatcccggg tggatgtgcg 114900
ccttggtctg cagcaccagt gaaactggtg agattttgta taacatggcg gccagcgtca 114960
taactgagtg caacacgttg ggacaggtgg ccgagtagcg cgaaaagggc gagcgtagcc 115020
agttgtggta ctcgtgtgcg aaggctgtgg gtagcggaaa accaccgtcg tgacggtgat 115080
agtgcgggaa ctcggtcacg tagcgtttaa tgtcgtcgct caacgccgcg cagatggtgg 115140
ggtttgagta gaaacggtgg aaaggtacgg gtaggctgta ctcgatcagc gtcttaggcg 115200
ccgtcacgac gcagcagccg ttgtaaagca cgtgctgacg tgagataaag tccggcaggc 115260
cctgacgttg cgcgtgatcc agaggcgcgc gcacttcgag caccttgacg tgctcgccca 115320
cgaattgcac ggccaaaaac agctcacgac aggcctgcag cagcggcgta tgcgcgtcgg 115380
tggcgacgtc ctccaccagc tcggtcagca tctcgcctac ggcttgacgt tgcgccgcta 115440
ccgagtcttc gggggtgacg ccgcttgtgc tctctttcga cgtcgtacct gacgtggaga 115500
ccgcggtggc ggccggcatc aggagaaacg ccggtcggta aaagaggtct actagcagcg 115560
tcttgaggtt gagtcccagg ccgcaggccc ggttgttggt catggcgggt atgaggcaga 115620
gataaaagac cttttgtaac gtccattcgt cgtcggtggc acggtaatcg tccacaaaca 115680
gcggctcgtc ggcatccatg gcgcccaaac gcggtacgtc agaaacgccg tggtgtcgcg 115740
cctcgatgtt ggccgggttc aacggttgcc ggtcggccac tacctgtacg ccttccatat 115800
tacgcggcag gtgcgtaacg aagggggccc acagccggtg gtcgtgcagc gcgttcacgt 115860
aagccgatag cggttcctcg gccagttgac cgttgttaag ccccggcagc gctgagatgc 115920

-continued

```
gcgttaccag acgcagcacg gcgactagat tgcggtagtg aaagagcaac tgcggtggta 115980
gggcgccatc ggccaggtgt tcggcgatca acgtcaccag cgcgtagctg tgtgcaaaaa 116040
ccagcagctg acgtgtgtga aacatgttga cgatacaacg tgctatgaaa gcgcggatta 116100
gcaaaaaagc gtcggcgttg ccgtgtacca gtacgtcgac caggtagcag agctcggggt 116160
aattggggct ggtcacggtg gttttgaaaa gtcgcaacgt ctcttcgtag tcgggtggtg 116220
gccgcagtcg catgtgttcc atgatctccc aggtgcgcag ttcgtggaag gggcccggtg 116280
ccagtccatc tggcaaatta ccgatgacga tacgcggcgt acacagcgcc accgtttcgc 116340
tgttttcctg gcagtgcgta aagtcgaaga aggggtgcag ctcggtgtag agcgtgatgt 116400
tgcccacctt gtagaagtcg gtgaccacaa aatcctgctt catttcgttc accgtgcgcg 116460
ggacctcacg ccgtacgcgg taaaaatgtg gtatgcggcg cgccgcaccg cccatgggct 116520
cctgctgaaa acgacattcg agcagccgtt gcatggcggg ttccgagggc ggtccgcgtt 116580
ccgtgaaggc ctgcagacag ggcgcgggtt catgcagcac cgggtggcac agcgtcttaa 116640
gcgcgtccac aaagtctatc ttttgcacgg cacggtcccg gtttagcagg taggccgtgg 116700
tgggcagcgc gttgcggacg gtgtcgttga gcttaacttt gctttccacc gtggtgtaac 116760
cgcgatcctc gggcagatac agccctacgg ggaagaaaaa cgtcaggtcc acgttacgtt 116820
ctagcggatc tttggtatcg gtgtttttgt agacgcgccg caagttttcc ataatcaccg 116880
ttttttcgcc cagtcgaatc acatccatgc ttagtggcgt taggctgtgc gccccggcct 116940
gcgaaagcga gtcgttgggc agatgcggtt gacccgaagt cagatgggcc ttgtatgagt 117000
tgaaatcggc caggatcgag tgataggaaa tggcggtgac ggcgttttcg ggactgagca 117060
caaagttgcc gtaggtggcc ggcgccgaga ccgtctcttt ggtgatgtgg cttgagagca 117120
gcgacatgat gatctgcata acgttggccg tgcttaccat cacgccgctg atcttggccc 117180
ccgagctcgt ggtatacgtg gtggggttgt ctaggatgct atcggtggcc gcttcggcca 117240
gacgcgtgag gaacttgagc acatagtcgc gatcgcgcgt gcgattcagc aaaaagagcg 117300
tggccagcat tttggccttg aagctctgca agatgttgct tcgctggatg cggttcaatg 117360
cctgtcgcgc cagcgtggcg ttttctacca gcgtctgcac cacaaagtac ggcggcgcct 117420
tgcgtagcag tgtctgtaaa aagctgtgaa tcaagccgcg ctccatggcg tcggccgtgt 117480
ttttaagcgc gcgcagcacc gtgtgcatgg cttccacgtt gaggatcttg tccaagatgg 117540
tgccctcgaa tgtctcgcgc agatacgtga ggcaggctgc gctgagctcg aaggggatgg 117600
tgatggggga tttttcactg tatttggtga ccataatggt ggtctgacga ctggtgggca 117660
aaccggcgcc gctggccaca cgcggcacct gcacgtggaa cagcattttg cccgtagtca 117720
gtttattgag gtcgtggaac ttgatggcgt gcgccgccgc ggccaagccg ctggtcaaaa 117780
aataaaccca ttccaggcga ttgcagaagg tgccgaagat ggcttcgaag tgaatattgt 117840
aacgctcggg gtcgtcgccg tagtagatgc gtaaggcctc gaacatctcc tcgccggcgc 117900
tggtcttgac gtgcgtcaga aagtcagtgg gaatgcctac tttaggcagg agctcgagcg 117960
ccgaccagtt ctccatcgcg gcggcggcgt gagcgcgagg cgtcggagct cggggaaagc 118020
agcgcgaccc ggagaatggc cggcgctgcg ccgcgccgcc tcggctgcga cgctctaata 118080
gtcgtcggcg gctccgctac gccgcgccgg gttttacacg tccccgtgca cgttcgcgcc 118140
tgcaacctca cccaagagct atcgacgggc gaggacgccc gcttctgtcg tccgcgaccc 118200
gttaacgtcg aacgggtacg cgctgttttc gcggctctct accgtgcctg tcccgtacac 118260
gcgaggaccg agtccgagcg tgtcaagctg gtactgggtc gtctgttgct gggacccgtg 118320
```

-continued gccgtaccct gtttttgcga cggtgaagtg gagggccacg gcgagcatct ggtacccacg 118380
acgcagtttt gtcgcgggcc gctgctctac gtgcaccgac gttgttgttg cggatccgtg 118440
accgccgggc gcgcgctgtc ctaccacgtt ctcgaaaacc acgtggccac gcatgtgtta 118500
cgcggattgc tctcgctgac ggaatggaat cgagagttgc cgggcctttt ttgcgactgt 118560
cctggcagcg gtggcgcctt gggaaccgag gaacgctacg ccatggcctg cttgccgcgc 118620
gacctcagcc tgcacctgga cgactatcct tacctgatgg tggaaatcgg acgcgtactc 118680
agcgtcagcg aggtagacga ctacgtaacc gccgtctccg gctacctggg cgaggccgcg 118740
gcgccgcgca ttcaggttca ctacaagctg ctctttggac tcaacgtgcg tccgcaagcg 118800
ccgtgcgcgt tggacgctac acgcgacttt tttctgctgg agctgcaaaa gctttggctg 118860
ggcgttgaat atcaccacga agtcacgtcg gagtttttcg gtcgcgtact ggctcagctg 118920
catcgcgacc gcgcccgcgt catgatggca cttcgcttgc ccgagcagac ggtgtgccac 118980
ctaagcacct tcgttctcag tcgcttcaag cgacaggtac tgtacttcaa gttacaggtg 119040
agctacggca agtgccggac tggccacgct gacagaagtg ggggaggggg aaacggtgga 119100
agtcagggac accacaacct actgtgttat cgacgtctta gcgtcacgtt tgccgacacg 119160
gacacggtgt ggagaaacct tttctacgtt tattatgaac tagctcggga tctggggtcc 119220
catgggacag aggaccgatc cgtaagccgc ggttacggtg tttcttgcgc tccgaggacg 119280
tcgcggctac caccgtcaga accgacggtg gtttcagcca acggacacgc gctgtcttcc 119340
accgcgctcc cgacgacgag cgcgggtcac aagctgtcgc tgccgcgcga cccggccgca 119400
gatcgcgttc gacgttacgt gtgcattatc tcgcgtctca tgttcgcccg gtatggggag 119460
agatggcgta aacaccgtcg acggcggtcg gagacgggag aagaggagga ggaagagacg 119520
gtggaatcgg gggagactga cgccacgccg ccatttgact ttacggggca gcagctgcgc 119580
cgggcctatc aggaacaccg acgtcgtaaa catctagccg tgcagcgtta cgcgccgtgc 119640
cgtcgtaagc tcatcggcgg gatggagttt gccgaggtga cgggcgttag tctggaccgc 119700
atcgccgtca acgctttcaa caccaaccgc gttatcaata tgaaggccgc actctcgtcc 119760
atcgccgcgt cgggtctcgg cgtgcgcgcg ccgcggcttc ccaagaacat gacccacagt 119820
tttgtgatgt acaagcacac cttcaaggag cccgcttgca ccgtcagcac ttttgtttcc 119880
aacgacgccg tctacatcaa ctcgctcaac gtcaatattc gcggttccta tcccgagttt 119940
ctgtactcgc tgggcgtgta ccggctgcac gttaatatcg atcacttctt tctgccggcc 120000
gtggtgtgca acagcaactc ctcgctggac gtgcatgggc tggaggacca ggcggtgatc 120060
cgctcggagc gcagcaaggt gtactggacc accaactttc cgtgcatgat ctcgcatact 120120
aacaacgtca acgtgggttg gttcaaagcg gctacggcca ttgtgccgcg cgtctcgggc 120180
gctgacctgg aagccattct gctcaaagaa ctctcgtgca tcaagaacat gcgcgacgtg 120240
tgcatcgatt acggtctgca tcgcgttttc acgcaactag agctgcgcaa ttcgtaccag 120300
atccccttcc tggccaagca gttggtgctg tttctgcgtg cttgcctgct caagctgcac 120360
ggtcgagaga agcggctgca gttggaccgc ctagtatttg aggcggcaca gcggggtctc 120420
tttgactaca gcaagaacct cacggcgcac accaagatca agcacacttg cgcgctcatc 120480
ggcagtcgtc tagccaacaa cgtgcccaag atcctggccc ggaacaaaaa agtcaaattg 120540
gatcacctgg gccggaacgc caacgtgctg acggtgtgtc ggcacgtgga agcccacaag 120600
atccctcgca cgcgcctcaa agtgttagtc gaggtgctgg gcgcgttgca gagtatcagc 120660

-continued ggtacgccgc acacgcgtga agtgatccac cagacgttgt ttcgattgtg ctcggcggcc 120720
gcagccacct cgggcctgtg ttcatcccct cccccattgt gtgtgtcctc atcttcctcc 120780
gccccttctg tcccaacctc cgtcagcgtt gacggcagtt ctgaacccac gtcgccgcga 120840
gcgcggtttg catcacgatg atggaagccg cggccgctgc cgccgcggcg tttcgtccgg 120900
aggagcgtcc gacgccgggt tggcacgacg cagcgttgtt aatggacgac ggtacggtgc 120960
gcgagcacgc gtttcgcaac ggaccgctgt cgcaactgat tcgccgtgtg ttaccgccgc 121020
cgcccgacgc cgaagatgac gtggtttttg cttcagaact gtgtttttat tgcagcggtc 121080
gttttaaccg caggtcgtcc gtcttctcca tctattggca gaagcatagc gatctggtat 121140
acgcgcttac gggcattacc cattgcgcta agttggtggt ggaatgcggt cagttgggga 121200
gtggtaggct acggtggcgc gacggtgacg tgggtggtga ggagcgccgg ggagacgacg 121260
acagcaggga cgagctgtac gacgtgccgg gaatttacat gatccgcgtc aacgacggcg 121320
gcagcaccgg ccccaggcac gttatttggc cgggtaccag cgtgctttgg gcgccggacg 121380
tggtgatcac tacggtgcag cgacgaatct cggcggcgcg cgccctggtg aacacgttcc 121440
gccagtattt ttttttgctg gaacggcgct cgcacgagga gctggttctt tgtccgcccg 121500
agatggagga gcgtctagcg ccgttgttgc agagtgccac gcgtggtgat tcggacatgt 121560
ttgacggtgt ggtggccagc gcttatcacc gtttgcgaat aagtaatatt ccgcgttcat 121620
ccgcccgtct gctggagcac tgcgtggggc tggcaggtgc taagaagctg ctcttgctcg 121680
acgtgccgcg tctggagaac tattttcttt gtcaagtctg tctttacgag ctggacgagg 121740
acgagatggg cgaggagatg ctgggtatgt tggccggaaa gcccgaggac gccgccgtct 121800
cgggcgcaag cggcggtttt ctgctacatc gcaagacgat gaagctggcc gcctgtctat 121860
gtttgctgct caattcgctg catttgcacc aggaggcgct ggaggccttg gatcctccgc 121920
cgccgcgcgt cgaggagaac gaccttgtca acgtggtgct gcgccgttac tatcgcagtc 121980
acggcggcgt gcaggcgcgg acgttggcgg cggcccgggc tttgttagcc gactacgccg 122040
aaacgttttc gcccttgggg agttttacgc gcctgggtta cgatcgtctc gtttctgccg 122100
atgccggcgt cagtcgccgg cacctggtgg ctctgctgcg tgcctagctg accctgaaac 122160
ggatggcgtg tatctcgtca cacaggtagg tggccatgat gacggctatg ataagatcgt 122220
ccgagatacg attctggcgc ttggccgagt agcgtgccgt cgtgccttcg gccagcgtga 122280
cgcggtgcag gttctgaatc tgctccagaa gatactcgat ggggtcgtgg ctcagcttga 122340
tggtgtagga gacgagctct tgcgaggctt tgatgtagcc cgagttgaaa cgcgagatga 122400
actgttctac ggccagcgcc ttgtcgcggc ccatgaggta gaagggctgt tcgatgtggt 122460
tctggtcggg cgtgtggtag aagagcacgc ggatgagcgt gctactctgc acgctctgtc 122520
ggatgaggca ggcgatgcgc acggccgccg cctggttagt gttgccctcc acggcgatac 122580
gcagttcgtc caggtaaggg tgcaggctca gcaccgagat gatcatgtgc gccgcgcact 122640
cggcgatggc tacctcagaa ctctcggaga ggtcgcgcaa aaagaaatgc tctaggccgt 122700
aaatgagaaa ctggtgtcgg taggcgccta cggccgccac gcccgtgccc gaggccttgc 122760
ggttggtggt gaaggccggg tccagatata cgtagagcgt cttgccgaaa taatcgtagg 122820
cgttggtgtt gagcgtgctg taacgcaaaa tatcgaactc ttcgcggctc tggtccgtga 122880
tgagcacggt gttttgcgag atcttattgg taccgccgat gatctcgtcc atgaaggcgc 122940
ccggcataaa catgttggcc gtcttgcgca cctgcgagtt gaggctgatg aaggtgggct 123000
tgtgcagtcg gtagcaagga caggccgtgg cgtcgccctt ctccgtgaag ctgtgcaggt 123060

-continued gctcttcgca cacgtaagag accacgttga gcatgtcaaa gggcgcattg ttgaggcgcg 123120
tcaagaaaca cgtggcgtca ctggtagtgt tggtggacga tatgaagatg atcttggtgg 123180
tattctgtgc caggaacccc agaatggtgt tgaaggcctc tttcttgatg aagtgcgcct 123240
cgtccaccag cagcaagtgg aagttttgtc ctcggatgct ctgtgtagag aggagacaga 123300
aaagggactc ttatgattac gcacgctcgg ctggaagcct acagagtcgg ggtggggccg 123360
gacaggtgag ccaggtgagc cgccaggtga ggcgggatcg ccgtgtgcca accgggctgc 123420
gacctgaaaa ccggaaccaa tccgccgaca ccggcgccgc gtgacgcgcg cccataaaaa 123480
cgaaagtgtc gtcgtcgcga cccgccacag ccgccatgaa ctcgttgctg gcggaactca 123540
accgactggg ggtcgcgcac gccactacgg aggatgtttt tatctttgtc gaccgcctct 123600
ttcaacactt ttccttcctt ttccaggccg aggagtcagg cccgcgccgc ttggaactgg 123660
tcgcgtccgt gttcgagcac ctgacggtgg agtgcgtcaa cgacatcctg gacgcctgca 123720
gccacccgga cgtgaacgtc gcggagacaa gcaacacctg tcgtccctgc ccttctcctg 123780
ttccctccgc ccccaaaact gtcagcgacg ctcagacgtc atgtgcgacg tctcgggcgc 123840
ctgtgacatg aggcacgtcc agaacgcgtt taccgaggag atccagttac actcgctcta 123900
cgcgtgcacg cgctgctttc gcacgcacct gtgtgatctg ggcagcggct gcgcgctcgt 123960
ctccacgctc gagggctccg tctgcgtcaa gacgggcctg gtatacgagg ctctttatcc 124020
ggtggcgcgt agccacctgt tggaacccat cgaggaggcc gcactggacg acgtcaacat 124080
catcagcgcc gtgctcagcg gcgtgtacag ctacctcatg acgcacgccg gccgttacgc 124140
cgacgtgatc caagaggtgg tcgagcgcga ccgcctcaaa aagcaggtgg aggacagtat 124200
ttacttcacc tttaataagg ttttccgttc tatgcataac gtcaaccgta tttcggtgcc 124260
cgtcatcagc caacttttta ttcagcttat catcggtatc tactcaaagc agaccaagta 124320
cgacgcgtgt gtcatcaagg ttagtcgtaa gaagcgcgag gacgcgcttc tgaaacagat 124380
gcgttccgaa tatggaaacg cacctgtatt cggatctggc gtttgaggcg cggttcgctg 124440
acgatgagca attgcctcta catctggtgc tcgaccagga ggtgctgagt aacgaggagg 124500
ccgagacgct gcgctacgtc tactatcgta atgtagacag cgctggccga tccgcgggcc 124560
gcgctccggg tggagatgag gacgacgcac cggcctccga cgacgccgag aacgccgtgg 124620
gcggcgatcg cgcttttgac cgcgagcggc ggacttggca gcgtgcctgt tttcgtgtac 124680
taccgcgccc actggagttg ctcgattacc tacgtcaaag cggtctcact gtgacgttag 124740
agaaagagca gcgcgtgcgc atgttctatg ccgtcttcac tacgttaggt ctgcgctgcc 124800
ccgataatcg gctctcaggc gcgcagacgc tacacctgag actggtctgg cccgacggca 124860
gctatcgtga ctgggaattt ttagcgcgtg acctgttacg agaagaaatg gaagcgaaca 124920
agcgcgaccg gcagcaccaa ttggccacgg ccacgaatca ccgtcggcgg ggcggactgc 124980
gtaacaattt agacaatggg tcggatcgcc gattgcccga aacggctatg gcttctttgg 125040
agacggccgt cagtactcca tttttcgaaa ttccgaacgg agcaggaacc tcctccgcga 125100
atggcggcgg cagattcagt aacctggagc agcgggtagc gcgtttgttg cgcggcgacg 125160
aggaattcat ctatcacgcg ggtccattgg agccgccttc caagatacgc ggtcacgagt 125220
tggtgcagct gcgcctggac gtaaatccag acctcatgta cgccaccgat ccgcacgacc 125280
gagacgaggt cgcgcgtacg gacgagtgga agggcgccgg cgtctcgcgt ctccgcgagg 125340
tttgggatgt gcagcatcgc gtgcgcctcc gtgtgctgtg gtacgtcaat tccttttggc 125400

-continued gcaatcgcga gctgagctac gatgatcacg aagtcgaact ataccgggcg ttggacgctt 125460
atcgggcgcg cattgccgtc gagtacgtgc tgattcgcgc cgtgcgcgac gagatctatg 125520
ctgtactacg acgggacggc ggcgcgttgc cacagcgttt cgcctgccac gtgccacgga 125580
acatgtcctg gcgcgttgtt tgggaacttt gccgtcatgc cttggtgctc tggatggatc 125640
gggcggacgt gcgtagctgt attattaagg cgctgacgcc tcgtctgagc cggggtgccg 125700
ccgctgccgc tcagcgagct cgtcgccagc gcgagcgccc ggcgcccaaa ccgcaggagc 125760
tgcttttcgg gccgcggaac gagagcggtc cgcccgccga acggacttgg tacgctgacg 125820
tggtgcgctg cgttcgcgcg caagtggatt tgggcgtgga agtgcgcgcg gcgcgttgtc 125880
ctcgcaccgg gctttggatc gttcgtgatc gccgcggacg cctgcgacgt tggctctcgc 125940
agcccgaggt gtgcgtgctc tacgtcacgc cagacttgga cttttactgg gtgctgccgg 126000
gcggctttgc tgtgttctcg cgcgtcactc ttcatggctt ggcgcagcgg gctttgcgag 126060
accgattcca gaactttgaa gcagttcttg caagaggaat gcatgtggaa gctggtcggc 126120
aagagtcgga aacaccgcga gtatcgggcc gtcgcttgcc gttcgacgat ctttagtccg 126180
gaggacgaca gctcgtgtat cttatgccag ttgctgttgc tctaccgcga cggcgaatgg 126240
atcatctgtt tttgctgcaa cggccgttat caaggccact atggcgtgaa tcacgtacat 126300
cggcgtcgtc gacgcatctg tcatctacct accttgtacc aactgagctt cggaggtcct 126360
ttgggtccag ccagcatcga tttcttgccg agctttagcc aggtgaccag cagtatgacg 126420
tgcgatggta ttacgcccga cgtgatttac gaggtctgca tgttggtgcc ccaggatgaa 126480
gccaagcgta tcctggtcaa gggtcacggt gccatggacc tgacctgtca gaaggcagtg 126540
acgctaggcg gcgccggcgc ctggttgctg ccgcgtcccg aaggctacac gcttttcttt 126600
tacattctgt gttacgacct gtttacctca tgcggcaatc ggtgcgatat cccttccatg 126660
acgcgcctca tggcggcggc cacggcctgc gggcaggcgg gttgcagctt ttgcacggat 126720
cacgagggac acgtagatcc cactggcaat tacgtgggtt gcacccccga tatgggccgt 126780
tgtctttgtt acgtgccctg tgggcccatg acgcagtcgc tcatccacaa cgaggaaccc 126840
gcgacttttt tctgtgagag cgatgacgcc aagtacctat gcgccgtagg ttctaagacc 126900
gcggcgcagg tcacactggg agacggcctg gattatcaca tcggtgttaa ggattctgag 126960
ggccgatggc tgcccgtcaa gaccgatgtg tgggacctgg tcaaggtaga ggaacctgtg 127020
tcacgtatga tagtgtgttc ctgtccggtg cttaagaacc tagtgcacta acggggtctg 127080
acagttcacg gggagaagaa acaagaaaca acaaaaaaag gaggacatgg actcgccacg 127140
gtttgtggca aggcgtatgt tatcatcatg gagctactca cgttggtgtt gtagcaactg 127200
gcaaaaagcg ccgtgctctt ggcgccgcgg tggtcgatgc tgatcacgtt gtccttgttc 127260
tcgaccacgt agtcgcgcgc gaaggtgtgg cggcagcgga actcgacctc tttgagcaca 127320
aactgcgaca cgtgcttttg gtgcgccacg tagccgatgc tgatgccgat catgtgctta 127380
agcagaaacg agataatggg gatgatgaac caagtcttgc cgtgacgtcg cggcaccagg 127440
aacacggtgg ctttctgctt aaagatgtcg atggaggtct gcgagaggaa gtcgatctgg 127500
aaggcgtgga tgaggtactg cagcacgcga ttggccagca cggggatctt ggtcacggct 127560
ataaaaaaga tgacgtgtat caataaattc ttttgaaacg gttcgagtcg gatggctttt 127620
gcgtcgccct cgacggcggt actgaagccg ccgtcgagcc actttttaaa gtcggtcatg 127680
aagttgttga tctgctgaaa ctgcggatcg cggtagagct cggtcaacgc gtccagcttc 127740
tggtaggagg cgcgctgctc ctcggagcac gggcgaaacg tcagttcatc gagcgcgctc 127800

-continued

```
ttgaggcgct cgtgaaacag cagctcgcgc tggctttcct cgggcgagtt gtagtcgcgg 127860
tggcggccgc agaaggccat gagcggcagg aaggcctcgt tgcacgagtg ggccagcccg 127920
agttcggggt gcatcatctg gtagcgcttg cggcacagcg ccgccacatt ggtgaaggcc 127980
gtggagatgc aggaggtggg gtggctcttg cgcttctgca gctccgcgta gcgctcctgg 128040
atcttggcgg ccgagtctcc gcgcaacatg atggcggcgg cggtggtgcg agcggaggtt 128100
aggcggcagc ggcgagagga gaggaaaaag atggcggccg cgaggacgac ggaggatcca 128160
cccgaaaacc acgttgttgc ggacgtggct tgtgggacgg gcgccgtcac tcgttcgtct 128220
tcgtcgtccc tagtggtgtc gtcttcctcg gcgtcaggct cggacgaacc ttcctccgcc 128280
tctcctctca gtttccccgt ctgctccccc tcaactgccg tcaggtctcc ggggtccgcc 128340
ggggtttcaa cgtccctgtg ctcggtggaa cggatggtcg agctgtcggc gcagtctccg 128400
gccgccgatt tctcggtctc cgaggcttgg cgcttcgagg aggccgtaaa tatggcgctg 128460
gtggcctgcg aggccgtgtc accttacgat cgctttcgcc taattgaaac gcccgacgag 128520
aatttcttgt tggtcaccaa cgtaattccg cgcgagtcgg ccgaggtgcc ggtgttggat 128580
agcagtagca gcggtggcga tagcgggccg gaggacaaaa agaaaaacgt cgggaataaa 128640
accgcggggg aaaagaacgg cggtgggtct cgggccaaac gccgtcgtag acgacgcgct 128700
ccgaaaaacg acgccgccac gccgtctttt ctacgtcgac acgacgtgct ggagcgtttc 128760
gcggccgcgg ctgagccttt gccgtcgctt tgtgtgcgtg attatgcgtt acgcaatgct 128820
gaccgtgtta cctacgacgg cgaattaatc tacggcagtt acctgttgta tcgcaaggct 128880
cacgtggagc tgtcactctc cagcaacaag gtgcaacacg tggaagccgt gctgcgacag 128940
gtgtacacgc cgggcttgtt agatcatcac aacgtgtgcg acgtggaggc cctgctgtgg 129000
ctgctgtact gcggaccgcg tagcttttgc gcgcgtgaca cctgtttcgg tcgcgaaaaa 129060
aacggttgtc ctttccccgc gttgttgccc aaactctttt acgaacccgt gcgggactat 129120
atgacctaca tgaatctggc tgagctgtac gtctttgttt ggtatcgcgg ctacgaattc 129180
cctgcgccga cgccgcaggc gacgacggcg ggtagtggtg gcggcggcgg ggccggcgct 129240
tgtgcggtcg agacgagcgc gtcagcaggc cgggtcgatg acgccggcga cgaggtgcat 129300
ttgcctttaa agcccgtctc gctggaccgt ctcagagagg tgttgcaggc ggtgcgcggc 129360
cgcttctcgg ggcgcgaggt gcccgcctgg ccggcctcgt cgcgcacctg tttgttgtgc 129420
gcgctctaca gtcagaaccg tctctgttta gatctcgcgc gtgacgaggc gcggaccgtg 129480
agttatagcc ccatcgttat ccaagactgc gccgcggctg tcaccgacgt cactttgagc 129540
cacatcttgc ccggccagag caccgtctcg cttttccccg tctaccacgt cggaaagttg 129600
ctggacgccc tctcgctgaa cgacgcgggt ctcatcacgt tgaatctatg acgtcggtca 129660
acaaacagct cttaaaggac gtgatgcgcg tcgaccttga gcgacagcag catcagtttc 129720
tgcggcgtac ctacggaccg cagcaccggc ttaccacgca gcaggctttg acggtgatgc 129780
gtgtggccgc tcgggaacag acccgataca gtcagcgaac gacgcagtgc gtggccgcac 129840
acctgttgga gcaacgggcg gccgtgcagc aagagttgca acgcgcccga cagctgcaat 129900
ccggtaacgt ggacgacgcg ctggactctt taaccgagct gaaggacacg gtagacgacg 129960
tgagagccac cttggtggac tcggtttcgg cgacgtgcga tttggacctg gaggtcgacg 130020
acgccgtcta acaggtatag caatccccgt cacgcctctg ttcagatttt attaaaaaaa 130080
aaaaacacaa cataacgaca gtgtcggtgt ggtagctagt gcagctctag gaacagggaa 130140
```

-continued gactgtcgcc actatgtcct ccgcacttcg gtctcgggct cgctcggcct cgctcggaac 130200
gacgactgag ggctgggatc cgccgccatt gcgtcgtccc agcagggcgc gccggcgcca 130260
gtggatgcgc gaagctgcgc aggccgccgc tcaagccgcg gtgcaggccg cgcaggccgc 130320
cgccgctcag gtcgcccagg ctcacgtcga tgaagacgag gtcgtggatc tgatggccga 130380
cgaggccggc ggcggcgtca ccactttgac caccctgagt tccgtcagca caaccaccgt 130440
gcttggacac gcgacttttt ccgcatgcgt tcgaaatgac gtgatgcgtg acggagaaaa 130500
agaggacgcg gcttcggaca aggagaacct gcgtcggccc gtggtgccgt ccacgtcgtc 130560
tcgcggcagc gccgccagcg gcgacggtta ccacggcttg cgctgccgcg aaacctcggc 130620
catgtggtcg ttcgagtacg atcgcgacgg cgacgtgacc agcgtacgcc gcgctctctt 130680
caccggcggc agcgacccct cggacagcgt gagcggcgtc cgcggtggac gcaaacgccc 130740
gttgcgtccg ccgttggtgt cgctggcccg caccccgctg tgccgacgtc gtgtgggcgg 130800
cgtggacgcg gtgctcgaag aaaacgacgt ggagctgcgc gcggaaagtc aggacagcgc 130860
cgtggcatcg ggcccgggcc gcgttccgca gccgctcagc ggtagttccg gggaggaatc 130920
cgccacggcg gtggaggccg actccacgtc acacgacgac gtgcattgca cctgttccaa 130980
cgaccagatc atcaccacgt ccatccgcgg ccttacgtgc gacccgcgta tgttcttgcg 131040
ccttacgcat cccgagctct gcgagctctc tatctcctac ctgctggtct acgtgcccaa 131100
agaggacgat ttttgccaca agatctgtta tgccgtggac atgagcgacg agagctaccg 131160
cctgggccag ggctccttcg gcgaggtctg gccgctcgat cgctatcgcg tggtcaaggt 131220
ggcgcgtaag cacagcgaga cggtgctcac ggtctggatg tcgggcctga tccgcacgcg 131280
cgccgctggc gagcaacagc agccgccgtc gctggtgggt acgggcgtgc accgcggtct 131340
gctcacggcc acgggctgct gtctgctgca caacgtcacg gtacatcgac gtttccacac 131400
agacatgttt catcacgacc agtggaagct ggcgtgcatc gacagctacc gacgtgcctt 131460
ttgcacgttg gccgacgcta tcaaatttct caatcaccag tgtcgtgtat gccactttga 131520
cattacaccc atgaacgtgc tcatcgacgt gaacccgcac aaccccagcg agatcgtgcg 131580
cgccgcgctg tgcgattaca gcctcagcga gccctatccg gattacaacg agcgctgtgt 131640
ggccgtcttt caggagacgg gcacggcgcg ccgcatcccc aactgctcgc accgtctgcg 131700
cgaatgttac caccctgctt tccgacccat gccgctgcag aagctgctca tctgcgaccc 131760
gcacgcgcgt ttccccgtag ccggtctacg gcgttattgc atgtcggagc tgtcggcgct 131820
gggcaacgtg ctgggctttt gcctcatgcg gctgttggac cggcgcggtc tggacgaggt 131880
gcgcatgggc acggaggcgt tgctctttaa gcacgccggc gcggcctgcc gcgcgttgga 131940
gaacggcaag ctcacgcact gctccgacgc ctgtctgctc attctggcgg cgcaaatgag 132000
ctacggcgcc tgtctcctgg gcgagcatgg cgccgcgctg gtgtcgcaca cgctgcgctt 132060
tgtggaggcc aagatgtcct cgtgtcgcgt acgcgccttt cgccgcttct accacgaatg 132120
ctcgcagacc atgctgcacg aatacgtcag aaagaacgtg gagcgtctgt tggccacgag 132180
cgacgggctg tatttatata acgcctttcg gcgcaccacc agcataatct gcgaggagga 132240
ccttgacggt gactgccgcc aactgttccc cgagtaaccg ggacgcggaa cgtgacggtt 132300
gctgagggga aaggcgacag agaaggtaca aacccaccgg cggggaaaat accgaggcgc 132360
cgccatcatc atgtggggcg tctcgagttt ggactacgac gacgatgagg agctcacccg 132420
gctgctggcg gtttgggacg atgagcccct cagtctcttt ctcatgaaca cctttttgct 132480
gcaccaggag ggcttccgta atctgccctt tacggtgctg cgtctgtctt acgcctaccg 132540

-continued catcttcgcc aagatgctgc gggcccacgg tacgccagta gccgaggact ttatgacgcg 132600
cgtggccgcg ttggctcgcg acgagggtct gcgcgacatt ttgggtcagc ggcacgccgc 132660
cgaagcctcg cgcgccgaga tcgccgaggc cctggagcgc gtggccgagc ggtgcgacga 132720
ccggcacggc ggctcggacg actacgtgtg gctcagccgg ttgctggatt tggcgcccaa 132780
ctatcggcag gtcgagctct tccagttgct ggaaaaggaa tcgcgcggac agtcgcgcaa 132840
ctcggtgtgg catctgttgc gtatggacac ggtttcggcc accaagttct acgaggcctt 132900
cgtcagcggc tgtctgcccg gcgccgcggc ggcggacggt tcgggtggcg gcggctcgca 132960
ctacacgggc tcgcgcgccg gcgtctcgcc aggcatccag ttcggtatca aacacgaggg 133020
tttagtcaaa acgctggtgg aatgttacgt gatgcacggg cgcgagccgg tgcgcgacgg 133080
cctcggtctg ctcatcgacc ccacgtcggg gctgctgggc gcttccatgg acctgtgctt 133140
cggcgtgctc aagcagggca gcggtcgcac cttgctggtg gaaccgtgcg cgcgcgtcta 133200
cgagatcaag tgccgctaca aatatttgcg caaaaaggag gacccctttg tgcagaacgt 133260
gctgcggagg cacgacgcgg cggccgtggc ctcgctgttg cagtcacacc cggtgccggg 133320
cgtggagttt cgcggtgaac gcgagacccc gtcggcacgc gagtttctgc tttcgcacga 133380
cgcggcgctc ttcagggcca cgctcaagcg cgcgcgcccg ctcaagccgc ctgaaccgct 133440
gcgcgagtac ctggccgatc tgctgtatct caataaggcc gagtgttcgg aagtgatcgt 133500
gtttgacgcc aagcacctga atgacgacaa cagcgacggg gacgccacga ccactattaa 133560
cgcgagtctc ggcctagccg cgggcgacgc cgctggcggc ggcgctgatc accacctgcg 133620
gggcagcccg ggcgattcgc cgccgccgat acctttcgag gacgaaaaca cgcccgagct 133680
gctgggccgg ctcaacgtgt acgaggtagc gcgcttttca ctgccggctt ttgtcaatcc 133740
gcgtcaccag tattactttc agatgctcat tcagcagtac gtgctcagcc aatactatat 133800
aaagaagcat ccggacccgg agcggatcga tttccgcgac ctgcctaccg tctacctggt 133860
ctcggccatc ttccgcgagc gcgaggaaag cgaactgggc tgcgagttgc tggccggcgg 133920
tcgcgttttc cactgcgacc acatcccgct cctgctcatc gtcacgcccg tggtctttga 133980
ccctcagttt acgcgccatg ccgtctctac cgtgctagac cgttggagtc gcgacctgtc 134040
ccgcaagacg aacctaccga tatgggtgcc gaactctgca aacgaatatg ttgtgagttc 134100
ggtaccacgc ccggtgagcc cctgaaagat gctctgggtc gccaggtgtc tctacgctcc 134160
tacgacaaca tccctccgac ttcctcctcg gacgaagggg aggacgatga cgacggggag 134220
gatgacgata acgaggagcg gcaacagaag ctgcggctct gcggtagtag ctgcggggga 134280
aacgacaata gtagcggcag ccaccgcgag gccgcccacg acggctccaa gaaaaatgcg 134340
gtgcgctcga cgtttcgcga ggacaaggct ccgaaaccga gcaagcagtc aaaaaagaaa 134400
aagaaaccct caaaacatca ccaccatcag caaagctcca ttatgcagga gacggacgac 134460
ctagacgaag aggacacctc aatttacctg tccccgcccc cggtccccccc cgtccaggtg 134520 gtggctaagc gactgccgag gcccgacaca cccaggactc cgcgccaaaa gaagatttca 134580
caacgtccac ccaccccccgg gacaaaaaag cccgccgcct ccttgccctt ttaacccata 134640
aactttcagg tctcgcgtac gattcgcgag tcgggaatgg gacacccgtg ggtgtttctc 134700
cgtgtgtata ttattttttt tttgtgtgtg tttgcgcccc cgtgtgtcta atgtgctgtt 134760
tgaaacacgt aaagtagctg gtggaagaac agataaacct ttaataaaaa aaaaagtatg 134820
tgctcccgac ccacggtctg cgtgtctctt ttttatgtcc atgtctccaa gtctggtgcg 134880

-continued

```
ggtggcggcg gggtcaagcg tcctcgaagt cttcatcatc gtcgtcgtcc tcttcttcgc 134940
ggaggcgacg gctttccaag ctgtcgtggt gactgagtgc agcgacttct tcgccggagg 135000
ctgtggccag cgcctggtac ttaacactgc cgctaccgcg tccgcgaaag taacggacgg 135060
cgcgacacgt cgtaaacatg gcccatatga aaaagagcat gccgaacgac cagctgatgc 135120
cggtgcggta ttcgttgctg aggaaggtat cgtactgcac gatggggtag atgaggccgc 135180
agagtccaaa gaaggcgccc aggtggtagc cgaattgcac cttgacgtat tgaaaaaaga 135240
cggcctcgat cagtaaaaag tagatgatgg agatgatagc gtagaccacg aagacggcta 135300
acaccatgtg gcctgtacgc acgaaaaagt tgtttctgaa gccgtagcat agggccatgg 135360
ctaccacggt ggtgttgaaa ccaagcgcta cctccaccag gttgacgatg agcgtgcgga 135420
actgcaccgt acctttgagc ttggggtgca gacgcgagaa gaaaaagagc gagcgtttgt 135480
agctgcggta ctgcgtgacc atgctcacgt tgaaaatggt caggcagaaa aagtgcacgg 135540
cggccatgaa ggcgatcatg ctgggcagcc gaaatgacat ggtcagtgtg aatagttgga 135600
atgtgtccat gctgaggatg aaaaggaagg ctgtgaggct gtcgcccatg tacgagatgt 135660
cgcgtgtcga ctggtttagg ctcatgcctt tgtccttgcg catgctgatc ttgatccagc 135720
ataccaggta gtagatggtc acggctaaaa agacgagctg catgaacacg gcgtagcaca 135780
ccagctgcac cgagtctaag aaaagcatag gcgtgtgcag gtgcattacg ttgtaggccg 135840
acatgttgag cctttcaaag tccacgacgt gatagtagac gcaggggtag cccaggtgcg 135900
gaaaattgct cagcaccaga tgcacgctga cgttgacaaa agtcagcacc atgaaaacga 135960
tagaagcgct ccatgtccgt gtattcacct tatccacgtg cgagggggcc atggcgatag 136020
cggcggcccg ctcgctcggg aggcgatggg ggcgcgccga tgacgacagg ctcgcgggtc 136080
gttaaatact acgatgggag ccgccgcggc tcacgacgcg gtttgagcgc gtccgggcgg 136140
tcggcgaaaa aagaccccgc gggccttcgc gactctcttc tgtccgagga tgaccgctca 136200
gccgccgctg caccaccgcc accacccgta cgccctgttc gggaccagct gtcatctcag 136260
ctggtacggc cttctggagg cctcggtgcc catcgtacaa tgtctgtttt tggatctggg 136320
tggcggccgt gccgaaccgc ggcttcacac gttcgtggtg cgcggtgacc gtctgccgcc 136380
ggctgaggtg cgtgctgtgc atcgcgccag ctacgccgcg ctggcctcgg ccgtgactac 136440
ggacgccgac gagcgccggc gcggcctaga gcagcgtagc gccgtgttgg cgcgcgtgtt 136500
gctagaaggc agcgcgttaa tccgcgtgtt ggcgcgcacc ttcacgccgg tgcagattca 136560
gacggacgct agcggcgtgg agatcttgga ggccgcgccg gcattgggcg tggaaaccgc 136620
agcgctgtcg aacgcgctta gtcttttcca cgtagccaag ttagtggtca tcggctcgta 136680
tcccgaagtg cacgagtcgc gtgtggtcac gcatgccgcg gaacgcgtct ccgaagagta 136740
tggcacccac gcgcacaaaa aattgcgtcg cggttactac gcctacgatt tggccatgtc 136800
gtttcgcgtc ggcactcaca agtatgtgct ggagcgcgac gacgaggccg tcctggcacg 136860
cctctttgag gtgcgcgagg tgtgtttttt gcgcacctgt ctgcgtctgg tcacgcccgt 136920
cggtttcgtg gccgtggcag tgaccgatga gcagtgttgt ttattgctgc agtcggcctg 136980
gactcacctt tacgacgtgc tttttcgtgg tttcgctggg cagccgccgc tacgcgacta 137040
cctggggccg gacctctttg agacgggcgc tgcccgttct ttcttttttc ccggtttccc 137100
gcccgtgccc gtctacgcgg tccacggtct gcacacgtta atgcgcgaga cggcgttgga 137160
cgcggcggct gaggtgctct cgtggtgcgg cctgcccgac atcgtgggct cggccggcaa 137220
gctggaggtg gaaccctgcg cgctctcgct cggcgtgccc gaggatgagt ggcaggtctt 137280
```

-continued cggcaccgag gccggcggcg gcgccgtgcg tctcaatgcc acggcttttc gcgagcgacc 137340
ggccggcagc gatcgtcgct ggctgttgcc gccgctgccg cgtgacgacg gcgacggtga 137400
aaacaacgtc gtggaagtca gcagcagcac cggcggtgcg cacccgccga gcgacgacgc 137460
cactttcacc gtgcacgttc gcgacgccac gctacatcga gtgctcatcg tggatttggt 137520
cgagcgcgtg ctggccaagt gtgtacgcgc gcgcgacttc aatccctacg tgcgttatag 137580
tcatcgactc cacacttatg cggtttgtga aaagtttatt gaaaatctgc gttttcgctc 137640
gcgacgcgcc ttctggcaga tccagagtct gctgggctac atctccgagc acgttacgtc 137700
agcctgcgct tcggccggcc ttttgtgggt tctgtcgcgc ggccaccgcg agttttatgt 137760
ctacgacggc tattcgggtc acggacccgt ctcggccgaa gtgtgcgtgc ggactgtggt 137820
cgactgttat tggcgcaaac tttttggcgg cgacgatcca ggtcccacct gtcgtgttca 137880
agagagcgcg cccggcgtgc tgttggtctg gggcgacgag cggttggtgg gtcccttcaa 137940
cttcttctac ggcaacggcg gcgccggtgg tagtccgctc cacggggtgg tgggtggttt 138000
cgcggcggga cattgcggcg gcgcttgttg cgcgggctgc gtcgtcactc accgccattc 138060
tagcggcggc ggtggtagtg gcgtgggcga cgcggaccac gcgagtggcg gcggtctaga 138120
tgccgctgcc gggagtggtc ataacggcgg tagtgatcgg gtttctccct ccacgccgcc 138180
cgcggcgttg ggtggctgtt gctgcgcggc cggtggcgac tggctctcgg ccgtgggtca 138240
tgtcctgggc cggctgccgg cgctgttacg ggagcgcgtg agcgtgtccg agctggaagc 138300
cgtgtaccgc gagatcctct ttcgcttcgt ggctcgccgc aacgacgtgg acttttggtt 138360
actgcgcttc cagcccggtg aaaacgaagt aaggccgcac gccggggtga ttgactgcgc 138420
gcccttccac ggcgtgtggg ccgagcaggg ccagatcatc gtacagtcac gcgatacggc 138480
gttggcggcc gatattggct acggcgtcta tgtggacaag gcctttgcca tgctcacggc 138540
ttgcgtggag gtctgggcgc gagagttatt gtcgtcctcc accgcttcca ccaccgcttg 138600
ttcttcttct tccgttctct cctccgcctt gccgtccgtc acttcgtcct cttcgggcac 138660
ggcgacggtg tctcctccgt cttgttcttc ttcgtcggcg acttggctcg aggagcgcga 138720
cgagtgggtg cgttcgctgg cggttgacgc gcaacacgct gctaagcggg tggcttccga 138780
gggcctgcgg tttttccggc tcaacgctta acgagtcacg taggggaact acgtgggtaa 138840
gtgacgtgga tactagtaaa aaaaagtgcg tcaaagctct cagcgtgtga cgtggatact 138900
agtaaaaggg acgtcaaagc tcactacgtg ttgcgtgttt ttttttctat gatatgcgtg 138960
tctagttcgc ttctcactct tcctctcccc gttcccagcg cggtggcagc ttggggggtg 139020
agggcaaatt ggggtagttg gcgttgagca cgtctagcag gcccaggccc acgggccaac 139080
cgtccacggt cttacgctcg gtcagcttga ggctgaacga gtgtgcctcg tcttgaccgg 139140
taaggcggaa aaagaagcgt gctaccagct gcaggcaggt atgctgcgtc tgctggaaga 139200
gcacgaaggt agcgggtacg tactgcacaa tgtgcggttc tttttcctca aagagtaggt 139260
agagcgcgct gcagatcagc cgccgggcgc tgtggtgcag cagccggccg aagctttcgc 139320
gcacgttcac cgcgtccagg tactggagca ggtcgtgcag gcacttgcgc gttaagttgc 139380
aattttccac gcatgaaata acggtacaga gcgcgaagtg cagcaggttg tcggccttga 139440
cgatgccgca gcggtgtttg agccgcagat ccgagagcct cacctgcgtg acggcgtctt 139500
cggtctcgag caaaaacacg gcggagtagc ccagaaaggc cgaggtgcac agcagctcgc 139560
tgcggtactc ggccatggag accagcagcc cgtgctccgt gtgcagccac agcttgtcgc 139620

-continued cgcgcaccgt aaagtcgagc acttgcggct ccatgatcat cacattctgt ctagtgaaat 139680
ccgtatggac ctccagcacg ccgcggatca tcagggcctc catttcgaaa tcggccgaca 139740
cgctctgggc cgcgccgctc ctcgtctgcc gtgatcaggc ggcgcggcgc ggacctttca 139800
agcgttcctg ggccgccgct cgaggcagtt cccctttctg gcactccgcc cgccgcttcg 139860
cggctcattt ggcgtcggcg cgccttctcg cggctgcaaa tcagctccac gtatcggcaa 139920
aacttgctgt cgtcgtaggc ggcggccacg atctcgccga aggagagctg caggtaggcc 139980
tcgggtacgg ggtccagcgt gcccagcgcc aggatgtgac acagataggg cagggtcacg 140040
cgctctaccg tgtaattgga gtagacgatg gcctcttcgg ccccctgatg cgtgaccaga 140100
cgccgcaggc gaaaggtgcg gaaatactcg ttttcccaca gctgcgtgag gaagcgttcc 140160
agcgactcgg tgccgggcac gaactgcgag aagaagctgt tggccaccag gcggttgtcc 140220
tccaccgcca acggacggaa aggcgccgcg tcgcgcgcct tgcgcacggc ctccaacacg 140280
ggcaggtggt agagttcggc gtcgcgcgcg cccaggctca tggagtcctc gcggcgcgag 140340
gcgtagcgcg tgagcaggtc gcgcagttcg cgcacgcgat tctcccaggt ctggttgagc 140400
gtgcgcaggt cctggatctc gtctacctgc gactggatct gctcctccag gcacttgatg 140460
acctgcttct taaacaggtc gcggatgtcc cgctcgggcg ccgccgggcc gggtggcggc 140520
ggcatcagcc cgacgtggcc cgcgggtcct cccaccacgg caccgccggg ccccaccacg 140580
ccgggtccac ccggaccacg cgcgggtagc agacggtttt ggtccaccag cgaaggggtc 140640
aagtcctgca ggaaggactc gacgctgtcc tcgatgccga tgcgcgattt gctgtccgag 140700
acgttaagca aaaacttcat aatggacttt ttggcgtcgc tgccccggtc gtgctgctcc 140760
atcatctcca ccagcttctt gcagttgagc tcgtggcggc tggcggtcac cactttcaca 140820
ggaaaggtat tgagcaactg gcagatcttt tggtggcggc agagcccgtc gtagcgcaga 140880
atctcctcgt gcaggtgtgc caccggcgtg gtgaacagca gcttgtcgcg ctcataagcc 140940
agcggttcgg tcgccacgta caagcggatg tgcttgccgc gcagctgcgc ctccagccgc 141000
tccgagcgca ccttcttgaa gacgcgtacc tcgggcgcgt tggctacgcg cacagctccc 141060
aggcgctcgg ccacctgcag cagcagcgcc aggttagcct gcagcaggtc ctgcgccagc 141120
gggtgtgtct cggtggctcg ctgcacggcc gcgcgtacaa attgcgcccg ctcggccgcc 141180
tcgctcggct tggtcttcac gtccagcagc ggtaccagtc ccaccgttac gcaccaatcc 141240
acgtagagac catagtcgtc gttatcggcg tactgatata aaatgtcgcg gagcgcgccc 141300
agcacgcccg tttgcacgct ctggcgcaac gaggcgctcc acaccaacag atactgctcc 141360
aggtcctctt cgtccagcgc gcggtaggga aacagcgccg cgtgcaactt ccactcttcg 141420
gccacgcgcc gcaccgtgat ggtgtcaaag agcgttttgc acactccgta gagcagctgc 141480
ttgcgcagca cgcacgggtc gcgcagcact tggtgcatgc tttggccgcg acacgtcccc 141540
agaaagccgt gcagcaaccg caggaagctc atcgtctggc ccgtggggaa aatgtcgatg 141600
acggcctcgt catccacacc gcggcccacg cccaagtacg acgacgcctt gatcctcaac 141660
ctctcgtcgg ccgccaagat cgaacggatc gtcgacaagg tcaagtccct ctcgcgcgag 141720
cgctttgcgc ccgaggattt ttcgttccag tggtttcgct ccatcagtcg cgttgaacga 141780
acgacagata acaacccctc tgccgcaact accgccgcgg caacgacgac cgttcactcc 141840
tccgcctcct cttctgccgc cgctgccgct tcgtccgagg ccggcggcac gcgcgtgccc 141900
tgcgtcgacc gttggccctt ctttcccttc cgcgcgctgc tcgtcaccgg cacggcgggc 141960
gccggcaaga cttccagcat ccaggtgctg gcggccaatc tagattgcgt gatcaccggt 142020

-continued accacggtga tcgccgcgca gaacctcagc gcgatcctca accgcactcg ctcggcgcag 142080
gtcaagacca tctaccgcgt cttcggcttc gtcagcaagc acgtgccgct ggctgacagc 142140
gccgttagcc acgagacgct ggaacgctac cgcgtgtgcg agccgcacga ggagaccacc 142200
atccagcgcc tgcagatcaa cgatctgctc gcctactggc cggtcatcgc cgacatcgtg 142260
gacaaatgct taaatatgtg ggagcgcaag gccgcttcgg cctccgccgc ggccgcagcc 142320
gccgcctgcg aggacctctc ggagctgtgc gagagcaata tcatcgtcat cgacgagtgc 142380
ggccttatgc tgcgctacat gctgcaggtg gtggtgtttt tttactactt ttacaacgcc 142440
ctgggcgaca cgcgacttta ccgcgaacgc cgcgtgccct gcatcatctg cgtcggttcg 142500
cccacgcaga ccgaggcgct ggagagccgc tacgaccact acacgcaaaa caagagcgta 142560
cgcaagggtg ttgacgtgct ctcggcgctg attcagaacg aggtgctcat caactactgc 142620
gacatcgccg acaactgggt catgtttatt cacaacaagc gttgcaccga cctggacttt 142680
ggcgacctgc tcaagtacat ggagttcggt atcccgctca aggaggaaca cgtggcctac 142740
gtggaccgct tcgtgcggcc gcccagctcc atccgtaacc cctcgtacgc cgccgagatg 142800
acgcggcttt ttctctcgca cgtcgaggtg caggcttact tcaagcggct gcacgagcag 142860
atccgcctga gcgagcgcca ccgtctcttt gatctgcccg tctactgcgt ggtcaacaac 142920
cgcgcgtacc aggagctctg cgagctggcc gacccgctgg gtgactcgcc gcagcccgtc 142980
gagctctggt tccgccagaa cttggcgcgc atcattaact actcgcagtt tgtcgaccac 143040
aacctttcca gcgagatcac caaggaggcg ctgcgccccg cggccgacgt cgttgccacc 143100
aacaactcct ccgtccaggc tcacggaggg ggaggatctg taatcgggag caccggcggc 143160
aacgacgaga cggcgttttt ccaggacgat gataccacca ccgcgcccga tagccgtgag 143220
acgctgctca ccttgcgcat tacctacatc aagggcagtt cggtgggagt caactctaag 143280
gtgcgggcct gtgttatcgg ataccagggc acggtcgaac gtttcgtgga catcttgcaa 143340
aaggacacgt ttatcgaacg cacgccctgc gagcaggcgg cctacgccta ctcgttagtt 143400
tcgggcctgc tcttctcggc catgtactac ttctacgtgt cgccctacac gaccgaggag 143460
atgttgcgtg agctggcgcg cgttgagctg cccgacgtga gttcgctttg cgccgctgcc 143520
gccgccacgg ccgccgctcc cgcttggagc gggggagaga atccgataaa taatcacgtc 143580
gacgcggatt cttctcaggg cggccagagc gtgccggtat ctcaacggat ggaacatggc 143640
caagaggaga cccacgacat cccctgcctg tccaaccacc atgacgactc ggacgccatc 143700
acggacgccg aactcatgga ttacaccagt ctgtacgcgg atcccttttt tctcaaatac 143760
gtcaagccac ctagcctggc gctgctttct ttcgaggaga cggtgcacat gtacactacc 143820
ttccgcgaca tttttctcaa gcgctaccag ctcatgcagc gtctcacggg cggtcgcttc 143880
gccacgttgc cgctcgttac ctacaatcgc cgtaacgtgg tgttcaaggc caactgtcag 143940
atcagctcgc agaccggctc cttcgtgggc atgctttcgc atgtgtcgcc ggcgcagacg 144000
tacacgctcg agggctacac cagcgacaac gtgctcagtc tgcccagtga ccgccaccgc 144060
atccaccccg aggtggtgca gcgcggcctt tcgcggctgg tgctacgcga tgcgctcggg 144120
ttcctctttg tgctcgacgt taacgtttcg cgcttcgtcg agtcggcgca gggcaagagt 144180
ctgcacgtgt gcaccaccgt ggactacggc ctcacttcgc gcacggccat gaccatcgcc 144240
aagagtcagg gcctgtcgct cgagaaggtg gccgtggact ttggggacca tcccaagaac 144300
ctcaaaatga gccacatcta cgtggccatg tcgcgagtca cggaccccga gcacctcatg 144360

-continued atgaacgtta acccgttgcg actgccctat gagaagaaca ccgctatcac cccctatatc 144420
tgtcgcgcgc tcaaagacaa acgcaccacg cttatttttt gacacaacac cgtgtaagga 144480
aaacgtgact ttattgagca gggtaaaaac cacgtacaag aaccacgttg tctatcccca 144540
aaaaaacaca caccgtcagg gaacacatcg cctatagata gcggcacttt acataaaacc 144600
accgtacctg catcacggtg gctcgataca ctggaaattc aataaaaacc accgtatctc 144660
cgtgacagta cttatcgggt cagcgtcttt ctcttgagat ttctgttcgt aaacttatcc 144720
gtttccccgg tccgcggtgt ctcctcgcga ggctgacagt ctacgggtgg tacctgcaag 144780
agaagaaacc cgggtgggag cgacgccgtc gctgggtatc aaccccgcgg ctgaccgtcg 144840
tccggtaaag gaacgacccg tcgtcgcaag ccgggttcga ccaagagaaa aaacccgggt 144900
gcggggggag acgggtcgtc ctttggttgt tcgcggacgg cgtacatgcc gcgtgggtca 144960
gtcgacggcg tcgctccgtg cggtcggtca tcattctgct tcacatatat gggttgtttg 145020
tgtttttttt ataatgaata cgcactgatc ctatccgtga ctgcgcgtgt ggcagagagg 145080
atgccttata acatgtattt tgaaaaattg ccaacagcta taatttctct catgtagcag 145140
aatagagacc ttttgtcgtc tttttgtttg tcattacttg ttttccaggg aattagagag 145200
agggaaccgc gcctccggcg gcggtgcccg cggaccccgg ccccttctcg cgtgcgcggt 145260
gtgactggtt gagcgaatga gcagctaggc ttggtggtgc tccgcgtgcg ggggagaaga 145320
cgattaacaa caaaaaataa gtggaagtgg ccggtgggtc tttgtccgcg tgcgcgccca 145380
tccgtcgccg ggaccgagca gaaagtgatg tggtggtaca ttgatttttt ccttgacagg 145440
aaagaaaaaa aagagtttg ttttcctatg tgagaggaga aaggtatgtg aggagatgtt 145500
cgatgatcgt atgttacagt tatgctgtaa ggaagctttt atcgtgcgtc ctgtttttca 145560
tttgatgtat atgacacaat tgaaacctat cgataggcgt atatcgagga ttcatcaatt 145620
cttagaatcg tcgtcttttt ggctaattgg actttgccca tgttggttgt cattcgtggc 145680
ctgaggtcat cgtcgtccac gacgacgtgt ctatagcgtg cggtgtgatc attgtgtcga 145740
gccagagaaa gcgcgcctcg cacgacgttt gcggatcggc tcgcgggtgt gtggaattcc 145800
taagaacata atcagctggt cgtctttctt tgatgtgttg ttgtcgtcga ggtcttgctt 145860
cgttttcttt tttcttttta gtcgatggaa cttttcttcg gtacgggttc ttgttatgga 145920
agcttgtgtt ttcgaacatg aattcgaaaa aataaaaagg cctatcttcg tttcaaaaaa 145980
aggacagata tcaatcttct taacttatat catggtaaat tcagaatcct atggtgtctt 146040
attatctcta aagtagtcaa cattatggtc taacttgtat ttccctgacg agatatatat 146100
gatccttata acctggctac tatcatgaac aacaatatcc ttacttacag tcatcttcgt 146160
gagttaatga agtataatat cggtcatcta tcaacttatc tgctatgtaa cgtacccttt 146220
taggtatttt gcgtttctta acgagtgtac ccgcctgtgt gaggcgaaac tctgagaagt 146280
ctaccgagtc gagttacaag tcactaaaac acttacacga gttatctata ctaaaatcac 146340
tatctatgtt gtttgcttac ctaattatta tcctacatga cgaagctacc tcccaacgta 146400
aggtaggggg agaggagaca gaacaataaa aagtaactaa tgtttcttag aacttacccg 146460
ctaaggactt accaaactat attcaccaaa aaacaacagc tacgtgtttc atttgtttta 146520
atctaccgaa gtaaaaaaaa aaaagatgat tagctatcca gaacctactt acttcttaat 146580
gttttaacta aggatgccta tgggattgga aaaaaaatca cagcaacttg ctactaatca 146640
gttgacagcg aagagactca taacaaagat ttctgggtaa tacggttata ataatgctta 146700
tggactaaag gatacttgga aaaaaagaac gggctatgac tatagagatt cgtcgagata 146760

```
tcaaacttca aataggcggc tatcattcat ggttgtggtg actatatcgt ggagaaaaaa    146820
tgtgatcgtt agttagctag gtgagactta cagctatcca tccgtctagt ttttcgttgt    146880
aatgatgata gtacgtctat ggtggtgatc gattttggtt aacaatttgt tcgtttaaag    146940
gcttaatgta cttatgctac atgatgtatt attctttgat tcatcgttcc tcctaagggg    147000
gtgtatgtat gtatgtacta gtcgtatagt gttcctaaca tcatgactat tcagactatg    147060
gcttcatcta tcgtgtctaa agttcactta ttctactatt actatatata tgcactacta    147120
tgtaactagg atatggtcct ataaggtgtc ttctatcacg gtggcttgtt tatcgcttgg    147180
cggttacgag caagagttca tcacggacca gccgtgaggc agggcacacg cgggtcggcg    147240
gcgataatgt ccctcgcgaa ggggacaacg aaaacaagag gccgccggcc gcggccacgg    147300
acgcgtagcg gttacacaat gtttggttga gcgttttgtt tcatcgtcgt ggtggttttg    147360
ttgttctctg tatatatcgt gtggtggctt tatcgtcatc attattatca tcattcttgt    147420
ttccatcatc acgatgagtt ttctccgttt tcctctcctc cagtggtagt cgtgtatcat    147480
catcaatcat cgtagtgacg tcgttgctgc tgctgctctt gccttcatgg cggtatttct    147540
cttcctcccc cctaacccca tattaactcg tgagtgtgat ggttagagtg gctgcttgtt    147600
ttttttttct tttctctttg gaacaacaaa agaggataaa gatggtcggt gaatgtatta    147660
ttattattat catcattatg atacggtcgc ggtcttcttc tccgatgacg aaacctgcgc    147720
acatcgaaga aaagacgagc gcgcgaaccg atagccgtcc gtctgggacg aaggagaaga    147780
tgatggggag aggaggagag ccccagaagc cagagcgaga ggggagacga cagacatacg    147840
tcgtcaccgt cctctggagg aggcacggcg gcgctgtttg ttgtttggat gcttgattat    147900
atcctgttct atggggtaga ttattatcaa taggcttggt tttcaaaggt cagcctgtgt    147960
attgtcgtgt cttttttttc gttctcatga tcgcggagac cacacagacg tgcgcgtctc    148020
ccaatggcta ggcgttcttt ttaggtagta attttttgat cttttttttt cttaacaagt    148080
ctggcttgat ttcttttatc tatgatcgat tcttcttttt ctcgggggtt gcatcttccg    148140
tgaaagtaaa gtgacactac tctaaatggt aaccatatta tctgttgatt aggagaaaaa    148200
ataatttttt cgcacgaaat cgatcctaag tgaggtgatt tacttgctat cacacgaaat    148260
gattatcttt tgctgctaac gtactgaatt ttttaacaga attgcttctc cgtaactatt    148320
tccgcagatt cagacagatt gtcaaaaaaa aatacggcac agaaatagtg ggtctgtggc    148380
ttttggttcg tgtacattcg cgtttgcgtg tcgagatttc tacggtatgt ttattcttcc    148440
tgcgatgatg tagggtcctt ggtgtaagta ggatttcgag tatctctctt agagcgaaca    148500
aaataatcaa aaaacaacag ctaggaaatc gagggttact ctacgataaa gtgtctctac    148560
aaagtgaaga atgttacgtt gtggtggaat aataagactc gcgtgatcga tgagtgatcg    148620
agagcggctc gaaccttctt taagagcttt gtttagtgca actttaaatt acaaggagta    148680
gaaagctgaa atgaatctat gaaggtgcta ttctttgaat atcttacttt gtacgcttca    148740
cattcgttat ttggatagag agttgtctag agaaaatctg tgattctcta tgagtgttat    148800
ttttattatc cttttgggga ctacgatttt tcttcttgtt ctacatacca ctactactcg    148860
taatcacata catggacgaa aaaaaaattc gtcaggcagt agataccaga ttctccgacg    148920
ttacggcgtc tttttttctt ttgagagagt atctgctgag attgtccgtg gtgtatctag    148980
tcgctatttt tgttgttact agtagttttg cacacagttt attcagtata gttttcttc     149040
ttgccatgat caattgagcc caccacctttt tttttaagag aggaggaatt tcgtcttgat    149100
```

-continued

```
ctccagccgg agataacggc ggtggtggtg gtggcgggag agacttcaag gcaatgaaaa 149160
aaaaaaattt cgttttgcca tcaagtggtg acgataaccc gtcagattga taattggttc 149220
ctacagaaac tattctaacc gcggaagaaa gaaattgaaa aaaaaaaatt gacaaaaaac 149280
atcataacat aaaggaccac ctacctggga cgcgcagttg ggcggcggac tggggcggca 149340
tgctgcggtg atgctgtcgg tgatggtctc ttcctctctg gtcctgatcg tctttttttct 149400
aggcgcttcc gaggaggcga agccggcgac gacgacgacg ataaagaata caaagccgca 149460
gtgtcgtcca gaggattacg cgaccagatt gcaagatctc cgcgtcacct ttcatcgagt 149520
aaaacctacg ttggtaggtc acgtaggtac ggtttattgt gacggtcttt cttttccgcg 149580
tgtcgggtga cgtagttttc ctcttgtagc aacgtgagga cgactactcc gtgtggctcg 149640
acggtacggt ggtcaaaggc tgttggggat gcagcgtcat ggactggttg ttgaggcggt 149700
atctggagat cgtgttcccc gcaggcgacc acgtctatcc cggactcaag acggaattgc 149760
atagtatgcg ctcgacgcta gaatccatct acaaagacat gcggcaatgc gtaagtgtct 149820
ctgtggcggc gctgtccgcg cagaggtaac aacgtgttca tagcacgctg ttttactttt 149880
gtcgggctcc cagcctctgt taggttgcgg agataagtcc gtgattagtc ggctgtctca 149940
ggaggcggaa aggaaatcgg ataacggcac gcggaaaggt ctcagcgagt tggacacgtt 150000
gtttagccgt ctcgaagagt atctgcactc gagaaagtag cgttgcgatt tgcagtccgc 150060
tccggtgtcg ttcacccagt tactttaata aacgtactgt ttaaccacgt tgcgtcgtga 150120
cgttgtttgt gggtgttgct aggcgggctg gaaagatgat gtataaatag agtctgcgac 150180
ggggttcggc gctctgccgg ctgcggcggc actcgctcca cggcctccga cgagcgttgc 150240
gctcgcgctt tgcgccgccg cgtcatggat ctgcctacta ccgtcgtgcg aaaatactgg 150300
acttttacga atcctaaccg catcctgcat cagagcgtca atcagacttt cgacgtgcgc 150360
cagttcgtct ttgacaacgc ccgtctggtc aactgcgtgg acggcgatgg caaggtgctg 150420
cacctcaaca agggctggct ctgcgctacc attatgcagc acggcgaggc ttcggccggc 150480
gccaagacgc agcagggctt catgtccatt gacattacgg gcgacgggga acttcaggag 150540
cacctctttg tacgcggcgg tatcgtcttt aacaaatccg tctcctcggt ggtgggctcc 150600
agcggaccca atgagagcgc gctgctcact atgatttccg agaacggtaa tttgcaagtg 150660
acttacgtgc ggcattacct gaaaaaccac ggcgaatcct ccagcggagg cggtggttgc 150720
ggcgccgcgt ctactgcctc cgccgtctgc gtgtcctcgc tgggtggcag cggcgggact 150780
cgcgacggcc cttctgcgga ggaacagcaa cggcgaaggc aggaacagcg tcacgaagaa 150840
cggcgcaaaa aatcgtcctc gtctgccggt ggtggtggag gcggcggcgc tggtggtggc 150900
ggtggcggcg gcgggagcgg cggtcagcac tcctcggact ccgccaacgg actgctgcgg 150960
gatccccggt tgatgaaccg gcagaaggag cggcggccgc ctccctcctc cgagaacgac 151020
ggtgagtccc ggccctcctc gcgtcacggt gctttccgag tggactcgtg agcccccccgt 151080
agcgcacgag cgagcaggcg agcggtgttg gtgcgctggt ggttgtgtgg atgataacca 151140
tgtgcttttt cgtgcgctat gtgtcgtccc gtctgtaggc tctcctcccc tccgggaggc 151200
gaagagacaa aagaccaccg cacagcacga aggccatggc ggcggcggca agaacgagac 151260
ggagcagcag tccggtggtg ctggcggtgg tggtggcggc ggcagcggcc gcatgtcgct 151320
gccgctggac acgtctgaag cggtggcctt tctcaattac tcgtcctcat cctccgcggt 151380
ctcttcttcc tccaacaacc accaccacca tcatcaccac cataacgccg tgacggacgt 151440
ggccgccggc accgacggtg cgttacttct acccattgag cgcggagcgg tggtttcgtc 151500
```

-continued gccgtcgtcg acgtcgccgt cgtcacttct ttcgctccct cgacccggca gcgcccacag 151560
cgcgggcgag acggtgcagg agtccgaggc ggcggcgacg gcggcggctg cggggttaat 151620
gatgatgagg aggatgagga gggctccggc tgaggcggcg gaggcaccac cgcagtcgga 151680
ggaggagaat gattccacca ctccagtctc taactgccgt gttcctccga attcgcagga 151740
atccgcggcg cctcagcctc ctcgcagtcc gcgttttgat gacattatac agtcattgac 151800
caaaatgctc aatgattgta aggagaaaag attgtgcgat ctccccctgg tttccagcag 151860
actcttgcca gagacgtcgg gcgggactgt cgtcgtcaac cacagcagcg tcgcgaggac 151920
cgccgcagct gtctccacag ccggcgttgg ccccccagca gccgcatgtc cgccactcgt 151980
caccaccggt gttgtaccct caggttccgt cgccggtgtc gcgcccgttg ccgccgcagt 152040
cgaaacacca gctgctcctc cccggcccgt gtgtgaaatc aagccctacg tggtaaaccc 152100
cgttgtcgcc accgccgcgg ctgccagtaa ctcttcctcg tcttcttcgg ctccgctgcc 152160
gccgccgcca ccaccgccgg gcggacgtcg gggtcgggcc cggaataata cccgaggagg 152220
cggcggtggt agaaacagcc ggcggcaggc cgcatcgtcg tcgtcctcct cctctcggag 152280
atcgcgacgg agaaacaacc gccacgagga cgaggaggac aacgaccctc tgctccggtt 152340
gtcgcaagtc gccggcagcg gccgccggcg agggccctcg ttcctcgagg acggactcga 152400
aattatcgat cccagcgagg aagctgcgat cgccgccgcc tcgatcgcgg cgtttttcga 152460
cgattaaaaa accgagccga gaccggaaaa attatgaaac aggacgcgct tggacatttg 152520
ggtttccacc ccctttggtg tgtgtctata tatattggtc actgattttt tttacaataa 152580
agagatagac atcacagttc accaccttgt ctccccggtg tgtctattat catcaatcac 152640
ccacagagtc gccagtccat ggtctctcgg taatgcgtgt ccagatacgc gttggccagt 152700
ataaaatggt cgttgcccac aaaggcgcgg gtggtgttgc gcggcgacgg gtggcaggac 152760
ttgagtacca agtgccgccg tcggtcgatc aggtactcgc aggtgtgcgc gtcggcgccc 152820
catagcatga acaccagatg ctcccggcgc tctgacagcc tccggatcac atggttactc 152880
agcgtctgcc agcctaagtg acggtgagat ccaggctgtc cgtgcaccac ggtgaacacg 152940
gtgttgagca gcagcacgcc gcgtcgcgcc caggcgtcca ggcaacccga ggccggacgc 153000
tgaaacccgt ccaccgtacg cgccagttcg cgaaacacgt tgttgaggga gggtggcggc 153060
ggtcggcccg ccagcgtgcc gaaggccagg ccgctggcgc tgccgtcgca gtacgggtcc 153120
tggcccacga tcaccacgcg cacctgctcg ggcggacaca gatagctcca gcggtgtacg 153180
tgctcgggtg ccgggtacac catctcgagt tgccgcgcgc cctccaccgc cgccaccgtg 153240
tcgcgcagca gcaccgtgtc gtggtcgggc aagctgagga agcggatcca gtcggcgctc 153300
agacaaaaca cgcgagcctg ctcgtcgggg gttaacagag agcctttatt atcagcaatg 153360
ttagcgagca tccactgctt gagggccata gcgcgagtga gccggcaggt tgacgcgcgt 153420
ctgcttcagc tcgggcggca gtccggcgta gtatttatct aggtggcgta gcagcggcgg 153480
gtccagctgg tgacgcaggc agaattcctt cactgcgttg tacaggccgt aaaagagcgt 153540
gatgccctcg ggcgcggcag cggtgctcac gggcagacgc acggcgcggt tggtacgcgt 153600
ggcttcgttg cgtatggcca ccaccacgtt aaagagagac ggtggcacca gctcgaagcc 153660
taacacgtgt tccgtgaaga tgctgcgccc gtatgacagt cgcgtgaggt cgtagccgcg 153720
gcacaggtcg tccacgcacg tgtacacggc cggcgagcca tcgccgcact cgctgtaacc 153780
gcgcatcacc gtcatccagc gcggcgctgt gtccgagctc aacagcgtca gcaaggcccg 153840

-continued

```
caattgatcc ggattgttgt acagcagggc cagagtgtcc aggaaagcat cgtccaacag 153900
cacggagttg gcggcctccg gcgtaacggg acggtaacga ataagttgcg atagcgggcc 153960
atcgcgtctg gtaacattca ccaacgggcg cagccaactt tcatacttgt caccctgaaa 154020
cacctcaccc aacaggcatc gacgcgttag ttcggggcac tccgcgggaa ctttctcggc 154080
gacggtagga gcgacgctga cggtggctga ggaaacgatg ggcagcagaa ggcaacacca 154140
cagcagtgcc accggtccag gtgagaaaga gaagccgcaa tccgggcggc ggcacatcaa 154200
gtctgcggca cgatgagagt gtgacggtaa ggagccagtt ggcgccgaaa gttggcgctc 154260
aggtcttcga tccctaaaac gttatatatt gcatccagca ggtgagccag gctaaacgga 154320
ttcacgtacc aggtttggtt acccgcgacg ataacggcca gaccgtgggc gctacagttg 154380
gagaggttcc tgggtacgaa ggtaactgag tcgatgtcgc gccacggggg gaatgagaca 154440
gacgactggc gcacgctgta atcacaactg tgattgacgt attgtagcgt gtaatttagg 154500
ttgcactcag cctcgaagta gagggggaac cacagttcgt cgtactcgtc gtcgtcctcc 154560
agttctggct cttcttcatc caccgcaatg tctacgctgc tctgagattc ctcttcgtac 154620
aggatgattg acaggttatg gctacaaagg tcctgggcgg gaggacgcgt gggagcgcgg 154680
gtggtggtaa tgttttccag atcgtcaaaa gtcggagtgt agtctgacgc cgtgacgaca 154740
ccgtcgacgg agatagtaga agttgcggcc ggtgtcacgg tggtaagtat ggatacagaa 154800
ggggaggggg aagtagcgtt cgtaccgatg gttgtggtat tattattcct tgtatttctt 154860
gtttcagaaa ccgttgacgt tgagatggga atcgacgtgg cgctggacgt cagattgctg 154920
accgaggaaa ccgtggtggg agtggtgacg gtgttactcg tggttgaagt gacgttaggg 154980
gaggtagtag tggtaccggt ggtggcgacg gtagtgtttg tcgtggcggc ggcagcggtg 155040
gtactggtaa cggtggtcgc gttggtttcc accgcttcac acagtaagca aaagcacagg 155100
gccaggaaaa gcaaccagcc ccgccatcgc cgccgccgct tcatgaggtg ggcaggcgaa 155160
agctggtgaa ttcgttgtac agcggcaagt ggggcgccgc gatcgaaggg tacgtcaaca 155220
agctgacgtt gatattaaat acgtctggct gcttttctac gatggaagcg cacagggtta 155280
cggcgtcaaa caggtctttc ttggtggcgc ccgagaccca catctggtat acacccgtct 155340
cgtggtacga agtagagcgc ggcaccaccg gacggatgca gtccagaacg cggttgggat 155400
cctggtgaaa gaatttgaac gtggctacgg cctgtggcgt gtgcggcatc gtctgcgtga 155460
tgagctgctg gcccgctaac acggtgacgt tgtgcaactt gagcagggca ctcttgaggg 155520
cctggaaagc gttgccgcac gaggcgctga tctgcagctg cacggccgtg gagtcgtgca 155580
gccgcatgag acgtgatacc tcttcgaaga cgtacttgta tttgctggca aagagtggcg 155640
cgtaccgaca gtcggccggc aaaatgtagg tggcgttacc gccgttggtg gccacggcgg 155700
gcgcagcggc cgcggaggcc ggcgtaaaca gcgtcagcgg ccggtggtgg ctggtaaggt 155760
cgatcatggg cggcgtggtg accgtggcgg tggcgggcat gacggggttt gcggcgacgg 155820
gcactccggc cacagcggcg gcagcggcgg ccacggcggc gctggccgag cccacacccg 155880
ccggcagtcc tccgccaccc atgacgccgc cgggcagagc gtcgcccaga cagacttcca 155940
cagtggcggg cgcgctctcg gcggtcagta cggtttgccg atcgacctcg cgacgaaagc 156000
tggtgaggaa ctcactatga tccatggccg cagggcccga gatcccggga ttctgcgggt 156060
gctgaccgag tgcgggccga gttatatgga agacgattag cttggagcgg agttttgcgt 156120
ccctagctga cctgcggatc agcgacgtgc catagggata gactgtgagc ggcggccgca 156180
acggcggggt cggccgccgc tcgtcgtcac ggggcggcgc gagggaggag gaggtggtgg 156240
```

-continued

```
gtacgatctt gacgtggttg acgtcctgcc cgtccggggg aatacgcaaa aaaccccgcc 156300
gcggcgctac cacgatggtg cgatgggtct ttctcttgtt ggccggggcc agggacttgc 156360
agatgcgtgt ggagccgtag acgatctgga cgtggtcctg ggagaacatg accatcgccg 156420
ccaacgctca gcggggggac gggttgggaa cacagaggct gaggggaaac cccgtagaag 156480
tcagcgaaat aaagacaaca cagcagccgc tcctctcgtt tctggcccta ccactgcttg 156540
aagtagggca ccgggtgttt cttttcctca acgggctcct ccagtctctt ataggaccag 156600
tcccgccggc gcgccagcat gtaggtcacg tacaaaagaa taattaccat gaacaccagg 156660
aaagccagca cgccgtaggc cagcagccgg tcctcgaaca gcgggtcgct cttgataaac 156720
acgtaggtgg tggtaaaact tcggcccgcg atctgaacgt ggagacgcac gacagtatac 156780
gtgccgttga ggtagaagac aaactcgcgt aaccgttgtc cgttatacgt cacgttacta 156840
atattccacg gcggaatgag ctggtcgccc tgatgcagat gcacggtgct gtttgggtga 156900
tagaggctgc taccgttgag caagcagtgt tcgtgttcct gaagcagcac gcggacccgc 156960
atcgtggtag cgttcaagcg agtcccgtac acggcgtaga tgggataggt gaaaaggtcc 157020
caagtggcgt tgtgatggcg gccccagctg aaaaaagagc acgtgtactc agtggtctcc 157080
tgcggcctga gtcccgagat aagcagctct tgagcagtag cgttgtagga gagatgtagt 157140
tttcctgtgg ataaaattca tatgctgttt attctgttag caggttggtg ggggaggaag 157200
gggaatagaa cagaggcggt attacttacc tttatcaccg ggcgcaaaag cgctaagata 157260
ccccacctga gtgaagggac ccttgcagtc tgtccgtgca taacaggtaa tggacaaaat 157320
gtcgggattt acggtgttgt tcaacaggga cactttacag gtggcgttga gagacacctg 157380
gtcgtagctg tagctggctt cgcaattcac agtatacagg tgcccctctt tctgcgtcgt 157440
ggctgccacg gaggtagcgg cggatgtgaa ggtagagccg gacgtggaaa tagaggtttg 157500
taccgtggtg ctgacggcag aagtgacgtt attagaggta cttattgacg tagtggacgt 157560
gacggtggta ttaatggggg aagtgacggc gcttgtggtg ctactttcca ctcccgggtg 157620
cgtgtcgcct aagagcgtaa ccatgagcgc gatcgccagt acgggacaca tgttgccgtg 157680
tgacgagacg gagtgtggac gagctatatg tggcaggagg ccgcgtcacc tcttatgacg 157740
cttaaacgtc cagctccaga taaaagaggc gttaataatg aacactacaa aaaccacttg 157800
cgtcaatatg acgatcataa aggctcggtg atcgctgcgc ctaaagtatg cgggattctc 157860
caccagctca ctgtctttga caaagtggat agatgtacta gtgttaccgg ccgtttcgtt 157920
gaccatggat tgtactatga aagtcccggc gccaaaagtt ccattagagc cccagcaagt 157980
aacgctgccg tttacgtagg ttcccggctg gcctgtcagc atgtatgtca gttggtgggt 158040
ataattctgt ttaatgtttt ccatgtcctc gctgtagttg acttttctag tgagaaattg 158100
cgtacgatgc ggaaggacga tcatcatccc tgaggccaaa aagggcgaat cataagctgt 158160
cgtgttacaa aaaatagtca ggttagtatc gttgtgctca tagatataag ccatttttac 158220
ttgaggttca taccaccacc ctaccctaat tgtagttgcc accgtcaccg agtcccatct 158280
cccgaaacct accaccgcca ccactaatag cgtcaccccc gcacggtaca tagttaccct 158340
ctcgacgtcg ccggctgtca atgacgtgcc tgcgtcagtg gctatgattt atagcttttg 158400
gacacaaccg caacggatct gtcgtaatct accttccaca gggccgccgc gacgatgctg 158460
aacgacagga tcagacagac ggcgtatagg agtcctaggt cggcgtcgac gcggcaggtg 158520
cggatgtctc gcagggtggg tagatgggcg atgcacaact ccttctcccc ccgcccgtac 158580
```

-continued attccatccc gtatcagcag ccgtagcgtg gcattgatgg tcagcggggt aaccaaagaa 158640
atcacatagg gatgtgtaca ggaagtgcag tgacgggtat ccgtgagatg taagtcatca 158700
ccctcatcac cctcatcatg aaagaccagg actcgggtga gacgacccga tgaatactgg 158760
atctcccacc acagtctttg gtccaacacc gagagggcgc aggagattct aagtctccct 158820
gggttggggg agcagatgta agccccgtgt gtgccccttg ccatcaaagc catacacatg 158880
agggggagaa ggacaagtat ccgggaccac ccgcaccccc acatcacgag accagagacg 158940
gagatgtata aaaaaagcta cttttattaa acagcattct caccacacgt taatactgtc 159000
acggggaatc actatgtaca agagtccatg tctctctttc cagtttttca cttactgaga 159060
cttgttcctc aggtcctgga tggctgcctc gatggccagg ctcagggtgt ccaggtcttc 159120
gggaggggtc tcggtgggct gctcaaactg ccccacggcg taggccttcg tggccgtctc 159180
gtagataggc agcatgaacc caccctggtt ggtggagaag atgcgcacca tgacctgttt 159240
gggaaacttt tgcatcaggg gcaggcacag gttgagagcg cccaacaggt ccacgggggt 159300
ggcagcgtgg atgatcatgt tgcggtaatc ggaggaacgg gggcataatt ggtgggtgtg 159360
caattctttg aggctccacg cggccttgac gccttcgtta caagcatcgg ctgtgcgctg 159420
cgccactttg ggtggatgtg tcacgggcat ggtgtgctcc atgaggaagg gagtggagag 159480
ggccaggttg cacatggtgc ccaggcgaca ccgcaccgca tccacctcac tcttcacctc 159540
atgattgcgg gtgtagataa tctggatgcc cttgttgttc acctgcatgg ttttgcaggc 159600
tttgatggcc tcatctaaca cctggtgcat actgggaatc gtgaagggca ggttcttgta 159660
ctcaagagag cgattggtgt tgcggaacat gcggctcacc tcgtcaatct tgacgcgacc 159720
ccgccgagtc tgcacgttgg gtgtgcagaa gggggtgttc ttatctttca tgatattgcg 159780
caccttctcg ttgtccaact cggagatgcg tttgctcttc ttcttgcggg gtccggtgct 159840
cgccccgccg ctgctctgat ggccgcagct cagcagagag gaggaggccg cgccaccaaa 159900
accgccgcgc ccatggtggc tcgaggtcac ggatgctcct ccgccactgc tgcatttcat 159960
ctcctcggac tcactctccg agtccgaagc cgaactgcag gaggaagacg aagaggaact 160020
atcttcatcg ggccggccca agggatcggg aagaggaggg tggttcatct gggagagcgg 160080
gtgcgtggga gaggtcactc gcggcgtgcc gctgccggtg gaaggggaag acgcggtagc 160140
accgcgggtt tcgacttctt caccctgttc ttcctcgcta tcagagatca cgatacagcc 160200
ggcggtatcg ataatcttgt tgcggtactg gatggtaaag tcgggctcgg gcttgatgtc 160260
ttcctgtttg atgaggggca gcatgatagg cgcgggaggc acgggcggtt taataatcac 160320
cttgaaagga cgcgtggttt tgcgcggttt cttacgcggg ctgagctcgg gagtagcgga 160380
tgccccgggg agaggagtgt tagtaaccgc gacgctggtg ggggtcggct tgttaagagg 160440
ggcgctgcta acgctgcaag agtgggttgt cagcgtgggg ccggtgctac tggaatcgat 160500
accggcatga ttgacagcct gggcgaggat gtcacctgat ggtgataaga agacacggga 160560
gacttagtac ggtttcacag gcgtgacacg tttattgagt aggattacag agtataacat 160620
agagtataat atagagtata caatagtgac gtgggatcca taacagtaac tgatatatat 160680
atacaatagt ttactggtca gccttgcttc tagtcaccat agggtgggtg ctcttgcctc 160740
cagaggcggt gggttcctca gcaccatcct cctcttcctc tggggcaact tcctctatct 160800
cagacactgg ctcagacttg acagacacag tgtcctcccg ctcctcctga gcaccctcct 160860
cctcttcctc atcactctgc tcactttctt cctgatcact gttctcagcc acaattactg 160920
aggacagagg gatagtcgcg ggtacagggg actctggggg tgacaccaga gaatcagagg 160980

-continued

```
agctggcacc agcggtggcc aaagtgtagg ctacaatagc ctcttcctca tctgactcct 161040
cggcgatggc ccgtaggtca tccacactag gagagcagac tctcagagga tcggcccccca 161100
gaatgtactg ggcaaagacc ttcatgcaga tctcctcaat gcggcgcttc attacactga 161160
taacctcagg cttggttatc agaggccgct tggccagcat cacactagtc tcctctaaga 161220
catagcagca cagcacccga cagaactcac ttaagagaga gatgccccccg tacatggtca 161280
tcatacaagc gtcactagtg accttgtact cattacacat tgtttccaca catgtagtga 161340
ggatatccat aaatatgtga tcaatgtgcg tgagcacctt gtctctctcc tcatccaaaa 161400
tcttaaatat tttctgggca taagccataa tctcatcagg ggagcactga ggcaagttct 161460
gcaatgccgc catggcctga ctgcagccat tggtggtctt agggaaggct gagttcttgg 161520
taaagaactc tatattcctg tagcacatat acatcatctt tctcctaagt tcatcctttt 161580
tagcacgggc cttagcctgc agtgcacccc ccaacttgtt agcggcgccc ttgctcacat 161640
catgcagctc cttaatacaa gccatccaca tctcccgctt atcctcaggt acaatgtagt 161700
tctcatacat gctctgcata gttagcccaa tacacttcat ctcctcgaaa ggctcatgaa 161760
ccttatctaa gatatctaag gcattctgca aacatcctcc catcatatta aaggcgccag 161820
tgaatttctc ttccgtctgg gtatattttt tcagcatgtg ctccttgatt ctatgccgca 161880
ccatgtccac tcgaacctta atctgtttga ctgtagagga ggataacaac acatataagt 161940
atccgtcctc ctgactcatt tatcgctatc tcgatgcccc gctcacatgc aagagttaat 162000
ctttactcta tctgacatac acaagtaaat ccacgtccca tgcaggttag tatacatcac 162060
atacatgtca acagacttac cgagttctgc caggacatct ttctcggggt tctcgttgca 162120
atcctcggtc actcgttcaa aagttttgag ggattcttcg gccaactctg gaaacagcgg 162180
gtctcccaga ctcagctgac tgttaacctc cttcctcaac atagtctgca ggaacgtcgt 162240
ggccttggtc acgggtgtct cgggcctaaa cacatgagaa atagagtcat aagcacatgg 162300
gtcacataca ggagatatgt atataacatt aatacaattt tataaaaaaa aggggggggca 162360
caaaccccga cacgtaccgt ggcaccttgg aggaagggcc ctcgtcagga ttatcagggt 162420
ccatctttct cttggcagag gactccatcg tgtcaaggac ggtgactgca gaaaagaccc 162480
atggaaagga acagtctgtt agtctgtcag ctattatgtc tggtggcgcg cgcggcagca 162540
acgagtactg ctcagactac actgccctcc accgttaaca gcaccgcaac gggagttacc 162600
tctgactctt atcagaatac aacaactcag ctgcctgcat cttcttctgc cgctgcctta 162660
agtcttccat ctgcgtcagc ggtgcgagcc caatctccga gctcattttc agacacatac 162720
cctaccgcca cggccttgtg cggcacactg gtggtggtgg gcattgtgct gtgcctaagt 162780
ctggcctcca ctgttaggag caaggagctg ccgagcgacc atgagccgct ggaggcatgg 162840
gaccagggct cggatgtgga agctccgccg ctaccggaga agagcccatg tccggaacac 162900
gtacccgaga ttcgcgtgga gatcccacgc tatgtttaat aaaaactgcg ggcacggggg 162960
acggcgttgt tgtatatgtg aatttgtaaa taataaatgg gaccccatcc tgtaaaaata 163020
cagagtccgt gtcagtctct gaaggacaga gtattggcat atagccaata gagatagttg 163080
tggcaaagag ccatgttatg gattagtaat ggaaagtatc gtcaccaata ggggagtggt 163140
caataatggt caataaccca cacctatagg ctaagctata ccatcaccta tagcataagg 163200
aagcgggggt gtataggccc caagccaaaa acagtatagc atgcataaga gccaaagggg 163260
tgtgcctata gagtctatag gcggtactta cgtcactctt ggcacgggga atccgcgttc 163320
```

-continued caatgcaccg ttcccggccg cggaggctgg atcggtcccg gtgtcttcta tggaggtcaa 163380
aacagcgtgg atggcgtctc caggcgatct gacggttcac taaacgagct ctgcttatat 163440
agacctccca ccgtacacgc ctaccgccca tttgcgtcaa cggggcgggg ttattacgac 163500
attttggaaa gtcccgttga ttttggtgcc aaaacaaact cccattgacg tcaatggggt 163560
ggagacttgg aaatccccgt gagtcaaacc gctatccacg cccattggtg tactgccaaa 163620
accgcatcac catggtaata gcgatgacta atacgtagat gtactgccaa gtaggaaagt 163680
cccgtaaggt catgtactgg gcataatgcc aggcgggcca tttaccgtca ttgacgtcaa 163740
tagggggcgg acttggcata tgatacactt gatgtactgc caagtgggca gtttaccgta 163800
aatactccac ccattgacgt caatggaaag tccctattgg cgttactatg ggaacatacg 163860
tcattattga cgtcaatggg cgggggtcgt tgggcggtca gccaggcggg ccatttaccg 163920
taagttatgt aacgcggaac tccatatatg ggctatgaac taatgacccc gtaattgatt 163980
actattaata actagtcaat aatcaatgtc aacatggcgg tcatattgga catgagccaa 164040
tataaatgta catattatga tatagataca acgtatgcaa tggccaatag ccaatattga 164100
tttatgctat ataaccaatg actaatatgg ctaattgcca atattgattc aatgtataga 164160
tcgatatgca ttggccatgt gccagcttga tgtcgcctct atcggcgata tagcctcata 164220
tcgtctgtca cctatatcga aactgcgata tttgcgacac acagaatcgc ccaagtcgcc 164280
aaagtcgtct atcgccatcc cccgtaaacg atataagcgc tatcgccaga tatcgcgtat 164340
gcccaaaaat cacttttgga aaaatggcga tatcagttac acagaaactc acatcggcga 164400
cattttcaat atgccatatt ttcaaatatc gatttttcca atatcgccat ctctatcggc 164460
gataaacacc actatcgcgc gacatgaatt tagtcggcga cagaaatctc aaaacgcgta 164520
tttcggacaa acacacattt tattattcac tgcagcatat agcccatttt agcgcggcac 164580
acatccagcc gtttgtgttt cttaacgctc tccaggtact gatccaggcc cacgatccgg 164640
gttatcttgt cgtattccag gttgatccat cgatagggaa cgctgccagc ggcgcccagc 164700
aggtactgcg ccttgtcgtt cactttgccg cagcgtattc gcccgtcagc ttcgagatat 164760
aacctacaac acggagggga aggggggtac aaaacgtgaa attagacttt tttttaatga 164820
tgttttgtcc ctctctgtct tactctccca taggctgtaa ggccctcgag gaagagactt 164880
acggattgta gttgcagctc gtcagtttgt tgtgtacgac ctggcgtgtc aatgaatggg 164940
tcatggtggt gacgatcccg cgaatctcag ccgttttctc gggactgtag cagacttcgc 165000
cgtccggaca ccgcagcctg tggattcatg aaaatctact ctggcattcc cgaggatcgt 165060
cgatggaaca tggctatcag aaacgtcgag agacagatcc agacgcacca cagaacgcag 165120
acaatcatga aaatacgtac gcgacggtga agcgattgca cattttgaaa tcgtaacagc 165180
gttccggcgg gtggttgacg tttatgaatt cgcaacattc ttctgcgcgc acccgcggca 165240
cgcggctgtg acccaatagc agccacaacg ccgtcaagaa cggcgtcagg tttttgggac 165300
tcatgacgcg cggttttcaa aattccctgc gcgcgcgacg ggctcaaacg atgagattgg 165360
gatgggtgca gaaggtgtaa aagtctggtt attggcctcg gtgaacgtca atcgcacctg 165420
aaaagacacg ctgtagtccc ggaagacgtg agcccagctc tccagcttca tcacacacat 165480
ctgataacgt gtgccatcgt tgacgacgaa gcgtagcagc ttggtctgct tgggcaccat 165540
gtgcgctcca aaaatcttgg cgtcttccac gctgatctgc acgtttccgt cgctcggttt 165600
cgaagccgtt cggggcatcc gttgaaggat ggtctggttg cgaccgctca ggtaccagat 165660
cacctttttc acccaggtgg agcttctctc caccaaggtc tggccttccc ggttatacag 165720

-continued

```
cagatacagg gtctcgttgc gacactcggg acccgttaat acccgctgga accccgagaa 165780
ttgcaagggg gaccgtgggg gcgagggata gagaaaagga cagtaaaacg tcgccgcgtc 165840
atgcggtttg gaatacgtca gtttagacca tggcggggac ggattctggt ttgccgttag 165900
cgtcgaccag ggagacgcca gacagggcgt tgcccaaacc gcgcacagaa gcaggcagtg 165960
aaagtggtga cgaagcagaa gccgcagcat attatttccc gtgacgcagg ctagttggca 166020
aagagccgca cgctgaactc gaggctccgg gcgtgtggcg ccagcgaacc ggcggcgttg 166080
aacgtggtcc ttttgttggt gccgccgcga cggttctgac gtctaaagtc gctgatgagc 166140
aacgacacct cggtcacgtt gattctgcaa gcacaggttc caaacgtcat ttcatacccc 166200
atgcggttac ttagccgtta cccgttcgct cttaccttcc cgttgtcatg cacctttagc 166260
gcgtaccctc acctcttgag cacgtcaaag ttgtccaagc cgtggctcgc atcgtagtgg 166320
tagttcaacg tgaggtccac gagctgttcc acatacttgt aacgggtttg gtcgggcagc 166380
gcgcgagagc acgcgtccca gtaatgcggt actcggtaat aatcgttttt ttccgcggtt 166440
tcccgctggc actgacccag caccacggcg cacagacaaa cagacagcca cacccgacac 166500
agccgcatgt tgcagactga gaaagaaagc tttattatga gacatcatac acatagtata 166560
ggcgaggtga tggggcgggg aaagagttgg aaccgaaaga caaaaaaaaa agcctagtcg 166620
tactcgggat ctctgagcga gacgggttgc atggcaactt tcattagttt gggaatctgc 166680
cagctggtgc tgttcgaagg ttcttccatt tccgaggcgg tcagttcatc gtacaccgaa 166740
acgtagtacc tgatggggtc ctcctcattg tccgagaggt gagattcgat ggtcaaaggc 166800
gagcctctcc cataattggg attcacgaac gacgtgtcca agttgccatc ctttctgaaa 166860
tagatgacgt tctcaggatc atgtttcatg cgctcgcggg ccgcggacgc ctcctcctcc 166920
tcgtcccagt cccgagtttc caaccgctga taagggctcg aggaacaaaa tccggcgggg 166980
atctgagaac ctcgtcggga accgctgcca aacgggctgc tgccgccact gtcgtccgtg 167040
tcgtccaaca ggttgacggc ctcttcgtcg gcgaaacgaa agcggcccgg gtgcttgcaa 167100
cacgaggagt aaactaccgc gatcagtacc gctatgaagc tgaaaatgga ggtgcctgtc 167160
acgatgtaga agaggatagc cagcactttc atgatttcgt cattgcgcgc gtcgtgaacg 167220
gaagattcgc gggcggtggt catgttggtt tcggttgtag gttcgctact cgtggtgctc 167280
tcgacggtat ttctgctgct ggtgctagta gggacgtttg tgctgctggt catatttgta 167340
gcgtcgctga agtcgatgtg aagcagcaac ccgaacgcga ccaggaccag gaatgttgcg 167400
cgaaggagac cccgcggggc cggcattctt gagacgtggc gacgtggatt tctcgttatg 167460
tccgcgaacg acgtgtgacg aggacgtggt ttccgcaagc ctctaccgac gccgcgacac 167520
caggtaggtt atcaaaacgc gagcccatat cgccgccatc attgtaatca gcaatgtgtt 167580
gaggtactgc acgatgaatc tgtctagtga caccagccaa ccctctgctt ttgcgggcaa 167640
gcgcgctttc ggtgacaggg tgtatcgtac gtagccgcgg gtcaggcgcg cgttgtagcg 167700
gtacacgcag aaatctatcc acaggccaac gcccggctgt agcttaggat ggtggataat 167760
agcgcggtga cgtacgccac ggggctttag aatctccacc tgtaaggcca tctcctccag 167820
gtagtgggtc tgactgcgac gcagcgtcca gttcatgtaa aagtcggtct cgccgtgtcc 167880
ggccacgtag aggctgctta ctaaatcggg cgccagagct agatcaggcg tatcaaattc 167940
cactgccagg cgacctgatt ctaacggttc cacgatccgg gagagcgttt ctagatatag 168000
agcaaagcgt accacgtcta cctgcggtgt aaaaaactgt tgtgggcgtt caccgtcgtt 168060
```

-continued gaccacgtaa gccacgtaga ggccaacatt ttccaccacg ggttctagct gcaggcggca 168120
cgtaaagctt agaaacgacg gctgtacggt ttggttcccg tgaagctgaa gcgtcacttc 168180
cttgccgggg ctcaccgtgc tgtaacgccg caccgagtcg gtcatctgct ccagatcggt 168240
agaccagaag ggcgtgcaat gcatactgtc ccagtcgcga cacgcagccc agcctagctc 168300
ggtgaagggt cgacgcacac ccgaaaaagt gtgcttgaag accagggggt cgcctcggta 168360
gctcagtagc cgaacatgca catagtcgcg gctagcgttg acagacggcc cgtagagggc 168420
cagcaggaca agcgtgaaca gcaagcgcaa catgctgcgc gggttagaaa atgcggcgtg 168480
ccggccaccg cccgactcat aaacgctacc agcatgacgt ctcagatcac acaagtgacg 168540
aggagcgtac cgcaaatcac tagggaaaag gccagcagag cccgatagtc ttgctcttcg 168600
cgaacgatct cgtccggttc ctcgcagtct tcgtggtcca cagaagatga ggagcaggat 168660
tcttcgttaa tttctgccag gatactagtg ctgtaccaca ccagagcgct cagcgtgccc 168720
agggctaccg cacggtaaaa tagggacatg atcaccagcg caatctgaag tggtggtagt 168780
tcagtttctt ggcgtatttc cagagaaagg ctttgtaggc cgtagggact ggccaggcac 168840
cgaactcaat attggtagac actacgtcgt aaatgcgttg ttcctcgtct aagattaacc 168900
gaaaaaatag ccggttgatg tgacgacgca cggcttgcgc gttaggattg agacacttgg 168960
tgcccttgtc ctttaaaata gccagcactt cctgacgatt gcagctttcg ctcgccgcga 169020
ttggcttaag caattcagtt ccgattggca gagtattcaa cagaatttgg ttgttacaac 169080
gacagcgttt gtcgtaatct tccaattcta aaagatggac ggctagggga catacgacaa 169140
ataacatgta tgcagtcaat tgcatatatc gtaccgataa aatgttagtg tgcggattca 169200
gaatcggatg atgcaaccgt cttagcatca tatcgaaaaa gtatacatat taccgattca 169260
ttataattag ggaattattt ccaacgcgga cgtttgttag tgacagcgtt ttcttctaca 169320
tgcggtccat tactatcctt tacttttacc aatactctgt gccatgagtt gtcttttta 169380 ccatccagcc atttggacaa atgatgatcg ggagctaaac atacaggttt acctcgagga 169440
ggcaatagat aatgttgagg tttgtcacac tcaggaggat tgggagggtc acgaccaacc 169500
caaaataagc cacctatagg atgatgtaaa gctttgtggg tacacggaca acgcaattct 169560
ctactgtgaa ccccatggta atacataaat gccatcaaaa gactaatcag cgaaccaaaa 169620
attaatcgca ttctaatttt attaactacg tcactatcag taattcgtaa tatccggtat 169680
tcccggaaaa tcactcaaaa ctgcgtccat gacacatcaa ttcccgataa gtacccccct 169740
ttgaaatcgg atccccccac ataccaatca atcacacaac acacaggttt aaaaatcgat 169800
cacacgtcaa ttaggtttca aaatcgatac tgtttattat caggaatcta gactaattct 169860
acaatgacag ctctgaattt ctctctcgtc tttcttgtca ggttctcatc atcaatcttc 169920
acttccaccc atcgaggagt catcgtcgct ccaaaaccct ttggggtcgc tggttggaaa 169980
agtctctgac acgatccagg caccccgtac ccagtccgac tgatctagct tacggagcat 170040
ctcaacaggc atgagctgca gggccacggc tgtcacggca gggattatta ctaccgttca 170100
ggtaaactgt atctccctga gttaccgtga tgggtctttc tacatgttga ctttgcgtaa 170160
aaaatcgccg gtaaaatgtt ttttcttgtt catgtaaaag taccggaact aaaatgctag 170220
ttagaatggt tgcagttgct attagcgcgg ctagtaacag tagtttagtg ttacattgta 170280
tacccatgtt tttaataact atgaatattc tgcttcacac cataagtgct taacccacaa 170340
aaaccacacg gagacattat tggctaaaaa taaaaacaaa agtttattga tgtgcatgtt 170400
aggttttagt ctaaaattca tctgggtcgt atttgggaag ttttgtataa cgcggtcttc 170460

-continued tggggacgcg acggctaccc atgtataagg ctataagtgc cacagatacc actatacccg 170520
cccatacagc atgaattccc aggggaatgt tagtgttttt tacagttttt attacattgt 170580
cccacgttct gctattatgc tggtctgatt cctcttttgt tttacattta tcaggtatag 170640
gagacgatgt tgcagttcct gataacacgg ttaaatagta gttttccttt ttaccgtcac 170700
tgtaacgttg caaaacgtat tttccagcgt gttcggtagt tacgttgtat atagtgagag 170760
aggtcttatt gcagtctaaa cacatgccgt tcagtgggga agttgaataa taatgtccaa 170820
tgctgcacag ttggtgtgcg cgaggtccat attttatcca ttctatatcg tgccatacat 170880
ccgttctact gcagtttttc aaagtgacgt atccaccgac atatcctgtt acattaatta 170940
cttcgtaatt taaattagag tgtttataaa cggtgtacaa actgccattg caagttatgt 171000
tgctggtatt caaccaggga gtagtactat gaatggtaga aaacgttaat gttggcgtag 171060
cgcttgacga tgattttgaa agcgttgaag tggttgctga tgcgactgaa gaagcggtag 171120
agggtttgtg cgtggttcca tttgcgatag ctgaagtgct gttagcatcg gtgacagagt 171180
tagaagaatt tgtgatagtg gaggcggtgg aggtaaaggc aattgcacgg acaggagcac 171240
gtgtcattgc aaccttcaga tatcgtaatc atcagtaacg tccacttaac cgtaaatctc 171300
cagtccataa cgttattaaa tttcggttaa cgggcattga tgtttcttcg gacgttgttg 171360
atctttcttg cccgtttatt ttctgatatg gtctcataag acatttatcc ggaaacgttg 171420
cttagtcctc gtgctcagga ttgtatcgaa ctatgaattc tgattcactt atatcgtcac 171480
ttaatggatg atattttta tttagagctc gtcggacgaa aaataggaga atgcaggcta 171540
cacaaattaa tgctaacgtc cacgtagtgc gtctgccgtg tgatgtgtta gaatgattgt 171600
tatagcggta taaatgatct atagatgatg tggctgtatt gtcttcataa ttggtcggtt 171660
tatgagaagt gtcccattcg tgctttggtt cttcacatac ccagggattc acgtgtgtcc 171720
cgtttgtgtt gtttctagga tgtatttgca gattaaagtt ttgattttgt tcggagggat 171780
gcccagtttt ataacatcga aagctatatt taccagaatg agtaaaatta agaccgtaca 171840
gagataaaga taaattacga tcgcatgtaa aacataaatc atagtgatgt tttagataat 171900
ttgtgtgcca ctcacatagt atacgcgaat ggaggatttt caatgaatgg ttatgatatt 171960
ttccatttct tatgttggga tgggtgtatt ttccgtgtgt ggatatatta aaatgtctaa 172020
gccaggctgt tttgtagcac gatgtgatgg ttaggttgtg tgttatagta atattgtctc 172080
cttgtgccgc ctccaataat gtttcagatt cttttgatat cgtattattt gtactgttag 172140
gcgatgagca agttggaagc ggtgtagtga cgttttcatt tgcatttatc atagtagtag 172200
tgttggttga taatgatata gtttgcaaag tcacagtact atcggttaca tgctgtgtcg 172260
atgaattcgt gtcgccgttt ggtgaagttg ttattacagt tacgttagtt gtagatgttt 172320
gggtagatat ggtggaaata gttgaggtca cgtctgtgcc ttttacagag cttgcagtga 172380
atcctgtgga tgtgttgacg ttgccattgg aggatgtgaa catagtggta gacatttcgg 172440
tggtttgtaa cgtagatgtc agttgtgtag tagatattaa gcttgtgggt gtaatcgacg 172500
tggaagtatt ggcgatagtg gtgttgttac acttgctttt ctgcagaatc caaaaaataa 172560
taaacatgca tattatttgc gtatatgatg acttgttcca ccgtcgatgt tgtgtgcgca 172620
tcttttactc caaatccccg tccaccgtca acaacagagg ttccgtatct aggtccgtcc 172680
gcaaccgttc agcgtcctgt tccccgattc gttgcgaccg cagaaagcag atgaccagtg 172740
cgccaacaaa gatcatcagt cccgaaaccc aggcgcaatg gagtgagagg ccggaccact 172800

-continued

```
ggcgttttaa atccgagata attgctcggt ctgcctcttg ggaatccgta accacaactc 172860
tccctggtcc cggataaaag catcgacgcg tttccaaagc tcggcagaag ctacgtgggt 172920
ggatgatgag gtaaaaagcc tcgacatcac cggtatactg atcctgcagg aggtagactc 172980
ccgtatcttt aaccgtaaga ttgtacagcg tgagattttg gcgcgtgcac gtgaaagttg 173040
cgccaccctg atgcgtggtt tctttatagg cgtctgtaat gatgcaaagt ggcggcatac 173100
gacgcatgta tctgctgtag atatcataac gttgccagac tacgctgtga tggctagtgt 173160
taagcctggt aaccagagta cgtgtacggt cctcgcaggt ggcgcggtaa ttggcgagct 173220
ttaggggttt tttggttggt tcgacggcgt tcgatgaact tccctgagtt gtgaacaaaa 173280
acagcgacgt gactatgaca agcgtgaggg gggtgctgta ggtctgcatg gtgcaaaaca 173340
cgttctcgcc ttccttgtca gacgtcgtcg tcctcgtcct cttcgtcgtc tgtgcccgtc 173400
ggttcgatca acggggagtt atctttctgt ctggagggtc ggtatggaat ccgttcgtag 173460
atgttctgct ttttagccgc gtgttgttcc agctttttgc gtgtcaggct ccgataggcc 173520
agacattgat ctacctcggt gcccgtgttg tttttctcct cctcgcgcgc gtaaattacg 173580
aagaagacca ccagcaggac tatcagcgtg gccacgaacg agcccgcgcc ccaggccgag 173640
tatgcgccta gcattgtaat gggttctgtg acccggcatt tgcacatcgc gtggcacctg 173700
ctgccattgg tagatgtgct attcggattg cacttacatg ttaggtgggt attttctgtt 173760
ttcacgagac aattggtggt aaccgtgttt tcggcgcaaa cggccacgta gcttatcaaa 173820
ccgagtgcta aaaagcacac cgcgtgcatt acacgcggat acatattaaa acaccgtgtt 173880
ccacaagcac cgcacacgtc gatcctcccc gcacggtctt cagcccgccc atgacatgat 173940
ctccctcacg ttacccttca acactctgta gtactctgtc tcggcttccg gtccccatgt 174000
cctaatcata acaaaacacc gtgtcactgt ccatctccct gtcttttcgc gccgccggtc 174060
ccccccaaac catgtctcta gatgccgcca gccaccaacc ggcggcacgg cggctcttgg 174120
attcggcatt ggtgcgccgc gtcttggcct gcatgatcat cgtcatcatg atcgccatta 174180
gcatctggat cctgacctac gtgctgtttt tctaataaga accccggccc ctgacggtaa 174240
ttttcctttc ttctccgttt ctcctcagct gccgtacgtg atgcctcacg gccatctccg 174300
acaggccctc tccccgacct cctggacatg tgagggcttg ttgctcctcc tgggattgct 174360
ggtgctcttc tttcaccacc acaaccagtc ggccgtagag aggcgtcgcc gcgtctcgtt 174420
cgtcgaggtc gatcgactgc cgcatgagag cggatggtat tcttccgatg acgacggaga 174480
ccgggatggc gatgaggaaa ctggagagag ccacaacaga aacagcgtgg gactgtccgc 174540
tgtttttagc tgagactggc gtgcgacctg taaaccgtta ctcgggtctc aagatggttt 174600
ggaagttgtg actcatcttc ctgtgggcaa tgcccaaccg gacgcgagtg tcccataaaa 174660
gccgggcgct ccggcgagac catgccatcc tcgccttcgg acgccccgct cctcttctct 174720
ctcctctcct ccccgctgcc gcggccactg ccgccgccgc ccataccatc ggcatgtcgg 174780
ccgacaaatc gcagctgtcg tcgtcgccgc cgcagctgta gcagttaacg tcgccggcct 174840
tcaggaggag atggcgctct gcgtcgtctc ttcgtcccgc ctccctctgt ggtcgtgggt 174900
ggtgcgagag tacacgatgg gtggctctcg tctcggggga ccacaggggg aggggggtaa 174960
tttattattc gtattactgt aattttgtat cgcttaattt gtttagagcc gcacgcttga 175020
caacgccttg tatagcctta tttatcccga tgactttttt ctccgtacaa gaaatggacg 175080
tcacttgagc agacacagtt tcatcgacca cgacagtctc atgatctgac tacctctgac 175140
ccgccaatga gaaaaccgaa aagtaaaaga tgaccgcgcc ctcggagtcc tttttccctt 175200
```

-continued ttcaatcatg aaagcaagag gcagccgaga gaatgccagt aagagacgac catcgcagac 175260
acagtacgat actcatctta gaacgaacca gcgaataacc atcacacgta cagcagaatc 175320
tcatgaacta gtcaaccaac gtcataaaat cttcacacaa tcgtttttgc gaacttttag 175380
gaaccagcaa gtcaacaaaa gactaacaaa gaaaaaccat cttggaatta aaaaaagtag 175440
catcgttacc ttatgaacca gcagcattca gtatatacac cagatataat atatttatta 175500
atgtatcctc tctttctcct gatgtaattt tgtttttgta aattcaattg ttgaaagtct 175560
ctccctgggg gaattgcata tcttattgat gaagaagaaa tccctgccat atgtgttgtc 175620
aaactatcat tatttctcta tatgggtatt ttttttctaa gaagcaaaag actagcagca 175680
gccaaaataa acctgatgaa atctttaact gaactcccgg tggtctgtgt gtatatttct 175740
gttggtggtc ggttgtctga acccgggtgg gttgttcgga aacggcggga cggggaaacg 175800
ggtggaaaca gcgtcgctat atacgtgact tttgatctaa acggacgtcg ctaggctgac 175860
agtttacgaa ttgctaaaca aggtggtcag gaacacaaca agcggggctt tgcctggtag 175920
gatttcctgt ggaaacaatc accggatgtt atcgtggctg gtacataagc tggttctggc 175980
tgcaagcgct ttttactgca ttaggttcgg cgttagctct tgcttaggaa cgccatggct 176040
ataacgggaa ataaccggtt tggcagcatt ccattgtggg gggggggta cttatagcgt 176100 gtttcatgac ggtgtttata catgaaggtg cgggtttcaa taaagtagag gttaaaagtg 176160
gtgacaatgt aaccattgaa cacaaaaacg acccgatgac tacgaaatgg agccatctga 176220
atcaaggatg gttatgtaat gtaacaggga gacatgcacc tctagtgaat aatggatcaa 176280
gcgtttgtgt aacgaattgt actcatacat ctttagatct gtgcaatatc acgaagggta 176340
acgatggcgt tgtcgacctt ggtcgttggt tcggagagaa taaagacgag tacagcggtg 176400
aattatggta tttgactact aaaaaattagg tttagagagt gttaggttac gttgacctag 176460
ttagatttcc tgtgtagaac aatgaccgga cgtgcttgga ctggtacata cgcaggggct 176520
ggacgtggtt accggtcact ggactcggtt tcgctgtagc tgtggttcaa cctgaacatg 176580
gctcccagag ctgctaggaa ccggtccagt cacatttttt ggtgggtggg gggtactaaa 176640
aaagtgttta atattggggt ttaatgataa aatccaggtt atggatatga ggaaactgaa 176700
tacctcgcag ggtcgaaatc ttaccacagt tgatgataga agacggtttt ccatcgggtg 176760
ggaaacatgg gatgacggtg gagagtctct atacgatgtg actaataatg gtacaacggt 176820
catcaataca acagcctgtg tttcaagttg ttcgcatacg tcgcttgtgc tttgcaatat 176880
gacgcagcag actgattcgt tgtacggagt gggtcatcgg ttgaatgacg aagaagatgg 176940
tgaactgtgg agagtttcgg tttcttaata atcccatacg acatgtgttc atttatatct 177000
gaattttagg atgatgacta tagtataact ctggggaaca aatatcatac gttaatcact 177060
ttaagttacg ccgttaggaa aagaaaatca gtccgaatga agcatagtca gccgaatgat 177120
acagcaatag cttgtttaca acgtgttctt ttttacatta tgaacgtgcc ttgcttttta 177180
tacacacatg gagacagagg tccctcagcc cttgtcacga caactccctt tttctaaacc 177240
gtatgtgctc caaaccgcat ctcctcatcg tcacgtgaaa taccatggga cccctttttcg 177300 tcacacacgt ctttccgctt actcaacgcg tcagcccgcg ctcggcagag ctaccatata 177360
aaaacgcagg ggtttagcgg cttccccaga tcgctgctgc cccggcgttc tccagaagcc 177420
ccggcgggcg aatcggccgg ctggtcggtc ggcgctcgga cggatgggga gaacggcggt 177480
gacttagccg cccgtggccg ggagaagatg gaggagccga gatgacaacg gcagtcgtgg 177540

-continued aagggtcgcc aagccccggt ccttctcttc tgtctggtcg aatctcgttt tcttttttca 177600
accgctcttt ttatcacctt tttatgtgag tttctcttcc gcgtctcccg gccgtaccat 177660
ccacccatgc agcatgcacg cgtgtatgta tgcatcgtct ctcctccgtc ccgactacca 177720
tcagcagcac cactaccgcc acccccagcg ccaccaccgc tgccgtcgcc accgcgttat 177780
ccgttcctcg taggctggtc ctggggaacg ggtcggcggc cggtcggctt ctgttttatt 177840
attttttttt atttttatc ttctcctttc cttaatctcg gattatcatt tccctctcct 177900
acctaccacg aatcgcagat gataaacaag agggtaaaaa gaaaaaagct acagacattt 177960
gggtacctca gctttccgat aactcgaaga attcaaagtc gacgattccc aacgagagaa 178020
aacagaacaa aaacaaggtc atttttattt atcctcatcg tcaacaacaa ctaccgacaa 178080
caacgaaaca ccaccaagaa tgtcaatccg caagggtgtt cctgccccct cgacgcgcct 178140
gtcgcgatcc tcatggcgag gaccgcgatc tccgtatagg tagatgaaat tatcccgtgt 178200
ccggtcctga ttccccgcat gccctgcaca tcctgacgcg tcggtcagca gccaaacaat 178260
cataggaaat gaaccagaag aacaaaaaga tcatctctct cggtgtatag caacaccaac 178320
aacaaccgca tcgcaacatc ttcatccgca agacggaaag aaaacaacaa taatgagaat 178380
gaaatcacca caaccaagcc agatttcacg tccatgagtt tttattatat tattatcaaa 178440
acgaaaaaca gaaaaactgt catagataaa tataaaaaaa aatagaaacc acaaacgact 178500
actagtactc caatcttaga tgtatatgct cctagataag atttagtatt accataatca 178560
tcgaagaatg aaagacgacg atgattcctt accgctcctg ccacccggtc tgtatgtaga 178620
gagagaagag agaaaacggt gaatccaaga tccccgggtc ggcgtcggca tgccgctgat 178680
cgcagtggcc ccacctcggc atgccggcgc cgggcgagga attgctcatg aaaaaagtat 178740
ctttctgtaa aaaaagaaaa caatacatga ttaaccgaaa agaaaccaac aaaaagaacc 178800
cgagatcagt cgatttcgat cactacgata aacacatgga agatttcttg aaaaaagaaa 178860
agagaaagag accaccttcc cggcggcgga cacgctcctc tccgtcgccg ttctgcacca 178920
tgattcgatc aataacaaca tcatcatcgg agaccatctt ttaatcaatc agcgttgcag 178980
tagtcgactc cctggacacg aaggagtcat ccatttttat cctcgcactt cttcgctctc 179040
aaagccgcct ttaaagttga aatgaaagga tggaaacatg gaatacagtt ttaattgcac 179100
gtatcaccat tttactacaa aaagaaaaaa aaacaactta cacatagtat taccttaggt 179160
ttacggataa gtagagtgta ggcgtttttg aaacagttca gccaatgcaa tcttgtctcg 179220
gcataatcac tctttctgca tataatagta gtagtagatt tattcacatc aacacagcga 179280
aaaactccag catcaaagta cacctagaga cagcccttaa aatatagttt gcagctttta 179340
gatgtactta caccaaagaa gattaccgtc cttacgagaa aacagatact cggatatagg 179400
aatcaagaca gctctgcact gaaaacacac tctcctgtca cgacaccgcg ccacaccaga 179460
ggcgtacgcg tgacttcatc gcaacgatcc atcgtgatgt ccctcgcaga acctaaaaag 179520
accaaaaaaa aatcttggac cacagttgtc gattcttgaa gacaatattc tcgtgagaac 179580
tttgagattc gcacttgaaa cctcttagga tccacaaaaa caacaacctc tgtatggaaa 179640
atgcgctatt ttatctcagc ttttctccca aacctcggtt tcttcctatt cttaagtttt 179700
ccctagtata tttgcctcct tataacaaaa gaagcacaag ctcggtcgca cggattattc 179760
cttctgctaa tctattattt tgttcctttt ttttttgttt gccttcaccc ccttcactcc 179820
ctgtagcaac acagagtagt agacacaata aatgagaagt ttgcatgcat ttgccgtgtc 179880
cgtggtctgt tatagcgtgt ggagtgctcg ggatggatgg acgtggggac ggattcctga 179940

-continued ggctacaaag atacgcggag acgtcgtggc gaggggatgg gtttattgga tatcggtgaa 180000
gcagcgtggc ggcgaaatac gcgatccctg ggctggtaga tccccctacc ccgtctaccg 180060
gggacgttta tccttgggac atgtaaatgt ttcggccggc atccacgcgc cacgttcacc 180120
gcgtcgtgcc cagcgccatg tgcgggtcgt ttcggcgtga agttggacgg cgtggtttcg 180180
gggattgtga accgtggctg agggtgtaga agggatagga aagagcgtgt catgtgggcg 180240
agtcgtagca tgtgggtgcg atgcggtgga tatggtgggc tggggtggtt ttgggcgtgg 180300
agatgtggag atgggggtga tccggatgcg tggcaatagg cctcgagctt gggcttctcc 180360
cgcggatgga cgttctaact gtacacggcg gccgtggcct ccgagtaaaa aaaccaggtg 180420
ctgacgccag acacagacgc cgtcctcgga atcgtgtgcg cgaaagcctg tgccgcggca 180480
gcgtacgacg ttccagtcag cgaggccgtc gcgttggcgc gccaacagta aggtcacgat 180540
aggttggcgg cccatggttc cgaagcgtcc ccacatgcac cagcagtcgg cgtcgaagtc 180600
gcttgcgctg tcggcccggt cgccaccgcc gcggcggatt tccgcgcggg ggacggggta 180660
gccgagcgct gcgccttcgc caatgttgtg aagtagatgc gtcagttgat ggtgatgttc 180720
tgtggaaaaa tgagcgcttt cctgagggtt ggcgtcgggg tatgcgtgta gttggggttg 180780
tgttggagcg tagaggtgtt ggcgggcctg cgcgcaagcg gcgtaatccg cggcgtcgag 180840
ctccatctgc gtgcggtgtt cttcgttggc gtgtttgtcc gaggtttgga taggcggttg 180900
tgtgttgctg tggtgtaagg gtagcgtgtg ttggtactgt gggtgaagcg gcgtggtgtg 180960
ggtgctgttt gtggctgtgg ctggcatgat tgtgcggcag gtgtgtgttg aagtgggtgg 181020
aggttaaata ggcgagggcg agtccccgtc cccgcacacc cgcgtcctcg ccgcaaacac 181080
ccgcgccacc cccgtccctc ggtccggacc cgcaacaccc gcgtcgccaa cgtaaccccc 181140
gtacccgcaa cgccccggcc ctaccgccgt cacgcacacc ccccggcccg cagcccggta 181200
cccagcgcgc ccaaaaagcg ccgtggagac acccgtacag agatccctca gcgcgatgac 181260
gccccgcaaa cctcacgcag tccggtcccg cgaacagata ccgtgggacg acacgcaccg 181320
gtagtgcgca caaaggcagc cgcgcttacg ggcctcaaag ttccctcagc cccgtcccgc 181380
gccggcgtcg ggttgggtgt gccgggggcg cggctgggtg ggtgcgtgcg tgccgggtgt 181440
gtcgcgggcg tgtgtcgggt gtgtcggtcg ggtgtgtcgg tcgggtgtgt cggtcgggtg 181500
tgtcggtcgg gtgtgccgcg ggtgtgtcgg tcgggtgtgt cgcgggcgtg tgtcgggcgc 181560
gtggcgggtg tgtcgcgggt gtgtcggtcg ggtgtgccgc gggtgtgtca ggggtgtgtc 181620
agcggtgtgc gcggcttcgg ggtgcgtgtc ggcggccgga gggaacaaca agtgtgcccc 181680
ggggcccgcg agcccccccc cctcccctcg gccggacgcc tcttctgcgt gtgtcctcga 181740
cgcgggtcgc gccgtacttt gcggccgttg cttcccccgc ggtccccagg gtcgcgcggc 181800
gccgcgcgct tcctcttttc cgcgcgcggc cgtccccccg gggacttcct cttttccgcg 181860
tcgtttccgc gtcgctggcc cctgggaggc gttcttcgtg tgtccccggg gacccgcgct 181920
gccgtcgtcc cctggggact tcctccgttc cccggggaat caaacagaca cagacacgcg 181980
tcttcttttc gccgtgcgcg ccgcacgccg cttttatgcg ccgccgccgt cccaaccgca 182040
ccgcaacgcg actccaagac tccaaatttc acccccccgc taaaaacacc cccccgcccc 182100
acggggaccc aacacacggc ccggaatgga tgtcaggcgt ccacctagat gacagcgctc 182160
gagtgctgcg ggcctgtctc gcgtcttcct tcgggcgtct gcctttccca gtcgagtgcg 182220
tcgtcgcctg ccgggtggtt ttccacgggc ttccagactg cgcgtcgcca aggcggcgcc 182280

-continued agcaagcgcc gtgcacggcg ctgcctataa aagccaggtg cgtgtcggcc gtggcacacg 182340
gacaacggag acgtccgcgt gtgtaaacgg cgtgctcgct gacgcgggtt gtgttgctat 182400
atagtggacg tcgcctcgac gtcggaggtg tccggcggcc atggcccagc gcaacggcat 182460
gtcgccgcgc cccccgcccc tcggtcgcgg ccgcggtgcc ggagggcctt cgggggttgc 182520
ttcctctcct tcttcttgtg tgccgatggg agcgacgtca acggcgggaa ctggtgcaag 182580
tactgcgggt tcggcgacgc cgggccacgg cgtccaacgg gtagaacccc gcgggccgcc 182640
gggcgcccct ccgggtagcg gcaacaatag caacttttgg cacgggccgg agcgcctgtt 182700
gctgtctcag attccggtgg agcggcaggc gctgacggaa ctggaatacc aggccatggg 182760
cgccgtgtgg cgcgcggcgt ttctggccaa cagcacgggc cgcgccatgc gcaagtggtc 182820
gcagcgcgac gcgggcacgc tgctgccgct cggacggccg tacggattct acgcgcgggt 182880
gacgccgcgc agccagatga acggcgtggg cgcgacggac ctgcgtcagc tgtcgccgcg 182940
ggacgcgtgg atcgtgctgg tggcgaccgt ggtgcacgag gtagaccccg cggccgaccc 183000
gacggtgggc gacaaggccg gccatcccga gggtctgtgc gcgcaggacg gactgtacct 183060
ggcgctgggc gccggattcc gcgtgttcgt gtacgacctg gcgaacaaca cgctgatcct 183120
ggcggcgcgc gacgcggacg agtggtttcg gcacggcgcg ggcgaggtgg tgcgggtgta 183180
ccgctgcaac cggctgggcg tgggcacccc gcgcgcgacg ctgctgcctc agccggcgct 183240
tcgacagacc ttgctgcgcg ccgaggaggc gacggcgctc ggacgggagc tgcgccggcg 183300
gtgggccggc acgacggtgg cgctgcagac gccgggcagg cgactgcagc cgatggtact 183360
gctgggcgcg tggcaggagc tggcgcagta cgagccgttc gcgtcggcgc cgcaccccgc 183420
gtcgctgctg acggccgtgc gtcggcacct gaaccagcgt ctgtgctgcg gctggctggc 183480
gctgggcgcg gtgctgcccg cgcggtggct gggctgcgcg gcggggccgg cgacgatgac 183540
ggcggggacg acggcgatgg cgacggggac gacgttgccg gcgggggcga gcggcacgga 183600
gacggaggcc gccggcgggg acgcgccgtg cgcgatagcg ggagccgtgg ggtctgctgt 183660
gactttacct ccgcagccgt acggcgccgc cggcgggagc gcggtttgcg taccaaacgc 183720
ggacacgcac gcggtggtcg gaacggatgc ggcggcggcg gcagcggcgg cgccgacggt 183780
gatggtgggt ccgacggcga tggcgggtcc ggcggcgtcg gggaccgtgc cgcgcgccat 183840
gctggtggtg gtgctggacg agctgggcgc cgtgttcggg tactgcccgc tggacgggca 183900
cgtgtacccg ctggcggcgg agctgtcgca ctttctgcgc gcgggcgtgc tgggcgcgct 183960
ggcgctgggg cgcgagtcgg cgcccgccgc cgaggccgcg cggcggctgc tgcccgagct 184020
ggaccgcgag cagtgggagc ggccgcgctg ggacgcgctg cacctgcacc cgcgcgccgc 184080
gctgtgggcg cgcgagccgc acgggcagtg ggagttcatg tttcgcgaac aacgcggtga 184140
ccccataaat gatcccgtcg catttcgtgt ttcggacgct cgaactctcg gtctcgacct 184200
caccaccgtc atgacagagc gtcaaagtca attgcccgaa aagtatatcg gtttctatca 184260
gattaggaaa cctccttggc tcatggaaca acctccaccc ccatctcgcc aaaccaaacc 184320
ggacgctgca acgatgcccc caccgctcag tgctcaggca agcgtcagct acgcgctccg 184380
atacgatgac gagtcctggc gcccgctcag cacagttgac gaccacaaag cctggttgga 184440
tctcgacgaa tcacattggg tcctcgggga cagccgaccc gacgatataa aacaacgcag 184500
actgctgaag gccactcaac gacgaggcgc cgaaatcgac agacccatgc ctgtcgtgcc 184560
tgaagaatgt tacgaccaac gcttcactac cgaaggccac caggtcatcc cgttgtgcaa 184620
gcttatcgcg ataccgtcga cctcgagggg gggcccggta cccagctttt gttcccttta 184680

-continued gtgagggtta attgcgcgct tggcgtaatc atggtcatag ctgcttcctg tgtgaaattg 184740
ttatccgctc acaattccac acaacatacg agccgggagc ataaagtgta aagcctgggg 184800
tgcctaatga gtgagctaac tcacattaat tgcgttgcgc tcactgcccg ctttccagtc 184860
gggaaacctg tcgtgccagc tgcattaatg aatcggccaa cgcgcgggga gaggcggttt 184920
gcgtattggt cgaccaattc tcatgtttga cagcttatca tcgaatttct gccattcatc 184980
cgcttattat cacttattca ggcgtagcaa ccaggcgttt aagggcacca ataactgcct 185040
taaaaaaatt acgccccgcc ctgccactca tcgcagtact gttgtaattc attaagcatt 185100
ctgccgacat ggaagccatc acaaacggca tgatgaacct gaatcgccag cggcatcagc 185160
accttgtcgc cttgcgtata atatttgccc atggtgaaaa cgggggcgaa gaagttgtcc 185220
atattggcca cgtttaaatc aaaactggtg aaactcaccc agggattggc tgagacgaaa 185280
aacatattct caataaaccc tttagggaaa taggccaggt tttcaccgta acacgccaca 185340
tcttgcgaat atatgtgtag aaactgccgg aaatcgtcgt ggtattcact ccagagcgat 185400
gaaaacgttt cagtttgctc atggaaaacg gtgtaacaag ggtgaacact atcccatatc 185460
accagctcac cgtctttcat tgccatacgg aattccggat gagcattcat caggcgggca 185520
agaatgtgaa taaaggccgg ataaaacttg tgcttatttt tctttacggt ctttaaaaag 185580
gccgtaatat ccagctgaac ggtctggtta taggtacatt gagcaactga ctgaaatgcc 185640
tcaaaatgtt ctttacgatg ccattgggat atatcaacgg tggtatatcc agtgattttt 185700
ttctccattt tagcttcctt agctcctgaa aatctcgata actcaaaaaa tacgcccggt 185760
agtgatctta tttcattatg gtgaaagttg gaacctctta cgtgccgatc aacgtctcat 185820
tttcgccaaa agttggccca gggcttcccg gtatcaacag ggacaccagg atttatttat 185880
tctgcgaagt gatcttccgt cacaggtatt tattcgcgat aagctcatgg agcggcgtaa 185940
ccgtcgcaca ggaaggacag agaaagcgcg gatctgggaa gtgacggaca gaacggtcag 186000
gacctggatt ggggaggcgg ttgccgccgc tgctgctgac ggtgtgacgt tctctgttcc 186060
ggtcacacca catacgttcc gccattccta tgcgatgcac atgctgtatg ccggtatacc 186120
gctgaaagtt ctgcaaagcc tgatgggaca taagtccatc agttcaacgg aagtctacac 186180
gaaggttttt gcgctggatg tggctgcccg gcaccgggtg cagtttgcga tgccggagtc 186240
tgatgcggtt gcgatgctga aacaattatc ctgagaataa atgccttggc ctttatatgg 186300
aaatgtggaa ctgagtggat atgctgtttt tgtctgttaa acagagaagc tggctgttat 186360
ccactgagaa gcgaacgaaa cagtcgggaa aatctcccat tatcgtagag atccgcatta 186420
ttaatctcag gagcctgtgt agcgtttata ggaagtagtg ttctgtcatg atgcctgcaa 186480
gcggtaacga aaacgatttg aatatgcctt caggaacaat agaaatcttc gtgcggtgtt 186540
acgttgaagt ggagcggatt atgtcagcaa tggacagaac aacctaatga acacagaacc 186600
atgatgtggt ctgtcctttt acagccagta gtgctcgccg cagtcgagcg acagggcgaa 186660
gccctcgagt gagcgaggaa gcaccaggga acagcactta tatattctgc ttacacacga 186720
tgcctgaaaa aacttccctt ggggttatcc acttatccac ggggatattt ttataattat 186780
ttttttttata gtttttagat cttctttttt agagcgcctt gtaggccttt atccatgctg 186840
gttctagaga aggtgttgtg acaaattgcc ctttcagtgt gacaaatcac cctcaaatga 186900
cagtcctgtc tgtgacaaat tgcccttaac cctgtgacaa attgccctca gaagaagctg 186960
ttttttcaca aagttatccc tgcttattga ctctttttta tttagtgtga caatctaaaa 187020

-continued

```
acttgtcaca cttcacatgg atctgtcatg gcggaaacag cggttatcaa tcacaagaaa 187080
cgtaaaaata gcccgcgaat cgtccagtca aacgacctca ctgaggcggc atatagtctc 187140
tcccgggatc aaaaacgtat gctgtatctg ttcgttgacc agatcagaaa atctgatggc 187200
accctacagg aacatgacgg tatctgcgag atccatgttg ctaaatatgc tgaaatattc 187260
ggattgacct ctgcggaagc cagtaaggat atacggcagg cattgaagag tttcgcgggg 187320
aaggaagtgg ttttttatcg ccctgaagag gatgccggcg atgaaaaagg ctatgaatct 187380
tttccttggt ttatcaaacg tgcgcacagt ccatccagag ggctttacag tgtacatatc 187440
aacccatatc tcattccctt ctttatcggg ttacagaacc ggtttacgca gtttcggctt 187500
agtgaaacaa aagaaatcac caatccgtat gccatgcgtt tatacgaatc cctgtgtcag 187560
tatcgtaagc cggatggctc aggcatcgtc tctctgaaaa tcgactggat catagagcgt 187620
taccagctgc ctcaaagtta ccagcgtatg cctgacttcc gccgccgctt cctgcaggtc 187680
tgtgttaatg agatcaacag cagaactcca atgcgcctct catacattga gaaaaagaaa 187740
ggccgccaga cgactcatat cgtattttcc ttccgcgata tcacttccat gacgacagga 187800
tagtctgagg gttatctgtc acagatttga gggtggttcg tcacatttgt tctgacctac 187860
tgagggtaat ttgtcacagt tttgctgttt ccttcagcct gcatggattt tctcatactt 187920
tttgaactgt aatttttaag gaagccaaat ttgagggcag tttgtcacag ttgatttcct 187980
tctctttccc ttcgtcatgt gacctgatat cgggggttag ttcgtcatca ttgatgaggg 188040
ttgattatca cagtttatta ctctgaattg gctatccgcg tgtgtacctc tacctggagt 188100
ttttcccacg gtggatattt cttcttgcgc tgagcgtaag agctatctga cagaacagtt 188160
cttctttgct tcctcgccag ttcgctcgct atgctcggtt acacggctgc ggcgagcgct 188220
agtgataata agtgactgag gtatgtgctc ttcttatctc cttttgtagt gttgctctta 188280
ttttaaacaa ctttgcggtt ttttgatgac tttgcgattt tgttgttgct ttgcagtaaa 188340
ttgcaagatt taataaaaaa acgcaaagca atgattaaag gatgttcaga atgaaactca 188400
tggaaacact taaccagtgc ataaacgctg gtcatgaaat gacgaaggct atcgccattg 188460
cacagtttaa tgatgacagc ccggaagcga ggaaaataac ccggcgctgg agaataggtg 188520
aagcagcgga tttagttggg gtttcttctc aggctatcag agatgccgag aaagcagggc 188580
gactaccgca cccggatatg gaaattcgag gacgggttga gcaacgtgtt ggttatacaa 188640
ttgaacaaat taatcatatg cgtgatgtgt ttggtacgcg attgcgacgt gctgaagacg 188700
tatttccacc ggtgatcggg gttgctgccc ataaaggtgg cgtttacaaa acctcagttt 188760
ctgttcatct tgctcaggat ctggctctga aggggctacg tgttttgctc gtggaaggta 188820
acgaccccca gggaacagcc tcaatgtatc acggatgggt accagatctt catattcatg 188880
cagaagacac tctcctgcct ttctatcttg gggaaaagga cgatgtcact tatgcaataa 188940
agcccacttg ctggccgggg cttgacatta ttccttcctg tctggctctg caccgtattg 189000
aaactgagtt aatgggcaaa tttgatgaag gtaaactgcc caccgatcca cacctgatgc 189060
tccgactggc cattgaaact gttgctcatg actatgatgt catagttatt gacagcgcgc 189120
ctaacctggg tatcggcacg attaatgtcg tatgtgctgc tgatgtgctg attgttccca 189180
cgcctgctga gttgtttgac tacacctccg cactgcagtt tttcgatatg cttcgtgatc 189240
tgctcaagaa cgttgatctt aaagggttcg agcctgatgt acgtattttg cttaccaaat 189300
acagcaatag taatggctct cagtccccgt ggatggagga gcaaattcgg gatgcctggg 189360
gaagcatggt tctaaaaaat gttgtacgtg aaacggatga agttggtaaa ggtcagatcc 189420
```

-continued ggatgagaac tgtttttgaa caggccattg atcaacgctc ttcaactggt gcctggagaa 189480
atgctctttc tatttgggaa cctgtctgca atgaaatttt cgatcgtctg attaaaccac 189540
gctgggagat tagataatga agcgtgcgcc tgttattcca aaacatacgc tcaatactca 189600
accggttgaa gatacttcgt tatcgacacc agctgccccg atggtggatt cgttaattgc 189660
gcgcgtagga gtaatggctc gcggtaatgc cattactttg cctgtatgtg gtcgggatgt 189720
gaagtttact cttgaagtgc tccggggtga tagtgttgag aagacctctc gggtatggtc 189780
aggtaatgaa cgtgaccagg agctgcttac tgaggacgca ctggatgatc tcatcccttc 189840
ttttctactg actggtcaac agacaccggc gttcggtcga agagtatctg gtgtcataga 189900
aattgccgat gggagtcgcc gtcgtaaagc tgctgcactt accgaaagtg attatcgtgt 189960
tctggttggc gagctggatg atgagcagat ggctgcatta tccagattgg gtaacgatta 190020
tcgcccaaca agtgcttatg aacgtggtca gcgttatgca agccgattgc agaatgaatt 190080
tgctggaaat atttctgcgc tggctgatgc ggaaaatatt tcacgtaaga ttattacccg 190140
ctgtatcaac accgccaaat tgcctaaatc agttgttgct ctttttctc accccggtga 190200
actatctgcc cggtcaggtg atgcacttca aaaagccttt acagataaag aggaattact 190260
taagcagcag gcatctaacc ttcatgagca gaaaaaagct ggggtgatat ttgaagctga 190320
agaagttatc actcttttaa cttctgtgct taaaacgtca tctgcatcaa gaactagttt 190380
aagctcacga catcagtttg ctcctggagc gacagtattg tataagggcg ataaaatggt 190440
gcttaacctg gacaggtctc gtgttccaac tgagtgtata gagaaaattg aggccattct 190500
taaggaactt gaaaagccag caccctgatg cgaccacgtt ttagtctacg tttatctgtc 190560
tttacttaat gtcctttgtt acaggccaga aagcataact ggcctgaata ttctctctgg 190620
gcccactgtt ccacttgtat cgtcggtctg ataatcagac tgggaccacg gtcccactcg 190680
tatcgtcggt ctgattatta gtctgggacc acggtcccac tcgtatcgtc ggtctgatta 190740
ttagtctggg accacggtcc cactcgtatc gtcggtctga taatcagact gggaccacgg 190800
tcccactcgt atcgtcggtc tgattattag tctgggacca tggtcccact cgtatcgtcg 190860
gtctgattat tagtctggga ccacggtccc actcgtatcg tcggtctgat tattagactg 190920
gaaccacggt cccactcgta tcgtcggtct gattattagt ctgggaccac ggtcccactc 190980
gtatcgtcgg tctgattatt agtctgggac cacgatccca ctcgtgttgt cggtctgatt 191040
atcggtctgg gaccacggtc ccacttgtat tgtcgatcag actatcagcg tgagactacg 191100
attccatcaa tgcctgtcaa gggcaagtat tgacatgtcg tcgtaacctg tagaacggag 191160
taacctcggt gtgcggttgt atgcctgctg tggattgctg ctgtgtcctg cttatccaca 191220
acattttgcg cacggttatg tggacaaaat acctggttac ccaggccgtg ccggcacgtt 191280
aaccgggctg catccgatgc aagtgtgtcg ctgtcgagta caggtgttgg ccgttgtgcc 191340
cggacgggag atcgagtccc gtgatcggat cgccaagata tgcgacaatt ttgctattag 191400
caaagtagcc cgggatatgg agcagttgtt ggccaccaaa aatttggaga agccactgga 191460
gcagccggag aatgggtaca cctacaaggc cacctggttc atgcagttcc gggcggtcct 191520
gtggcgatcc tggctgtcgg tgctcaagga accactcctc gtaaaagtgc gacttattca 191580
gacaacggtg agtggttcca gtggaaacaa atgatataac gcttacaatt cttggaaaca 191640
aattcgctag attttagtta gaattgcctg attccacacc cttcttagtt tttttcaatg 191700
agatgtatag tttatagttt tgcagaaaat aaataaattt catttaactc gcgaacatgt 191760

-continued

```
tgaagatatg aatattaatg agatgcgagt aacattttaa tttgcagatg gttgccatct 191820
tgattggcct catctttttg ggccaacaac tcacgcaagt gggcgtgatg aatatcaacg 191880
gagccatctt cctcttcctg accaacatga cctttcaaaa cgtctttgcc acgataaatg 191940
taagtcttgt ttagaataca tttgcatatt aataatttac taactttcta atgaatcgat 192000
gcgatcgctg gttaattaag atccagacat gataagatac attgatgagt ttggacaaac 192060
cacaactaga atgcagtgaa aaaaatgctt tatttgtgaa atttgtgatg ctattgcttt 192120
atttgtaacc attataagct gcaataaaca agttaacggg cccgctagca cgcgtaagct 192180
taccggtctt aagctgcagg cggccgcttt acttgtacag ctcgtccatg ccgagagtga 192240
tcccggcggc ggtcacgaac tccagcagga ccatgtgatc gcgcttctcg ttggggtctt 192300
tgctcagggc ggactgggtg ctcaggtagt ggttgtcggg cagcagcacg gggccgtcgc 192360
cgatgggggt gttctgctgg tagtggtcgg cgagctgcac gctgccgtcc tcgatgttgt 192420
ggcggatctt gaagttcacc ttgatgccgt tcttctgctt gtcggccatg atatagacgt 192480
tgtggctgtt gtagttgtac tccagcttgt gccccaggat gttgccgtcc tccttgaagt 192540
cgatgccctt cagctcgatg cggttcacca gggtgtcgcc ctcgaacttc acctcggcgc 192600
gggtcttgta gttgccgtcg tccttgaaga agatggtgcg ctcctggacg tagccttcgg 192660
gcatggcgga cttgaagaag tcgtgctgct tcatgtggtc ggggtagcgg ctgaagcact 192720
gcacgccgta ggtcagggtg gtcacgaggg tgggccaggg cacgggcagc ttgccggtgg 192780
tgcagatgaa cttcagggtc agcttgccgt aggtggcatc gccctcgccc tcgccggaca 192840
cgctgaactt gtggccgttt acgtcgccgt ccagctcgac caggatgggc accaccccgg 192900
tgaacagctc ctcgcccttg ctcaccatgg tggcgaccgg tggatcgatc ctaggcctcc 192960
aaaaaagcct cctcactact tctggaatag ctcagaggcc gaggcggcct cggcctctgc 193020
ataaataaaa aaaattagtc agccatgggg cggagaatgg gcggaactgg gcggagttag 193080
gggcgggatg ggcggagtta ggggcgggac tatggttgct gactaattga gatgcatgct 193140
ttgcatactt ctgcctgctg gggagcctgg ggactttcca cacctggttg ctgactaatt 193200
gagatgcatg ctttgcatac ttctgcctgc tggggagcct ggggactttc cacaccctaa 193260
ctgacacaca ttccacagct ggttctttcc gcctcagaag gtacctaacc aagttcctct 193320
ttcagaggtt atttcaggcc atggtgctgc gccgaattgt taattaagac aataagtcta 193380
cgtagaagac taggccggcc atcgattcga tttaggtgtt cacctcagag ctgccagttt 193440
ttatgaggga ggcccgaagt cgatggcaag tgtagcggtc acgctgcgcg taaccaccac 193500
acccgccgcg cttaatgcgc cgctacaggg cgcgtcccat tcgccattca ggctgcgcaa 193560
ctgttgggaa gggcgatcgg tgcgggcctc ttcgctatta cgccagctgg cgaaaggggg 193620
atgtgctgca aggcgattaa gttgggtaac gccagggttt tcccagtcac gacgttgtaa 193680
aacgacggcc agtgagcgcg cgtaatacga ctcactatag ggcgaattgg agctccaccg 193740
cggtggcggc cgctctagaa ctagtggatc gatcccccgg gctgcaggaa ttcgatatca 193800
agcttagcaa acagaggatg gctaaccgtc gttgcatgtt ccaggccatg agccaggcta 193860
ggcccgtaca ccagacgcag agcatggatg acaggacata ggcctggatt accacggtgc 193920
gatcgaaaca cagcccgatg gtggacacgg atatcgtagt gagggtggta tataccatga 193980
ccagcatcag ggtcccgggt cggcgccgac gttccagcca gtacgcgtgg caacgcagag 194040
cgcagggtag cagtgtgctc cagaagggca gtgtatcgcg caggtagggg gtcgtcacgc 194100
gccacggtat gagcatgaaa aggatggtag tggctatggt agcgctggtc tggaacacga 194160
```

-continued

```
cggtgccgta gagacgtacc atccagagaa agtgttgaac gctccgcagg gtgtcttcat 194220
ctttggtgat tacggtgact cgacggatcg gcggtggtga cggcggcgac acgggtgggg 194280
gtttctcttt cttatggccg agtggctcgc cttggtgaaa ctggatctgt accatgacgg 194340
gtgctcgacg aacagtcgtc ggggcttcag gtacccggca agttttatag agaaaggggg 194400
acgatgggtg gtggctacga gccaccgcca ccttcgcaat acgaggatct gaaggcggca 194460
aagacggtcg tccagggcag gcgccagagg ttgggactga gcacgatcag cgtgatttta 194520
aacatggtca ccagtcctac gtagatcagc agcgagccgc gtaacgtctg agcggccggc 194580
agttcgtcgc ggatgtaacg cgtgccgtag aaagtcacgg tcatcataag gaagacgatg 194640
gcgccgtagc cgtagagtag aatacgctga tgatggaaca cggtctggtc gccgataacc 194700
cagagcgtga tgaaaaaaac gctggtgagc acccgtgagc atatgagctc ccaacgctta 194760
gcgcgaaaac tgtccccaac catgacagcg ccggtgcaag ctatccacag cgtgaggacc 194820
agtgtgtagt cgatgaggat ggcgggcagg tcggagcacc aggtgtagaa aaccgtggta 194880
acggagagga ggcctacgta gcccatggtc aataccacgt cgtcggggtg cctttcgccc 194940
tgtatcaaga ccaaacacca gagaagggag ggggcaaaaa ccagcagcag aggggaagat 195000
tcatgttgac atatgttgtg ggaatcgggg atacccagcc aaatcattcc gcagaaagcc 195060
gtactgatgg cgatgtgaaa gaccactagg gcgtagaccc ggacgaggac agcaaaacgg 195120
cgcagccaca taaggccgtg gtgcagctgc aggagggaag cccattgcgg cgaatgtagc 195180
gacggcagcg gcgggtccat gaggcgggtg atgcgcccga gtgaacgggt gagcgtctcg 195240
gtggagtctt cttataaacc agcggagctc aggcagcctt gctctggaac gtcgcggtgg 195300
tggtgttgag gatgacgctg agcgtgccgt tgtcaatcag gtaatgatga taggtgccga 195360
gcttggccag gtagctgaac atttggtccc agcgtgccga ccacaccacg ggcgtgagca 195420
ttaggagtgt ggtgtgataa atgagtgttt cggtggcgta aagtatcagc gagctgcgga 195480
tgatgtggct cacgggcatt ttggtggcga tgtagcgcac gtcttggaaa agaacggcca 195540
ggatgcagcc cacgaacacg gtgtagagac acagcagagt cttatgcaac caagtgtaag 195600
tagaagccag gacgctgacc atcaccgtca aaagtgtgga ggtaaaaagc gcgtcacgcc 195660
acacggagct gagacggtgc tcccaagcca cgccgttgca ggccacgaac aacgtccacg 195720
ttaagatgag actggaaacg ccaatgggcg ctgtggcgca caggttgagc ccggcggtgg 195780
tgaacgacag aagcgccaca tacagcgcaa acaccaggcc gttgctgggg tgtctgtgat 195840
cggtaagctc cagcgcgccc agaaccaaca ccggtgtgca gctaagcaat aacggcgaag 195900
gatcgtcgcg gcactcgtag cccagcgagg ggtaacccag ccaaaccagc gcgctaatga 195960
gcacgctgaa agcggtttcc agcgtcagca atccgtagac acgcatgacg atcgcggtcc 196020
gccgtagcca acacaccgca tcttcggaag ctgtggacgc tgtttccgaa taccgggagg 196080
agatcgtgct tccctcttct aaggatcgga aagtagcgtc cgtcgtttcc gcggacgcgg 196140
cttccctggt acgctccgtt tccgacgacg cggtttcccg ctgcgtggaa actgtctcca 196200
tgtcgggacc gcagcgcccg gcggcgtatc cgcaaggtct cgaagctaca gcttgtcaga 196260
ggaaaagtag gtttgcaaaa aggtgcgcag ggtcatgatt ctcagcacca tcagcagagt 196320
gaaaaccagg ctgagaaaca ccttgacggc cgccaaaagc gcgcgttcca gcggcgtctc 196380
gtagcgtaca gccagggccg cttcgtggaa atgcgagacg gctagacagg taatgagcac 196440
gctgaaggac aagacgatct taaagcacca ggaccaacca cgcctcaaga tgaccaccac 196500
```

-continued gattgccgtg aaggtcaacg tgatcaaagc atggacgacc acgatctgac ggcggacggt 196560
acgttcggga gccaacaacg ctacgccggt gcagctgaga aaggccagta aggtgaacaa 196620
cgcggccgag atgaccaacg taccgtccag gcagagacat atcacgatca acggcggcac 196680
gtgaagcagc gtgtaaaaga gcagaacgcc gatattgctg ggatgcgatg tttcgtaaca 196740
gtgaatgaag atcaccgacg tgacgggtat gacaaagacg aggctgggcg aggactccgt 196800
gagacacaga cgggaatggt gaaaccacgt cgcgggcgcc gcgtagcaga aggcgctcaa 196860
caacgcggtc aagccggcca gctgccaacc cacggcgcca taagtgtgca gcgccacgcg 196920
gcaacagtcg acccaagcca gactgcgggt cgccagccgg gtctcttgta tcccgggggg 196980
cacgtagatg accgtgccat cggtgggtac ttgaaaccct ttttctcttc tcatggtgcg 197040
ctgcgttctc tggaaacggc tgctctgtcc gaaaaccagt tccgaacgaa aatctagggc 197100
gagagggtgg acaacggcgt cgacgacgaa gcatgggaca ggtcgttcgg cgttaacgtc 197160
atcgcgtcgg acgacggtag ttctaagaga cgtagatcgc tcagcaggtc ctgacagttg 197220
cggattcgca agatcagaaa aaaaagggaa atgaacgtaa taaagagctg tagcgacgta 197280
tgcgccacat cgcgtggcat aagaacgtga cggacgaaaa ggacctgctg cgaaaagtgg 197340
ccggcgaaga taaggcccac cgtgctgtag aagcccaaaa gcagccgcag gggccaagtc 197400
cagggccgcg tgaagacgat gagaacgtta gccagaaaga ccacgaccca gacgccgttg 197460
atgagggtaa attgatcgga cagggtgcag ttgtcgcgac agatgaagac tacttccgcg 197520
cagagcaagg tgatgaccaa cgtgagcaca aacgacgtca acacctcgcg gggctcctgg 197580
caggcacacg tgacacctag cgccgggatg tgcgccagga ggccggcgag taatagcacc 197640
agctgtcgga acggacgacg gcagcgcggg tgccggtttc gctgagcgag aaccggtcgc 197700
tcatagcgga aatacacgaa gagcgcggag gccacaggca ccaggaggag cacctcgggc 197760
gcccagacaa cgtgacaagg aaagcccgga cgcgacttaa gagtcgctgt agggaagacc 197820
agagagaagc tacccaagac ggccaccgcc gcggagattt ggaagaggag caagccggcg 197880
attcggacga caacctcgaa gcgatgcacc cagcccagca cggccaccac ggccgcttca 197940
tcatagtcgt cgttgttgcc gctgtcgaac agccgccgaa acacgatctg tcgctgggtc 198000
gcggtgggaa agcgcagacc catgacagcc ggaggctata tgaccgtgcg tctaaggcgc 198060
gagatccgtg gggggacttt tagatgtttg ggcggcccgc ggttctaaca ggcttgattg 198120
gtggagacgg ccggcgcggc gggtggggga aacgacgagt ttttccgtta cgccatggtt 198180
cgcgtgaggt ttctctgtac ctcccgcaaa aggtcacagc ccgaaatgga ggccgcgttg 198240
gtggccccgg tggcgcgtga cgataaccag gtcatccaag cgatgagttt gtctaatgag 198300
tcctcggtgg tgaagaggat aagaatgagc aggtacaggt acaccaggtt ctcatagaga 198360
cacaaggtga gcaggtcggc ctcggaccac gcgatctcaa acaggcgcgt ggtgtcaaag 198420
accgtgacga ccagcatgaa gctgagcgcc atggcgtaat agcccaaaaa aagtttgtgc 198480
cctaacggta cgggttgcag gtaaagtgcg atcaagaacg cgataacgcc gatcacaaac 198540
agcgtgatga tgacctgcca tcgacggtga ttatgggcgg ctagacccgt gacgcagctg 198600
cagaggctaa aaagcacgca agccaagagg cccgagaagg tcaccagcgt agaggaggag 198660
caggcgctgg ccacgatcac cgaaagcgtc gtgagcacgc tgtaaatggt gagcaggccc 198720
gggctcggcg gcgacgtgaa cgatccctcg tcgcgtttgc cgtgcagcag agccagacag 198780
atggtgggca ccaccaaact caaaggcggc ataaagccag tgcaacagag aaagacggtg 198840
cttttgagat gcggaaaagc cagcaccagg cccagacaga gcaagaaggt gcaggtgccc 198900

-continued

```
tgcacggcca cggtgctgta gacccgcata caaagcaaaa agcgacgtac gtcgttcgtc 198960
gagacggagg aaatcataat gactccgcgc gagggtcgcg ggggtggggg cgcccaggcc 199020
gtcccggtgg cctctgagtt cggagacatg acggcggtgg cgatcaaaag gcgcgtatga 199080
aaaaccgttt atagagtgta atagaatcac cgtcatcccc acacggcgtt cccccataaa 199140
gtcacgtcac actcgagtaa gcgtgaaaaa gctttattgt tgaataaaaa acacgagtac 199200
aacaccgagt tgcggtgtcc tgtctgtcta ctgggtgggg gaggttcatc gtctgtctct 199260
ggagggaagg tggggaacgt ttaagcgagc aggagcgtgt catctccccc atctttttat 199320
aacaagctga ggagactcac gccgtcgatg cgtccgccgt gtttctcggc gtactgctgc 199380
acccagacgt ggccgctaaa gatggcgacg ctcatgttta ggagactcat gacgatggtg 199440
tacaacacga cgctgacaca gacgctgttt ttagacagcg ttccacgctg gtagatgaga 199500
tccagggtct cgtaaataag cacggccgaa gcggcggtca ccaccaggac gtagagtccg 199560
ctgtagatct tgctgaccca caacacgggc gaaaagtaaa gcaataggta aaagacgatg 199620
acggaccagc cgtaaccaat cccgatgact ttccagcgcg tgggattgtt gccggccagg 199680
taggtgagac cgctgcagag aacgaaaaag accatcacca gggcaaacga cagaccgatg 199740
acgcgccttt ctccgcaaaa gcccgtgcac acggtgatgc cggtgttgat cagcaggcac 199800
gccaccgtga gatgagcaaa attggtggtg tgtgggcgaa actcggcgaa accgcgtagc 199860
atagccagcg tggacacggg cacgatggag gacagggctg gcactatgcc gttggcgcac 199920
tgtccctgca catcggggaa ggcgagccaa gccagcaggc agaccgtgag ggtacaagcc 199980
agctgccaca cgagcccgtg atagacctcc atgagcagct tgaagcgttt caaccattgg 200040
aagagctgct gttcggccac cagcgcgtgg ctgcgatgga gcggcacgat ggtaaccgtc 200100
ggcgactcat ggtgttcgga aaccgaggcg gtgtcgccca tgctgccgct tacgaccgct 200160
gtcggtctaa ggtaggcgtc gatgaaacag tccgtcttat cagcacccgg ttaccgcgga 200220
tttgattgac gtcacgagtg tggtcaaacc gtggcggcac cctgtatccg acccgtcgtc 200280
atgggctcca caaccagagc ctcagaagat ggtacatgcc gatgaataaa gccacatttt 200340
cgacatagag gcgtagcgag ggctgaaaac tctccgggaa agaactctga caggtgatca 200400
gggacagatc gtgaattagc atcagcgtca ccgtcaacag cgtcgtcgcg tgtaaaccga 200460
gaaagaacgg ggccgcggcc cgcagcagcc aaagtcccag cgccgtagcg cagagcagag 200520
acaggaccga cggtagccac agccgccgga gagacgcgcc aggatcgcaa cccaaaagcg 200580
aggcccccag gcagctgaga tctaccgcca gggcgagaag agccgcgccg acaaaggcct 200640
gcggcgacgg ctggcacatc agcaaggtca gaaaggctag cgcgtgcggc aggcagtaag 200700
ccaacaggag tgggagtttg cggggacaac ggtcgatcga cggaccgcgt agcagcagga 200760
acaggcagcc gacgggcacg acgaggctga gatgagaaag cggcggtggg tcgtcgtccc 200820
gtccccgctc gcatagctcg gccaccggtg gcggcatgag ccaccagctg agcacgctga 200880
gggcgacggt ggcggtaagc tggaaggcga cgaggacgga ggcgcgcagc cataccgcca 200940
gcctctctag gtaggggact acctcctcga cggtccattc tagcgggacg acatgaagca 201000
tggcgacaag cgcggctgct gtgaaaacgg gcgcggtttt ataggcatta ggacttcccc 201060
gtcgtactgg cggctgtcaa agtcccgttg tccaaaggca cgccgtccga aagactaatc 201120
caacggggac ccgagagcat gagcaacaac gtgagaaaga tggccatgct gtccaggtag 201180
agacagacgg cgtgacggat gcattggtta ggtgggcaga aaaagatgac catgagactg 201240
```

-continued tcgtaggcca gaatacccaa aaagaagctg atagagaagg cgcacaacgt caccactatc 201300
ttctgcagcc aatcggcgtc gcttagcaga gcgagcgtga ggaacgaaag cagcatcacc 201360
acgtagacgc agctgatgca tttccagcga cgtcggtcac ggccacctag aaacgccagc 201420
cccgtaaagg agataaacaa cgccagggtc atcacgtagg aacctactag tacgcggctt 201480
tcagagcaca tctggaagat ggccgccgtc aggctgttgg ccaacagata gatgaaaagc 201540
accgtggcgt tactagggtg ttcgttgccc aacgtgtacg tgatgaacat gcagacgatg 201600
ggcacgagca cggtgagaaa gaagctgtag ttctcgacgc aaaagttgcg gttttgtggg 201660
aaccccaacc aaaaaacgct tcccaaaccg aagctgaaag ccagctgaaa gatgaagatg 201720
gcgtacacgc gcagccatac ggtgaacttt ttgaaccact cgagagcctc catgcgggag 201780
agcagcagcg cgttagcctc ctgcgcctgc atggtggcga cggtctcggc acaaagccgc 201840
tgcggcgcac ctacccttct cttatacaca agcgagcgag tggggcacgg tgacgtggtc 201900
acgccgcgga cacgtcgatt aggagacgaa ctggggcgac gccgctgctg tggcagcgac 201960
cgtcgtagcg accgtcgtct gagcagtgtg ggcgctgccg ggctcggagg gcatgaagta 202020
gagcacggag acaaagaggt acatgaggtc catgtacaag cagagcgcgc ccgggatata 202080
actctcatac tcgatgtcgt gcaggatgtc ctgcgtatcg cacaccaccg aggtcacgat 202140
gacggccaaa ccggctatca tcaccaggat ctcacttacc gcctcgggaa aaagagaaaa 202200
tacggcgaac agtaatagaa tcagcgtgga tgcgcccgtc aatagggaac gctgtaattc 202260
cacgtcgcgg gcaaacagat acgtagcgag cgtaaggaaa caaaatagcg ttactgtggc 202320
caccatggca taaatgactg aacgatgact aaagtggaag cctgacgccg tgacagccac 202380
gctggtaagc aacgtgtacg tcagtaagat ccatacgttt ttgggaaagt tgggctcggc 202440
ccaacgcaac agacctaggc acacgatgga gatcattaag caagacagcg tcagacgcac 202500
gctggaaaag agctgctcca gccggtgcgg caacaccagc cagcaaaagg cgcagacgct 202560
cataaggatg aggcattgca cccagataag gatgtagatg cgcagcagga agaccgaccg 202620
ggctatctgg acctgaccgc ggagcgacat ggcggcaacg ccggcggtta tcgccgagat 202680
tcgtctaaat acacaaagcg aactagaaaa cgcacacacg tgatttgcaa aaagaaagca 202740
gctgccggct tattatttta ttaaaaattt atctgtgcag aatcataagt ttatgatgaa 202800
taaaaacggg gaaagggaat ctgcttttag ggacccgggt ctggtccgtc gtctcccatc 202860
tggtcgggtt cggggatggg gacctgtttc agcgtgtgtc cgcgggcgtg catggctttt 202920
gctcgccggc cgcgctgtaa ccaggcctct ttctctgtgg tcggcgagtc ttccgacggg 202980
tagggagtct gggagtccat cgcttcaggc ccaccgctcg ctccctcgac cgtcgtgtcg 203040
tcctcgtttt cgctattaca cggggtttct ggagtatcgc ctatacggtt ggcgattctc 203100
cgggggcggc cgctctcgtc ctcgtcgctg ctatcgccgc ccggtaattc gacgccgcat 203160
tcgttgtacg gagcgcggca catgggcggc ggaaagaact tgggcatgcg aaagcagcgt 203220
tgtccatcca cggtctgcgt ggtttcatcg ttatcctccc ataatccccc ctgtagcgcc 203280
ggcagcgttt cgacgctgtg agaggggaag gcccagttct ggttgtcttg cagcgcgccc 203340
gtgggcagta ggtccgtgcg gccccaggcg ctgctgttgt tgggtacctt gtcagtgccg 203400
cgagtaggtc gcagaaacca gtccagagcg ctctctaact gcgagcgtgt gatggtgccc 203460
agtgcgccgt gccagcgcag cacgtctctt ttcagcgtgt ggtgacagac gggcagctcc 203520
tccaaccgac actcgccgcg caatccgcgg tcgaagcggc agagaccacg cagtttaagc 203580
agaccgcact tgagaaacat gtgaaaatta tcggcaatgc gatacaggtc tgagtcctcg 203640

-continued

```
atcttgtgta ggtagaccac gccaaacttg tcgagcagca ccaggccgct gggcacaaaa 203700
ggcccgtagg ccaggtaata gcccacgagg ccgacgacgt accactcgca gcataagcgt 203760
tgacgaataa agttcagaag atcgcgaaag tccgcggccg gcatgtggtc aaaaggccgg 203820
caggcgcgca ggccctcgat ggagcccagc atgagcaacg gctccacctc ggtgcgaccc 203880
ggcgtgcgga tgaccaggtt gagaccgctc atttcgcggg ccgtcttggc cacggccgca 203940
gcgtcagtgg ggtcggtgca gaggaatttt tgcacatgat agcgcggttc ggtggtggcg 204000
aacggcgttt gtgggtgccg atacacatat tcgcaccaga gtaggccgtt cttggaaaag 204060
gctttgatat cactggccac ctcgtagagc ccgtcggtct cccagtcgta gacgtagacg 204120
gtgccgtaat gacttagcat gagcacacag ggcagttcct gcgcctgctt ggtgtttcgt 204180
gttagatcgc tgtcgggtgg acgtacggct aatacaccga cggcttccag ggtgtcatcg 204240
cagcagagat agtcggcggc cagagaacgt gcgtaaatct gcgggatggc gacctgttcg 204300
cgcatcacta ggaaccagtt ggcggggttg cgcagtgcta cggtggttcc ttggtggcgc 204360
tgcacgtagg ttctcagcgc cggaggatcg tactggcgca gatagaggcc ttgcagcatc 204420
gataacgtct tttgaaagac ggtgtttcta aactgaaaaa cgccgtagtc gcagcggata 204480
gcatcttcgc agcgctcgtc gcgctgtcgg agataggtgc cccaggcttc ggcggcggct 204540
ttggtgagta gggacatgcc ggcggagccg tctcgacagc gagtcggata aagcgcgctg 204600
cgcgaaagct taatatagga gcagcgtcag acgaatcgcg gctggtggcc ctgggggtgg 204660
gacgcgccgc ctacacaaag tgctcccgaa aatcgaaact cttgacccac tccggagaca 204720
aatccgtatt cagattgatg cgtcgcgctt ccacttcggc ttccgaaacc tcggcctccg 204780
tccggtaggc gttaacgata cgctgaccca ggtgccaacg ctctttctct gccaaacgcc 204840
gttgctcaaa ccattcgtct acgtccttga ggtcaaagac agtgtcctcc tcaaggtcaa 204900
agcctaggtc ttcccactcg tcgtcatcgc tctcgtggcc ggcggccata cgcgcggcaa 204960
ccgcgtcctc ccctcctctt ctttcaacgt tgggtaccac gttattttct tcgggttcca 205020
taggttctgc gccactgtcg tcatcatcct ctccctgctc ctcatcgtcc gccaaggcgt 205080
cgtggattat ctccaggttc tgattgtcgg gtacgacgtg gttatcttcg tcgtcgtcgc 205140
gtggcatggg cggcggccga cggcggacga ccggcatggc gcggccgtcg tttccttcgt 205200
cttcctcttc accgtctccc aaggaacgcg gtcgacgacg ttccgcgaag tcgccgcgga 205260
ctacgcgcgc ctgccaaatg gtaaacgcgt cccaaccgtc ccagttattg agcatttcgg 205320
cgcgaaaacg gtcgcctcga cagagccagc gaaactgccg cgcgtagtcg cggtctacgc 205380
cgctgtcgaa catggtaaag tgcagacgcg ccgcctcgcc catgtgtacg cagcctccgt 205440
tgcgttccag cctggccgcg cgccgtagac cgtgttcgta gcggcgacgc acgtacacct 205500
tcatgaggcc ggcgcgaaaa agttcctcta ggctgtcggc cagacggtag atttcaccgg 205560
ctagacgctg cagaggcggc gagcggtcca gatgcgattt gacaatcacc acgtaaaaac 205620
gacagaaacg gtcgaagatg atgaggaagg acgtgtcaaa aaaaccaccg gcgcggtagg 205680
agcccacggc gcccagcagg taccagcggc aacgcagttg cagcgtgacg tacatttcgc 205740
actcggccaa gcgggcggct ggcgctacct cgaagggcca acagtccgtc aagcagccga 205800
aactggtcag gagtttcaac gttttggcat ggcgtccagg tgtatgaaag ttcacgtcgc 205860
gtccgtgatg ttcgccaacg caggcggcca acgcgtcggc gtcatgaccg tgacgcagca 205920
gcatcgctac cacgtcgtgc ggtacccgcg tagcaaacgg cgtctgtggc tgacggtata 205980
```

-continued cggcttcggt gtacatcata ccgtaacgcg ccagctcgtc cagatgacgc gcgcacagca 206040
gcagaatctc ttgcgagggt tcgtagatgt agaggcgcgt accgccaccc atgcagagca 206100
ccagctccgt ctcttcgtag tgatcttcca ccatgatcac gcacttgcct agcacgataa 206160
ggcgttcggg gcaacaaatc acgtcgtcca gcagctggtc gcgtagctcc ggcatggtgc 206220
tgccgggccg tacctgcagg aaccagttgt gcggaatgcc gagcgacagc acctggtcga 206280
cgtggttacg gacccagtcg cgaagcacgt cggcgctgta ctggcactca aagatgccct 206340
gaaagtcgcc catgacccgc agaaaagttt cgtagcgcgt gtggcaatag aggaattcat 206400
cgtttcgcgt aaacgtggga gctccgtctt cccaacgtgt acgccacatg tcaaaagagg 206460
ccgccagcta gacaccccag aaaagaagca gagaaagaga cttctttgtg cgacacgttt 206520
tattccgcgt tctccgctcg acgttcaaat ctggatgtac tcgcgcacac ccgtcaggct 206580
ctttaaggga aaagggtccg agtacgtcac taaccgcgac tgatgcacca gggcggtaat 206640
cacccgctcc gcgccctcgc gcgtcgacga acgcgtcgtc accaggcagt gcagccgcgg 206700
gcccgtatcg tcctgatgac cagcggcctc gcgctcggct gcttccacac cgacaatgtc 206760
gggatccaac acgtagctct gcgagttggt atcgtagcgg tgtagcacca acgtgttggg 206820
gtccagacgc tcccacgcgc cctcgtgcgg gtcaaaacgc tccgttaaac agagccagtc 206880
atactgctgc tgcagaatac gccgctcgcg ctcgcgtcgc tcatcgggca acgcggcgtc 206940
ttcgttgaag agaatgtccc gcttgtggtc tacggcacgc tcgtggtgat gcgggcacag 207000
atgacggtgt tccatacgcg tctgacgttg acgctcgcgc tcgaaacgcc ggtgtcgaaa 207060
gaccattttc agcaacccca tgcggaaaaa ctccgtgatg gtgttggcaa cgcgccgcac 207120
gtagtggttg gggtcgtcca tctggatggc gtacacggca ccgaaccagt ccaacagtac 207180
cagcacttcg gccacaaaac tgcgtcccgg tcgcggacgt cccgtcacgc ctagcacata 207240
ccacggcgtg gccagattag cacggacagc ccaccaccaa cgacggctct ccacctcggt 207300
gagcgcacaa aagggccaaa tgcggtgtaa ctgctgcacc gttttcatca gccgcataat 207360
caccgtgccg taacccggtg tatgcaactt cacgtcgcaa cccaggattc gttcggccgt 207420
ggcgtacgag ccctcaggtg tggtgtcatt gagaaacaaa acatgcatgg tacgcgcgcc 207480
cttagggtat cgtcgcggaa caggtaccgt cattctccgc agagtggtgt gaatcacgtc 207540
gcgatacgca atctccgaac gtgacacacc gtaacgtgcc agttcgtcca ggttgtgcga 207600
taccaacacc atgtactttt cacgagtgtc gtaggcgtag acgcgagaaa agcgacccat 207660
aaaaaccacg tacggggtag ccaccatgcc atcatggtga tcgcgacgtg gctcgggcaa 207720
caaaataaca gcgtatccca acggcgtcag cggctcgcgg caacagatga gctttgacgc 207780
cgcctgtttg gcggcggtaa tgatcccgtc ctccgtacgt aacatcacat gccagccctt 207840
gggggaccc aaggacagac agcgtccctc gttacgatga acgtaacgcg tgatttccat 207900
tggctccagg caaaagaaca gttccttaaa atctcgcaac acttgtcggt ataacgccat 207960
gggatcctcg gccgccacag gcagcgcggg gagctccggc ggcacaactg cagcgccgtc 208020
ggggccagaa cccgcagccg gatccatcat tgcgcgacac tctcagccgg acaaccggcg 208080
tcactgacag aagccgagcc aaatacagag aaagcaacgc cacaccgtca ccccgctccc 208140
aagcgccgcg gaaagtgctc cgatttttca ccgtcgttca cgacgttgat ttgcctcggt 208200
ctgagaaccg acctagcgtt cggaccggtg cgcagaaaca gccggcggtc cgagccactg 208260
agcggttcac agccccggcc gccgatagtt atcggagaga cgttcgagct gcaggtacat 208320
cggcgctccc cgcttcgcca ccccgcgccc gccccagttt atactctccg acgcccettc 208380

-continued caacgcgcct gtggagggcc aatcggaccg cgggagctct ccaagtggat gacaggcaca 208440
gccgggtgcc cgaccgtgaa gagccctcat ccacctgaac agaccgctaa ccgaaggacc 208500
ccgagtcgcg tccgtcagtc ccgacgtccg tcgccatctg gctccctgct gttggctacc 208560
tctcggattt caaaaaagag cacgtgccga tgacggtgca caggaaagag ccaaagtgtc 208620
acagcgtctt tttttatttg tattcctttc ctgttttgta ctcgtaaact gttgacgttg 208680
tttttacatc caaaagggca agtaagaaac aggatgaggc atggtaggtt tgggcgtggg 208740
gcggccctcc agcacggcgg cccgggccgc ccggcgggtg agcacccggc gttgcgccgt 208800
gtctatcttg tgtttcttct gtgtcttttt cctatcttgt tccgcgacgg cctctttcat 208860
cacgttcagc atgcgttcct cgacgccctc cagggatcct ggggaggagg gagtcctagt 208920
gaggcttcca atgttgtttt gtggattttc ggtttcctct tcttggtcgt catcgtcgga 208980
cgtgtcgtct tcctcttgat cctcttcttc gtccgagtag tagacgcata gtccttggtt 209040
catcaggctg ggattcatca ggttctgacg gggaatccgc tgttgtagac gtttaaccgc 209100
ccgttccagg cgagagctca tgccgcacca gacgctgtaa cgccgcacgg gcccgtagcg 209160
ggctgtttgt tcgcgtacat gatcgttgag ctcttgccaa tattgtttgg cacactccag 209220
atcggaggtt tgtggatagt cgggtcggat ccgtggatcc caactgacat cggcggtgcc 209280
ggagacttcg tccagactgt tacgcataga gcaccagtcg ggtcggacga taaacctgtc 209340
cttgcggatt aaccatttat aacgtagttc gtgatggcgt gtagaggccc gtacacgctc 209400
cacggtccca aagcggtccc agaagggaaa gttttcgtgg gggcagcgac ccggcacttc 209460
cagacgttcg gcgtcgtcca cggcgtagtg aaaacgccgg ccggcctggt aaattttgag 209520
cagacccact gttaacaaca tatccacgct gtcagccaac cgccagatct cgcggcgaga 209580
cacgtcaaaa tagaaaaatt cgcaggctcg gtcgaccagg atcacgaaat cggcgtgaaa 209640
gacgccggag ggtagcgatt cgcccaccac acccattatc atggtttcac agcataagcg 209700
gtccacaaag aacttcaaca ggtcgttgaa ttgctccgtc tccatacaga tgaagggcca 209760
gacgcctttg aggttctcgg cctggccgca gagcagtagc ggacgtgtca tctcgcccgg 209820
agtgcgcaga ggcacgcatt cgccgcgata acgacaggtc acacgctgta gttcgctgat 209880
gctgttgtcg tgcaggcgaa ggtcgcagat aatatgatcc ggttgcgtgg ttagcagcgg 209940
cgtgcgcatt tgctcgccgt agatggcctc gcagtgcaac agcccgtgtc gcgcaaaatc 210000
gtccagactg tgcgccaggt agtaaagcac cccgcgatcg cggtctagac accacacggt 210060
ttcgtaacgt cctaacagga gcaccagacg ggcctggcta ggtggctcaa tttcctctac 210120
atacacgaaa aagtcgtcat cgtccgagtc ctcgtcctca gaagaggacc gcggcccgtg 210180
tactctgggc aacacggtgg tagagaactg caggacgccc agagactcga gcgactcttc 210240
gcagcagatg agctgacccc agggcgtttc gggcccgtcg gtgacagccg cgctgccaaa 210300
gatgtcctca aactctacaa aatctagacg ccatccgggt ggcgctgaaa tgggaaggct 210360
aatgttcata tcagcataac tacgaactaa gtggcggatg tcctgccgca agtcttggca 210420
gagaatgagc tttcgtaaac ccttgagggt cctccgaaca acggccccag acgcgtagcg 210480
ataggactgg cgcatggtgc cgcggcgtgg agcggcactt ggcagcctat tttatggagt 210540
ttcttcagtg acgtggcttg ttcacgtcgt tcgtgggctg cggttggcag ctccggtctg 210600
taaaccaccc gaaaagactg acatcgacgt caaagactca cgtaatttgg aacatgtgcg 210660
accgcaaagt gcgtcagaat agcacgtggc tttaggacat aaaaagtacc gtgaggtcta 210720

-continued

```
gacgtggttt ttgtgattga cacttacacc aggtaagcca agggacggtg aaactgtatg 210780
tgaggaacct gggtgcttag acaactaacg tgtaatgctt tttacaggac cgttcaacag 210840
gtgatactac ctgcaaggta atgactacat ctactacaac taccactaat atcatgctac 210900
aggtgagcaa cgtaacgaat cacaccctga atagcaccga aatttatcag ttgttcgagt 210960
acactcggtt cggggtatgg ttgatgtgca tcgtgggcac gtttctgaac gtgctggtga 211020
ttaccaccat cctgtactac cgtcgtaaga aaaaatctcc gagcgatacc tacatctgca 211080
acctggctgt agccgatctg ttgattgtcg tcggcctgcc gttttttcta gaatatgcca 211140
agcatcaccc caaactcagc cgagaggtga tttgttcggg actcaacgct tgtttctaca 211200
tctgtctttt tgccggcgtt tgttttctca tcaacctgtc gatggatcgc tactgcgtca 211260
ttgtctgggg tgtagaattg aaccgcgttc gaaataacaa gcgggctacc tgttgggtgg 211320
tgatttttg gatactggcc gcgctcatgg ggatgccaca ctacctgatg tacagtcata 211380
ccaataacga gtgtgttggt gaatttgcta acgagacttc aggttggttc cccgtctttt 211440
tgaacaccaa agtcaacatt tgcggctacc tggcgcccat cgtgctgatg gcgtacacgt 211500
acaaccgtat ggtgcggttt atcattaact acgtgggtaa atggcacatg cagacgctcc 211560
acgttctttt agttgtggtt gtatcttttg ccagcttttg gttccccttc aacctggcac 211620
tatttttaga atccatccgt cttttagcgg gaacgcaaaa cgagactctc caaaccgtta 211680
ttactttctg tctatacgtc ggtcagtttt tggcctacgt tcgcgcttgt ctgaatcctg 211740
gaatctacat cctagtaggc actcaaatga ggaaggacat gtggacaacc ctaagggtat 211800
tcgcctgttg ctgcgtgaag caggagatac cttaccagga cattgatatt gagctacaaa 211860
aggacataca aagaagggcc aaacacacca aacgtaccca ttatgacaga aaaaatgcac 211920
ctatggagtc cggggaggag gaatttctgt tgtaattcga tcctctctca cgcgtccgcc 211980
gcacatctat ttttgctaat tgcacgtttc ttcgtggtca cgtcggctcg aagaggttgg 212040
tgtgaaaacg tcatctcgcc gacgtggtga accgctcata tagaccaaac cggacgctgc 212100
ctcagtctct cggtgcgtgg accagacggc gtccatgcac cgagggcaga actggtgcta 212160
tcatgacacc gacgacgacg accgcggaac tcacgacgga gtttgactac gatgaagacg 212220
cgactccttg tgttttcacc gacgtgctta atcagtcaaa gccagtcacg ttgtttctgt 212280
acggcgttgt ctttctcttc ggttccatcg gcaacttctt ggtgatcttc accatcacct 212340
ggcgacgtcg gattcaatgc tccggcgatg tttactttat caacctcgcg gccgccgatt 212400
tgcttttcgt ttgtacacta cctctgtgga tgcaatacct cctagatcac aactccctag 212460
ccagcgtgcc gtgtacgtta ctcactgcct gtttctacgt ggctatgttt gccagtttgt 212520
gttttatcac ggagattgca ctcgatcgct actacgctat tgtttacatg agatatcggc 212580
ctgtaaaaca ggcctgcctt ttcagtattt tttggtggat ctttgccgtg atcatcgcca 212640
ttccacactt tatggtggtg accaaaaaag acaatcaatg tatgaccgac tacgactact 212700
tagaggtcag ttacccgatc atcctcaacg tagaactcat gcttggtgct ttcgtgatcc 212760
cgctcagtgt tatcagctac tgctactacc gcatttccag aatcgttgcg gtgtctcagt 212820
cgcgccacaa aggtcgcatt gtacgggtac ttatagcggt cgtgcttgtc tttatcatct 212880
tttggctgcc gtaccaccta acgctgtttg tggacacgtt aaaactcctc aaatggatct 212940
ccagcagctg cgagttcgaa agatcgctca aacgtgcgct catcttgacc gagtcgctcg 213000
ccttttgtca ctgttgtctc aatccgctgc tgtacgtctt cgtgggcacc aagtttcggc 213060
aagaactgca ctgtctgctg gccgagtttc gccagcgact cttttcccgc gatgtatcct 213120
```

-continued ggtaccacag catgagcttt tcgcgtcgga gctcgccgag tcgaagagag acatcttccg 213180
acacgctgtc cgacgaggtg tgtcgcgtct cacaaattat accgtaataa aaaagcgcta 213240
cctcggcctt ttcatacaaa ccccgtgtcc gccccctcttt tccccgtgcc cgatatacac 213300
gatattaaac ccacgaccat ttccgtgcga ttagcgaacc ggaaaagttt atggggaaaa 213360
agacgtagga aaggatcatg tagaaaaaca tgcggtgttt ccgatggtgg ctctacagtg 213420
ggtggtggtg gctcacgttt ggatgtgctc ggaccgtgac ggtgggtttc gtcgcgccca 213480
cggtccgggc acaatcaacc gtggtccgct ctgagccggc tccgccgtcg gaaacccgac 213540
gagacaacaa tgacacgtct tacttcagca gcacctcttt ccattcttcc gtgtcccctg 213600
ccacctcagt ggaccgtcaa tttcgacgga ccacgtacga ccgttgggac ggtcgacgtt 213660
ggctgcgcac ccgctacggg aacgccagcg cctgcgtgac gggcacccaa tggagcacca 213720
actttttttt ctctcagtgt gagcactacc ctagtttcgt gaaactcaac ggggtgcagc 213780
gctggacacc tgttcggaga cctatgggcg aggttgccta ctacgggggt tgttgtatgg 213840
tgggcggggg taatcgtgcg tacgtgatac tcgtgagcgg ttacgggacc gccagctacg 213900
gcaacgcttt acgcgtggat tttggccgcg gcaactgtac ggcgccgaaa cgcacctacc 213960
ctcggcgctt ggaactgcac gatggccgca cagaccctag ccgttgcgat ccctaccaag 214020
tgtatttcta cggtctacag tgtcctgagc aactggttat caccgcccac ggcggcgtgg 214080
gtatgcgccg ctgtcctacc ggctctcgtc ccaccccgtc ccggccccac cggcatgact 214140
tggagaacga gctacatggt ctgtgtgtgg atcttctggt gtgcgtcctt ttattagctc 214200
tgctgctgtt ggagctcgtt cccatggaag ccgtgcgtca cccgctgctt ttctggcgac 214260
gcgtggcgtt atcgccgtcc acttccaagg tggatcgcgc cgtcaagctg tgtcttcggc 214320
gcatgctggg tctgccgccg ccaccgtcag tcgcaccacc tggggaaaag aaggagctac 214380
cggctcaggc ggccttgtcg ccgccactga ccacctggtc actaccgccg tttccgtcca 214440
cgcggatacc tgacagtccg ccgccaccgt accagcttcg tcacgccacg tcactagtga 214500
cggtacccac gctgctgtta tatacgtcat ccgacatcgg tgacacagct tcagaaacaa 214560
cgtgtgtggc gcacgctact tatggggaac ccccggagcc cgctcgatcg acggctacgg 214620
ttcaggaatg tgccgttctt accgccccaa attgcggcat cgtcaacaac gacggcgcgg 214680
tctctgaagg ccaagaccat ggagatacgg ttcaccatag cctggatgtg gtttcccagt 214740
gtgctgctga tactggggtt gttgacgcct ccgagtaacg gctgcactgt cgatgtcgga 214800
cgaaacatgt ccattcgaga acagtgccgt cttcgagacg gtgcgacgtt ctccaaggga 214860
gacatcgaag gtaacttcag tgggcccgtc gtcgtggagt tggactacga agacgtcgat 214920
attactggcg aacggcagcg acttcggttt catctcagcg gactcgggtg tcctacaaag 214980
gaaaatataa gaaaagacaa tgaaagcgac gtcagcggtg gaattcgctg ggctctatat 215040
atacaaaccg gcgacaccaa gtacggtatt cgtaatcagc atttgagtat acggttgatg 215100
tatcctgggg aaaaaaatac acaacagctg ttgggttctg atttcagttg cgaacgtcac 215160
cggagaccgt ccacgccgtt gggaaataac gccaaagtgc ctttcacgac ccgcacgtct 215220
tctacatacg gcgtcctcag cgcctttgtg gtgtggatcg gatccggcct caatatcatc 215280
tggtggaccg gcatcgtgct tctggcggcg gacgctctcg ggcttggcga gcgttggctg 215340
aggttggcgc tgtcccaccg ggacaaacat cacgcatcgc gaaccgcggc gctccagtgt 215400
caacgcgaca tgttacttcg gcaacgtcga cgggctcggc ggctgcacgc cgtttctgaa 215460

-continued

```
ggcaaactgc aggaagagaa gaaacgacag tctgctctgg tctggaacgt tgaggcgcga 215520
ccctttccgt ccacacatca gctgattgtg ctgccccctc ctgtagcgtc agctcctcct 215580
gcagttccct cgcagccccc cgagtattcg tctgtgtttc cgcctgtata aaaataaaga 215640
gacgggaggc tgatcgcggc cttcagcgtc tcatttgtct ttactctcga gtgcggtcgg 215700
tgtctcgtcg gtgagacgag gccgccgccc gacaagttcg atctcatgtc gctcttggag 215760
cgcgaagaga gttggcgtcg cgtagtcgac tactcgcaca acttgtggtg tacgtgcggt 215820
aactggcaga gccacgttga gattcaggac gaggagccca actgcgagca gccggagccc 215880
gcacactggc tggaatacgt ggcggtccag tggcaggccc gggttcgcga ttctcacgat 215940
cgctggtgtc tctgcaacgc ctggcgtgat cacgccttgc gcggccgttg gggtacggcg 216000
tattcctcgg gttcctcggc ctcttcctcc ggtttcgtcg cggagagcaa gttcacctgg 216060
tggaaacgac tgcgccacag tactcggcgc tggttgtttc gccgccggcg agctcgatac 216120
actccgtcta actgtgggga aagtagcact agcagcggcc agagtagcgg tgacgagagt 216180
aactgcagtc tacgcaccca cggcgtgtac acacggggtg aacaacacta atcgataagt 216240
cgcgtgtagg cgactggcta catcaaccgg atatctgcgg ggatttaaaa agacgacccg 216300
ttgtcatccg gcttagagca aaccgtcctt ttatcatctt ccgtcgccat ggctatgtac 216360
acatccgaat ccgaacgcga ctggcgtcgt gtaatccacg actcgcacgg cctgtggtgc 216420
gactgcggcg actggcgaga gcacctctat tgtgtgtacg acagccattt tcagcgacga 216480
cccacgaccc gagccgaacg gagggccgcc aattggcggc gacagatgcg gcggttacac 216540
cgtctgtggt gtttttgtca ggactggaag tgtcacgcgt tatacgccga gtgggacggc 216600
aaagaatccg acgacgagtc gtcggcgtct tcctcgggcg aagcgccaga gcaacaggtc 216660
cccgcttgga agaccgtgcg agccttctcg cgggcctacc atcaccgcat taaccggggt 216720
ctgcggggca cgccccccacc gcgcaacttg ccgggatacg agcacgcctc cgagggctgg 216780
cggttttgca gtcgacggga acggcgagag gacgatcttc gcacgcgggc tgagccggac 216840
cgcgtggtgt tccagttagg gggagtgccg cctcgccgtc accgggaaac ttacgtgtaa 216900
gaacacggca tgacaataaa caacatagcg taaatccccg tgtgatgtgt gtgattgacg 216960
ttcaggaaac atgtccccat catcagcgtc acaactgacg tgggttgggt actgacgtgc 217020
aggatattac gcgagtcaga gaatcgcata agaacggggt ggtgagcggg ttcccacagg 217080
agtttctggc acagaggcac catgagcctt aagttccccg agagggtggg ttacgagaaa 217140
ttgggacacc gcccgtatac caaacgcgtg cgggtgcatg acccgttggg attgacgcgg 217200
tttatcatga ggcaactcat gatgtacccg ctggtgttgc cgttcacttt tccgttttac 217260
gtgccgcggt cctagcacgt cagtggtgac gctgataatt gcaacatggc ccatgacgaa 217320
cccgcttggg acgaacgtca ataccacgtc aaaccaccgt gacttggctg aacgttgaaa 217380
cataaagcca aagcgccgtc ggcacttggc ttcagagcag cgcctcgggg cgatgcgacg 217440
gcgatgaact tagagcaact catcaacgtc cttggtctgc tcgtctggat tgccgctcgt 217500
gctgtcagcc gcgttggtcc gcatggctcc ggactcgttt atcgtgagct tcatgatttc 217560
tacgggtatt tgcagctgga ccttctggga ccagtggtgg cggggaatcg ctcagtccgg 217620
acctggagag agcaggcgga ccgagccaga gggaccttcg ctcggcgttc aggccttaat 217680
actagccaca tcttacctgt cggcagcatg tatcggggct ccgacacctt atccgccggc 217740
ctgtatcgtt ccaaagaaga ggtgttcctc ctcttgaacc gctgtcacgg gccactgtca 217800
acgccgaaaa acgcttgtct ggctgaggtt ggtgtcgtta atggaacttt tttgtctcgc 217860
```

-continued

```
ttcaatgtcg gtgattttca cggagcgtca tgggaaaacg gtaccgctcc cgatggagag 217920

cccggggtat gctgaaattc ttcttaaaat tacgtaaacg acgtcgtcca gtcgttgtgc 217980

cgcgattcgt acggttcatc gtctacgtcg ttttgttcac cgtcgctgtg caacgtgtga 218040

aacaagagcg cgatgcgcac cttcggcggt atgaagaacg gttacggaaa aatcacgcac 218100

ggcgtcggca gtcttttccg tgacttgggg cgatgggtcc gagctgcggt atgggtcacg 218160

gcggcgtgtg tcttagtgac gaagatgccg atgtgtgact aaaaacgtcc cagccccaga 218220

gcgatgtgtt tcaataaaaa aatatgtagt atcatattat gcgtgtcctg gtttttcatt 218280

tctggatgta tttgttacat aaaaggcggt gggatatggg gatgaaacat atgtagatac 218340

gcagtttgat tatccgaaca aagctcgtgt gatgcgaaaa acggtactgc aggatgaaag 218400

tcccgttggg ggggggggaa gcagagaata gtcgcttttg ccgctgggca tacgctatgc 218460

ttgtatttgt gactatacta tgtgcagtcg tgtgtcgatg ttcctattgg gaagggtgtg 218520

aatgtacgag gtataaagaa tggtgggacg tagagaggca tcgctagaca caggttgatc 218580

gttgtgctag ccccacgtga gcagcgtcat gggtaaagcg gtgattaagc gtgaaaacac 218640

cgtaaggggg ggggggcagg aagcttggtg gcagtggccg ttagatacct tacgtgtctg 218700

attggtaca tttgcgactt gtcgggtacg acggtatagt ttaactatga ttatattatg  218760

atgcgcagg atacaatgcc ctaaaacatt gtaacacgaa ac                     218802
```